US012637661B2

(12) United States Patent
Pagliuca et al.

(10) Patent No.: US 12,637,661 B2
(45) Date of Patent: May 26, 2026

(54) METHODS OF ENHANCING STEM CELL DIFFERENTIATION INTO BETA CELLS

(71) Applicant: Vertex Pharmaceuticals Incorporated, Boston, MA (US)

(72) Inventors: Felicia Pagliuca, Boston, MA (US); George Harb, Boston, MA (US); Mads Gurtler, Cambridge, MA (US); Austin Thiel, Southborough, MA (US); Jihad Yasin, Gardner, MA (US); Evrett Thompson, Woburn, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 18/054,860

(22) Filed: Nov. 11, 2022

(65) Prior Publication Data

US 2023/0146780 A1 May 11, 2023

Related U.S. Application Data

(63) Continuation of application No. 17/010,346, filed on Sep. 2, 2020, now abandoned, which is a continuation of application No. PCT/US2019/020430, filed on Mar. 1, 2019.

(60) Provisional application No. 62/637,923, filed on Mar. 2, 2018.

(51) Int. Cl.
*C12N 5/071* (2010.01)

(52) U.S. Cl.
CPC ........ *C12N 5/0676* (2013.01); *C12N 2501/11* (2013.01); *C12N 2501/15* (2013.01); *C12N 2501/16* (2013.01); *C12N 2501/999* (2013.01)

(58) Field of Classification Search
CPC .................................................... C12N 5/0676
See application file for complete search history.

(56) References Cited

U.S. PATENT DOCUMENTS

| | | | |
|---|---|---|---|
| 3,773,919 | A | 11/1973 | Boswell et al. |
| 4,378,016 | A | 3/1983 | Loeb |
| 4,391,909 | A | 7/1983 | Lim |
| 5,674,289 | A | 10/1997 | Fournier et al. |
| 5,843,780 | A | 12/1998 | Thomson |
| 6,090,622 | A | 7/2000 | Gearhart et al. |
| 6,200,806 | B1 | 3/2001 | Thomson |
| 6,436,704 | B1 | 8/2002 | Roberts et al. |
| 6,667,176 | B1 | 12/2003 | Funk et al. |
| 6,800,480 | B1 | 10/2004 | Bodnar et al. |
| 7,029,913 | B2 | 4/2006 | Thomson |
| 7,033,831 | B2 | 4/2006 | Fisk et al. |
| 7,049,296 | B2 | 5/2006 | Castro et al. |
| 7,084,246 | B2 | 8/2006 | Coco et al. |
| 7,153,684 | B1 | 12/2006 | Hogan |
| 7,157,278 | B2 | 1/2007 | Jin |
| 7,163,918 | B2 | 1/2007 | Piccariello et al. |
| 7,297,539 | B2 | 11/2007 | Mandalam et al. |
| 7,326,572 | B2 | 2/2008 | Fisk et al. |
| 7,410,798 | B2 | 8/2008 | Mandalam et al. |
| 7,432,104 | B2 | 10/2008 | Mitalipova et al. |
| 7,510,876 | B2 | 3/2009 | D'Amour et al. |
| 7,534,608 | B2 | 5/2009 | Martinson et al. |
| 7,541,185 | B2 | 6/2009 | D'Amour et al. |
| 7,625,753 | B2 | 12/2009 | Kelly et al. |
| 7,695,963 | B2 | 4/2010 | Agulnick et al. |
| 7,695,965 | B2 | 4/2010 | Martinson et al. |
| 7,704,738 | B2 | 4/2010 | D'Amour et al. |
| 7,964,402 | B2 | 6/2011 | Terskikh et al. |
| 7,985,585 | B2 | 7/2011 | D'Amour et al. |
| 7,993,916 | B2 | 8/2011 | Agulnick et al. |
| 7,993,920 | B2 | 8/2011 | Martinson et al. |
| 8,008,075 | B2 | 8/2011 | Green et al. |
| 8,129,182 | B2 | 3/2012 | D'Amour et al. |
| 8,153,429 | B2 | 4/2012 | Robins et al. |
| 8,187,878 | B2 | 5/2012 | Dalton et al. |
| 8,211,699 | B2 | 7/2012 | Robins et al. |
| 8,216,836 | B2 | 7/2012 | D'Amour et al. |
| 8,247,531 | B2 | 8/2012 | Cochran et al. |
| 8,278,106 | B2 | 10/2012 | Martinson et al. |
| 8,334,138 | B2 | 12/2012 | Robins et al. |
| 8,338,170 | B2 | 12/2012 | Kelly et al. |
| 8,415,153 | B2 | 4/2013 | Majumdar et al. |
| 8,445,273 | B2 | 5/2013 | Green et al. |
| 8,481,499 | B2 | 7/2013 | Watkins et al. |
| 8,501,813 | B2 | 8/2013 | Abe et al. |
| 8,603,811 | B2 | 12/2013 | D'Amour et al. |
| 8,623,645 | B2 | 1/2014 | D'Amour et al. |
| 8,647,873 | B2 | 2/2014 | D'Amour et al. |
| 8,658,151 | B2 | 2/2014 | Kelly et al. |
| 8,785,184 | B2 | 7/2014 | Xu |
| 8,785,185 | B2 | 7/2014 | Xu et al. |
| 8,859,286 | B2 | 10/2014 | Agulnick |

(Continued)

FOREIGN PATENT DOCUMENTS

| | | | |
|---|---|---|---|
| EP | 1456356 | A2 | 9/2004 |
| EP | 1676574 | A2 | 7/2006 |

(Continued)

OTHER PUBLICATIONS

Peterson et al. (2020, Nature Communications, vol. 11:2241, pp. 1-14). (Year: 2020).*

(Continued)

*Primary Examiner* — Anoop K Singh
*Assistant Examiner* — David A Montanari
(74) *Attorney, Agent, or Firm* — Klarquist Sparkman, LLP; Susan Alpert Siegel; Sheree Lynn Rybak

(57) ABSTRACT

Disclosed herein are compositions and methods of enhancing stem cell differentiation into beta cells with use of one or more epigenetic modification compounds. The present disclosure also relates to compositions and methods of sorting and enriching the differentiated beta cells. The present disclosure also relates to compositions and methods of irradiating cell population for reducing proliferation.

60 Claims, 47 Drawing Sheets

Specification includes a Sequence Listing.

(56) References Cited

U.S. PATENT DOCUMENTS

| | | | |
|---|---|---|---|
| 9,096,832 | B2 | 8/2015 | Xu |
| 9,109,245 | B2 | 8/2015 | Agulnick et al. |
| 9,186,381 | B2 | 11/2015 | Zender et al. |
| 9,650,610 | B2 | 5/2017 | Agulnick |
| 9,974,784 | B2 | 5/2018 | Groppe |
| 9,982,235 | B2 | 5/2018 | Agulnick et al. |
| 10,030,229 | B2 | 7/2018 | Peterson et al. |
| 10,138,465 | B2 | 11/2018 | Rezania |
| 10,190,096 | B2 | 1/2019 | Melton et al. |
| 10,253,298 | B2 | 4/2019 | Melton et al. |
| 10,443,042 | B2 | 10/2019 | Melton et al. |
| 10,457,916 | B2 | 10/2019 | Kume et al. |
| 10,655,106 | B2 | 5/2020 | Peterson et al. |
| 11,085,027 | B2 | 8/2021 | Melton et al. |
| 11,466,256 | B2 | 10/2022 | Pagliuca et al. |
| 11,525,120 | B2 | 12/2022 | Pagliuca et al. |
| 2001/0049130 | A1 | 12/2001 | Spielberg |
| 2002/0094569 | A1 | 7/2002 | Yu et al. |
| 2003/0138948 | A1 | 7/2003 | Fisk et al. |
| 2004/0047837 | A1 | 3/2004 | Fong et al. |
| 2004/0060568 | A1 | 4/2004 | Dudek et al. |
| 2004/0121460 | A1 | 6/2004 | Lumelsky et al. |
| 2004/0191901 | A1 | 9/2004 | Assady et al. |
| 2004/0259244 | A1 | 12/2004 | Scharp et al. |
| 2005/0053588 | A1 | 3/2005 | Yin |
| 2006/0040385 | A1 | 2/2006 | Itskovitz-Eldor et al. |
| 2006/0040387 | A1 | 2/2006 | Fisk et al. |
| 2006/0194321 | A1 | 8/2006 | Colman et al. |
| 2006/0276391 | A1 | 12/2006 | Auricchio et al. |
| 2007/0142376 | A1 | 6/2007 | Fleenor et al. |
| 2008/0145889 | A1 | 6/2008 | Fisk et al. |
| 2008/0299582 | A1 | 12/2008 | Mandalam et al. |
| 2009/0047263 | A1 | 2/2009 | Yamanaka et al. |
| 2009/0068742 | A1 | 3/2009 | Yamanaka |
| 2009/0155218 | A1 | 6/2009 | Hayek et al. |
| 2009/0170198 | A1 | 7/2009 | Rezania |
| 2009/0186076 | A1 | 7/2009 | Kataoka et al. |
| 2009/0191159 | A1 | 7/2009 | Sakurada et al. |
| 2009/0227032 | A1 | 9/2009 | Yamanaka et al. |
| 2009/0246875 | A1 | 10/2009 | Yamanaka et al. |
| 2009/0263896 | A1 | 10/2009 | Kelly et al. |
| 2009/0298178 | A1 | 12/2009 | D'Amour |
| 2009/0304646 | A1 | 12/2009 | Sakurada et al. |
| 2009/0325180 | A1 | 12/2009 | Fisk et al. |
| 2010/0015100 | A1 | 1/2010 | Xu |
| 2010/0015711 | A1 | 1/2010 | Davis et al. |
| 2010/0112693 | A1 | 5/2010 | Rezania et al. |
| 2010/0144033 | A1 | 6/2010 | Mandalam et al. |
| 2010/0240130 | A1 | 9/2010 | Majumdar et al. |
| 2010/0255580 | A1 | 10/2010 | Rezania |
| 2010/0260728 | A1 | 10/2010 | Martinson et al. |
| 2010/0267731 | A1 | 10/2010 | Nakamura |
| 2010/0311166 | A1 | 12/2010 | Florio et al. |
| 2011/0008819 | A1 | 1/2011 | Chipperfield et al. |
| 2011/0014702 | A1 | 1/2011 | Xu |
| 2011/0053930 | A1 | 3/2011 | Yu et al. |
| 2011/0151560 | A1 | 6/2011 | Xu |
| 2011/0280842 | A1 | 11/2011 | Melton et al. |
| 2011/0281355 | A1 | 11/2011 | Xu |
| 2011/0305672 | A1 | 12/2011 | Dalton et al. |
| 2012/0009675 | A1 | 1/2012 | Martinson et al. |
| 2012/0021519 | A1 | 1/2012 | Ichida et al. |
| 2012/0052571 | A1 | 3/2012 | Fryer |
| 2012/0052575 | A1 | 3/2012 | Rezania |
| 2012/0052576 | A1 | 3/2012 | Rezania |
| 2012/0135015 | A1 | 5/2012 | Noguchi et al. |
| 2012/0141436 | A1 | 6/2012 | Bonner-Weir et al. |
| 2013/0034526 | A1 | 2/2013 | Itskovitz-Eldor et al. |
| 2013/0071931 | A1 | 3/2013 | Ishikawa |
| 2013/0189777 | A1 | 7/2013 | Rezania |
| 2013/0316357 | A1 | 11/2013 | D'Amour et al. |
| 2013/0330823 | A1 | 12/2013 | Rezania |
| 2013/0337564 | A1 | 12/2013 | Davis et al. |
| 2014/0029704 | A1 | 1/2014 | Becker |
| 2014/0080210 | A1 | 3/2014 | Davis et al. |
| 2014/0134726 | A1 | 5/2014 | D'Amour et al. |
| 2014/0154801 | A1 | 6/2014 | D'Amour et al. |
| 2014/0154802 | A1 | 6/2014 | Robins et al. |
| 2014/0162359 | A1 | 6/2014 | Rezania |
| 2014/0186305 | A1 | 7/2014 | Rezina |
| 2014/0186948 | A1 | 7/2014 | Schulz et al. |
| 2014/0186953 | A1 | 7/2014 | Rezania |
| 2014/0193902 | A1 | 7/2014 | D'Amour et al. |
| 2014/0193904 | A1 | 7/2014 | D'Amour et al. |
| 2014/0199700 | A1 | 7/2014 | Kume et al. |
| 2014/0242693 | A1 | 8/2014 | Fryer et al. |
| 2014/0271566 | A1 | 9/2014 | Agulnick et al. |
| 2014/0287944 | A1 | 9/2014 | Hrvatin et al. |
| 2014/0329704 | A1 | 11/2014 | Melton et al. |
| 2014/0335611 | A1 | 11/2014 | Chen et al. |
| 2015/0017135 | A1 | 1/2015 | Agulnick |
| 2015/0104430 | A1 | 4/2015 | Keller et al. |
| 2015/0218522 | A1 | 8/2015 | Peterson et al. |
| 2015/0240212 | A1 | 8/2015 | Peterson et al. |
| 2015/0247123 | A1 | 9/2015 | Ekberg et al. |
| 2015/0329828 | A1 | 11/2015 | Rezania |
| 2015/0376574 | A1 | 12/2015 | Talavera-Adame et al. |
| 2016/0022742 | A1 | 1/2016 | Zender et al. |
| 2016/0040130 | A1 | 2/2016 | Rezania |
| 2016/0152950 | A1 | 6/2016 | Zhang et al. |
| 2016/0175363 | A1 | 6/2016 | Melton et al. |
| 2016/0177268 | A1 | 6/2016 | Melton et al. |
| 2016/0177269 | A1 | 6/2016 | Melton et al. |
| 2016/0186143 | A1 | 6/2016 | Melton et al. |
| 2016/0208215 | A1 | 7/2016 | Doehn et al. |
| 2016/0326495 | A1 | 11/2016 | Ekberg et al. |
| 2016/0369239 | A1 | 12/2016 | Agulnick et al. |
| 2017/0029778 | A1 | 2/2017 | Peterson et al. |
| 2017/0233700 | A1 | 8/2017 | Kunisada |
| 2017/0240866 | A1 | 8/2017 | Wells et al. |
| 2017/0349884 | A1 | 12/2017 | Karp et al. |
| 2017/0362572 | A1 | 12/2017 | Rieck et al. |
| 2018/0087033 | A1 | 3/2018 | Xu et al. |
| 2018/0153941 | A1 | 6/2018 | Melton et al. |
| 2018/0179593 | A1 | 6/2018 | Melton et al. |
| 2019/0017031 | A1 | 1/2019 | Peterson et al. |
| 2019/0085295 | A1 | 3/2019 | Christophersen et al. |
| 2019/0119649 | A1 | 4/2019 | Melton et al. |
| 2019/0136197 | A1 | 5/2019 | Iwata et al. |
| 2019/0185817 | A1 | 6/2019 | Melton et al. |
| 2019/0338250 | A1 | 11/2019 | Melton et al. |
| 2020/0199539 | A1 | 6/2020 | Melton et al. |
| 2020/0332262 | A1 | 10/2020 | Poh et al. |
| 2020/0347355 | A1 | 11/2020 | Melton et al. |
| 2020/0347356 | A1 | 11/2020 | Melton et al. |
| 2020/0347357 | A1 | 11/2020 | Melton et al. |
| 2020/0347358 | A1 | 11/2020 | Peterson et al. |
| 2020/0385681 | A1 | 12/2020 | Peterson et al. |
| 2021/0017157 | A1 | 1/2021 | Thiel et al. |
| 2021/0198632 | A1 | 7/2021 | Pagliuca et al. |
| 2021/0198633 | A1 | 7/2021 | Nostro et al. |
| 2021/0214690 | A1 | 7/2021 | Melton et al. |
| 2021/0238553 | A1 | 8/2021 | Pagliuca et al. |
| 2021/0353686 | A1 | 11/2021 | Ito et al. |
| 2021/0403876 | A1 | 12/2021 | Pagliuca et al. |
| 2022/0090020 | A1 | 3/2022 | Harb et al. |
| 2022/0162562 | A1 | 5/2022 | Peterson et al. |
| 2022/0233646 | A1 | 7/2022 | Carey |
| 2022/0235327 | A1 | 7/2022 | Harb et al. |
| 2023/0075375 | A1 | 3/2023 | Pagliuca et al. |
| 2023/0085395 | A1 | 3/2023 | Pagliuca et al. |
| 2023/0092449 | A1 | 3/2023 | Harb et al. |
| 2023/0218676 | A1 | 7/2023 | Harb et al. |
| 2023/0332107 | A1 | 10/2023 | Pagliuca et al. |
| 2024/0425818 | A1 | 12/2024 | Harb et al. |
| 2025/0011723 | A1 | 1/2025 | Harb et al. |
| 2025/0122478 | A1 | 4/2025 | Harb et al. |

FOREIGN PATENT DOCUMENTS

| | | | |
|---|---|---|---|
| EP | 2267116 | A1 | 12/2010 |
| EP | 2292734 | A1 | 3/2011 |
| EP | 2341147 | A2 | 7/2011 |
| EP | 2377922 | A2 | 10/2011 |

(56) References Cited

FOREIGN PATENT DOCUMENTS

| | | | | | |
|---|---|---|---|---|---|
| EP | 2569419 | A2 | | 3/2013 | |
| EP | 2283117 | B1 | | 10/2013 | |
| EP | 2650359 | A1 | | 10/2013 | |
| EP | 2650360 | A2 | | 10/2013 | |
| EP | 2664669 | A1 | | 11/2013 | |
| EP | 2674485 | A1 | | 12/2013 | |
| EP | 2970899 | A1 | | 1/2016 | |
| JP | 2006506047 | A | | 2/2006 | |
| JP | 2016503654 | A | | 2/2016 | |
| JP | 2016506246 | A | | 3/2016 | |
| JP | 2016-532436 | A | | 10/2016 | |
| JP | 2017-515507 | A | | 6/2017 | |
| RU | 2011121843 | A | | 12/2012 | |
| WO | WO-9631242 | A1 | | 10/1996 | |
| WO | WO-9920740 | A2 | | 4/1999 | |
| WO | WO-9920741 | A1 | | 4/1999 | |
| WO | WO-0151616 | A2 | | 7/2001 | |
| WO | WO-0188104 | A2 | | 11/2001 | |
| WO | WO-0242445 | A2 | | 5/2002 | |
| WO | WO-03020920 | A1 | | 3/2003 | |
| WO | WO-03050249 | A2 | | 6/2003 | |
| WO | WO-03100026 | A2 | | 12/2003 | |
| WO | WO-2004058764 | A1 | | 7/2004 | |
| WO | WO-2007002136 | A2 | | 1/2007 | |
| WO | WO-2007075807 | A2 | | 7/2007 | |
| WO | WO-2007103282 | A2 | | 9/2007 | |
| WO | WO-2007127927 | A2 | | 11/2007 | |
| WO | WO-2008083331 | A2 | | 7/2008 | |
| WO | WO-2008102000 | A1 | | 8/2008 | |
| WO | WO-2009012428 | A2 | | 1/2009 | |
| WO | WO-2009018453 | A1 | | 2/2009 | |
| WO | WO-2009070592 | A2 | | 6/2009 | |
| WO | WO-2010057039 | A2 | | 5/2010 | |
| WO | WO-2010059778 | A1 | | 5/2010 | |
| WO | WO-2011059725 | A2 | | 5/2011 | |
| WO | WO-2011079017 | A2 | | 6/2011 | |
| WO | WO-2011109279 | A2 | | 9/2011 | |
| WO | WO-2011123572 | A1 | | 10/2011 | |
| WO | WO-2011139628 | A1 | | 11/2011 | |
| WO | WO-2011143299 | A2 | | 11/2011 | |
| WO | WO-2012020845 | A1 | | 2/2012 | |
| WO | WO-2012021698 | A2 | | 2/2012 | |
| WO | WO-2012025725 | A1 | | 3/2012 | |
| WO | WO-2012030540 | A2 | | 3/2012 | |
| WO | 2012/060315 | A1 | | 5/2012 | |
| WO | WO-2012168930 | A2 | | 12/2012 | |
| WO | WO-2013052700 | A1 | | 4/2013 | |
| WO | WO-2013057164 | A1 | | 4/2013 | |
| WO | WO-2013071282 | A1 | | 5/2013 | |
| WO | WO-2013095953 | A1 | | 6/2013 | |
| WO | WO-2014033322 | A1 | | 3/2014 | |
| WO | WO-2014062138 | A1 | | 4/2014 | |
| WO | WO-2014105543 | A1 | | 7/2014 | |
| WO | WO-2014105546 | A1 | | 7/2014 | |
| WO | WO-2014106141 | A1 | | 7/2014 | |
| WO | WO 2014/124172 | A1 | | 8/2014 | |
| WO | WO-2014151871 | A2 | | 9/2014 | |
| WO | WO-2014160413 | A1 | | 10/2014 | |
| WO | WO-2014201167 | A1 | | 12/2014 | |
| WO | WO-2015002724 | A2 | | 1/2015 | |
| WO | WO-2015013653 | A1 | | 1/2015 | |
| WO | WO-2015028614 | A1 | | 3/2015 | |
| WO | WO-2015173576 | A1 | | 11/2015 | |
| WO | WO-2015175307 | A1 | | 11/2015 | |
| WO | 2016/021734 | A1 | | 2/2016 | |
| WO | WO-2016100035 | A1 | | 6/2016 | |
| WO | WO-2016100898 | A1 | | 6/2016 | |
| WO | WO-2016100909 | A1 | | 6/2016 | |
| WO | WO-2016100921 | A1 | | 6/2016 | |
| WO | WO-2016100925 | A1 | | 6/2016 | |
| WO | WO-2016100930 | A1 | | 6/2016 | |
| WO | WO-2016101010 | A1 | | 6/2016 | |
| WO | WO-2016172564 | A1 | | 10/2016 | |
| WO | WO 2017/019702 | A1 | | 2/2017 | |
| WO | WO-2017091943 | A1 | | 6/2017 | |
| WO | WO-2017094001 | A1 | * | 6/2017 | C12N 5/0676 |
| WO | WO-2017144695 | A1 | | 8/2017 | |
| WO | WO-2017177163 | A1 | * | 10/2017 | A61K 35/39 |
| WO | WO-2017222879 | A1 | | 12/2017 | |
| WO | WO-2018159805 | A1 | | 9/2018 | |
| WO | WO-2019018818 | A1 | | 1/2019 | |
| WO | WO-2019099725 | A1 | | 5/2019 | |
| WO | WO-2019169351 | A1 | | 9/2019 | |
| WO | WO-2020033879 | A1 | | 2/2020 | |
| WO | WO-2020264072 | A1 | | 12/2020 | |
| WO | 2022/026933 | A2 | | 2/2022 | |
| WO | 2022/147056 | A1 | | 7/2022 | |
| WO | 2022/192300 | A1 | | 9/2022 | |

OTHER PUBLICATIONS

Schweicher et al. (2014, Front. Biosci., vol. 29, pp. 49-76) (Year: 2014).*

Liu et al. (1999, Biochemical and Biophysical Res. Comm., vol. 260, pp. 712-717) (Year: 1999).*

Lee et al. (2008, Horm. Metab. Res., vol. 40(2), pp. 147-154) (Year: 2008).*

Banerjee et al. (2009, Diabetelogia, vol. 52, pp. 621-625) (Year: 2009).*

Antfolk et al. (2017, Analytica Chimica Acta, vol. 965, pp. 9-35) (Year: 2017).*

Pagliuca et al. (2014, Cell, vol. 159, pp. 428-439). (Year: 2014).*

Co-pending U.S. Appl. No. 18/051,721, inventors George Harb et al., filed on Nov. 1, 2022.

Co-pending U.S. Appl. No. 17/988,257, inventors George Harb et al., filed on Nov. 16, 2022.

Abraham et al.: Glucagon action in the brain. Diabetologia 59(7):1367-1371 doi:10.1007/s00125-016-3950-3 (2016).

Aguayo-Mazzucato, et al., "Mafa Expression Enhances Glucose-Responsive Insulin Secretion in Neonatal Rat Beta Cells," Diabetologia, 54(3):583-593, (Mar. 2011).

Aguayo-Mazzucato, et al., "Thyroid Hormone Promotes Postnatal Rat Pancreatic β-Cell Development and Glucose-Responsive Insulin Secretion Through MAFA," Diabetes, 62:1569-1580, (2013).

"Agulnick, et al., "Insulin-Producing Endocrine Cells Differentiated In Vitro From Human Embryonic Stem Cells Function in Macroencapsulation Devices In Vivo" (2015) Cells Translation Medicine 4:1214-1222".

Amariglio, et al., "Donor-Derived Brain Tumor Following Neural Stem Cell Transplantation in an Ataxia Telangiectasia Patient," PLOS Medicine, 6(2):1-3, (2009). (2 pages of translation of relevance).

Apelqvist, et al., Notch Signaling Controls Pancreatic Cell Differentiation, Nature 400, (1999): 877-881.

Arda et al.: Age-Dependent Pancreatic Gene Regulation Reveals Mechanisms Governing Human β Cell Function. Cell Metab. 23(5):909-920 doi:10.1016/j.cmet.2016.04.002 (2016).

Ashery-Padan, et al. Conditional inactivation of Pax6 in the pancreas causes early onset of diabetes. Developmental Biology, 269 (2004): 479-488.

Assady, et al. Insulin Production by Human Embryonic Stem Cells. Diabetes, 50 (2001): 1691-1697.

Axxora.com Product Search Results for "Alk5 Inhibitor." Retrieved from URL: https://www.axxora.com/product-listing/ on Oct. 21, 2020 [1-2](Year: 2020).

Baetge, E. E., Production of β-cells from human embryonic stem cells, Diabetes, Obesity and Metabolism 10 (2008): 186-194.

Basford, et al., The Functional and molecular Characterisation of Human Embryonic Stem Cell-Derived Insulin-Positive Cells Compared with Adult Pancreatic Beta Cells, Diabetologia, 55 (2012): 358-371.

Beattie, et al., Sustained proliferation of PDX-1+ cells derived from human islets, Diabetes, 1999, 48:1013-9.

Bellin, et al. Potent induction immunotherapy promotes long-term insulin independence after islet transplantation in type 1 diabetes. Am J Transplant. Jun. 2012; 12(6):1576-83. doi: 10.1111/j.1600-6143.2011.03977.x. Epub Apr. 11, 2012.

(56) References Cited

OTHER PUBLICATIONS

Bennett, et al. SP600125, An Anthrapyrazolone Inhibitor of Jun N-Terminal Kinase. PNAS, vol. 98, No. 24, 20, 2001, pp. 13681-13686.
Biressi et al.: The homeobox gene Arx is a novel positive regulator of embryonic myogenesis. Cell Death Differentiation 15(1):94-104 doi:10.1038/sj.cdd.4402230 (2008).
Blazhevich, et al., "Cell Culturing: Lecture Course," 6 pages (1 page of translation of relevance) (2004).
Boretti, et al., Induced cell clustering enhances islet beta cell formation from human cultures enriched for pancreatic ductal epithelial cells, 2003 Summer Bioengineering Conference, Jun. 25-29, Sonesta Beach Res ort in Ke Bisca ne, Florida.
Boretti, et al. Induced cell clustering enhances islet beta cells formation from human cultures enriched for pancreatic ductal epithelial cells, Tissue Engg. 12.4 (2006): 939-948.
Bose, et al., Human embryonic stem cell differentiation into insulin secreting beta-cells for diabetes, Cell Bioi Int., 3611 (2012): 1013-1020.
Brolen, et al. Signals From the Embryonic Mouse Pancreas Induce Differentiation of Human Embryonic Stem Cells Into Insulin-Producing r3-cell-like Cells. Diabetes 54 (2005): 2867-2874.
Cai, et al., Generation of Homogeneous PDX1ρ Pancreatic Progenitors from Human ES Cell-derived Endoderm Cells, Journal of Molecular Cell Biology (2010), 2:50-60.
Cai et al.: Isl1 identifies a cardiac progenitor population that proliferates prior to differentiation and contributes a majority of cells to the heart. Dev. Cell 2003 5(6):877-889 doi:10.1016/s1534-5807(03)00363-0 (2003).
Campbell-Thompson, et al., "Collection Protocol for Human Pancreas," Journal of Visualized Experiments, 63:1-5, (May 2012).
Cerf, Transcription factors regulating β-cell function, European Journal of Endocrinology, 155 (2006): 671-679.
Chakrabarti, et al., Transcription factors direct the development and function of pancreatic beta cells, Trends Endocrinol Metab., 14.2 (Mar. 2003): 78-84.
Chawla et al.: Production of islet-like structures from neonatal porcine pancreatic tissue in suspension bioreactors. Biotechnol Prog. 22(2):561-567 doi:10.1021/bp050261i (2006).
Chen, et al., Scalable GMP complain suspension culture system for human ES cells, Stem Cell Research 8 (2012): 388-402.
Cheng, et al. Self-renewing endodermal progenitor lines generated from human pluripotent stem cells. Cell Stem Cell 10 (2012): 371-384.
"Chiang, et al., Single-Cell Transcript Analysis of Pancreas Development, Developmental Cell, Mar. 2003, 4:383-393".
Choi, et al. A comparison of genetically matched cell lines reveals the equivalence of human iPSCs and ESCs. Nat Biotechnol. Nov. 2015;33(11):1173-81. doi: 10.1038/nbt.3388. Epub Oct. 26, 2015.
CMRL-1066 Data Sheet. Retrieved online Sep. 30, 2017. https://www.sigmaaldrich.com/content/dam/sigma aldich/docs/sigma/datasheet/c0422dat.pdf (1998).
Cohen, et al., Antibiotics Reduce the Growth Rate and Differentiation of Embryonic Stem Cell Cultures, Tissue Eng., 12.7 (2006): 2025-2030.
Co-pending U.S. Appl. No. 17/985,746, inventors Pagliuca; Felicia et al., filed on Nov. 11, 2022.
Co-pending U.S. Appl. No. 18/055,312, inventors Pagliuca; Felicia J. et al., filed on Nov. 14, 2022.
Co-pending U.S. Appl. No. 18/055,327, inventors Pagliuca; Felicia J. et al., filed on Nov. 14, 2022.
Corkey, et al., A Role for Malonyl-CoA in Glucose-Stimulated Insulin Secretion from Clonal Pacreatic β-Cells, J. Bioi. Chem., 254.36 (Dec. 1989): 21608-21612.
D'Amour, et al., Efficient differentiation of human embryonic stem cells to definitive endoderm, Nat. Biotech., 23(12):1534-41 (2005).
D'Amour, et al. Production of pancreatic hormone-expressing endocrine cells from human embryonic stem cells. Nat Biotechnol. Nov. 2006;24(11):1392-401.
Docherty, "Pancreatic Stellate Cells Can Form New 13-Like Cells," Biochem, J., 421:e1-e4, (2009).
Dror, et al., Notch Signaling Suppresses Apoptosis in Adult Human and Mouse Pancreatic Islet Cells, Diabetlogia 50 (2007): 2504-2515.
DW Engers, et al., Synthesis and structure-activity relationships of a novel and selective bone morphogenetic protein receptor (BMP) inhibitor derived from the pyrazolo[1.5-a]pyrimidine scaffold of dorsomorphin: the discovery of ML347 as an ALK2 versus ALK3 selective MLPCN probe. Bioorg. Med. Chem. Lett. 2013, 23, 3248-3252.
Eberhardt, et al. Multipotential nestin and Isl-1 positive mesenchymal stem cells isolated from human pancreatic islets. Biochem Biophys Res Commun. Jul. 7, 2006; 345.3, 1167-76. Epub May 11, 2006.
Eisenberg et al.: Establishment of the mesodermal cell line QCE-6. A model system for cardiac cell differentiation. Circ Res. 78(2):205-216 (1996).
Falzacappa et al., "3,5,3'-Triiodothyronine (T3) is a Survival Factor for Pancreatic Beta-Cells Undergoing Apoptosis," J. Cell Physiol., 206(2):309-321, (Feb. 2006).
Gotoh et al., Gamma-Irradiation as a Tool to Reduce Immunogenicity of Islet Allo-and-Xeonograpfs, Horm Metab Res Suppl., Jan. 1, 1990, vol. 25, pp. 89-96. Abstract only.
Greggio, et al., Artificial Three-Dimensional Niches Deconstruct Pancreas Development in vitro, Development, 140 (2013): 4452-4462.
Habener, et al., Minireview: transcriptional regulation in pancreatic development Endocrinol., 146:1025-34 (2005).
Hamamoto et al.: Lack of evidence for recipient precursor cells replenishing β-cells in transplanted islets. Cell Transplant 19(12):1563-1572 doi:10.3727/096368910X515881 (2010).
Hanley, "Closing in on Pancreatic Beta Cells," Nature Biotechnology, 32(11):1100-1102, (Nov. 2014).
Hao, et al., In Vivo Structure Activity Relationship Study of Dorsomorphin Analogs Identifies Selective VEGF and BMP Inhibitors, ACS Chem Biol., Feb. 19, 2010, vol. 5, No. 2, pp. 245-253.
Haycock, John W., 3D Cell Culture: A Review of Current Approaches and Techniques, Molecular Biolo 695 (2011): 1-15.
"Heremans, et al., Recapitulation of embryonic neuroendocrine differentiation in adult human pancreatic duct cells expressing neurogenin 3, The Journal of Cell Biology, Oct. 28, 2002, 159(2):303-311".
Hernandez, et al., Microcapsules and microcarriers for in situ cell delivery, Advanced Drug Deliver Reviews 62 (2010): 711-730.
Hess et al., Bone Marrow-Derived Stem Cells Initiate Pancreatic Regeneration, Nature Biotechnology, Jun. 22, 2003, vol. 21, Issue 7, pp. 763-770.
"Hilderink, et al., "Controlled aggregation of primary human pancreatic islet cells leads to glucose-responsive pseudoislets comparable to native islets" (2015) J. Cell. Mol. Med., vol. 19, No. 8, pp. 1836-1846".
Hrvatin, et al. Differentiated human stem cells resemble fetal, not adult, β-cells. PNAS, 111.8, 3038-3043 (2014).
Hrvatin: Exploring the Use of Human Pluripotent Stem Cells to Create Functional Pancreatic Beta Cells. Doctoral dissertation, Harvard University, pp. 1-165 URL:http://nrs.harvard.edu/urn-3:HUL.InstRepos:10433470 (2013).
Hur et al.: New method to differentiate human peripheral blood monocytes into insulinproducing cells: Human hematosphere culture. Biochem Biophys Res Commun. 418(4): 765-769 (2012).
Huynh, et al., "Screening and Identification of a Novel Class of TGF-13 Type 1 Receptor Kinase Inhibitor," Society for Laboratory Automation and Screening, 16(7):724-733, (2011).
International Search Report and Written Opinion for PCT/US2018/043179 dated Oct. 16, 2018.
Isayeva, et al. Characterization and performance of membranes designed for macroencapsulation/implantation of pancreatic islet cells. Biomaterials. Sep. 2003;24(20):3483-91.
Jahansouz, et al., Evolution of β-Cell Replacement Therapy in Diabetes Mellitus: Islet Cell Transplantation, Journal of Transplantation, (2011): 1-21.

(56) References Cited

OTHER PUBLICATIONS

Jeon et al.: Differentiation and Transplantation of Functional Pancreatic Beta Cells Generated from Induced Pluripotent Stem Cells Derived from a Type 1 Diabetes Mouse Model. Stem Cells Dev., 21(14): 2642-2655, (2012).
Jiang, et al. In vitro derivation of functional insulin-producing cells from human embryonic stem cells. Cell Res. Apr. 2007;17(4):333-44.
"Kelly, et al., "Cell-surface markers for the isolation of pancreatic cell types derived from human embryonic stem cells" (2011) Nature Biotechnology, p. 1-19".
Kieffer et al.: Beta-cell replacement strategies for diabetes. J Diabetes Investig. 9(3):457-463 doi:10.1111/jdi.12758 (2017).
Kim et al.: Functional Diversification of Motor Neuron-specific Isl1 Enhancers during Evolution. PLoS Genetics 11(10):e1005560, pp. 1-27 doi:10.1371/journal.pgen.1005560 (2015).
"Kojima, Nobuhiko "In vitro reconstitution of pancreatic islets" (2014) Organogenesis 10:2, pp. 225-230".
Korytnikov: Role of Tankyrase Inhibitors in the Generation of NKX6-1+ Endoderm. Dissertation, University of Toronto, pp. 1-84 URL: https://hdl.handle.net/1807/92864 (2016).
Koshimizu et al.: Functional requirement of gp130-mediated signaling for growth and survival of mouse primordial germ cells in vitro and derivation of embryonic germ (EG) cells. Development 122(4):1235-1242 (1996).
Kozhukharova et al.: Novel Human Embryonic Stem Cell Lines C612 and C910. Cytology, 51(7): 551-558 (2009).
"Kroon, et al., Pancreatic endoderm derived from human embryonic stem cells generates glucose-responsive insulin-secreting cells in vivo, Nat. Biotech, Apr. 2008, 26(4):443-452".
Kumar, et al., Recent Developments in β-Cell Differentation of Pluripotent Stem Cells Induced by Small and Large Molecules, Int. J. Mol. Sci., 15.12 (2014): 23418-23447.
Kumar, et al. Signals from lateral plate mesoderm instruct endoderm toward a pancreatic fate. Dev Bioi. 259.1 (2003): 109-22.
Kunisada, et al., Small molecules induce efficient differentiation into insulinproducing cells from human induces pluripotent stem cells, Stem Cell Research, 2012, 8:274-284.
Lee et al.: All-Trans-Retinoic Acid as a Novel Therapeutic Strategy for Alzheimer's Disease. Expert Rev. Neurother, 9(11): 1615-1621 (2009).
Lee et al., Differentiation into Endoderm Lineage: Pancreatic differentiation from Embryonic Stem Cells, International Journal of Stem Cells, Apr. 4, 2011, vol. 4, No. 1, pp. 35-42.
Lim et al., Microencapsulated islets as bioartificial endocrine pancreas, Science 210(4472):908-10 (1980).
Lima et al., Generation of Functional Beta-Like Cells from Human Exocrine Pancreas, PLoS One, May 31, 2016, vol. 11, No. 5, pp. 1-19.
Lin et al.: Transforming growth factor-beta/Smad3 signaling regulates insulin gene transcription and pancreatic islet beta-cell function. J Biol Chem. 284(18): 12246-12257 (2009).
Lopez et al.: Staurosporine-derived inhibitors broaden the scope of analog-sensitive kinase technology. J Am Chem Soc. 135(48):18153-18159 doi:10.1021/ja408704u (2013).
Lumelsky, et al., Differentiation of Embryonic Stem Cells to Insulin-Secreting Structures Similar to Pancreatic Islets, Science, 292:1389-94 (May 2001).
Madsen, et al. Towards cell therapy for diabetes. Nat Biotechnol. 24.12 (2006): 1481-3.
Maehr, et al., Generation of pluripotent stem cells from patients with type 1 diabetes, Proc Natl Acad Sci. 106.37 (2009): 15768-15773.
Manning et al. The Protein Kinase Complement of the Human Genome. Science. 298:1912-1934. 2002.
Marzorati, et al., Culture Medium Modulates Proinflammatory Conditions of Human Pancreatic Islets Before Transplantation, Am. J. Transplant, 6.11 (2006): 2791-2795.
Massumi et al.: An abbreviated protocol for in vitro generation of functional human embryonic stem cell-derived beta-like cells. PLoS One 11(10):e0164457 DOI:10.1371/journal.pone.0164457 [1-24] (2016).
Matschinsky, Assessing the potential of glucokinase activators in diabetes therapy, Nature Reviews Drug Discovery, 8 (2009): 399-416.
Matsui, Y., et al., (1992), Derivation of pluripotential embryonic stem cells from murine primordial germ cells in culture, Cell 70:841.
Mclean, et al., Activin a Efficiently Specifies Definitive Endoderm from Human Embryonic Stem Cells Only When Phosphatidylinositol 3-Kinase Signaling Is Suppressed. Stem Cells, 2007, 25: 29-38.
Mcquilling et al.: New Alginate Microcapsule System for Angiogenic Protein Delivery and Immunoisolation of Islets for Transplantation in the Rat Omentum Pouch. Transplantation Proceedings, 43(9): 3262-3264 (Nov. 2011).
"Smelt, et al., "Pancreatic Beta-Cell Purification by Altering FAD and NAD(P)H Metabolism" (2018) Experimental Diabetes Research vol. 2008, Article ID 165360, pp. 1-11".
Michael, et al., Pancreatic β-Cells Secrete Insulin in Fast- and Slow-Release Forms, Diabetes, 55 (2006): 600-607.
Moens, et al., Dual glucagon recognition by pancreatic beta-cells via glucagon and glucagon-like peptide 1 receptors, Diabetes, 47 (1998): 66-72.
Mollard, et al. Design, Synthesis and Biological Evaluation of a Series of Novel Axl Kinase Inhibitors. ACS Med Chem Lett. Dec. 8, 2011;2(12):907-912.
Moore et al.: Noninvasive in vivo measurement of beta-cell mass in mouse model of diabetes. Diabetes 50(10):2231-2236 doi:10.2337/diabetes.50.10.2231 (2001).
Morrison et al.: Regulatory Mechanisms in Stem Cell Biology. Cell 88(3):287-298 (1997).
Motte, et al. Composition and function of macroencapsulated human embryonic stem cell-derived implants: comparison with clinical human islet cell grafts. Am J Physiol Endocrinol Metab. Nov. 1, 2014;307(9):E838-46. doi: 10.1152/ajpendo.00219.2014. Epub Sep. 9, 2014.
Mudduluru, et al. Regulation of Axl receptor tyrosine kinase expression by miR-34a and miR-199a/b in solid cancer. Oncogene. Jun. 23, 2011;30(25):2888-99. doi: 10.1038/onc.2011.13. Epub Feb. 14, 2011.
Murua, et al., Cell microencapsulation technology: Towards clinical application, Journal of Controlled Release, 132.2 (2008): 76-83.
Narayanan, et al. Extracellular Matrix-Mediated Differentiation of Human Embryonic Stem Cells: Differentiation to Insulin-Secreting Beta Cells. Tissue Engineering, Part A, 20.1 & 2, 424-433.
Natalicchio et al.: Exendin-4 Protects Pancreatic Beta Cells from Palmitate-Induced Apoptosis by Interfering with GPR40 and the MKK4/7 Stress Kinase Signaling Pathway. Diabetologia, 56: 2456-2466 (2013).
Neely et al., DMH1, a Highly Selective Small Molecule BGMP Inhibitor Promotes Neurogenesis of hiPSCs: Comparison of PAX6 and SOX1 Expression During Neural Induction, ACS Chem Neurosci, Mar. 5, 2012, vol. 3, No. 6, pp. 482-491.
Nishimura, et al., "A Switch from MafB to MafA Expression Accompanies Differentiation to Pancreatic 13-Cells," Developmental Biology, 293:526-539, (2006).
Nohe et al.: Signal transduction of bone morphogenetic protein receptors. Cell Signal. 16(3):291-299 doi:10.1016/j.cellsig.2003.08.011 (2004).
Nostro, et al., Generation of beta cells from human pluripotent stem cells: Potential for regenerative medicine, Seminars in Cell & Developmental Biology, 23 (2012): 701-710.
Nostro, et al. Stage-specific signaling through TGFβ-family members and WNT regulates patterning and pancreatic specification of human pluripotent stem cells. Development 138 (2011): 861-871.
O'Brien, et al., Suspended in culture—Human pluripotent cells for scalable technologies, Stem cell Research 9 (2012): 167-170.
Okazaki et al.: Staurosporine, a novel protein kinase inhibitor, enhances HL-60-cell differentiation induced by various compounds. Exp. Hemtaol. 16(1):42-48 (1988).

(56) References Cited

OTHER PUBLICATIONS

Orive, et al., Application of cell encapsulation for controlled delivery of biological therapeutics, Advanced Dru Delive Reviews 1-12 2013.
Pagliuca, et al. Generation of functional human pancreatic β cells in vitro. Cell. Oct. 9, 2014;159(2):428-39. doi: 10.1016/j.cell.2014.09.040.
Pagliuca et al.: How to make a functional β-cell. Development 140, 2472-2483 (2013).
Papas et al.: Islet assessment for transplantation. Curr Opin Organ Transplant 14(6):674-682 doi:10.1097/MOT.0b013e328332a489 (2009).
Parsons, et al., Notch-Responsive Cells Initiate the Secondary Transition in Larval Zebrafish Pancreas, Mechanism of Development, 126.10 (2009): 898-912.
PCT/US2018/061364 International Search Report and Written Opinion dated Apr. 29, 2019.
PCT/US2019/020430 International Search Report and Written Opinion dated May 8, 2019.
PCT/US2019/045985 International Search Report and Written Opinion mailed Dec. 17, 2019.
PCT/US2020/039487 International Search Report and Written Opinion dated Sep. 22, 2020.
Phillips, et al., Directed Differentiation of Human Embryonic Stem Cells into the Pancreatic Endocrine Lineage, Stem Cells and Dev., 16 (2007): 561-578.
"Spijker, et al., "Conversion of Masture Human B-Cells Into Glucagon-Producing a-Cells" (2013) Diabetes, vol. 62, p. 2471-2480".
Piran, et al., "Pharmacological Induction of Pancreatic Islet Cell Transdifferentiation; Relevance Type I Diabetes," Cell Death and Disease, 5(e1357):1-13, (2014).
Prakash et al.: Nkx6-1 controls the identity and fate of red nucleus and oculomotor neurons in the mouse midbrain. Development 136(15):2545-2555 doi:10.1242/dev.031781 (2009).
Qi et al.: PVA Hydrogel Sheet Macroencapsulation of the Bioartificial Pancreas. Biomaterials, 24(27): 5885-5892 (2004).
"Ramachandran, et al., "Assessment of re-aggregated human pancreatic islets for secondary drug screening" British Journal of Pharmacology (2014) 171 3010-3022".
Ratanasavanh, et al. Immunocytochemical evidence for the maintenance of cytochrome PC33 450 isozymes, NADPH cytochrome C reductase, and epoxide hydrolase in pure and mixed primary cultures of adult human hepatocytes. J Histochem Cytochem. 34.4 (1986): 527-33.
Rathaore, et al., Microencapsulation of Microbial cells, Journal of Food Engineering, 116 (2013): 369-381.
Ravassard, et al. A genetically engineered human practical β cell line exibiting glucose-inducible insulin secretion. The Journal of clinical investigation 121.9 (2011): 3589-3597.
Reyes et al.: (Retracted) Purification and ex vivo expansion of postnatal human marrow mesodermal progenitor cells. Blood 98:2615-2625 [1-1] (2001).
Rezania, et al., Enrichment of Human Embryonic Stem Cell-Derived NKX6.1-Expressing Pancreatic Progenitor Cells Accelerates the Maturation of InsulinSecretin Cells in Vivo, Stem Cells, 31 (2013): 2432-2442.
Rezania, et al. Maturation of human embryonic stem cell-deprived pancreatic progenitors into functional islets capable of treating pre-existing diabetes in mice. Diabetes 61 (2012): 2016-2029.
Rezania, et al. Production of functional glucagon-secreting α-cells from human embryonic stem cells. Diabetes, 60 (Jan. 2011): 239-247.
Rezania, et al. Reversal of diabetes with insulin-producing cells derived in vitro from human pluripotent stem cells. Nat Biotechnol. Nov. 2014;32(11):1121-33. doi: 10.1038/nbt.3033. Epub Sep. 11, 2014.
Roche. Protocols to differentiate embryonic stem cells into insulin producing cells. Av. Diabetol. 24.2 (2008): 128-137.
Ropiquet et al.: FGF7/KGF triggers cell transformation and invasion on immortalised human prostatic epithelial PNT1A cells. Int. J. Cancer 82(2):237-243 (1999).
Roskoski: A historical overview of protein kinases and their targeted small molecule inhibitors. Pharmalogical Res. 100:1-23 (2015).
Rovira, et al., Chemical Screen Identifies FDA-Approved Drugs and Target Pathways That Induce Precocious Pancreatic Endocrine Differentiation, Proc Natl Acad Sci USA. 108.48 (2011): 19264-19269.
Russ et al.: Controlled induction of human pancreatic progenitors produces functional beta-like cells in vitro. EMBO J. 34(13):1759-1772 (2015).
Sander, et al. Homeobox gene Nkx6.1 lies downstream of Nkx2.2 in the major pathway of β-cell formation in the pancreas. Development 127 (2000): 5533-5540.
Sander, et al. The β-cell transcription factors and development of the pancreas. J Mol Med, 75 (1997): 327-340.
Schuldiner, et al., Effects of eight growth factors on the differentiation of cells derive from human embryonic stem cells, Proc. Nat. Acad. Sci., 97:11307-12 (2000).
Schulz, et al., A scalabe system for production of functional pancreatic progenitors from human embryonic stem cells, PLoS One, 7.5 (May 2012): 1-17.
Schumacher et al.: Staurosporine is a Potent Activator of Neuronal, Glial, and "CNS Stem Cell-Like" Neurosphere Differentiation in Murine Embryonic Stem Cells. Molecular and Cellular Neuroscience 23(4): 669-680 (2003).
Sebald et al.: Molecular recognition in bone morphogenetic protein (BMP)/receptor interaction. Biol Chem. 385(8):697-710 doi:10.1515/BC.2004.086 (2004).
Segerstople et al.: Single-cell transcriptome profiling of human pancreatic islets in health and type 2 diabetes. Cell Metab. 24(4):593-607 (2016).
Segrev, et al., Differentiation of Human Embryonic Stem Cells into Insulin-Producing Clusters, Stem Cells, 2004, 22:265-274.
Shaer, et al. Differentiation of human-induced pluripotent stem cells into insulin-producing clusters. Exp Clin Transplant. Feb. 2015;13(1):68-75. doi: 10.6002/ect.2013.0131. Epub Jan. 13, 2014.
Shahjalal, et al., Generation of insulin-producing B-like cells from human iPS cells in a defined and completely xeno-free culture system. Journal of Molecular cell biology, Jun. 2014; 6(5):394-408.
Shamblott, et al. Derivation of pluripotent stem cells from cultured human primordial germ cells, Proc. Natl. Acad. Sci. USA, vol. 95, pp. 13726-13731 (1998).
Shamblott, et al. Human embryonic germ cell derivatives express a broad range of developmentally distinct markers and proliferate extensively in vitro, Proc. Natl. Acad. Sci., vol. 98 No. 1, pp. 113-118 (2001).
Shapiro et al.: International trial of the Edmonton protocol for islet transplantation. N Engl J Med. 355(13): 1318-1330 (2006).
Shi, et al. Inducing Embryonic Stem Cells to Differentiate into Pancreatic β-cells by a Novel Three-Step Approach with Activin A and All-Trans Retinoic Acid. Stem Cells 23 ( 2005): 656-662.
Shim, et al., Directed differentiation of human embryonic stem cells towards a pancreatic cell fate, Diabetologia, 50 (2007): 1128-1138.
Sneddon, et al. Self-renewal of embryonic-stem-cell-derived progenitors by organ-matched mesenchyme. Nature. Nov. 29, 2012;491(7426):765-8. doi: 10.1038/nature11463. Epub Oct. 7, 2012.
Sorelle, et al., Beta Cell Replacement Therapy, Type 1 Diabetes-Pathogenesis, Genetics and Immunothera 22 (2011): 503-526.
Soria et al.: From stem cells to beta cells: new strategies in cell therapy of diabetes mellitus. Diabetologia 44(4):407-415 doi:10.1007/s001250051636 (2001).
Soria, et al., In-Vitro Differentiation of Pancreatic Beta-Cells, Differentiation, 68(4-5):205-19 (Oct. 2001).
Spence, et al. Sox17 regulates organ lineage segregation of ventral foregut progenitor cells. Dev Cell. Jul. 2009;17(1):62-74. doi: 10.1016/j.devcel.2009.05.012.
Sui et al.: Stem Cell Therapy for Diabetes: A Call for Efficient Differentiation of Pancreatic Progenitors. J. Regen. Med. 2(1):1-4 (2013).

(56) References Cited

OTHER PUBLICATIONS

Takahashi, et al. Induction of pluripotent stem cells from adult human fibroblasts by defined factors. Cell. Nov. 30, 2007;131(5):861-72.
Takahashi et. al.: Induction of pluripotent stem cells from fibroblast cultures. Nat Protoc. 2(12):3081-3089 (2007).
Taylor, et al. NKX6.1 Is Essential for Maintaining the Functional State of Pancreatic Beta Cells. Cell Rep 4 (2013): 1262-275.
Thatava, et al., Indolactam V/GLP-1-mediated Differentiation of Human iPS Cells into Glucose-Responsive Insulin-Secreting Progeny, 18.3 (2011): 283-293.
Thermo Fisher Scientific, B-27 Serum-Free Supplement (50X) liquid, ThermoFisher Scientific Website, Retrieved from the Internet: URL: thermofisher.com/order/catalog/product/17504044?SID=srch-srp-17504044#/17504044?SID=srch-srp-17504044, on Sep. 15, 2021.
Thomson et al. Embryonic stem cell lines derived from human blastocysts. Science. Nov. 6, 1998;282(5391):1145-7.
Thomson, et al. Isolation of a primate embryonic stem cell line. Proc Natl Acad Sci U S A. Aug. 15, 1995;92(17):7844-8.
Thomson et al., Pluripotent Cell Lines Derived from Common Marmoset (*Callithrix jacchus*) Blastocysts, (1996) Biol. Reprod. 55:254-259.
Thowfeequ, et al., Betacellulin inhibits amylase and glucagon production and promotes beta cell differentiation in mouse embryonic pancreas, Diabetologia, 50 (2007): 1688-1697.
Tian et al.: Protein kinase C and calcium regulation of adenylyl cyclase in isolated rat pancreatic islets. Diabetes 50(11):2505-2513 (2001).
Treff, et al., Differentiation of Embryonic Stem Cells Conditionally Expressing Neurogenin 3, Stem Cells, 24.11 (1999): 2529-37.
Trott et al. "Long-Term Culture of Self-renewing Pancreatic Progenitors Derived from Human Pluripotent Stem Cells," Stem Cell Reports, Jun. 6, 2017 (Jun. 6, 2017), vol. 8, No. 6, pp. 1675-1688. entire document.
Tsaniras, et al., "Generating Pancreatic Beta-Cells from Embryonic Stem Cells by Manipulating Signaling Pathways," Journal of Endocrinology, 206:13-26, (2010).
Tsuchida, et al., Activin signaling as an emerging target for therapeutic interventions, Cell Communication & Signaling, 7.15 (2009): 1-11.
Urquhart et al.: Rate-controlled delivery systems in drug and hormone research. Annu Rev Pharmacol Toxicol. 24:199-236 doi:10.1146/annurev.pa.24.040184.001215 (1984).
Vegas, et al., Long term glycemic control using polymer encapsulated, human stem-cell derived B-cells in immune competent mice, Nat Med. Jan. 25, 2016, vol. 22, No. 3, pp. 306-311.
Veres et al.: Charting cellular identity during human in vitro β-cell differentiation. Nature 569(7756):368-373 [1-36] (2019).
Wachs, et al., High Efficacy of Clonal Growth and Expansion of Adult Neural Stem Cells, LaboratoryInvestigation, 83.7 (Jul. 2003): 949-962.
Wimalasena: Vesicular monoamine transporters: structure-function, pharmacology, and medicinal chemistry. Med. Res. Rev.31(4):483-519 doi:10.1002/med.20187 (2011).
Xie, et al. Dynamic chromatin remodeling mediated by polycomb proteins orchestrates pancreatic differentiation of human embryonic stem cells. Cell Stem Cell 12 (2013): 224-237.
Xu et al. Feeder-free growth of undifferentiated human embryonic stem cells. Nat. Biotechnol. 19(10):971-974 (2001).
Xu et al.: Revealing a core signaling regulatory mechanism for pluripotent stem cell survival and self-renewal by small molecules. PNAS 107(18):8129-8134 (2010).
Yu, et al. Induced pluripotent stem cell lines derived from human somatic cells. Science. Dec. 21, 2007;318(5858):1917-20. Epub Nov. 20, 2007.
Zanin, et al., The development of encapsulated cell technologies as therapies for neurological and sensor diseases, Journal of Controlled Release 160 (2012): 3-13.
Zhang et al.: Highly efficient differentiation of human ES cells and iPS cells into mature pancreatic insulin-producing cells. Cell Research 19(4):429-438 (2009).
Zhdanov, et al., "The Secrets of the Third Kingdom," Publishing House "Znanie" Moscow:pp. 124-125, (1975). (2 pages of translation).
Zhu, et al., Generation of Pancreatic Insulin-Producing Cells from Rhesus Monkey Induced Pluripotent Stem Cells, Diabetologia, 54 (2011): 2325-2336.
Zhu et al.: Preventive effect of Notch signaling inhibition by a gamma-secretase inhibitor on peritoneal dialysis fluid-induced peritoneal fibrosis in rats. Am J Pathol. 176(2): 650-659 (2010).
Zulewski, Stem Cells with potential to generate insulin-producing cells in man, Swiss Med. Wkly, 136 (2006): 647-654.
Zweigerdt, et al., Scalable expansion of human pluripotent stem cells in suspension culture, Nature Protocols, 6.5 (2011): 689-700.
Co-pending U.S. Appl. No. 18/051,721, inventors Pagliuca; Felicia J. et al., filed Nov. 2022.
Hering B.J. et al., "Phase 3 Trial of Transplantation of Human Islets in Type 1 Diabetes Complicated by Severe Hypoglycemia", Diabetes Care 39:1230-1240 (Jul. 2016).
Street C.N. et al., "Islet Graft Assessment in the Edmonton Protocol", Diabetes 53:3107-3114 (2004).
Street C.N. et al., "Stem Cell-Based Approaches to Solving the Problem of Tissue Supply for Islet Transplantation in Type 1 Diabetes", The International Journal of Biochemistry & Cell Biology 36:667-683 (2004).
Xu C-R et al., "Dynamics of Genomic H3K27me3 Domains and Role of EZH2 During Pancreatic Endocrine Specification", The EMBO Journal 33:2157-2170 (2014).
Vertex Press Release, "Vertex to Acquire ViaCyte, With the Goal of Accelerating its Potentially Curative VX-880 Programs in Type 1 Diabetes", (Jul. 11, 2022).
Anlauf M. et al., "Expression of the Two Isoforms of the Vesicular Monoamine Transporter (VMAT1 and VMAT2) in the Endocrine Pancreas and Pancreatic Endocrine Tumors", The Journal of Histochemistry & Cytochemistry 51(8):1027-1040 (2003).
Liu H-S et al., "Is Green Fluorescent Protein Toxic to the Living Cells?", Biochemical and Biophysical Research Communications 260(3):712-717 (1999).
Schaffer A.E. et al., "Nkx6.1 Controls a Gene Regulatory Network Required by Establishing and Maintaining Pancreatic Beta Cell Identity", PLOS Genetics 9(1):e1003274 (Jan. 2013).
Veres A., "Charting and Navigating Fate Decisions in Directed Differentiation of Stem Cell-Deirved Human Beta Cells", Harvard University, Dissertation (2016).
Wang D. et al., "Targeted Disruption of the β2-Microglubulin Gene Minimizes the Immunogenicity of Human Embryonic Stem Cells", Stem Cells Translational Medicine 4:1234-1245 (2015).
Akinci E. et al., "Reprogramming of Various Cell Types to a Beta-Like State by Pdx1, Ngn3 and MafA", PLoS One 8(11):e82424 (Nov. 2013).
Bottino R. et al., "Pancreas and Islet Cell Transplantation", Best Practice & Research Clinical Gastroenterology 16(3):457-474 (2002).
Bruin J.E. et al., "Maturation and Function of Human Embryonic Stem Cell-Derived Pancreatic Progenitors in Macroencapsulation Devices Following Transplant into Mice", Diabetologia 56:1987-1998 (2013).
Ehrhart M. et al., "Chromogranin A in the Pancreatic Islet: Cellular and Subcellular Distribution", The Journal of Histochemistry and Cytochemistry 34(12):1673-1682 (1986).
Germanos M. et al., "Inside the Insulin Secretory Granule", Metabolites 11:515 (2021).
Ma X. et al., "Chemical Strategies for Pancreatic [beta] Cell Differentiation, Reprogramming, and Regeneration", Acta Biochimica Biophysica Sinica 49(4):289-301 (Feb. 22, 2017).
Pileggi A. et al., "Reversal of Diabetes by Pancreatic Islet Transplantation into a Subcutaneous, Neovascularized Device", Transplantation 81(9):1318-1324 (Mar. 15, 2006).
Shultz M.D. et al., "Identification of NVP-TNKS656: The Use of Structure-Efficiency Relationships to Generate a Highly Potent, Selective, and Orally Active Tankyrase Inhibitor", Journal of Medicinal Chemistry 56:6495-6511 (2013).

(56) References Cited

OTHER PUBLICATIONS

Xin Y. et al., "Pseudotime Ordering of Single Human Beta-Cells Reveals States of Insulin Production and Unfolded Protein Response", Diabetes 67:1783-1794 (Sep. 2018) (including single-cell sequencing data stored in the Gene Expression Omnibus database under accession No. GSE114297; https://www.ncbi.nlm.nih.gov/geo/query/acc.cgi?acc=GSE114297).
Co-pending U.S. Appl. No. 18/391,799, inventors George Harb et al., filed on Dec. 21, 2023.
Co-pending U.S. Appl. No. 18/391,831, inventors Yeh-Chuin Poh et al., filed on Dec. 21, 2023.
Co-pending U.S. Appl. No. 18/391,867, inventors Yeh-Chuin Poh et al., filed on Dec. 21, 2023.
Co-pending U.S. Appl. No. 18/018,787, inventors George Harb filed on Jan. 30, 2023.
Co-pending U.S. Appl. No. 18/270,314, inventors Bryce Carey filed on Jun. 29, 2023.
Co-pending U.S. Appl. No. 18/281,154, inventors Evrett Thompson et al., filed on Sep. 8, 2023.
U.S. Appl. No. 19/000,973, filed Dec. 24, 2024, Pagliuca et al.
Ravassard, et al., "A genetically engineered human pancreatic β cell line exhibiting glucose-inducible insulin secretion", *J. Clin. Invest.* 121(9):3589-3597, Sep. 2011.
Veres, et al., "Charting cellular identity during human in vitro β-cell differentiation", *Nature* 569(7756)368-373, 24 pages, May 2019.
Cuesta-Gomez et al., "Characterization of stem-cell-derived islets during differentiation and after implantation," *Cell Reports* 40(8):1-13, Aug. 23, 2022.
Ediger et al., "Islet-1 Is Essential for Pancreatic Beta-Cell Function," *Diabetes* 63(12):4206-4217, E-pub Jul. 15, 2014.
Wang et al., "Pdx1 Level Defines Pancreatic Gene Expression Pattern and Cell Lineage Differentiation," *The Journal of Biological Chemistry* 276(27):25279-25286, E-pub Apr. 17, 2001.
Jensen J. et al., "Independent Development of Pancreatic α- and β-Cells from Neurogenin3-Expressing Precursors", Diabetes 49:163-176 (Feb. 2000).
Velazco-Cruz L. et al., "Acquisition of Dynamic Function in Human Stem Cell-Derived β Cells", Stem Cell Reports 12:351-365 (Feb. 12, 2019).

* cited by examiner

EPZ6438
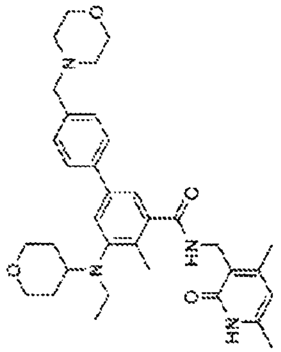
GSK126
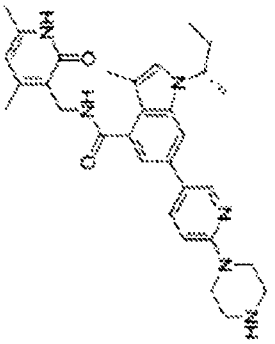
DZNep:
3-Deazaneplanocin A hydrochloride
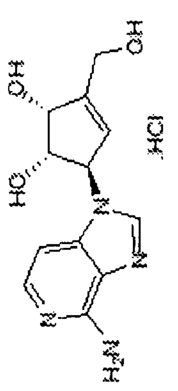
FIG. 1

KD5170
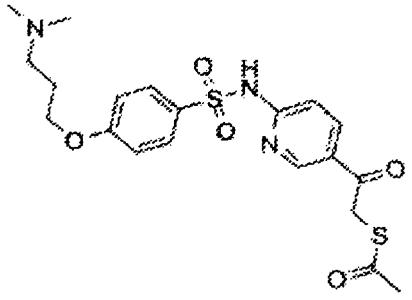
Class I and II HDAC inhibitor
MC1568
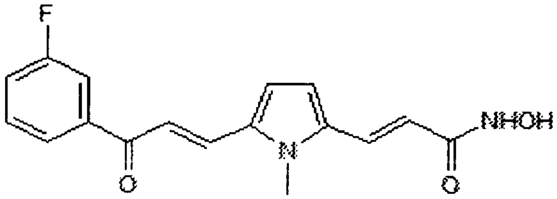
Class IIa HDAC inhibitor
FIG. 2

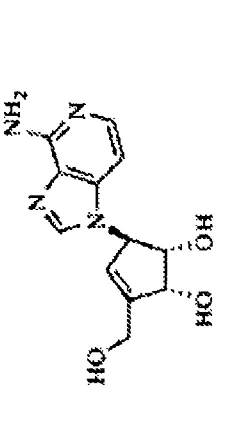
DZNep
(AdoHcy Hydrolase)
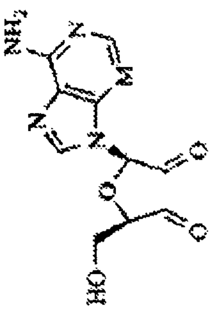
Adox
(AdoHcy Hydrolase)
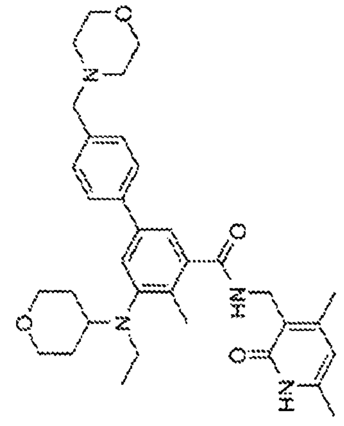
EPZ-6438
(PRC2, EZH2)
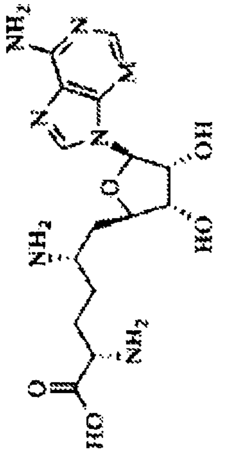
Sinefungin
(Methyltransferase)
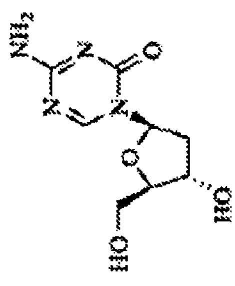
5-Aza-CdR
(DNA Methyltransferase)
FIG. 3

DZA

DZNep

Nep A

| | Stage 1 | Stage 2 | Stage 3 | Stage 4 | Stage 5 |
|---|---|---|---|---|---|
| Wash step | | | | | Wash with S5 media |
| Complete media | S1 | S2 | S3 | S3 | S5 (+ ZnSO4) |
| Basal media | MCDB131 | MCDB131 | MCDB131 | MCDB131 | MCDB131 |
| Media supplements | 1% Pen/Strep<br>2.46g/L NaHCO3<br>2mM Glutamax<br>8mM Glucose<br>0.25mM Vit C<br>0.05% HSA<br>1:50.000 ITS-X | 1% Pen/Strep<br>1.23g/L NaHCO3<br>2mM Glutamax<br>8mM Glucose<br>0.25mM Vit C<br>0.05% HSA<br>1:50.000 ITS-X | 1% Pen/Strep<br>1.23g/L NaHCO3<br>2mM Glutamax<br>8mM Glucose<br>0.25mM Vit C<br>0.05% HSA<br>1:200 ITS-X | 1% Pen/Strep<br>1.23g/L NaHCO3<br>2mM Glutamax<br>8mM Glucose<br>0.25mM Vit C<br>0.05% HSA<br>1:200 ITS-X | 1% Pen/Strep<br>1.75g/L NaHCO3<br>2mM Glutamax<br>25mM Glucose<br>0.25mM Vit C<br>0.05% HSA<br>1:200 ITS-X<br>10ug/ml Heparin<br>10uM ZnSO4 |
| Growth factors | 100ng/ml ActivinA | 50ng/ml KGF | 50ng/ml KGF | 50ng/ml KGF<br>5ng/ml ActivinA | 20ng/ml Betacellulin |
| Small molecules | 3uM Chir99021 (1st 24hrs) | | 2.5uM Thiazovivin<br>2uM RA<br>250nM SANT1<br>500nM PdBu | 2.5uM Thiazovivin<br>100nM RA<br>250nM SANT1 | 2.5uM Thiazovivin<br>50nM RA (1st 3 days)<br>250nM SANT1 (1st 3 days)<br>2uM XXI<br>10uM Alk5i II<br>1uM GC-1<br>100nM LDN<br>3nM Staurosporine |
| Number of days | 3 | 3 | 2 | 6 | 7 |
| Feeding schedule | each day | Days 1, 3 (or each day) | each day | every 2nd day | Days 1, 2, 4, 6 |

FIG. 5

Plate 3

Plate 4

| | 1 | 2 | 3 | 4 | 5 | 6 | 7 | 8 | 9 | 10 | 11 | 12 |
|---|---|---|---|---|---|---|---|---|---|---|---|---|
| A | Empty | ChemR23 ??? | CLA | CLEC2A | CLEC12A | CLEC9A | CLIP | CXICR1 | DCIR | DLL1 | DLL4 | DR3 |
| B | Erb6-3 (Her-3) | ??? | Fibroblast | ??? | Galactin 3 | Galactin 9 | GARP ??? | GITR | GLAST (ACSA-1) | GPR56 | HLA Class 188 | HLA Class1 ??? |
| C | MLA Class | MLA-A2 | HLA-A2 ??? | HLA-A9 | HLA-B12 | HLA-B7, B27 | HLA-CM | HLA-DQ | HLA-DQ | HLA-DR, DR,DQ | HLA-E | IFNAR2 |
| D | IL-IRAcP | IL-12R β2 | IL-17RC | INKT | Integrin β7 | Jagged2 | KR2D | KLRG1 (MAFA) | LAP ??? | LGR5 | LT-GR | Melanoma (MCSP) |
| E | HLA-ABC | MICA/MICB | MSCA-1 ??? | NKpiiO | Notch1 | Notch2 | Notch3 | O4 | OSCAR | Perforin | ??? | PSA-NCAM |
| F | PSMA | PTICT (CCR-4) | RDR1 | Siglec-10 | Siglec-5/ Siglec-14 | Siglec-8 | Silan ??? | SSEA-3 | SSEA-4 | SSEA-5 | SUSCO | TCR-Vo7.2 |
| G | TCR V311 | TCR V314 | TCR V316 | TCR Vβ23 | TCR Vγ9 | TCR-V51 | TCR-V52 | TCRα/β | TCRw/β | TdT | TIM-8 | TIM-3 |
| H | TLT-2 | TRA-I-85 (CD147) | TSRAN8 | ??? | ??? | ??? | ??? | ??? | ??? | ??? | ??? | ??? |

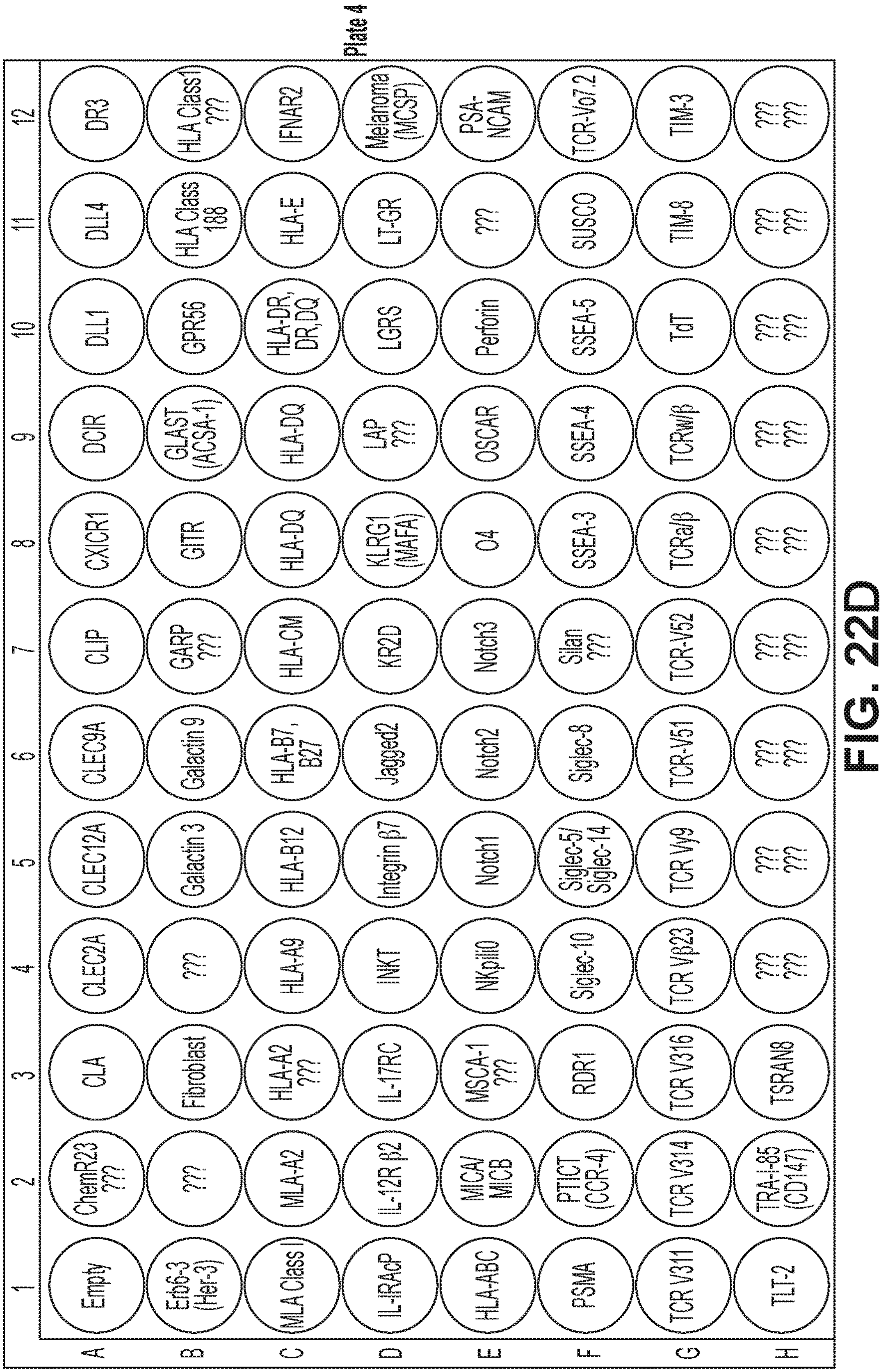

FIG. 22D

| S6d4 | PSA-NCAM+ | VMAT1+ | NKX+/CPEP+ | CHGA+ | Sox9+ | NKX - /SOX9+ |
|---|---|---|---|---|---|---|
| Pre-sorted | 22.2 | 78.8 | 18.7 | 77.9 | 9.7 | 5.8 |
| Positive | 68.6 | 55.9 | 23.6 | 93.1 | 6.9 | 2.1 |
| Negative | 8.5 | 35.4 | 18.2 | 69 | 9.3 | 6.4 |

| S6d18 | PSA-NCAM+ | VMAT1+ | NKX+/CPEP+ | CHGA+ | Sox9+ | NKX -/SOX9+ |
|---|---|---|---|---|---|---|
| RA | 33 | 72.8 | 14.5 | 95 | 6.8 | 0.2 |
| Positive | Not enough cells | 65.2 | 20.1 | 98.1 | 4 | 0.3 |

| S6d5 | PSA-NCAM+ | PSA-NCAM+ /VMAT1+ | NKX+/CPEP+ | CHGA+ | Sox9+ | NKX -/SOX9+ |
|---|---|---|---|---|---|---|
| RA | 24.3 | 22 | 25.4 | 84 | 6.4 | 0.9 |
| RA+ Endo-N | 3.5 | 2.4 | 25 | 84.5 | 6.8 | 0.9 |
| Positive | 15.8 | 14.5 | 25.1 | 88.7 | 6.9 | 1 |
| Positive + Endo-N | 2.4 | 1.9 | 25.1 | 88.3 | 6.8 | 0.9 |

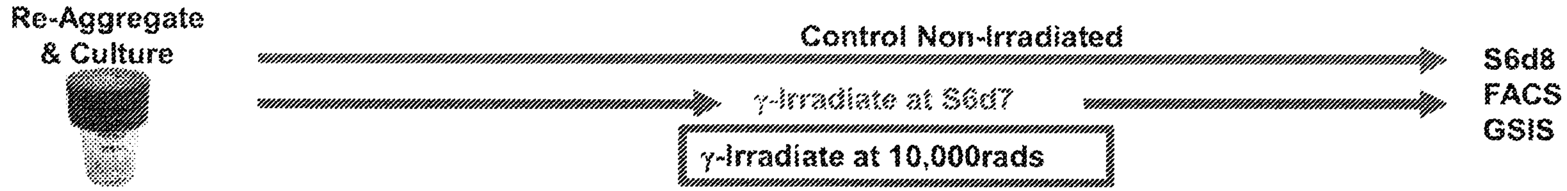
| | NKX6.1+C-pep | CHGA | CDX2 | SOX2 | SOX9 |
|---|---|---|---|---|---|
| SEM01 (D431) Control | 19% | 98.2% | 13% | 8.1% | 10.7% |
| SEM01 (D431) Irradiated | 21.7% | 95.2% | 8.6% | 6.6% | 6.6% |
| | | | | | |
| HUES8 (D495) Control | 29.4% | 97.1% | 12.4% | 6.4% | 6.9% |
| HUES8 (D495) Irradiated | 22.6% | 98.2% | 7.3% | 6.9% | 7.8% |
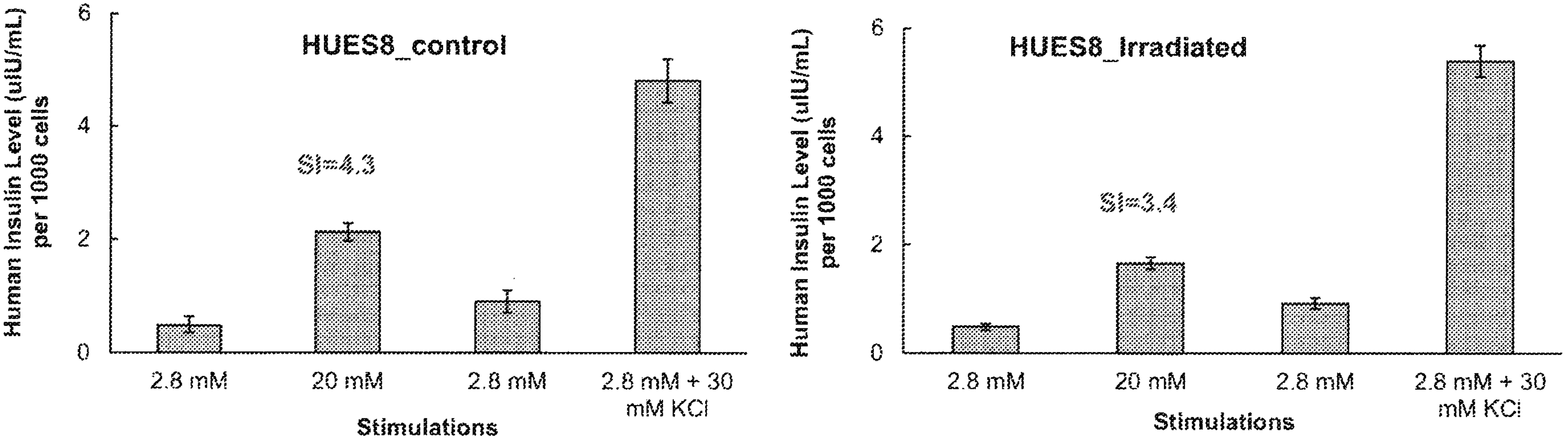
FIG. 34

| | NKX6.1+ C-Pep+ | CHGA | NKX6.1- Cdx2+ | NKX6.1- SOX9+ | SOX2+ | Vimentin | VMAT1+ Cpep- | VMAT1+ Cpep+ | VMAT1 |
|---|---|---|---|---|---|---|---|---|---|
| Control | 43.5 | 96.8 | 2.2 | 13.5 | 5.6 | 0.7 | 42.4 | 3 | 44.2 |
| Pre thaw Irradiation | 36.2 | 99 | 3.8 | 1.1 | 13 | 0.9 | 49.1 | 2.9 | 52.8 |
| mRA Irradiation | **79.2** | 98.3 | 2.5 | 1.4 | 0.8 | 1.4 | - | - | - |

| | NKX6.1+ C-Pep+ | CHGA | NKX6.1- Cdx2+ | NKX6.1- SOX9+ | SOX2+ | Vimentin | VMAT1+ Cpep- | VMAT1+ Cpep+ | VMAT1 |
|---|---|---|---|---|---|---|---|---|---|
| mRA ICRT – Irr | 37 | 99.8 | 0.1 | 0.1 | 1.6 | 0.8 | 43.1 | 6.2 | 48 |
| mRA – Irr | 37.2 | 99.9 | 0.1 | 0 | 1.1 | 1.3 | 44.3 | 2.7 | 47 |

METHODS OF ENHANCING STEM CELL DIFFERENTIATION INTO BETA CELLS

CROSS-REFERENCE

This application is a continuation of U.S. patent application Ser. No. 17/010,346, filed on Sep. 2, 2020, which is a continuation of International Patent Application No. PCT/US2019/020430, filed Mar. 1, 2019, which claims the benefit of U.S. Provisional Application No. 62/637,923, filed on Mar. 2, 2018, each of which is incorporated herein by reference in its entirety.

SEQUENCE LISTING

The instant application contains a Sequence Listing which has been submitted electronically in XML format and is hereby incorporated by reference in its entirety. Said XML copy, created on Nov. 10, 2022, is named 47380-718_303_SL.xml and is 22,906 bytes in size.

BACKGROUND OF THE DISCLOSURE

Deciphering the molecular mechanisms that direct islet cell regeneration, plasticity and function can improve and expand the β cell replacement strategies for treating diabetes. The generation of stem cell derived β-cells can provide a potentially useful step toward the generation of islets and pancreatic organs. One of the rapidly growing diseases that may be treatable by stem cell derived tissues is diabetes. Type 1 diabetes results from autoimmune destruction of β-cells in the pancreatic islet. Type 2 diabetes results from peripheral tissue insulin resistance and β-cell dysfunction. Diabetic patients, particularly those suffering from type 1 diabetes, can potentially be cured through transplantation of new β-cells. Patients transplanted with cadaveric human islets can be made insulin independent for 5 years or longer via this strategy, but this approach is limited because of the scarcity and quality of donor islets. The generation of an unlimited supply of human β-cells from stem cells can extend this therapy to millions of new patients and can be an important test case for translating stem cell biology into the clinic.

INCORPORATION BY REFERENCE

All publications, patents, and patent applications mentioned in this specification are herein incorporated by reference to the same extent as if each individual publication, patent, or patent application was specifically and individually indicated to be incorporated by reference. Absent any indication otherwise, publications, patents, and patent applications mentioned in this specification are incorporated herein by reference in their entireties.

SUMMARY OF THE DISCLOSURE

In some aspects, provided herein is a method comprising: contacting a population of pancreatic progenitor cells or precursors thereof with an epigenetic modifying compound, wherein the contacting results in a population of endocrine cells with an increased proportion of chromogranin A-positive (CHGA+) cells or an increased proportion of C-peptide-positive and NKX6.1-positive (C-PEP+, NKX6.1+) cells as compared to a corresponding population of endocrine cells which is not contacted with the epigenetic modifying compound.

In some aspects, provided herein is a method comprising: contacting a population of pancreatic progenitor cells or precursors thereof with an epigenetic modifying compound, wherein the contacting results in a population of endocrine cells with a reduced proportion of cells expressing VMAT or Cdx2 as compared to a corresponding population of endocrine cells which is not contacted with the epigenetic modifying compound.

In some cases, the epigenetic modifying compound comprises one or more of a DNA methylation inhibitor, a histone acetyltransferase inhibitor, a histone deacetylase inhibitor, a histone methyltransferase inhibitor, or a bromodomain inhibitor. In some cases, the epigenetic modifying compound comprises a histone methyltransferase inhibitor. In some cases, the histone methyltransferase inhibitor is an EZH2 inhibitor. In some cases, the histone methyltransferase inhibitor is selected from the group consisting of DZNep, GSK126, and EPZ6438. In some cases, the histone methyltransferase inhibitor is DZNep. In some cases, a concentration of the DZNep that is contacted to the population of pancreatic progenitor cells or precursors thereof is from about 0.05 μM to about 50 μM, about 0.1 μM to about 10 μM, about 0.5 μM to about 5 μM, about 0.75 μM to about 2.5 μM, or about 1 μM to about 2 μM. In some cases, the concentration of the DZNep is at least about 0.5 μM. In some cases, the concentration of the DZNep is about 1 μM. In some cases, the epigenetic modifying compound comprises a histone deacetylase (HDAC) inhibitor. In some cases, the HDAC inhibitor is a Class I HDAC inhibitor, a Class II HDAC inhibitor, or a combination thereof. In some cases, the HDAC inhibitor is selected from the group consisting of KD5170, MC1568, and TMP195. In some cases, the HDAC inhibitor is KD5170. In some cases, the epigenetic modifying compound comprises an HDAC inhibitor and an EZH2 inhibitor. In some cases, the epigenetic modifying compound comprises DZNep and KD5170. In some cases, the method is performed in vitro.

In some cases, the method further comprises contacting the population of pancreatic progenitor cells or precursors thereof with an agent selected from the group consisting of (i) a SHH pathway inhibitor, (ii) a retinoic acid (RA) signaling pathway activator, (iii) a γ-secretase inhibitor, (iv) a growth factor from the epidermal growth factor (EGF) family, (v) a bone morphogenetic protein (BMP) signaling pathway inhibitor, (vi) a TGF-β signaling pathway inhibitor, (vii) a thyroid hormone signaling pathway activator, (viii) a protein kinase inhibitor, and (ix) a ROCK inhibitor. In some cases, (A) the SHH pathway inhibitor comprises SANT1; (B) the RA signaling pathway activator comprises retinoic acid; (C) the γ-secretase inhibitor comprises XXI; (D) the growth factor from the EGF family comprises betacellulin; (E) the BMP signaling pathway inhibitor comprises LDN; (F) the TGF-β signaling pathway inhibitor comprises Alk5i II; (G) the thyroid hormone signaling pathway activator comprises GC-1; (H) the protein kinase inhibitor comprises staurosporine; or (I) the ROCK inhibitor comprises thiazovinin. In some cases, the method comprises contacting the population of pancreatic progenitor cells or precursors thereof with an agent selected from the group consisting of betacellulin, thiazovinin, retinoic acid, SANT1, XXI, Alk5i II, GC-1, LDN and staurosporine. In some cases, the contacting is for at least three days. In some cases, the contacting comprises contacting the population of pancreatic progenitor cells or precursors thereof with the epigenetic modifying compound for a period of more than three days, and removing the SHH pathway inhibitor, the RA signaling pathway activator, or the growth factor from the EGF family after the contacting with the population of pancreatic progenitor cells or precursors thereof for first three days of the period. In some cases, the contacting is for at least five days. In some cases, the contacting is for about seven days. In some cases, at least one cell of the population of pancreatic progenitor cells expresses at least one of PDX1 and NKX6-1. In some cases, at least one cell of the population of pancreatic progenitor cells expresses both PDX1 and NKX6-1. In some cases, at least one cell of the population of endocrine cells expresses CHGA. In some cases, at least one cell of the population of endocrine cells expresses C-peptide and NKX6.1. In some cases, the population of endocrine cells comprises a proportion of CHGA+ cells that is at least about 10%, 20%, 30%, 40%, 50%, 60%, 70%, 80%, 90%, 100%, 120%, 150%, 180%, 200%, 220%, 250%, 280%, 300%, 320%, 350%, 380%, 400%, 420%, 450%, 480%, or 500% higher than a corresponding population of endocrine cells which is not contacted with the epigenetic modifying compound, as measured by flow cytometry. In some cases, the population of endocrine cells comprises a proportion of C-PEP+, NKX6.1+ cells that is at least about 10%, 20%, 30%, 40%, 50%, 60%, 70%, 80%, 90%, 100%, 120%, 150%, 180%, 200%, 220%, 250%, 280%, 300%, 320%, 350%, 380%, 400%, 420%, 450%, 480%, or 500% higher than a corresponding population of endocrine cells which is not contacted with the epigenetic modifying compound, as measured by flow cytometry. In some cases, the population of endocrine cells comprises a proportion of cells expressing VMAT or Cdx2 that is at least about 10%, 20%, 30%, 40%, 50%, 60%, 70%, 80%, 90%, 100%, 120%, 150%, 180%, 200%, 220%, 250%, 280%, 300%, 320%, 350%, 380%, or 400% lower than a corresponding population of endocrine cells which is not contacted with the at least one epigenetic modifying compound, as measured by flow cytometry.

In some aspects, provided herein is a cell produced by any method provided herein.

In some aspects, provided herein is a composition comprising a cell population, wherein the cell population comprises: (a) at least about 20% cells expressing C-peptide and NKX6.1; (b) at least about 60% cells expressing CHGA; (c) at most about 20% cells expressing Cdx2; or (d) at most about 45% cells expressing VMAT1, as measured by flow cytometry.

In some aspects, provided herein is a composition comprising a cell population that comprises at least about 30% ISL1-positive, NKX6.1-positive cells and at most about 20% ISL1-negative, NKX6.1-negative cells, as measured by flow cytometry.

In some cases, the cell population comprises at least about 35% ISL1-positive, NKX6.1-positive cells. In some cases, the cell population comprises at least about 40% ISL1-positive, NKX6.1-positive cells. In some cases, the cell population comprises at most about 15% ISL1-negative, NKX6.1-negative cells. In some cases, the composition comprises: (a) at least about 20% cells expressing C-peptide and NKX6.1; (b) at least about 60% cells expressing CHGA; and (c) at most about 20% cells expressing Cdx2, as measured by flow cytometry. In some cases, the composition comprises at most about 45% cells expressing VMAT1, as measured by flow cytometry. In some cases, the composition further comprises an epigenetic modifying compound. In some cases, the epigenetic modifying compound comprises one or more of a DNA methylation inhibitor, a histone acetyltransferase inhibitor, a histone deacetylase inhibitor, a histone methyltransferase inhibitor, or a bromodomain inhibitor. In some cases, the epigenetic modifying compound comprises a histone methyltransferase inhibitor. In some cases, the histone methyltransferase inhibitor is an EZH2 inhibitor. In some cases, the histone methyltransferase inhibitor is selected from the group consisting of DZNep, GSK126, and EPZ6438. In some cases, the histone methyltransferase inhibitor is DZNep. In some cases, a concentration of the DZNep that is contacted to the population of pancreatic progenitor cells or precursors thereof is from about 0.05 μM to about 50 μM, about 0.1 μM to about 10 μM, about 0.5 μM to about 5 μM, about 0.75 μM to about 2.5 μM, or about 1 μM to about 2 μM. In some cases, the concentration of the DZNep is at least about 0.5 μM. In some cases, the concentration of the DZNep is about 1 μM. In some cases, the epigenetic modifying compound comprises a histone deacetylase (HDAC) inhibitor. In some cases, the HDAC inhibitor is a Class I HDAC inhibitor, a Class II HDAC inhibitor, or a combination thereof. In some cases, the HDAC inhibitor is selected from the group consisting of KD5170, MC1568, and TMP195. In some cases, the HDAC inhibitor is KD5170. In some cases, the epigenetic modifying compound comprises an HDAC inhibitor and an EZH2 inhibitor. In some cases, the epigenetic modifying compound comprises DZNep and KD5170. In some cases, the composition further comprises an agent selected from the group consisting of (i) a SHH pathway inhibitor, (ii) a retinoic acid (RA) signaling pathway activator, (iii) a γ-secretase inhibitor, (iv) a growth factor from the epidermal growth factor (EGF) family, (v) a bone morphogenetic protein (BMP) signaling pathway inhibitor, (vi) a TGF-β signaling pathway inhibitor, (vii) a thyroid hormone signaling pathway activator, (viii) a protein kinase inhibitor, and (ix) a ROCK inhibitor. In some cases of the compositions, (A) the SHH pathway inhibitor comprises SANT1; (B) the RA signaling pathway activator comprises retinoic acid; (C) the γ-secretase inhibitor comprises XXI; (D) the growth factor from the EGF family comprises betacellulin; (E) the BMP signaling pathway inhibitor comprises LDN; (F) the TGF-β signaling pathway inhibitor comprises Alk5i II; (G) the thyroid hormone signaling pathway activator comprises GC-1; (H) the protein kinase inhibitor comprises staurosporine; or (I) the ROCK inhibitor comprises thiazovinin. In some cases, the composition comprises an agent selected from the group consisting of betacellulin, thiazovinin, retinoic acid, SANT1, XXI, Alk5i II, GC-1, LDN and staurosporine.

In some aspects, provided herein is a composition that comprises a pancreatic progenitor cell, and at least one of a histone deacetylase (HDAC) inhibitor or a histone methyltransferase inhibitor.

In some cases, the composition further comprises an endocrine cell. In some cases of the composition, the HDAC inhibitor is a Class I HDAC inhibitor, a Class II HDAC inhibitor, or a combination thereof. In some cases, the HDAC inhibitor is selected from the group consisting of KD5170, MC1568, and TMP195. In some cases, the HDAC inhibitor is KD5170. In some cases, a concentration of the KD5170 in the composition is from about 0.05 μM to about 50 μM, about 0.1 μM to about 10 μM, about 0.5 μM to about 5 μM, about 0.75 μM to about 2.5 μM, or about 1 μM to about 2 μM. In some cases, the concentration of the KD5170 is at least 0.5 μM. In some cases, the concentration of the KD5170 is about 1 μM. In some cases, the histone methyltransferase inhibitor is an EZH2 inhibitor. In some cases, the histone methyltransferase inhibitor is selected from the group consisting of DZNep, GSK126, and EPZ6438. In some cases, the histone methyltransferase inhibitor is DZNep. In some cases, a concentration of the DZNep in the composition is from about 0.05 μM to about 50 μM, about 0.1 μM to about 10 μM, about 0.5 μM to about 5 μM, about 0.75 μM to about 2.5 μM, or about 1 μM to about 2 μM. In some cases, the concentration of the DZNep is at least 0.5 μM. In some cases, the concentration of the DZNep is about 1 μM. In some cases, the HDAC inhibitor is KD5170 and the histone methyltransferase inhibitor is DZNep. In some cases, the composition is an in vitro composition. In some cases, the composition further comprises an agent selected from the group consisting of (i) a SHH pathway inhibitor, (ii) a retinoic acid (RA) signaling pathway activator, (iii) a γ-secretase inhibitor, (iv) a growth factor from the epidermal growth factor (EGF) family, (v) a bone morphogenetic protein (BMP) signaling pathway inhibitor, (vi) a TGF-β signaling pathway inhibitor, (vii) a thyroid hormone signaling pathway activator, (viii) a protein kinase inhibitor, and (ix) a ROCK inhibitor. In some cases, (A) the SHH pathway inhibitor comprises SANT1; (B) the RA signaling pathway activator comprises retinoic acid; (C) the γ-secretase inhibitor comprises XXI; (D) the growth factor from the EGF family comprises betacellulin; (E) the BMP signaling pathway inhibitor comprises LDN; (F) the TGF-β signaling pathway inhibitor comprises Alk5i II; (G) the thyroid hormone signaling pathway activator comprises GC-1; (H) the protein kinase inhibitor comprises staurosporine; or (I) the ROCK inhibitor comprises thiazovinin. In some cases, the composition further comprises an agent selected from the group consisting of betacellulin, thiazovinin, retinoic acid, SANT1, XXI, Alk5i II, GC-1, LDN and staurosporine.

In some aspects, provided herein is a method comprising: contacting a cell population comprising pancreatic progenitor cells or precursors thereof with a histone methyltransferase inhibitor and generating a cell population comprising endocrine cells; and maturing the cell population comprising endocrine cells to obtain at least one pancreatic β cell that exhibits an in vitro glucose-stimulated insulin secretion response to a glucose challenge.

In some cases, the method comprises contacting the cell population with an agent selected from the group consisting of (i) a SHH pathway inhibitor, (ii) a retinoic acid (RA) signaling pathway activator, (iii) a γ-secretase inhibitor, (iv) a growth factor from the epidermal growth factor (EGF) family, (v) a bone morphogenetic protein (BMP) signaling pathway inhibitor, (vi) a TGF-β signaling pathway inhibitor, (vii) a thyroid hormone signaling pathway activator, (viii) a protein kinase inhibitor, and (ix) a ROCK inhibitor. In some cases, (A) the SHH pathway inhibitor comprises SANT1; (B) the RA signaling pathway activator comprises retinoic acid; (C) the γ-secretase inhibitor comprises XXI; (D) the growth factor from the EGF family comprises betacellulin; (E) the BMP signaling pathway inhibitor comprises LDN; (F) the TGF-β signaling pathway inhibitor comprises Alk5i II; (G) the thyroid hormone signaling pathway activator comprises GC-1; (H) the protein kinase inhibitor comprises staurosporine; or (I) the ROCK inhibitor comprises thiazovinin. In some cases, the method comprises contacting the cell population with an agent selected from the group consisting of betacellulin, thiazovinin, retinoic acid, SANT1, XXI, Alk5i II, GC-1, LDN and staurosporine. In some cases, the method further comprises contacting the cell population with a histone deacetylase (HDAC) inhibitor. In some cases, the HDAC inhibitor is KD5170. In some cases, the histone methyltransferase inhibitor is selected from the group consisting of DZNep, GSK126, and EPZ6438. In some cases, the histone methyltransferase inhibitor is DZNep. In some cases, the contacting with the histone methyltransferase inhibitor results in a population comprising the endocrine cells and having an increased proportion of chromogranin A-positive (CHGA+) cells or an increased proportion of C-peptide-positive and NKX6.1-positive (C-PEP+; NKX6.1+) cells as compared to a corresponding population of endocrine cells which is not contacted with the histone methyltransferase inhibitor. In some cases, the contacting with the histone methyltransferase inhibitor results in a population comprising the endocrine cells and having a reduced proportion of cells expressing VMAT or Cdx2 as compared to a corresponding population of endocrine cells which is not contacted with the histone methyltransferase inhibitor. In some cases, the at least one cell of the pancreatic progenitor cells or precursors thereof expresses both Pdx1 and NKX6.1. In some cases, the method further comprises differentiating a plurality of stem cells in vitro to obtain the cell population comprising the pancreatic progenitor cells or precursors thereof.

In some aspects, provided herein is a pancreatic β cell generated according to any method provided herein.

In some aspects, provided herein is a method, comprising: (a) contacting a population of Pdx1-negative, NKX6.1-negative primitive gut tube cells with a bone morphogenetic protein (BMP) signaling pathway inhibitor and a growth factor from transformation growth factor β (TGF-β) superfamily, thereby generating a cell population that comprises Pdx1-positive, NKX6.1-positive pancreatic progenitor cells; and (b) contacting the cell population comprising the Pdx1-positive, NKX6.1-positive pancreatic progenitor cells with an epigenetic modifying compound and generating a cell population comprising endocrine cells.

In some cases, the BMP signaling pathway inhibitor comprises DMH-1, a derivative, analogue, or variant thereof. In some cases, a concentration of the DMH-1 that is contacted to the population of Pdx1-negative, NKX6.1-negative primitive gut tube cells is about 0.01 μM to about 10 μM, about 0.05 μM to about 5 μM, about 0.1 μM to about 1 μM, or about 0.15 μM to about 0.5 μM. In some cases, a concentration of the DMH-1 that is contacted to the population of Pdx1-negative, NKX6.1-negative primitive gut tube cells is about 0.25 μM DMH-1. In some cases, the growth factor from TGF-β superfamily comprises Activin A. In some cases, a concentration of the Activin A that is contacted to the population of Pdx1-negative, NKX6.1-negative primitive gut tube cells is about 0.5 ng/mL to about 200 ng/mL, about 1 ng/mL to about 100 ng/mL, about 2 ng/mL to about 50 ng/mL, or about 5 ng/mL to about 30 ng/mL. In some cases, a concentration of the Activin A that is contacted to the population of Pdx1-negative, NKX6.1-negative primitive gut tube cells is at least about 5 ng/mL or at least about 10 ng/mL Activin A. In some cases, a concentration of the Activin A that is contacted to the population of Pdx1-negative, NKX6.1-negative primitive gut tube cells is about 20 ng/mL Activin A. In some cases, the contacting the population of Pdx1-negative, NKX6.1-negative primitive gut tube cells further comprises contacting with an agent selected from the group consisting of: a growth factor from FGF family, a SHH pathway inhibitor, a RA signaling pathway activator, a protein kinase C activator, and a ROCK inhibitor. In some cases, the epigenetic modifying compound comprises a compound selected from the group consisting of a DNA methylation inhibitor, a histone acetyltransferase inhibitor, a histone deacetylase inhibitor, a histone methyltransferase inhibitor, and a bromodomain inhibitor. In some cases, the epigenetic modifying compound comprises a histone methyltransferase inhibitor. In some cases, the histone methyltransferase inhibitor is an EZH2 inhibitor. In some cases, the histone methyltransferase inhibitor is selected from the group consisting of DZNep, GSK126, and EPZ6438. In some cases, the histone methyltransferase inhibitor is DZNep. In some cases, a concentration of the DZNep that is contacted to the population of pancreatic progenitor cells or precursors thereof is from about 0.05 μM to about 50 μM, about 0.1 μM to about 10 μM, about 0.5 μM to about 5 μM, about 0.75 μM to about 2.5 μM, or about 1 μM to about 2 μM. In some cases, the concentration of the DZNep is at least about 0.5 μM. In some cases, the concentration of the DZNep is about 1 μM. In some cases, the epigenetic modifying compound comprises a histone deacetylase (HDAC) inhibitor. In some cases, the HDAC inhibitor is a Class I HDAC inhibitor, a Class II HDAC inhibitor, or a combination thereof. In some cases, the HDAC inhibitor is selected from the group consisting of KD5170, MC1568, and TMP195. In some cases, the HDAC inhibitor is KD5170. In some cases, the method is performed in vitro. In some cases, the method further comprises contacting the population comprising the Pdx1-positive, NKX6.1-positive pancreatic progenitor cells with an agent selected from the group consisting of: (i) a SHH pathway inhibitor, (ii) a retinoic acid (RA) signaling pathway activator, (iii) a γ-secretase inhibitor, (iv) a growth factor from the epidermal growth factor (EGF) family, (v) a bone morphogenetic protein (BMP) signaling pathway inhibitor, (vi) a TGF-β signaling pathway inhibitor, (vii) a thyroid hormone signaling pathway activator, (viii) a protein kinase inhibitor, and (ix) a ROCK inhibitor. In some cases, (A) the SHH pathway inhibitor comprises SANT1; (B) the RA signaling pathway activator comprises retinoic acid; (C) the γ-secretase inhibitor comprises XXI; (D) the growth factor from the EGF family comprises betacellulin; (E) the BMP signaling pathway inhibitor comprises LDN; (F) the TGF-β signaling pathway inhibitor comprises Alk5i II; (G) the thyroid hormone signaling pathway activator comprises GC-1; (H) the protein kinase inhibitor comprises staurosporine; or (I) the ROCK inhibitor comprises thiazovinin. In some cases, the method comprises contacting the population comprising the Pdx1-positive, NKX6.1-positive pancreatic progenitor cells with an agent selected from the group consisting of: betacellulin, thiazovinin, retinoic acid, SANT1, XXI, Alk5i II, GC-1, LDN, and staurosporine. In some cases, the contacting is for at least three days. In some cases, the contacting comprises contacting the population comprising the Pdx1-positive, NKX6.1-positive pancreatic progenitor cells with the epigenetic modifying compound for a period of more than three days, and removing the SHH pathway inhibitor, the RA signaling pathway activator, or the growth factor from the EGF family after the contacting with the population of pancreatic progenitor cells or precursors thereof for first three days of the period. In some cases, the contacting is for at least five days. In some cases, the contacting is for about seven days. In some cases, the cell population that comprises Pdx1-positive, NKX6.1-positive pancreatic progenitor cells comprises at most about 10% cells expressing Cdx2, as measured by flow cytometry. In some cases, the cell population that comprises Pdx1-positive, NKX6.1-positive pancreatic progenitor cells comprises a smaller proportion of cells expressing Cdx2 as compared to a corresponding cell population without contacting with the bone morphogenetic protein (BMP) signaling pathway inhibitor and the growth factor from transformation growth factor β (TGF-β) superfamily. In some cases, the cell population comprising endocrine cells comprises at least about 40% cells expressing ISL1 and NKX6.1, as measured by flow cytometry. In some cases, the cell population comprising endocrine cells comprises a higher proportion of cells expressing ISL1 and NKX6.1 as compared to a corresponding cell population without the contacting with the bone morphogenetic protein (BMP) signaling pathway inhibitor and the growth factor from transformation growth factor 13 (TGF-β) superfamily. In some cases, the cell population comprising endocrine cells comprises at most about 15% ISL1-negative, NKX6.1-negative cells, as measured by flow cytometry. In some cases, the cell population comprising endocrine cells comprises a smaller proportion of ISL1-negative, NKX6.1-negative cells as compared to a corresponding cell population without the contacting with the bone morphogenetic protein (BMP) signaling pathway inhibitor and the growth factor from transformation growth factor β (TGF-β) superfamily. In some cases, the method further comprises cryopreserving the cell population comprising endocrine cells. In some cases, the cell population comprising endocrine cells is a cell cluster, and the method further comprises: (a) dissociating a plurality of cells from the cell cluster; and (b) culturing the plurality of cells from (a) in a reaggregation culture medium and allowing at least a portion of the plurality of cells to form a second cell cluster. In some cases, the dissociating does not comprise subjecting the plurality of cells to flow cytometry. In some cases, the reaggregation culture medium is serum-free. In some cases, the reaggregation culture medium does not comprise exogenous differentiation factors. In some cases, the method further comprises maturing the endocrine cells in vitro to obtain at least one pancreatic β cell that exhibits an in vitro glucose-stimulated insulin secretion response to a glucose challenge. In some cases, the maturing is performed in a serum-free medium. In some cases, the maturing is performed in a xeno-free medium. In some cases, the maturing is performed in a culture medium that does not comprise exogenous differentiation factors. In some cases, the maturing is performed in a presence of human serum albumin (HSA). In some cases, the HSA is present at a concentration of about 0.1% to about 5%, about 0.5% to about 2%. In some cases, the HSA is present at a concentration of about 1%.

In some cases, the methods provided herein comprise A method, comprising: (a) differentiating pluripotent stem cells in a population into definitive endoderm cells by contacting the pluripotent stem cells with a growth factor from TGF-β superfamily and a WNT signaling pathway activator; (b) differentiating at least some of the definitive endoderm cells into primitive gut tube cells by contacting the definitive endoderm cells with a growth factor from FGF family; (c) differentiating at least some of the primitive gut tube cells into Pdx1-positive pancreatic progenitor cells by contacting the primitive gut tube cells with a ROCK inhibitor, a growth factor from FGF family, a BMP signaling pathway inhibitor, a PKC activator, a retinoic acid signaling pathway activator, a SHH pathway inhibitor, and a growth factor from TGF-β superfamily; (d) differentiating at least some of the Pdx1-positive pancreatic progenitor cells into Pdx1-positive, NKX6.1-positive pancreatic progenitor cells by contacting the Pdx1-positive pancreatic progenitor cells with a ROCK inhibitor, a growth factor from TGFβ superfamily, a growth factor from FGF family, a RA signaling pathway activator, and a SHH pathway inhibitor; and (e) differentiating at least some of the Pdx1-positive, NKX6.1-positive pancreatic progenitor cells into a cell population comprising at least one NKX6.1+ and C-peptide+ cell by contacting the Pdx1-positive, NKX6.1-positive pancreatic progenitor cells with a TGF-β signaling pathway inhibitor, a growth factor from EGF family, a RA signaling pathway activator, a SHH pathway inhibitor, a TH signaling pathway activator, a γ-secretase inhibitor, a protein kinase inhibitor, a ROCK inhibitor, a BMP signaling pathway inhibitor, and an epigenetic modifying compound.

In some aspects, provided herein is a cell population comprising endocrine cells generated according to any method provided herein. In some aspects, provided herein is a cell population comprising SC-β cells that are generated according to any method provided herein.

In some aspects, provided herein is a method, comprising: exposing an in vitro cell population comprising endocrine cells to irradiation at a dose of about 100 rads to about 100,000 rads for a time period of about 1 min to about 60 min.

In some aspects, provided herein is a method of reducing cell proliferation, comprising exposing to irradiation a cell population comprising stem cells, definitive endoderm cells, primitive gut tube cells, pancreatic progenitor cells, or endocrine cells, wherein the irradiation results in a cell population that has reduced proliferative capability as compared to a corresponding cell population that is not subject to irradiation.

In some cases, the cell population is exposed to irradiation at about 100 rads to about 50,000 rads, about 100 rads to about 25,000 rads, about 100 rads to about 10,000 rads, about 250 rads to about 25,000 rads, about 500 rads to about 25,000 rads, about 1,000 rads to about 25,000 rads, about 2,500 rads to about 25,000 rads, about 5,000 rads to about 25,000 rads, or about 10,000 rads to about 15,000 rads. In some cases, the cell population is exposed to irradiation at about 10,000 rads. In some cases, the cell population is exposed to irradiation for about 1 min to about 55 min, about 1 min to about 50 min, about 1 min to about 45 min, about 1 min to about 40 min, about 1 min to about 35 min, about 1 min to about 30 min, about 1 min to about 25 min, about 1 min to about 20 min, about 1 min to about 10 min, about 1 min to about 5 min, about 10 min to about 55 min, about 15 min to about 55 min, about 20 min to about 55 min, about 25 min to about 55 min, about 30 min to about 55 min, about 20 min to about 40 min, or about 25 min to about 35 min. In some cases, the cell population is exposed to irradiation for about 30 min. In some cases, the irradiation comprises ionizing irradiation. In some cases, the ionizing irradiation comprises gamma ray, x-ray, ultraviolet radiation, alpha ray, beta ray, or neutron ray. In some cases, the irradiation results in a cell population with reduced proliferation as compared to a corresponding cell cluster that is not subject to the irradiation. In some cases, the cell population comprises a second cell cluster having a diameter of about 50 μm to about 500 μm, about 50 μm to about 300 μm, about 50 μm to about 200 μm, about 50 μm to about 150 μm, about 600 μm to about 150 μm, about 700 μm to about 150 μm, about 80 μm to about 150 μm, or about 60 μm to about 100 μm. In some cases, the method further comprises (a) dissociating a plurality of cells from a first cell cluster; and (b) culturing the plurality of cells from (a) in a reaggregation culture medium and allowing at least a portion of the plurality of cells to form the second cell cluster. In some cases, the dissociating does not comprise subjecting the plurality of cells to flow cytometry. In some cases, the first cell cluster is obtained by dissociating a third cell cluster and culturing cells dissociated from the third cell cluster to form the first cell cluster. In some cases, the cell cluster is cryopreserved prior to the irradiation, wherein the method further comprises thawing the cryopreserved cell cluster prior to the irradiation. In some cases, the cell cluster is cryopreserved while being subject to the irradiation. In some cases, method further comprises thawing the cryopreserved cell cluster after irradiation and differentiating at least some of the endocrine cells. In some cases, the method further comprises obtaining the cell population comprising the endocrine cells by differentiating pancreatic progenitor cells or precursor thereof in vitro. In some cases, the method further comprises differentiating stem cells in vitro, thereby generating the cell population comprising the endocrine cells. In some cases, the method further comprises maturing at least some of the endocrine cells in vitro into pancreatic β cells, thereby generating a cell population comp. In some cases, the method further comprises implanting the pancreatic β cells into a subject in need thereof. In some cases, the implanted pancreatic β cells are configured to control blood glucose level in the subject for at least about 50 days, 60 days, 70 days, 80 days, 90 days, or longer.

In some aspects, provided herein is a cell population comprising endocrine cells generated according to any method of irradiation as described herein. In some aspects, provided herein is a cell population comprising pancreatic β cells generated according to any method of irradiation as described herein.

In some aspects, provided herein is a method comprising: contacting a population of pancreatic progenitor cells or precursors thereof with a composition comprising at least one epigenetic modifying compound, wherein the contacting results in a population of endocrine cells with a reduced proportion of cells expressing VMAT or Cdx2 as compared to a corresponding population of endocrine cells which is not contacted with the at least one epigenetic modifying compound.

In some embodiments, the at least one epigenetic modifying compound comprises one or more of a DNA methylation inhibitor, a histone acetyltransferase inhibitor, a histone deacetylase inhibitor, a histone methyltransferase inhibitor, or a bromodomain inhibitor. In some embodiments, the at least one epigenetic modifying compound comprises a histone methyltransferase inhibitor. In some embodiments, the histone methyltransferase inhibitor is an EZH2 inhibitor.

In some embodiments, the histone methyltransferase inhibitor is at least one of DZNep, GSK126, or EPZ6438. In some embodiments, the histone methyltransferase inhibitor is DZNep. In some embodiments, a concentration of the DZNep in the composition is greater than 0.1 μM. In some embodiments, the concentration of the DZNep is at least 0.5 μM. In some embodiments, the concentration of the DZNep is about 1 μM. In some embodiments, the at least one epigenetic modifying compound comprises a histone deacetylase (HDAC) inhibitor. In some embodiments, the HDAC inhibitor is a Class I HDAC inhibitor, a Class II HDAC inhibitor, or a combination thereof. In some embodiments, the HDAC inhibitor is at least one of KD5170, MC1568, or TMP195. In some embodiments, the HDAC inhibitor is KD5170. In some embodiments, the at least one epigenetic modifying compound comprises an HDAC inhibitor and an EZH2 inhibitor. In some embodiments, the at least one epigenetic modifying compound comprises DZNep and KD5170.

In some embodiments, at least one of the cells expressing VMAT is $INS^-$ in the method provided herein. In some embodiments, at least some cells of the population of pancreatic progenitor cells differentiate into a population of PH cells. In some embodiments, an increased proportion of cells of the population of endocrine cells are $NKX6.1^-$ or $ChromA^+$ as compared to the corresponding population of endocrine cells which is not contacted with the at least one epigenetic modifying compound. In some embodiments, at least one cell of the increased proportion of cells is $NKX6.1^-$ and $ChromA^+$ In some embodiments, at least some cells of the population of pancreatic progenitor cells differentiate into a population of β cells. In some embodiments, the β cells are stem-cell derived β (SC-β) cells. In some embodiments, the β cells express C-PEP and NKX6-1. In some embodiments, the β cells exhibit an in vitro glucose-stimulated insulin secretion response to a glucose challenge.

In some embodiments, the composition of the method described herein comprises at least one of betacellulin, thiazovinin, retinoic acid, SANT1, XXI, Alk5i II, GC-1, LDN or staurosporine. In some embodiments, the contacting is for at least three days. In some embodiments, the contacting is for at least five days. In some embodiments, the contacting is for about seven days.

In some embodiments, at least one pancreatic progenitor cell of the population of pancreatic progenitor cells expresses at least one of PDX1 and NKX6-1. In some embodiments, at least one endocrine cell of the population of endocrine cells expresses CHGA.

Provided herein is an endocrine cell produced by any of the method described herein.

Provided herein is a composition that comprises a pancreatic progenitor cell, a histone deacetylase (HDAC) inhibitor, a histone methyltransferase inhibitor and optionally an endocrine cell. In some embodiments, the HDAC inhibitor is a Class I HDAC inhibitor, a Class II HDAC inhibitor, or a combination thereof. In some embodiments, the HDAC inhibitor is at least one of KD5170, MC1568, or TMP195. In some embodiments, the HDAC inhibitor is KD5170. In some embodiments, a concentration of the KD5170 in the composition is at least 0.1 μM. In some embodiments, the concentration of the KD5170 is at least 0.5 μM. In some embodiments, the concentration of the KD5170 is about 104. In some embodiments, the histone methyltransferase inhibitor is an EZH2 inhibitor. In some embodiments, the histone methyltransferase inhibitor is at least one of DZNep, GSK126, or EPZ6438. In some embodiments, the histone methyltransferase inhibitor is DZNep. In some embodiments, a concentration of the DZNep is at least 0.1 μM. In some embodiments, the concentration of the DZNep is at least 0.5 μM. In some embodiments, the concentration of the DZNep is about 1 μM. In some embodiments, the HDAC inhibitor is KD5170 and the histone methyltransferase inhibitor is DZNep. In some embodiments, the composition is an in vitro composition. In some embodiments, the composition further comprises at least one of betacellulin, thiazovinin, retinoic acid, SANT1, XXI, Alk5i II, GC-1, LDN or staurosporine.

Provided herein is a method comprising contacting a pancreatic progenitor cell or precursor thereof with a histone deacetylase (HDAC) inhibitor and a histone methyltransferase inhibitor, wherein the contacting induces differentiation of the pancreatic progenitor cell. In some embodiments, the pancreatic progenitor cell differentiates into a β cell. In some embodiments, the β cell is a stem-cell derived β (SC-β) cell. In some embodiments, C-PEP and NKX6-1. In some embodiments, the β cells exhibit an in vitro glucose-stimulated insulin secretion response to a glucose challenge. In some embodiments, the HDAC inhibitor is a Class I HDAC inhibitor, a Class II HDAC inhibitor, or a combination thereof. In some embodiments, the HDAC inhibitor is at least one of KD5170, MC1568, or TMP195. In some embodiments, the HDAC inhibitor is KD5170. In some embodiments, the histone methyltransferase inhibitor is an EZH2 inhibitor. In some embodiments, the histone methyltransferase inhibitor is at least one of DZNep, GSK126, or EPZ6438. In some embodiments, the histone methyltransferase inhibitor is DZNep. In some embodiments, the HDAC inhibitor is KD5170 and the histone methyltransferase inhibitor is DZNep. In some embodiments, the method is performed in vitro.

Provided herein is a method comprising contacting a pancreatic progenitor cell or precursor thereof with KD5170 in an amount sufficient to result in differentiation of the cell. In some embodiments, the method further comprises contracting the pancreatic progenitor cell with a histone methyltransferase inhibitor. In some embodiments, the histone methyltransferase inhibitor is at least one of DZNep, GSK126, or EPZ6438. In some embodiments, the histone methyltransferase inhibitor is DZNep. In some embodiments, the pancreatic progenitor cell differentiates into an endocrine cell. In some embodiments, the pancreatic progenitor cell differentiates into a β cell. In some embodiments, the β cell is a stem-cell derived β (SC-β) cell. In some embodiments, the β cell expresses C-PEP and NKX6-1. In some embodiments, the β cell exhibits an in vitro glucose-stimulated insulin secretion response to a glucose challenge.

Provided herein is a method comprising: (a) differentiating a plurality of stem cells in vitro to obtain a cell population comprising pancreatic progenitor cells or precursors thereof (b) contacting in vitro the cell population with a histone deacetylase (HDAC) inhibitor to generate at least one endocrine cell; and (c) maturing the endocrine cell in vitro to obtain at least one SC-β cell. In some embodiments, the stem cells are human pluripotent stem cells. In some embodiments, the method further comprises contacting the cell population with at least one of betacellulin, thiazovinin, retinoic acid, SANT1, XXI, Alk5i II, GC-1, LDN or staurosporine. In some embodiments, the SC-β cell expresses C-PEP and NKX6-1. In some embodiments, the SC-β cell exhibits an in vitro glucose-stimulated insulin secretion response to a glucose challenge. In some embodiments, the method further comprises contracting the cell population with a histone methyltransferase inhibitor. In some embodiments, the histone methyltransferase inhibitor is at least one of DZNep, GSK126, or EPZ6438. In some embodiments, the histone methyltransferase inhibitor is DZNep. In some embodiments, the HDAC inhibitor is KD5170.

Provided herein is a method comprising contacting a cell population comprising pancreatic progenitor cells or precursors thereof with a histone methyltransferase inhibitor in vitro in an amount sufficient to generate endocrine cells; and maturing the endocrine cells in vitro to obtain at least one SC-β cell that exhibits an in vitro glucose-stimulated insulin secretion response to a glucose challenge. In some embodiments, the method further comprises differentiating a plurality of stem cells in vitro to obtain the cell population comprising the pancreatic progenitor cells or precursors thereof. In some embodiments, the method further comprises contacting the cell population with at least one of betacellulin, thiazovinin, retinoic acid, SANT1, XXI, Alk5i II, GC-1, LDN or staurosporine. In some embodiments, the method further comprises contacting the cell population with a histone deacetylase (HDAC) inhibitor. In some embodiments, the HDAC inhibitor is KD5170. In some embodiments, the histone methyltransferase inhibitor is at least one of DZNep, GSK126, or EPZ6438. In some embodiments, the histone methyltransferase inhibitor is DZNep.

Provided herein is a method for selecting a target cell from a population of cells comprising (i) contacting the target cell with a stimulating compound, wherein the contacting induces a selectable marker of the target cell to localize to a cell surface of the target cell; and (ii) selecting the target cell based on the localization of the selectable marker at the cell surface. In some embodiments, the selectable marker comprises PSA-NCAM. In some embodiments, the selecting the target cell is by cell sorting. In some embodiments, the selecting comprises contacting the selectable marker of the target cell with an antigen binding polypeptide when the selectable marker is localized to the surface of the target cell. In some embodiments, the antigen binding polypeptide comprises an antibody. In some embodiments, the antigen binding polypeptide binds to the PSA-NCAM. In some embodiments, the method further comprises treating the population of cells with a compound that removes the selectable marker from a cell surface of at least one cell of the population of cells. In some embodiments, the population of cells is treated with the compound prior to the contacting the target cell with the stimulating compound. In some embodiments, the compound cleaves the selectable marker from the cell surface of the at least one cell. In some embodiments, the compound is an enzyme. In some embodiments, the compound is an endosialidase. In some embodiments, the endosialidase is endoneuraminidase (Endo-N). In some embodiments, the target cell is an endocrine cell. In some embodiments, the stimulating compound comprises at least one of arginine or glucose. In some embodiments, the endocrine cell is a β cell. In some embodiments, the β cell is an SC-β cell. In some embodiments, the stimulating compound comprises isoproterenol. In some embodiments, the endocrine cell is an EC cell. In some embodiments, one or more cells of the population of cells fails to localize the selectable marker to a cell surface when contacted with the stimulating compound. In some embodiments, the stimulating compound is at least one of glucose or arginine and the one or more cells is an EC cell. In some embodiments, the stimulating compound is isoproterenol and the one or more cells is a β cell. In some embodiments, the selecting the target cell separates the target cell from the one or more cells of the population of cells.

Provided herein is a method comprising: contacting a population of pancreatic progenitor cells or precursors thereof with a composition comprising at least one epigenetic modifying compound, wherein the contacting results in an increased proportion of islet cells as compared to a corresponding population of pancreatic progenitor cells which is not contacted with the at least one epigenetic modifying compound. In some embodiments, the islet cells comprise at least one β cell. In some embodiments, the β cell comprises an SC-β cell. In some embodiments, the SC-β cell exhibits an in vitro glucose-stimulated insulin secretion response to a glucose challenge. In some embodiments, the islet cells comprise at least one alpha cell. In some embodiments, the islet cells comprise a delta cell. In some embodiments, the islet cells comprise a polyhormonal (PH) cell. In some embodiments, the method further comprises differentiating a plurality of stem cells in vitro to obtain the population of pancreatic progenitor cells or precursors thereof. In some embodiments, the stem cells are human pluripotent stem cells. In some embodiments, the at least one epigenetic modifying compound comprises one or more of a DNA methylation inhibitor, a histone acetyltransferase inhibitor, a histone deacetylase inhibitor, a histone methyltransferase inhibitor, or a bromodomain inhibitor. In some embodiments, the at least one epigenetic modifying compound comprises a histone methyltransferase inhibitor. In some embodiments, the histone methyltransferase inhibitor is an EZH2 inhibitor. In some embodiments, the histone methyltransferase inhibitor is at least one of DZNep, GSK126, or EPZ6438. In some embodiments, the histone methyltransferase inhibitor is DZNep. In some embodiments, a concentration of the DZNep in the composition is greater than 0.1 μM. In some embodiments, the concentration of the DZNep is at least 0.5 μM. In some embodiments, the concentration of the DZNep is about 1 μM. In some embodiments, the at least one epigenetic modifying compound comprises a histone deacetylase (HDAC) inhibitor. In some embodiments, the HDAC inhibitor is a Class I HDAC inhibitor, a Class II HDAC inhibitor, or a combination thereof. In some embodiments, the HDAC inhibitor is at least one of KD5170, MC1568, or TMP195. In some embodiments, the HDAC inhibitor is KD5170. In some embodiments, the at least one epigenetic modifying compound comprises an HDAC inhibitor and an EZH2 inhibitor. In some embodiments, the at least one epigenetic modifying compound comprises DZNep and KD5170.

BRIEF DESCRIPTION OF THE DRAWINGS

The features of the present disclosure are set forth with particularity in the appended claims. A better understanding of the features and advantages of the present will be obtained by reference to the following detailed description that sets forth illustrative embodiments, in which the principles of the disclosure are utilized, and the accompanying drawings of which:

FIG. 1 shows chemical structures of 3-deazaneplanocin A hydrochloride (DZNep), GSK126, EPZ6438.

FIG. 2 shows chemical structures of KD5170 and MC1568.

FIG. 3 shows chemical structures of methyltransferase inhibitors.

FIG. 5 is a summary of differentiation stages as described herein.

FIG. 34 shows that high dose gamma irradiation had no significant impact on SC-islet composition and function.

DETAILED DESCRIPTION OF THE DISCLOSURE

Figure 4:
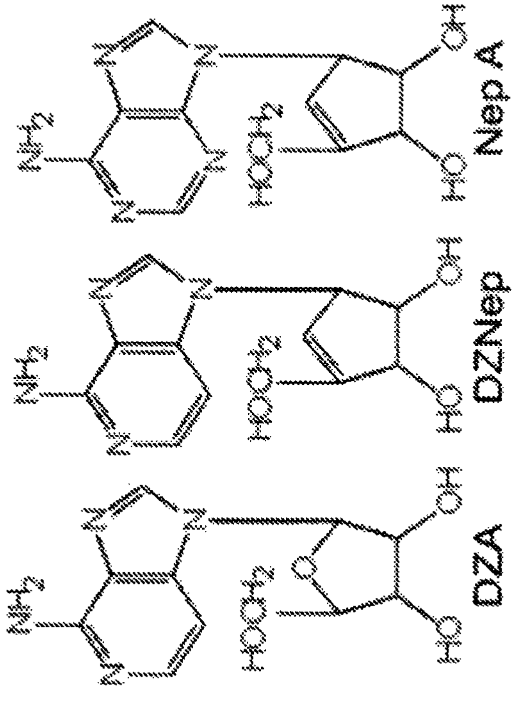
FIG. 4 shows a chemical structure of DZNep analogues.

The following description and examples illustrate embodiments of the present disclosure in detail. It is to be understood that this disclosure is not limited to the particular embodiments described herein and as such can vary. Those of skill in the art will recognize that there are numerous variations and modifications of this disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the present disclosure can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

Definitions

In this application, the use of the singular includes the plural unless specifically stated otherwise. It must be noted that, as used in the specification, the singular forms "a," "an" and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

Furthermore, use of the term "including" as well as other forms, such as "include", "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The term "about" in relation to a reference numerical value and its grammatical equivalents as used herein can include the numerical value itself and a range of values plus or minus 10% from that numerical value.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "diabetes" and its grammatical equivalents as used herein can refer to is a disease characterized by high blood sugar levels over a prolonged period. For example, the term "diabetes" and its grammatical equivalents as used herein can refer to all or any type of diabetes, including, but not limited to, type 1, type 2, cystic fibrosis-related, surgical, gestational diabetes, and mitochondrial diabetes. In some cases, diabetes can be a form of hereditary diabetes.

The term "endocrine cell(s)," if not particularly specified, can refer to hormone-producing cells present in the pancreas of an organism, such as "islet", "islet cells", "islet equivalent", "islet-like cells", "pancreatic islets" and their grammatical equivalents. In an embodiment, the endocrine cells can be differentiated from pancreatic progenitor cells or precursors. Islet cells can comprise different types of cells, including, but not limited to, pancreatic α cells, pancreatic β cells, pancreatic δ cells, pancreatic F cells, and/or pancreatic cells. Islet cells can also refer to a group of cells, cell clusters, or the like.

The terms "progenitor" and "precursor" cell are used interchangeably herein and refer to cells that have a cellular phenotype that is more primitive (e.g., is at an earlier step along a developmental pathway or progression than is a fully differentiated cell) relative to a cell which it can give rise to by differentiation. Often, progenitor cells can also have significant or very high proliferative potential. Progenitor cells can give rise to multiple distinct differentiated cell types or to a single differentiated cell type, depending on the developmental pathway and on the environment in which the cells develop and differentiate.

A "precursor thereof" as the term related to an insulin-positive endocrine cell can refer to any cell that is capable of differentiating into an insulin-positive endocrine cell, including for example, a pluripotent stem cell, a definitive endoderm cell, a primitive gut tube cell, a pancreatic progenitor cell, or endocrine progenitor cell, when cultured under conditions suitable for differentiating the precursor cell into the insulin-positive endocrine cell.

The term "exocrine cell" as used herein can refer to a cell of an exocrine gland, i.e. a gland that discharges its secretion via a duct. In particular embodiments, an exocrine cell can refer to a pancreatic exocrine cell, which is a pancreatic cell that can produce enzymes that are secreted into the small intestine. These enzymes can help digest food as it passes through the gastrointestinal tract. Pancreatic exocrine cells are also known as islets of Langerhans, which can secrete two hormones, insulin and glucagon. A pancreatic exocrine cell can be one of several cell types; α-2 cells (which can produce the hormone glucagon); or β cells (which can manufacture the hormone insulin); and α-1 cells (which can produce the regulatory agent somatostatin). Non-insulin-producing exocrine cells, as the term is used herein, can refer to α-2 cells or α-1 cells. The term pancreatic exocrine cells encompasses "pancreatic endocrine cells" which can refer to a pancreatic cell that produces hormones (e.g., insulin (produced from β cells), glucagon (produced by alpha-2 cells), somatostatin (produced by delta cells) and pancreatic polypeptide (produced by F cells) that are secreted into the bloodstream.

The terms "stem cell-derived β cell," "SC-β cell," "functional β cell," "functional pancreatic β cell," "mature SC-β cell," and their grammatical equivalents can refer to cells (e.g., non-native pancreatic β cells) that display at least one marker indicative of a pancreatic β cell (e.g., PDX-1 or NKX6.1), expresses insulin, and display a glucose stimulated insulin secretion (GSIS) response characteristic of an endogenous mature β cell. In some embodiments, the terms "SC-β cell" and "non-native β cell" as used herein are interchangeable. In some embodiments, the "SC-β cell" comprises a mature pancreatic cell. It is to be understood that the SC-β cells need not be derived (e.g., directly) from stem cells, as the methods of the disclosure are capable of deriving SC-β cells from any insulin-positive endocrine cell or precursor thereof using any cell as a starting point (e.g., one can use embryonic stem cells, induced-pluripotent stem cells, progenitor cells, partially reprogrammed somatic cells (e.g., a somatic cell which has been partially reprogrammed to an intermediate state between an induced pluripotent stem cell and the somatic cell from which it was derived), multipotent cells, totipotent cells, a transdifferentiated version of any of the foregoing cells, etc, as the invention is not intended to be limited in this manner). In some embodiments, the SC-β cells exhibit a response to multiple glucose challenges (e.g., at least one, at least two, or at least three or more sequential glucose challenges). In some embodiments, the response resembles the response of endogenous islets (e.g., human islets) to multiple glucose challenges. In some embodiments, the morphology of the SC-β cell resembles the morphology of an endogenous β cell. In some embodiments, the SC-β cell exhibits an in vitro GSIS response that resembles the GSIS response of an endogenous β cell. In some embodiments, the SC-β cell exhibits an in vivo GSIS response that resembles the GSIS response of an endogenous β cell. In some embodiments, the SC-β cell exhibits both an in vitro and in vivo GSIS response that resembles the GSIS response of an endogenous β cell. The GSIS response of the SC-β cell can be observed within two weeks of transplantation of the SC-β cell into a host (e.g., a human or animal). In some embodiments, the SC-β cells package insulin into secretory granules. In some embodiments, the SC-β cells exhibit encapsulated crystalline insulin granules. In some embodiments, the SC-β cells exhibit a stimulation index of greater than 1. In some embodiments, the SC-β cells exhibit a stimulation index of greater than 1.1. In some embodiments, the SC-β cells exhibit a stimulation index of greater than 2. In some embodiments, the SC-β cells exhibit cytokine-induced apoptosis in response to cytokines. In some embodiments, insulin secretion from the SC-β cells is enhanced in response to known antidiabetic drugs (e.g., secretagogues). In some embodiments, the SC-β cells are monohormonal. In some embodiments, the SC-β cells do not abnormally co-express other hormones, such as glucagon, somatostatin or pancreatic polypeptide. In some embodiments, the SC-β cells exhibit a low rate of replication. In some embodiments, the SC-β cells increase intracellular Ca2+ in response to glucose.

As used herein, the term "insulin producing cell" and its grammatical equivalent refer to a cell differentiated from a pancreatic progenitor, or precursor thereof, which secretes insulin. An insulin-producing cell can include pancreatic β cell as that term is described herein, as well as pancreatic β-like cells (e.g., insulin-positive, endocrine cells) that synthesize (e.g., transcribe the insulin gene, translate the proinsulin mRNA, and modify the proinsulin mRNA into the insulin protein), express (e.g., manifest the phenotypic trait carried by the insulin gene), or secrete (release insulin into the extracellular space) insulin in a constitutive or inducible manner. A population of insulin producing cells e.g., produced by differentiating insulin-positive, endocrine cells or a precursor thereof into SC-β cells according to the methods of the present disclosure can be pancreatic β cell or (β-like cells (e.g., cells that have at least one, or at least two least two) characteristic of an endogenous β cell and exhibit a glucose stimulated insulin secretion (GSIS) response that resembles an endogenous adult β cell. The population of insulin-producing cells, e.g. produced by the methods as disclosed herein can comprise mature pancreatic β cell or SC-β cells, and can also contain non-insulin-producing cells (e.g., cells of cell like phenotype with the exception they do not produce or secrete insulin).

The terms "insulin-positive β-like cell," "insulin-positive endocrine cell," and their grammatical equivalents can refer to cells (e.g., pancreatic endocrine cells) that displays at least one marker indicative of a pancreatic β cell and also expresses insulin but lack a glucose stimulated insulin secretion (GSIS) response characteristic of an endogenous β cell.

The term "β cell marker" refers to, without limitation, proteins, peptides, nucleic acids, polymorphism of proteins and nucleic acids, splice variants, fragments of proteins or nucleic acids, elements, and other analyte which are specifically expressed or present in pancreatic β cells. Exemplary β cell markers include, but are not limited to, pancreatic and duodenal homeobox 1 (Pdx1) polypeptide, insulin, c-peptide, amylin, E-cadherin, Hnf3β, PCI/3, B2, Nkx2.2, GLUT2, PC2, ZnT-8, ISL1, Pax6, Pax4, NeuroD, 1 Inf1b, Hnf-6, Hnf-3beta, and MafA, and those described in Zhang et al., Diabetes. 50(10):2231-6 (2001). In some embodiment, the β cell marker is a nuclear 3-cell marker. In some embodiments, the β cell marker is Pdx1 or PH3.

The term "pancreatic endocrine marker" can refer to without limitation, proteins, peptides, nucleic acids, polymorphism of proteins and nucleic acids, splice variants, fragments of proteins or nucleic acids, elements, and other analyte which are specifically expressed or present in pancreatic endocrine cells. Exemplary pancreatic endocrine cell markers include, but are not limited to, Ngn-3, NeuroD and Islet-1.

The term "pancreatic progenitor," "pancreatic endocrine progenitor," "pancreatic precursor," "pancreatic endocrine precursor" and their grammatical equivalents are used interchangeably herein and can refer to a stem cell which is capable of becoming a pancreatic hormone expressing cell capable of forming pancreatic endocrine cells, pancreatic exocrine cells or pancreatic duct cells. These cells are committed to differentiating towards at least one type of pancreatic cell, e.g. β cells that produce insulin; a cells that produce glucagon; δ cells (or D cells) that produce somatostatin; and/or F cells that produce pancreatic polypeptide. Such cells can express at least one of the following markers: NGN3, NKX2.2, NeuroD, ISL-1, Pax4, Pax6, or ARX.

The term "Pdx1-positive pancreatic progenitor" as used herein can refer to a cell which is a pancreatic endoderm (PE) cell which has the capacity to differentiate into SC-β cells, such as pancreatic β cells. A Pdx1-positive pancreatic progenitor expresses the marker Pdx1. Other markers include, but are not limited to Cdcp1, or Ptf1a, or HNF6 or NRx2.2. The expression of Pdx1 may be assessed by any method known by the skilled person such as immunochemistry using an anti-Pdx1 antibody or quantitative RT-PCR. In some cases, a Pdx1-positive pancreatic progenitor cell lacks expression of NKX6.1. In some cases, a Pdx1-positive pancreatic progenitor cell can also be referred to as Pdx1-positive, NKX6.1-negative pancreatic progenitor cell due to its lack of expression of NKX6.1. In some cases, the Pdx1-positive pancreatic progenitor cells can also be termed as "pancreatic foregut endoderm cells."

The term "Pdx1-positive, NKX6-1-positive pancreatic progenitor" as used herein can refer to a cell which is a pancreatic endoderm (PE) cell which has the capacity to differentiate into insulin-producing cells, such as pancreatic β cells. A Pdx1-positive, NKX6-1-positive pancreatic progenitor expresses the markers Pdx1 and NKX6-1. Other markers include, but are not limited to Cdcp1, or Ptf1a, or HNF6 or NRx2.2. The expression of NKX6-1 may be assessed by any method known by the skilled person such as immunochemistry using an anti-NKX6-1 antibody or quantitative RT-PCR. As used herein, the terms "NKX6.1" and "NKX6-1" are equivalent and interchangeable. In some cases, the Pdx1-positive, NKX6-1-positive pancreatic progenitor cells can also be termed as "pancreatic foregut precursor cells."

The term "Ngn3-positive endocrine progenitor" as used herein can refer to precursors of pancreatic endocrine cells expressing the transcription factor Neurogenin-3 (Ngn3). Progenitor cells are more differentiated than multipotent stem cells and can differentiate into only few cell types. In particular, Ngn3-positive endocrine progenitor cells have the ability to differentiate into the five pancreatic endocrine cell types (α, β, δ, ε and PP). The expression of Ngn3 may be assessed by any method known by the skilled person such as immunochemistry using an anti-Ngn3 antibody or quantitative RT-PCR.

The terms "NeuroD" and "NeuroD1" are used interchangeably and identify a protein expressed in pancreatic endocrine progenitor cells and the gene encoding it.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. The term "selectable marker" as used herein can refer to a gene or to an expression product of the gene, e.g., an encoded protein. In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions." To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

The term "epigenetics" refers to heritable changes in gene function that do not involve changes in the DNA sequence. Epigenetics most often denotes changes in a chromosome that affect gene activity and expression, but can also be used to describe any heritable phenotypic change that does not derive from a modification of the genome. Such effects on cellular and physiological phenotypic traits can result from external or environmental factors, or be part of normal developmental program. Epigenetics can also refer to functionally relevant changes to the genome that do not involve a change in the nucleotide sequence. Examples of mechanisms that produce such changes are DNA methylation and histone modification, each of which alters how genes are expressed without altering the underlying DNA sequence. Gene expression can be controlled through the action of repressor proteins that attach to silencer regions of the DNA. These epigenetic changes can last through cell divisions for the duration of the cell's life, and can also last for multiple generations even though they do not involve changes in the underlying DNA sequence of the organism. One example of an epigenetic change in eukaryotic biology is the process of cellular differentiation. During morphogenesis, totipotent stem cells become the various pluripotent cells, which in turn can become fully differentiated cells.

The term "epigenetic modifying compound" refers to a chemical compound that can make epigenetic changes genes, i.e., change gene expression(s) without changing DNA sequences. Epigenetic changes can help determine whether genes are turned on or off and can influence the production of proteins in certain cells, e.g., beta-cells. Epigenetic modifications, such as DNA methylation and histone modification, alter DNA accessibility and chromatin structure, thereby regulating patterns of gene expression. These processes are crucial to normal development and differentiation of distinct cell lineages in the adult organism. They can be modified by exogenous influences, and, as such, can contribute to or be the result of environmental alterations of phenotype or pathophenotype. Importantly, epigenetic modification has a crucial role in the regulation of pluripotency genes, which become inactivated during differentiation. Non-limiting exemplary epigenetic modifying compound include a DNA methylation inhibitor, a histone acetyltransferase inhibitor, a histone deacetylase inhibitor, a histone methyltransferase inhibitor, a bromodomain inhibitor, or any combination thereof.

The term "differentiated cell" or its grammatical equivalents is meant any primary cell that is not, in its native form, pluripotent as that term is defined herein. Stated another way, the term "differentiated cell" can refer to a cell of a more specialized cell type derived from a cell of a less specialized cell type (e.g., a stem cell such as an induced pluripotent stem cell) in a cellular differentiation process. Without wishing to be limited to theory, a pluripotent stem cell in the course of normal ontogeny can differentiate first to an endoderm cell that is capable of forming pancreas cells and other endoderm cell types. Further differentiation of an endoderm cell leads to the pancreatic pathway, where ~98% of the cells become exocrine, ductular, or matrix cells, and ~2% become endocrine cells. Early endocrine cells are islet progenitors, which can then differentiate further into insulin-producing cells (e.g. functional endocrine cells) which secrete insulin, glucagon, somatostatin, or pancreatic polypeptide. Endoderm cells can also be differentiate into other cells of endodermal origin, e.g. lung, liver, intestine, thymus etc.

As used herein, the term "somatic cell" can refer to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for converting at least one insulin-positive endocrine cell or precursor thereof to an insulin-producing, glucose responsive cell can be performed both in vivo and in vitro (where in vivo is practiced when at least one insulin-positive endocrine cell or precursor thereof are present within a subject, and where in vitro is practiced using an isolated at least one insulin-positive endocrine cell or precursor thereof maintained in culture).

As used herein, the term "adult cell" can refer to a cell found throughout the body after embryonic development.

The term "endoderm cell" as used herein can refer to a cell which is from one of the three primary germ cell layers in the very early embryo (the other two germ cell layers are the mesoderm and ectoderm). The endoderm is the innermost of the three layers. An endoderm cell differentiates to give rise first to the embryonic gut and then to the linings of the respiratory and digestive tracts (e.g. the intestine), the liver and the pancreas.

The term "a cell of endoderm origin" as used herein can refer to any cell which has developed or differentiated from an endoderm cell. For example, a cell of endoderm origin includes cells of the liver, lung, pancreas, thymus, intestine, stomach and thyroid. Without wishing to be bound by theory, liver and pancreas progenitors (also referred to as pancreatic progenitors) are develop from endoderm cells in the embryonic foregut. Shortly after their specification, liver and pancreas progenitors rapidly acquire markedly different cellular functions and regenerative capacities. These changes are elicited by inductive signals and genetic regulatory factors that are highly conserved among vertebrates. Interest in the development and regeneration of the organs has been fueled by the intense need for hepatocytes and pancreatic β cells in the therapeutic treatment of liver failure and type I diabetes. Studies in diverse model organisms and humans have revealed evolutionarily conserved inductive signals and transcription factor networks that elicit the differentiation of liver and pancreatic cells and provide guidance for how to promote hepatocyte and β cell differentiation from diverse stem and progenitor cell types.

The term "definitive endoderm" as used herein can refer to a cell differentiated from an endoderm cell and which can be differentiated into a SC-β cell (e.g., a pancreatic β cell). A definitive endoderm cell expresses the marker Sox17. Other markers characteristic of definitive endoderm cells include, but are not limited to MIXL2, GATA4, HNF3b, GSC, FGF17, VWF, CALCR, FOXQ1, CXCR4, Cerberus, OTX2, goosecoid, C-Kit, CD99, CMKOR1 and CRIP1. In particular, definitive endoderm cells herein express Sox17 and in some embodiments Sox17 and HNF3B, and do not express significant levels of GATA4, SPARC, APF or DAB. Definitive endoderm cells are not positive for the marker Pdx1 (e.g. they are Pdx1-negative). Definitive endoderm cells have the capacity to differentiate into cells including those of the liver, lung, pancreas, thymus, intestine, stomach and thyroid. The expression of Sox17 and other markers of definitive endoderm may be assessed by any method known by the skilled person such as immunochemistry, e.g., using an anti-Sox17 antibody, or quantitative RT-PCR.

The term "pancreatic endoderm" can refer to a cell of endoderm origin which is capable of differentiating into multiple pancreatic lineages, including pancreatic β cells, but no longer has the capacity to differentiate into non-pancreatic lineages.

The term "primitive gut tube cell" or "gut tube cell" as used herein can refer to a cell differentiated from an endoderm cell and which can be differentiated into a SC-β cell (e.g., a pancreatic β cell). A primitive gut tube cell expresses at least one of the following markers: HNP1-β, HNF3-β or HNF4-α. Primitive gut tube cells have the capacity to differentiate into cells including those of the lung, liver, pancreas, stomach, and intestine. The expression of HNF1-β and other markers of primitive gut tube may be assessed by any method known by the skilled person such as immunochemistry, e.g., using an anti-HNF1-β antibody.

The term "stem cell" as used herein, can refer to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" can refer to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retro-differentiation" by persons of ordinary skill in the art. As used herein, the term "pluripotent stem cell" includes embryonic stem cells, induced pluripotent stem cells, placental stem cells, etc.

The term "pluripotent" as used herein can refer to a cell with the capacity, under different conditions, to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g. iPS cells as that term is defined herein) also have the characteristic of the capacity of extended passaging without loss of growth potential, relative to primary cell parents, which generally have capacity for only a limited number of divisions in culture.

As used herein, the terms "iPS cell" and "induced pluripotent stem cell" are used interchangeably and can refer to a pluripotent stem cell artificially derived (e.g., induced or by complete reversal) from a non-pluripotent cell, typically an adult somatic cell, for example, by inducing a forced expression of one or more genes.

The term "phenotype" can refer to one or a number of total biological characteristics that define the cell or organism under a particular set of environmental conditions and factors, regardless of the actual genotype.

The terms "subject," "patient," or "individual" are used interchangeably herein, and can refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject can refer to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g, dog, cat, horse, and the like, or production mammal, e.g. cow, sheep, pig, and the like. "Patient in need thereof" or "subject in need thereof" is referred to herein as a patient diagnosed with or suspected of having a disease or disorder, for instance, but not restricted to diabetes.

"Administering" used herein can refer to providing one or more compositions described herein to a patient or a subject. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device. In an embodiment, a composition of the present disclosure can comprise engineered cells or host cells expressing nucleic acid sequences described herein, or a vector comprising at least one nucleic acid sequence described herein, in an amount that is effective to treat or prevent proliferative disorders. A pharmaceutical composition can comprise the cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

The terms "treat," "treating," "treatment," and their grammatical equivalents, as applied to an isolated cell, include subjecting the cell to any kind of process or condition or performing any kind of manipulation or procedure on the cell. As applied to a subject, the terms refer to providing medical or surgical attention, care, or management to an individual. The individual is usually ill or injured, or at increased risk of becoming ill relative to an average member of the population and in need of such attention, care, or management.

As used herein, the term "treating" and "treatment" can refer to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health.

The term "therapeutically effective amount", therapeutic amount", or its grammatical equivalents can refer to an amount effective, at dosages and for periods of time necessary, to achieve a desired therapeutic result. The therapeutically effective amount can vary according to factors such as the disease state, age, sex, and weight of the individual and the ability of a composition described herein to elicit a desired response in one or more subjects. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject of can be "prophylactic," e.g., the effect completely or partially prevents a disease or symptom thereof. A "prophylactically effective amount" can refer to an amount effective, at dosages and for periods of time necessary, to achieve a desired prophylactic result (e.g., prevention of disease onset).

Some numerical values disclosed throughout are referred to as, for example, "X is at least or at least about 100; or 200 [or any numerical number]." This numerical value includes the number itself and all of the following:

i) X is at least 100;
ii) X is at least 200;
iii) X is at least about 100; and
iv) X is at least about 200.

All these different combinations are contemplated by the numerical values disclosed throughout. All disclosed numerical values should be interpreted in this manner, whether it refers to an administration of a therapeutic agent or referring to days, months, years, weight, dosage amounts, etc., unless otherwise specifically indicated to the contrary.

The ranges disclosed throughout are sometimes referred to as, for example, "X is administered on or on about day 1 to 2; or 2 to 3 [or any numerical range]." This range includes the numbers themselves (e.g., the endpoints of the range) and all of the following:

i) X being administered on between day 1 and day 2;
ii) X being administered on between day 2 and day 3;
iii) X being administered on between about day 1 and day 2;
iv) X being administered on between about day 2 and day 3;
v) X being administered on between day 1 and about day 2;
vi) X being administered on between day 2 and about day 3;
vii) X being administered on between about day 1 and about day 2; and viii) X being administered on between about day 2 and about day 3.

All these different combinations are contemplated by the ranges disclosed throughout. All disclosed ranges should be interpreted in this manner, whether it refers to an administration of a therapeutic agent or referring to days, months, years, weight, dosage amounts, etc., unless otherwise specifically indicated to the contrary.

I. Overview

In aspects, the present disclosure provides compositions and methods of differentiating pancreatic progenitor cells. The compositions and methods provided herein can offer pancreatic β cells, cell populations, or cell clusters that have high purity of pancreatic β cells, high insulin content, and superior glucose-dependent insulin secretion response that can resemble native pancreatic β cells or native pancreatic islets.

In some aspects, provided herein is a method that comprises contacting a population of pancreatic progenitor cells or precursors thereof with an epigenetic modifying compound, wherein the contacting results in a population of endocrine cells with an increased proportion of chromogranin A-positive (CHGA+) cells or an increased proportion of C-peptide-positive and NKX6.1-positive (C-PEP+, NKX6.1+) cells as compared to a corresponding population of endocrine cells which is not contacted with the epigenetic modifying compound.

In some aspects, the present disclosure provides a method comprising: contacting a population of pancreatic progenitor cells or precursors thereof with an epigenetic modifying compound, wherein the contacting results in a population of endocrine cells with a reduced proportion of cells expressing VMAT or Cdx2 as compared to a corresponding population of endocrine cells which is not contacted with the epigenetic modifying compound.

In some aspects, the present disclosure provides a composition comprising a cell population, wherein the cell population comprises: (a) at least about 20% cells expressing C-peptide and NKX6.1; (b) at least about 60% cells expressing CHGA; (c) at most about 20% cells expressing Cdx2; or (d) at most about 45% cells expressing VMAT1, as measured by flow cytometry. In some cases, the composition comprises: (a) at least about 20% cells expressing C-peptide and NKX6.1;

(b) at least about 60% cells expressing CHGA; and (c) at most about 20% cells expressing Cdx2, as measured by flow cytometry. In some cases, the composition also comprises at most about 45% cells expressing VMAT1, as measured by flow cytometry. In some cases, the composition further comprises an epigenetic modifying compound.

In some aspects, the present disclosure provides a composition comprising a cell population that comprises at least about 30% ISL1-positive, NKX6.1-positive cells and at most about 20% ISL1-negative, NKX6.1-negative cells, as measured by flow cytometry. The composition of claim 34, wherein the cell population comprises at least about 35% ISL1-positive, NKX6.1-positive cells. In some cases, the cell population comprises at least about 40% ISL1-positive, NKX6.1-positive cells. In some cases, the cell population comprises at most about 15% ISL1-negative, NKX6.1-negative cells. In some cases, the composition further comprises an epigenetic modifying compound.

In some aspects, the present disclosure provides a composition that comprises a pancreatic progenitor cell, and at least one of a histone deacetylase (HDAC) inhibitor or a histone methyltransferase inhibitor. In some aspects, the present disclosure provides a method comprising: contacting a cell population comprising pancreatic progenitor cells or precursors thereof with a histone methyltransferase inhibitor and generating a cell population comprising endocrine cells; and maturing the cell population comprising endocrine cells to obtain at least one pancreatic β cell that exhibits an in vitro glucose-stimulated insulin secretion response to a glucose challenge. In some cases, the maturation step is conducted after the cell population comprising endocrine cells is implanted into a subject in vivo. In some cases, the maturation step is performed in vitro.

In some aspects, the present disclosure provides a method, comprising: (a) contacting a population of Pdx1-negative, NKX6.1-negative primitive gut tube cells with a bone morphogenetic protein (BMP) signaling pathway inhibitor and a growth factor from transformation growth factor 13 (TGF-β) superfamily, thereby generating a cell population that comprises Pdx1-positive, NKX6.1-positive pancreatic progenitor cells; and (b) contacting the cell population comprising the Pdx1-positive, NKX6.1-positive pancreatic progenitor cells with an epigenetic modifying compound and generating a cell population comprising endocrine cells.

In some cases, the methods provided herein comprise A method, comprising: (a) differentiating pluripotent stem cells in a population into definitive endoderm cells by contacting the pluripotent stem cells with a growth factor from TGF-β superfamily and a WNT signaling pathway activator; (b) differentiating at least some of the definitive endoderm cells into primitive gut tube cells by contacting the definitive endoderm cells with a growth factor from FGF family; (c) differentiating at least some of the primitive gut tube cells into Pdx1-positive pancreatic progenitor cells by contacting the primitive gut tube cells with a ROCK inhibitor, a growth factor from FGF family, a BMP signaling pathway inhibitor, a PKC activator, a retinoic acid signaling pathway activator, a SHH pathway inhibitor, and a growth factor from TGF-β superfamily; (d) differentiating at least some of the Pdx1-positive pancreatic progenitor cells into Pdx1-positive, NKX6.1-positive pancreatic progenitor cells by contacting the Pdx1-positive pancreatic progenitor cells with a ROCK inhibitor, a growth factor from TGFβ superfamily, a growth factor from FGF family, a RA signaling pathway activator, and a SHH pathway inhibitor; and (e) differentiating at least some of the Pdx1-positive, NKX6.1-positive pancreatic progenitor cells into a cell population comprising at least one NKX6.1+ and C-peptide+ cell by contacting the Pdx1-positive, NKX6.1-positive pancreatic progenitor cells with a TGF-β signaling pathway inhibitor, a growth factor from EGF family, a RA signaling pathway activator, a SHH pathway inhibitor, a TH signaling pathway activator, a γ-secretase inhibitor, a protein kinase inhibitor, a ROCK inhibitor, a BMP signaling pathway inhibitor, and an epigenetic modifying compound.

In some aspects, the present disclosure provides a method of irradiating cells to reduce proliferation. In some cases, the methods comprise exposing an in vitro cell population comprising endocrine cells to irradiation at a dose of about 100 rads to about 100,000 rads for a time period of about 1 min to about 60 min.

In some cases, the methods of reducing cell proliferation comprise exposing to irradiation a cell population comprising stem cells, definitive endoderm cells, primitive gut tube cells, pancreatic progenitor cells, or endocrine cells, wherein the irradiation results in a cell population that has reduced proliferative capability as compared to a corresponding cell population that is not subject to irradiation.

II. Method of Generating Endocrine Cells

In aspects, the present disclosure relates to compositions and methods of generating endocrine cells from pancreatic progenitor cells or precursors. Certain exemplary detailed protocols of generating endocrine cells the stem cells to provide at least one SC-β cell are described in U.S. Patent Application Publication No. US20150240212 and US20150218522, each of which is herein incorporated by reference in its entirety.

Figure 8:
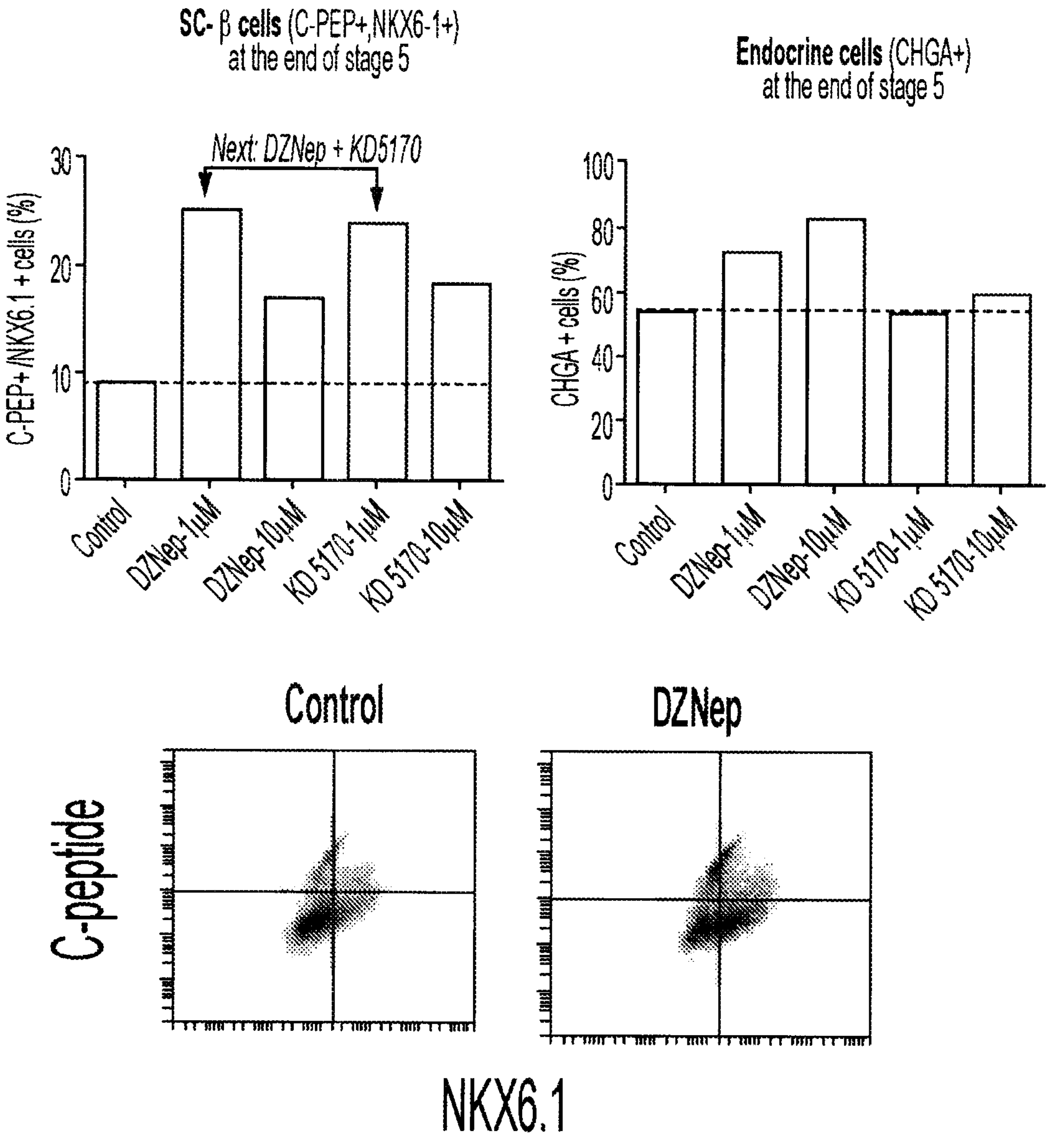
FIG. 8 shows that inhibition of EZH2 or HDAC in stage 5 increases endocrine cells and SC-β cell.

In some cases, a method for generating a first population of endocrine cells comprises contacting a population of pancreatic progenitor cells or precursors thereof with a first composition comprising at least one epigenetic modifying compound to generate the first population of endocrine cells, wherein a reduced proportion of cells of the first population of endocrine cells express $VMAT^+$ or $Cdx2^+$ as compared to a second population of endocrine cells generated using a second composition that lacks the at least one epigenetic modifying compound. In some embodiments, an epigenetic modifying compound is added at stage 5 (FIGS. 5-6), which can induce endocrine cells to shift the proportion of endocrine cells in following ways: (1) reducing an endocrine population marked by VMAT1 marker (FIG. 19) or by Cdx2; (2) increasing the proportion of cells fated to the alpha cell and other non-beta cell pancreatic islet cell fates (FIG. 20); and (3) increasing the proportion of beta cells in the composition (FIG. 8).

In some embodiments, the first population of endocrine cells is VMAT+ and INS−. In some embodiments, the population of pancreatic progenitor cells differentiate into a population of PH cells. In some embodiments, an increased proportion of cells of the first population of endocrine cells are $NKX6.1^-$ or $ChromA^+$ as compared to the second population of endocrine cells generated using the second composition that lacks the epigenetic modifying compound. In some embodiments, the increased proportion of cells is $NKX6.1^-$ and $ChromA^+$ In some embodiments, the first population of pancreatic progenitor cells differentiates into a population of β cells. In some embodiments, the β cells are stem-cell derived β (SC-β) cells. In some embodiments, the β cells express C-PEP and NKX6-1. In some embodiments, the β cells exhibit an in vitro glucose-stimulated insulin secretion response to a glucose challenge. In some embodiments, the methods described herein are performed in vitro.

In some cases, the first composition and the second composition comprise at least one of i) a SHH pathway inhibitor, ii) a RA signaling pathway activator, iii) a γ-secretase inhibitor, iv) at least one growth factor from the epidermal growth factor (EGF) family, v) a protein kinase inhibitor, vi) a BMP signaling pathway inhibitor, vii) a TGF-β signaling pathway inhibitor, viii) a thyroid hormone signaling pathway agonist, or ix) a ROCK inhibitor. In some embodiments, the first composition and the second composition comprise at least one of betacellulin, thiazovinin, retinoic acid, SANT1, XXI, Alk5i II, GC-1, LDN, staurosporine, or any combination thereof. In some cases, the first composition comprises and the second composition both comprise betacellulin, thiazovinin, retinoic acid, SANT1, XXI, Alk5i II, GC-1, LDN, and staurosporine.

Provided herein is a method of generating an endocrine cell comprising contacting a pancreatic progenitor cell or precursor thereof with a histone methyltransferase inhibitor, wherein the contacting induces the pancreatic progenitor cell to differentiate into the endocrine cell. In some cases, the histone methyltransferase inhibitor comprises DZNep. In some cases, the method further comprises contacting the pancreatic progenitor cell or precursor thereof with at least one of i) a SHH pathway inhibitor, ii) a RA signaling pathway activator, iii) a γ-secretase inhibitor, iv) at least one growth factor from the epidermal growth factor (EGF) family, v) a protein kinase inhibitor, vi) a BMP signaling pathway inhibitor, vii) a TGF-β signaling pathway inhibitor, viii) a thyroid hormone signaling pathway agonist, or ix) a ROCK inhibitor.

Provided herein is a method of generating an endocrine cell comprising contacting a pancreatic progenitor cell or precursor thereof with a histone deacetylase (HDAC) inhibitor and a histone methyltransferase inhibitor, wherein the contacting induces the pancreatic progenitor cell to differentiate into the endocrine cell. In some cases, the method further comprises contacting the pancreatic progenitor cell or precursor there of with at least one of i) a SHH pathway inhibitor, ii) a RA signaling pathway activator, iii) a γ-secretase inhibitor, iv) at least one growth factor from the epidermal growth factor (EGF) family, v) a protein kinase inhibitor, vi) a BMP signaling pathway inhibitor, vii) a TGF-β signaling pathway inhibitor, viii) a thyroid hormone signaling pathway agonist, or ix) a ROCK inhibitor.

In some embodiments, the endocrine cell differentiates into a β cell. In some embodiments, the β cell is a stem-cell derived β (SC-β) cell. In some embodiments, the β cell expresses C-PEP and NKX6-1. In some embodiments, the β cells exhibit an in vitro glucose-stimulated insulin secretion response to a glucose challenge. In some embodiments, the HDAC inhibitor is a Class I HDAC inhibitor, a Class II HDAC inhibitor, or a combination thereof.

Provided herein is a method of generating an endocrine cell comprising contacting a pancreatic progenitor cell or precursor thereof with a histone deacetylase (HDAC) inhibitor, wherein the HDAC inhibitor is KD5170. In some embodiments, the method further comprises contracting the pancreatic progenitor cell with a histone methyltransferase inhibitor. In some embodiments, the endocrine cell expresses CHGA. In some embodiments, the endocrine cell differentiates into a β cell. In some embodiments, the β cell is a stem-cell derived β (SC-β) cell. In some embodiments, the β cell expresses C-PEP and NKX6-1. In some embodiments, the β cell exhibits an in vitro glucose-stimulated insulin secretion response to a glucose challenge.

Also provided herein is a composition that comprises a population of cells and a culturing medium, wherein the cells comprise a pancreatic progenitor cell, and wherein the culturing medium comprises a histone deacetylase (HDAC) inhibitor and a histone methyltransferase inhibitor. In some embodiments, the pancreatic progenitor cell when contacted with the culturing medium is induced to differentiate into an endocrine cell.

Non-limiting exemplary epigenetic modifying compound include a DNA methylation inhibitor, a histone acetyltransferase inhibitor, a histone deacetylase inhibitor, a histone methyltransferase inhibitor, a bromodomain inhibitor, or any combination thereof.

In an embodiment, the histone methyltransferase inhibitor is an inhibitor of enhancer of zeste homolog 2 (EZH2). EZH2 is a histone-lysine N-methyltransferase enzyme. Non-limiting examples of an EZH2 inhibitor include 3-deazaneplanocin A (DZNep), EPZ6438, EPZ005687 (an S-adenosylmethionine (SAM) competitive inhibitor), EIL GSK126, and UNC1999. DZNep inhibits the hydrolysis of S-adenosyl-L-homocysteine (SAH), which is a product-based inhibitor of all protein methyltransferases, leading to increased cellular concentrations of SAH which in turn inhibits EZH2. DZNep is not specific to EZH2 and also inhibits other DNA methyltransferases. GSK126 is a SAM-competitive EZH2 inhibitor that has 150-fold selectivity over EZH1. UNC1999 is an analogue of GSK126, and it is less selective than its counterpart GSK126.

In an embodiment, the histone methyltransferase inhibitor is DZNep. In an embodiment, the HDAC inhibitor is a class I HDAC inhibitor, a class II HDAC inhibitor, or a combination thereof. In an embodiment, the HDAC inhibitor is KD5170 (mercaptoketone-based HDAC inhibitor), MC1568 (class IIa HDAC inhibitor), TMP195 (class IIa HDAC inhibitor), or any combination thereof. In some embodiments, the HDAC inhibitor is vorinostat, romidepsin (Istodax), chidamide, panobinostat (farydak), belinostat (PXD101), panobinostat (LBH589), valproic acid, mocetinostat (MGCD0103), abexinostat (PCI-24781), entinostat (MS-275), SB939, resminostat (4SC-201), givinostat (ITF2357), quisinostat (JNJ-26481585), HBI-8000, (a benzamide HDI), kevetrin, CUDC-101, AR-42, CHR-2845, CHR-3996, 4SC-202, CG200745, ACY-1215, ME-344, sulforaphane, or any variant thereof.

In some cases, the concentration of the histone methyltransferase inhibitor (e.g., DZNep) can be from or from about 0.01 to 10 μM. For example, the concentration of the histone methyltransferase inhibitor (e.g., DZNep) can be about 0.01 to 1, 0.1 to 1, 0.25 to 1, 0.5 to 1, 1 to 5; or 1 to 10 μM. The concentration of the histone methyltransferase inhibitor (e.g., DZNep) can be less than about: 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, 0.05, or 0.01 μM.

In some embodiment, the method comprises contacting the pancreatic progenitor cells or precursors with the first or second composition for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, or at least 20 days. In some embodiment, the method comprises contacting the pancreatic progenitor cells or precursors with the first or second composition for about 1 day, about 2 days, about 3 days, about 4 days, about 5 days about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days.

In some embodiments, the pancreatic progenitor cell expresses at least one of PDX1 and NKX6.1. In some embodiments, the pancreatic progenitor cell expresses both PDX1 and NKX6.1. In some embodiments, the endocrine cell expresses CHGA.

Epigenetics Modifications

Epigenetics can refer to heritable alterations that are not due to changes in DNA sequence. Rather, epigenetic modifications, such as DNA methylation and histone modification, can alter DNA accessibility and chromatin structure, thereby regulating patterns of gene expression. These processes can be crucial to normal development and differentiation of distinct cell lineages in the adult organism. They can be modified by exogenous influences, and, as such, can contribute to or be the result of environmental alterations of phenotype or pathophenotype. Importantly, epigenetic programming can have a crucial role in the regulation of pluripotency genes, which become inactivated during differentiation.

Chromatin is the complex of chromosomal DNA associated with proteins in the nucleus. DNA in chromatin is packaged around histone proteins, in units referred to as nucleosomes. A nucleosome can have 147 base-pairs of DNA associated with an octomeric core of histone proteins, consisting of two H3-H4 histone dimers surrounded by two H2A-H2B dimers. N-terminal histone tails can protrude from nucleosomes into the nuclear lumen. H1 histone can associate with the linker DNA located between the nucleosomes. Nucleosome spacing determines chromatin structure which can be broadly divided into heterochromatin and euchromatin. Chromatin structure and gene accessibility to transcriptional machinery can be regulated by modifications to both DNA and histone tails.

In differentiated mammalian cells, the principal epigenetic modification found in DNA can be that of covalent attachment of a methyl group to the C5 position of cytosine residues in CpG dinucleotide sequences (DNA methylation). In undifferentiated stem cells, cytosines, other than those in CpG, can be methylated, as well and that methylation of non-CpG cytosines can be crucial for gene regulation in embryonic stem cells in particular. CpG methylation can be, however, an important mechanism to ensure the repression of transcription of repeat elements and transposons, and also can play a crucial role in imprinting and X-chromosome inactivation. Transcriptional gene silencing by CpG methylation can also restrict the expression of some tissue-specific genes during development and differentiation by repressing them in non-expressing cells.

CpG methylation can suppress transcription by several mechanisms. The presence of the methyl group at a specific CpG may directly block DNA recognition and binding by some transcription factors. Alternatively, other factors may preferentially bind to methylated DNA, blocking transcription factor access. For example MeCP2 and other family members can bind to methyl CpG and contribute to transcriptional repression by the recruitment of histone-modifying proteins, such as histone deacetylases (HDAC). Subsequently, histone deacetylation can promote chromatin condensation, further repressing transcription. This sequence of events illustrates how DNA methylation and certain histone modifications function together to contribute to the transcriptional on or off state of genes subject to epigenetic modification.

A family of DNA methyltransferase enzymes (DNMTs) is involved in de novo DNA methylation and its maintenance. During embryogenesis, de novo methylation can be carried out by DNMT3A and DNMT3B 15. The ubiquitously expressed DNMT1 can be predominantly responsible for maintaining cellular levels of CpG methylation. DNMT1 can function in a complex to recognize hemi-methylated DNA and to add methyl groups to the non-methylated daughter strand formed during replication. The base pairing of CpG can allow for the reciprocal maintenance of methylation during subsequent replication cycles. In this manner, a non-genetic trait (DNA methylation) can be passed from cell to cell and, with it, the contextual effects on gene expression. Thus, methylation can be considered a long-term, relatively stable, epigenetic trait, the effects of which can contribute to maintaining the cellular phenotype.

DNA methylation can promote the persistence of certain histone states, such as deacetylation, thus providing a mechanism for perpetuating post-translational histone modifications. Histones can be post-translationally modified to restructure chromatin in many ways, including phosphorylation, ubiquitination, acetylation, and methylation. Of these histone modifications, histone acetylation, at the ε-amino group of lysine residues in H3 and H4 tails, can be highly consistently associated with promoting transcription. Acetylated, open-chromatin structure can also allow access of transcriptional repressors. For example, some bromodomain-containing factors, such as BRG1 and Brd4, target to acetylated histones where they can mediate the formation of repressor (or activator) complexes. Acetylation can be targeted to regions of chromatin by the recognition and binding of DNA sequence-specific transcription factors that recruit one of a growing family of histone acetyl transferase (HAT) cofactors such as CREB binding protein (CBP), and p300, MYST, and GNAT.

Deacetylation of histones can correlate with CpG methylation and the inactive state of chromatin. There are 4 classes of histone deacetylase enzymes (HDACs), with members capable of deacetylation of histones and/or other protein targets. These regulatory proteins can be themselves subject to regulation by acetylation, phosphorylation, and sumoylation, which can affect their function, subcellular distribution, and protein-protein associations. Interactions with sequence-specific DNA binding proteins and co-repressor complexes can target certain HDAC proteins to histones in a gene-specific manner.

Most histone lysine methyltransferases can have a SET homology domain, a vast family of proteins that can be grouped into 7 subfamilies based on their structural similarities. SET1 family members can specifically foster active chromatin by methylating H3K4. Other histone lysine methyltransferase families can methylate several histone targets. In addition, some of these methyl transferases can have additional domains that specify binding to methylated DNA or to other proteins, such as CBP 39. HDAC proteins can comprise a family of 18 members in humans and are separated into four classes based on their size, cellular localization, number of catalytic active sites, and homology to yeast HDAC proteins. Class I includes HDAC1, HDAC2, HDAC3, and HDAC8. Class II consists of six HDAC proteins that are further divided into two subclasses. Class IIa includes HDAC4, HDAC5, HDAC7, and HDAC9, which each contains a single catalytic active site. Class IIb includes HDAC6 and HDAC10, which both contain two active sites, although only HDAC6 has two catalytically competent active sites. HDAC11 is the sole member of class IV, based on phylogenetic analysis. Class I, II, and IV HDAC proteins can operate by a metal ion-dependent mechanism, as indicated by crystallographic analysis. In contrast, class III HDAC proteins, referred to as sirtuins (SIRT1-7), can operate by a NAD+-dependent mechanism unrelated to the other HDAC proteins. In an embodiment, HDAC inhibitors of HDAC proteins induce cell differentiation. In an embodiment, HDAC inhibitors upregulate crucial genes associated with cell differentiation.

Epigenetic Modifying Compounds

The term "epigenetic modifying compound" can refer to a chemical compound that can make epigenetic changes genes, i.e., change gene expression(s) without changing DNA sequences. Epigenetic changes can help determine whether genes are turned on or off and can influence the production of proteins in certain cells, e.g., beta-cells. Epigenetic modifications, such as DNA methylation and histone modification, can alter DNA accessibility and chromatin structure, thereby regulating patterns of gene expression. These processes can be crucial to normal development and differentiation of distinct cell lineages in the adult organism. They can be modified by exogenous influences, and, as such, can contribute to or be the result of environmental alterations of phenotype or pathophenotype. Importantly, epigenetic modification can have a crucial role in the regulation of pluripotency genes, which become inactivated during differentiation. Non-limiting exemplary epigenetic modifying compound include a DNA methylation inhibitor, a histone acetyltransferase inhibitor, a histone deacetylase inhibitor, a histone methyltransferase inhibitor, a bromodomain inhibitor, or any combination thereof.

In an embodiment, the histone methyltransferase inhibitor is an inhibitor of enhancer of zeste homolog 2 (EZH2). EZH2 is a histone-lysine N-methyltransferase enzyme. Non-limiting examples of an EZH2 inhibitor that can be used in the methods provided herein include 3-deazaneplanocin A (DZNep), EPZ6438, EPZ005687 (an S-adenosylmethionine (SAM) competitive inhibitor), EI1, GSK126, and UNC1999. DZNep can inhibit the hydrolysis of S-adenosyl-L-homocysteine (SAH), which is a product-based inhibitor of all protein methyltransferases, leading to increased cellular concentrations of SAH which in turn inhibits EZH2. DZNep may not be specific to EZH2 and can also inhibit other DNA methyltransferases. GSK126 is a SAM-competitive EZH2 inhibitor that has 150-fold selectivity over EZH1. UNC1999 is an analogue of GSK126, and it is less selective than its counterpart GSK126.

In an embodiment, the histone methyltransferase inhibitor is DZNep. In an embodiment, the HDAC inhibitor is a class I HDAC inhibitor, a class II HDAC inhibitor, or a combination thereof. In an embodiment, the HDAC inhibitor is KD5170 (mercaptoketone-based HDAC inhibitor), MC1568 (class IIa HDAC inhibitor), TMP195 (class IIa HDAC inhibitor), or any combination thereof. In some embodiments, HDAC inhibitor is vorinostat, romidepsin (Istodax), chidamide, panobinostat (farydak), belinostat (PXD101), panobinostat (LBH589), valproic acid, mocetinostat (MGCD0103), abexinostat (PCI-24781), entinostat (MS-275), SB939, resminostat (4SC-201), givinostat (ITF2357), quisinostat (JNJ-26481585), HBI-8000, (a benzamide HDI), kevetrin, CUDC-101, AR-42, CHR-2845, CHR-3996, 4SC-202, CG200745, ACY-1215, ME-344, sulforaphane, or any variant thereof.

III. Methods of Generating Pancreatic Progenitor Cells

In aspects, the present disclosure relates to compositions and methods of differentiating a primitive gut tube cell into a Pdx1-positive pancreatic β cell. In some cases, the method comprises contacting the primitive gut tube cell with a composition comprising a bone morphogenetic protein (BMP) signaling pathway inhibitor and a growth factor from transformation growth factor 13 (TGF-β) superfamily. In some cases, the composition further comprises one or more additional differentiation factors, which include, but not limited to, a growth factor from fibroblast growth factor (FGF) family, a Sonic Hedgehog (SHH) pathway inhibitor, a retinoic acid (RA) signaling pathway activator, a protein kinase C (PKC) activator, and a Rho-associated protein kinase (ROCK) inhibitor.

In some cases, a method provided herein comprises generating a population of cells or cell cluster that comprises a Pdx1-positive pancreatic progenitor cell by contacting a population of cells comprising a primitive gut tube cell with a first composition comprising a BMP signaling pathway inhibitor and a growth factor from TGF-β superfamily, wherein the primitive gut tube cell is differentiated in the Pdx1-positive, NKX6.1-positive pancreatic progenitor cell. In some cases, the contacting takes place for about 1 day, 2 days, or 3 days. In some cases, the contacting takes place about 1 day. In some cases, the primitive gut tube cell is differentiated into a Pdx1-positive, NKX6.1-negative pancreatic progenitor cell by contacting with a composition comprising BMP signaling pathway inhibitor and a growth factor from TGF-β superfamily. In some cases, the generating step further comprises differentiating the Pdx1-positive, NKX6.1-negative pancreatic progenitor cell into a Pdx1-positive, NKX6.1-positive pancreatic progenitor cell by contacting the Pdx1-positive, NKX6.1-negative pancreatic progenitor cell with a second composition comprising one or more differentiation factors, which include, but not limited to, a growth factor from TGF-β superfamily, a growth factor from FGF family, a SHH pathway inhibitor, a RA signaling pathway activator, and a ROCK inhibitor. In some cases, the second composition does not comprise BMP signaling pathway inhibitor.

In some cases, the method provided herein can obtain a population of cells or cell cluster that comprises at most about 30%, at most about 25%, at most about 20%, at most about 15%, at most about 10%, at most about 5%, at most about 4%, at most about 3%, at most about 2%, or at most about 1% CHGA-positive cells by differentiating a population of cells comprising primitive gut tube cells into a population of cells or cell cluster comprising Pdx1-positive, NKX6.1-positive pancreatic progenitor cells. In some cases, the method provided herein can obtain a population of cells or cell cluster that comprises at most about at most about 25%, at most about 20%, at most about 15%, or at most about 10% CDX2-positive cells as measured by flow cytometry by differentiating a population of cells comprising primitive gut tube cells into a population of cells or cell cluster comprising Pdx1-positive, NKX6.1-positive pancreatic progenitor cells. In some cases, the method provided herein can obtain a population of cells or cell cluster that comprises at most about 30% CHGA-positive cells and at most about 30% CDX2-positive cells by differentiating a population of cells comprising primitive gut tube cells into a population of cells or cell cluster comprising Pdx1-positive, NKX6.1-positive pancreatic progenitor cells. In some cases, the method provided herein can obtain a population of cells or cell cluster that comprises at most about 20% CHGA-positive cells and at most about 5% CDX2-positive cells by differentiating a population of cells comprising primitive gut tube cells into a population of cells or cell cluster comprising Pdx1-positive, NKX6.1-positive pancreatic progenitor cells. In some cases, the method provided herein can obtain a population of cells or cell cluster that comprises at most about 15% CHGA-positive cells and at most about 3% CDX2-positive cells by differentiating a population of cells comprising primitive gut tube cells into a population of cells or cell cluster comprising Pdx1-positive, NKX6.1-positive pancreatic progenitor cells.

In some cases, the BMP signaling pathway inhibitor provided herein comprises DMH-1, derivative, analogue, or variant thereof. In some embodiments, the BMP signaling pathway provided herein comprises DMH-1. In some embodiments, the method comprises contacting primitive gut tube cell with about 0.01 μM to about 10 μM, about 0.05 μM to about 5 μM, about 0.1 μM to about 1 μM, or about 0.15 μM to about 0.5 μM DMH-1. In some embodiments, the method comprises contacting primitive gut tube cell with about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.4, 0.42, 0.45, 0.48, 0.50, 0.55, 0.60, 0.65, 0.70, 0.75, 0.80, 0.85, 0.90, 0.95, 1, 1.2, 1.4, 1.5, 1.6, 1.7, 1.8, 2.0, 4.0, 6.0, 8.0, or 10 μM. In some embodiments, the method comprises contacting primitive gut tube cell with about 0.25 μM. In some cases, the BMP signaling pathway inhibitor as used in differentiating the primitive gut tube cell does not comprise LDN193189 (also named "LDN" herein).

In some cases, the methods provided herein comprise generating a population of cells or cell cluster that comprise a Pdx1-positive, NKX6.1-positive pancreatic progenitor cell by contacting a population of cells comprising a primitive gut tube cell with DMH-1, or derivative, analogue, or variant thereof.

Figure 15:
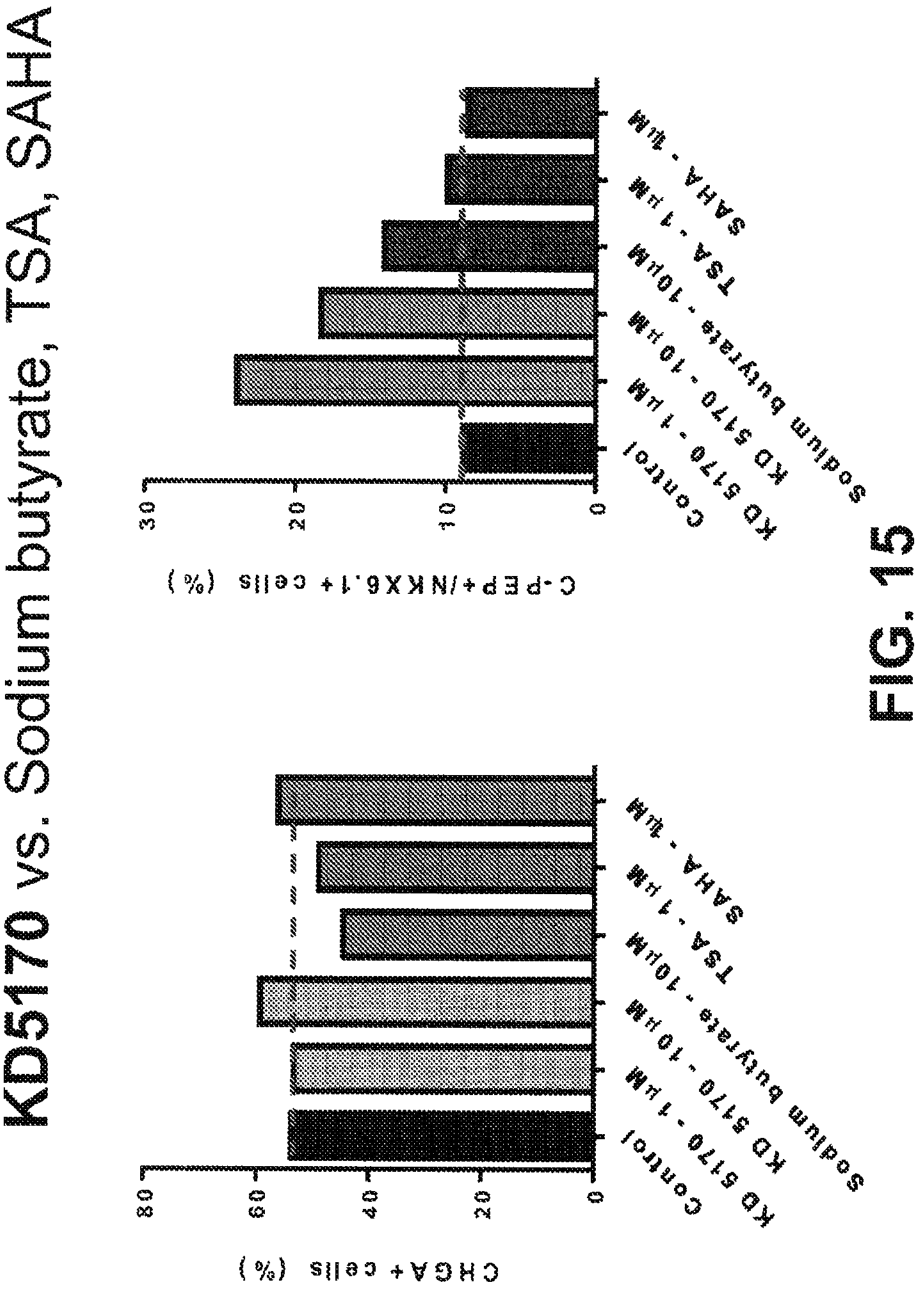
FIG. 15 shows that KD5170 outperforms other HDAC inhibitors.

Without wishing to be bound to a particular theory, in some embodiments of the methods disclosed herein, during differentiation of a primitive gut tube cell to a Pdx1-positive pancreatic progenitor cell, inhibition of BMP signaling pathway can contribute to reduction in generation of off-target cells, for instance, cells of intestine lineage or cells positive for CDX2 gene expression. On the other hand, in some cases, during differentiation of a primitive gut tube cell to a Pdx1-positive pancreatic progenitor cell or Pdx1-positive, NKX6.1-positive pancreatic progenitor cell, activation of Type II receptor-mediated TGF-β signaling pathway can contribute to reduction of early induction of neurogenin 3 (Ngn3) or chromogranin A (CHGA), which can, in some cases, lead to generation of polyhormonal cells rather than mature SC-β cells, which, in some cases, are monohormonal, e.g., secreting only insulin, but not other pancreatic hormones like somatostatin or glucagon. There can be cross-talk between BMP signaling pathway and TGF-β signaling pathway. In some cases, an inhibitor of BMP signaling pathway can have side effect, for instance, blockage of, among others, Type II receptor-mediated TGF-β signaling pathway. The inhibition of Type II receptor-mediated TGF-β signaling pathway, as illustrated in FIG. 15, for instance by a relatively less selective BMP signaling pathway inhibitor, LDN193189, can lead to early NGN3/CHGA induction, thereby generation of polyhormonal cells. Without wishing to be bound by a certain theory, in some cases, use of a highly selective BMP signaling pathway inhibitor, for instance, DMH-1 or its derivate, analogue, or variant, can have less inhibitory effect on Type II receptor-mediated TGF-β signaling pathway. In some other cases, without wishing to be bound to a particular theory, co-incubation with a growth factor from TGF-β superfamily together with a BMP signaling pathway inhibitor can result in selective inhibition of BMP signaling pathway, while maintaining relatively high activation level of Type II receptor-mediated TGF-β signaling pathway. In some cases, co-incubation with a growth factor from TGF-β superfamily together with a BMP signaling pathway inhibitor result in reduced generation of off-target cells, e.g., CDX2-positive cells, as well as reduced generation of polyhormonal cells, for instance, as a result of early induction of NGN3 or CHGA in the cells differentiated from the primitive gut tube cells.

In some aspects, the present disclosure provides a method of producing a NKX6 positive pancreatic progenitor cell from a Pdx1-positive pancreatic progenitor cell comprising contacting a population of cells comprising Pdx1-positive pancreatic progenitor cells or precursors under conditions that promote cell clustering with at least two β cell-maturation factors comprising a) at least one growth factor from the fibroblast growth factor (FGF) family, b) a sonic hedgehog pathway inhibitor, and optionally c) a low concentration of a retinoic acid (RA) signaling pathway activator, for a period of at least five days to induce the differentiation of at least one Pdx1-positive pancreatic progenitor cell in the population into NKX6-1-positive pancreatic progenitor cells, wherein the NKX6-1-positive pancreatic progenitor cells express NKX6-1.

In some embodiments, at least 10% of the Pdx1-positive pancreatic progenitor cells in the population are induced to differentiate into NKX6-1-positive pancreatic progenitor cells. In some embodiments, at least 95% of the Pdx1-positive pancreatic progenitor cells in the population are induced to differentiate into NKX6-1-positive pancreatic progenitor cells. In some embodiments, the NKX6-1-positive pancreatic progenitor cells express Pdx1, NKX6-1, and FoxA2. In some embodiments, the Pdx1-positive pancreatic progenitor cells are produced from a population of pluripotent stem cells selected from the group consisting of embryonic stem cells and induced pluripotent stem cells.

IV. Stem Cells and Reprogramming

Provided herein is use of stem cells for producing SC-β cells (e.g., mature pancreatic β cells or (3-like cells) or precursors thereof. In an embodiment, germ cells may be used in place of, or with, the stem cells to provide at least one SC-β cell, using similar protocols as described in U.S. Patent Application Publication No. US20150240212 and US20150218522, each of which is herein incorporated by reference in its entirety. Suitable germ cells can be prepared, for example, from primordial germ cells present in human fetal material taken about 8-11 weeks after the last menstrual period. Illustrative germ cell preparation methods are described, for example, in Shamblott et al., Proc. Natl. Acad. Sci. USA 95:13726, 1998 and U.S. Pat. No. 6,090,622.

Provided herein are compositions and methods of generating SC-β cells (e.g., pancreatic β cells). Generally, the at least one SC-β cell or precursor thereof, e.g., pancreatic progenitors produced according to the methods disclosed herein can comprise a mixture or combination of different cells, e.g., for example a mixture of cells such as primitive gut tube cells, Pdx1-positive pancreatic progenitors, Pdx1-positive, NKX6-1-positive pancreatic progenitors, Ngn3-positive endocrine progenitor cells, insulin-positive endocrine cell (e.g., (3-like cells), and/or other pluripotent or stem cells.

The at least one SC-β cell or precursor thereof can be produced according to any suitable culturing protocol to differentiate a stem cell or pluripotent cell to a desired stage of differentiation. In some embodiments, the at least one SC-β cell or the precursor thereof are produced by culturing at least one pluripotent cell for a period of time and under conditions suitable for the at least one pluripotent cell to differentiate into the at least one SC-β cell or the precursor thereof.

In some embodiments, the at least one SC-β cell or precursor thereof is a substantially pure population of SC-β cells or precursors thereof. In some embodiments, a population of SC-β cells or precursors thereof comprises a mixture of pluripotent cells or differentiated cells. In some embodiments, a population SC-β cells or precursors thereof are substantially free or devoid of embryonic stem cells or pluripotent cells or iPS cells.

In some embodiments, a somatic cell, e.g., fibroblast can be isolated from a subject, for example as a tissue biopsy, such as, for example, a skin biopsy, and reprogrammed into an induced pluripotent stem cell for further differentiation to produce the at least one SC-β cell or precursor thereof for use in the compositions and methods described herein. In some embodiments, a somatic cell, e.g., fibroblast is maintained in culture by methods known by one of ordinary skill in the art, and in some embodiments, propagated prior to being converted into SC-β cells by the methods as disclosed herein.

In some embodiments, the at least one SC-β cell or precursor thereof are maintained in culture by methods known by one of ordinary skills in the art, and in some embodiments, propagated prior to being converted into SC-β cells by the methods as disclosed herein.

Further, at least one SC-β cell or precursor thereof, e.g., pancreatic progenitor can be from any mammalian species, with non-limiting examples including a murine, bovine, simian, porcine, equine, ovine, or human cell. For clarity and simplicity, the description of the methods herein refers to a mammalian at least one SC-β cell or precursor thereof but it should be understood that all of the methods described herein can be readily applied to other cell types of at least one SC-β cell or precursor thereof. In some embodiments, the at least one SC-β cell or precursor thereof is derived from a human individual.

Stem Cells

Embodiments of the present disclosure can related to use of stem cells for generation of pancreatic β cells or precursors thereof. The term "stem cell" as used herein can refer to a cell (e.g., plant stem cell, vertebrate stem cell) that has the ability both to self-renew and to generate a differentiated cell type (Morrison et al., (1997) Cell 88:287-298). In the context of cell ontogeny, the adjective "differentiated", or "differentiating" is a relative term. A "differentiated cell" can be a cell that has progressed further down the developmental pathway than the cell it is being compared with. Thus, pluripotent stem cells can differentiate into lineage-restricted progenitor cells (e.g., mesodermal stem cells), which in turn can differentiate into cells that are further restricted (e.g., neuron progenitors), which can differentiate into end-stage cells (e.g., terminally differentiated cells, e.g., neurons, cardiomyocytes, etc.), which play a characteristic role in a certain tissue type, and can or cannot retain the capacity to proliferate further. Stem cells can be characterized by both the presence of specific markers (e.g., proteins, RNAs, etc.) and the absence of specific markers. Stem cells can also be identified by functional assays both in vitro and in vivo, particularly assays relating to the ability of stem cells to give rise to multiple differentiated progeny. In an embodiment, the host cell is an adult stem cell, a somatic stem cell, a non-embryonic stem cell, an embryonic stem cell, hematopoietic stem cell, an include pluripotent stem cells, and a trophoblast stem cell.

Stem cells of interest, e.g., that can be used in the method provided herein, can include pluripotent stem cells (PSCs). The term "pluripotent stem cell" or "PSC" as used herein can refer to a stem cell capable of producing all cell types of the organism. Therefore, a PSC can give rise to cells of all germ layers of the organism (e.g., the endoderm, mesoderm, and ectoderm of a vertebrate). Pluripotent cells can be capable of forming teratomas and of contributing to ectoderm, mesoderm, or endoderm tissues in a living organism. Pluripotent stem cells of plants can be capable of giving rise to all cell types of the plant (e.g., cells of the root, stem, leaves, etc.).

Embodiments of the present disclosure can related to use of PSCs for generation of pancreatic β cells or precursors thereof. PSCs of animals can be derived in a number of different ways. For example, embryonic stem cells (ESCs) can be derived from the inner cell mass of an embryo (Thomson et. al, Science. 1998 Nov. 6; 282(5391):1145-7) whereas induced pluripotent stem cells (iPSCs) can be derived from somatic cells (Takahashi et. al, Cell. 2007 Nov.

30; 131(5):861-72; Takahashi et. al, Nat Protoc. 2007; 2(12):3081-9; Yu et. al, Science. 2007 Dec. 21; 318(5858): 1917-20. Epub 2007 Nov. 20). Because the term PSC can refer to pluripotent stem cells regardless of their derivation, the term PSC can encompass the terms ESC and iPSC, as well as the term embryonic germ stem cells (EGSC), which are another example of a PSC. PSCs can be in the form of an established cell line, they can be obtained directly from primary embryonic tissue, or they can be derived from a somatic cell.

Embodiments of the present disclosure can related to use of ESCs for generation of pancreatic β cells or precursors thereof. By "embryonic stem cell" (ESC) can be meant a PSC that is isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells can be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs can grow as flat colonies with large nucleo-cytoplasmic ratios, defined borders and prominent nucleoli. In addition, ESCs can express SSEA-3, SSEA-4, TRA-1-60, TRA-1-81, and Alkaline Phosphatase, but not SSEA-1. Examples of methods of generating and characterizing ESCs can be found in, for example, U.S. Pat. Nos. 7,029,913, 5,843,780, and 6,200,806, each of which is incorporated herein by its entirety. Methods for proliferating hESCs in the undifferentiated form are described in WO 99/20741, WO 01/51616, and WO 03/020920, each of which is incorporated herein by its entirety.

By "embryonic germ stem cell" (EGSC) or "embryonic germ cell" or "EG cell", it can be meant a PSC that is derived from germ cells and/or germ cell progenitors, e.g. primordial germ cells, e.g. those that can become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, each of which are incorporated herein by its entirety.

Embodiments of the present disclosure can related to use of iPSCs for generation of pancreatic β cells or precursors thereof. By "induced pluripotent stem cell" or "iPSC", it can be meant a PSC that is derived from a cell that is not a PSC (e.g., from a cell this is differentiated relative to a PSC). iPSCs can be derived from multiple different cell types, including terminally differentiated cells. iPSCs can have an ES cell-like morphology, growing as flat colonies with large nucleo-cytoplasmic ratios, defined borders and prominent nuclei. In addition, iPSCs can express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs can be found in, for example, U.S. Patent Publication Nos. US20090047263, US20090068742, US20090191159, US20090227032, US20090246875, and US20090304646, each of which are incorporated herein by its entirety. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

Embodiments of the present disclosure can related to use of somatic cells for generation of pancreatic β cells or precursors thereof. By "somatic cell", it can be meant any cell in an organism that, in the absence of experimental manipulation, does not ordinarily give rise to all types of cells in an organism. In other words, somatic cells can be cells that have differentiated sufficiently that they may not naturally generate cells of all three germ layers of the body, e.g. ectoderm, mesoderm and endoderm. For example, somatic cells can include both neurons and neural progenitors, the latter of which is able to naturally give rise to all or some cell types of the central nervous system but cannot give rise to cells of the mesoderm or endoderm lineages In certain examples, the stem cells can be undifferentiated (e.g. a cell not committed to a specific lineage) prior to exposure to at least one differentiation factor or composition according to the methods as disclosed herein, whereas in other examples it can be desirable to differentiate the stem cells to one or more intermediate cell types prior to exposure of the at least one differentiation factor or composition described herein. For example, the stems cells can display morphological, biological or physical characteristics of undifferentiated cells that can be used to distinguish them from differentiated cells of embryo or adult origin. In some examples, undifferentiated cells can appear in the two dimensions of a microscopic view in colonies of cells with high nuclear/cytoplasmic ratios and prominent nucleoli. The stem cells can be themselves (for example, without substantially any undifferentiated cells being present) or can be used in the presence of differentiated cells. In certain examples, the stem cells can be cultured in the presence of) suitable nutrients and optionally other cells such that the stem cells can grow and optionally differentiate. For example, embryonic fibroblasts or fibroblast-like cells can be present in the culture to assist in the growth of the stem cells. The fibroblast can be present during one stage of stem cell growth but not necessarily at all stages. For example, the fibroblast can be added to stem cell cultures in a first culturing stage and not added to the stem cell cultures in one or more subsequent culturing stages.

Stem cells used in all aspects of the present invention can be any cells derived from any kind of tissue (for example embryonic tissue such as fetal or pre-fetal tissue, or adult tissue), which stem cells can have the characteristic of being capable under appropriate conditions of producing progeny of different cell types, e.g. derivatives of all of at least one of the 3 germinal layers (endoderm, mesoderm, and ectoderm). These cell types can be provided in the form of an established cell line, or they can be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, FISF-6 (University of California at San Francisco); and H1, H7, H9, H13, H14 (Wisconsin Alumni Research Foundation (WiCell Research Institute)). In some embodiments, the source of human stem cells or pluripotent stem cells used for chemically-induced differentiation into mature, insulin positive cells did not involve destroying a human embryo. In some embodiments, the source of human stem cells or pluripotent stem cells used for chemically-induced differentiation into mature, insulin positive cells do not involve destroying a human embryo.

In another example, the stem cells can be isolated from tissue including solid tissue. In some embodiments, the tissue is skin, fat tissue (e.g. adipose tissue), muscle tissue, heart or cardiac tissue. In other embodiments, the tissue is for example but not limited to, umbilical cord blood, placenta, bone marrow, or chondral.

Stem cells that can be used in the methods provided herein can also include embryonic cells of various types, exemplified by human embryonic stem (hES) cells, as described by Thomson et al, (1998) Science 282:1145; embryonic stem cells from other primates, such as Rhesus stem cells (Thomson et al. (1995) Proc. Natl. Acad. Sci. USA 92:7844); marmoset stem cells (Thomson et al. (1996) Biol. Reprod. 55:254); and human embryonic germ (hEG) cells (Shambloft et al., Proc. Natl. Acad. Sci. USA 95:13726, 1998). Also applicable to the methods provided herein can be lineage committed stem cells, such as mesodermal stem cells and other early cardiogenic cells (see Reyes et al, (2001) Blood 98:2615-2625; Eisenberg & Bader (1996) Circ Res. 78(2):205-16; etc.) The stem cells can be obtained from any mammalian species, e.g. human, equine, bovine, porcine, canine, feline, rodent, e.g. mice, rats, hamster, primate, etc. In some embodiments, a human embryo was not destroyed for the source of pluripotent cell used on the methods and compositions as disclosed herein. In some embodiments, a human embryo is not destroyed for the source of pluripotent cell used on the methods and compositions as disclosed herein.

A mixture of cells from a suitable source of endothelial, muscle, and/or neural stem cells can be harvested from a mammalian donor for the purpose of the present disclosure. A suitable source is the hematopoietic microenvironment. For example, circulating peripheral blood, preferably mobilized (e.g., recruited), may be removed from a subject. In an embodiment, the stem cells can be reprogrammed stem cells, such as stem cells derived from somatic or differentiated cells. In such an embodiment, the de-differentiated stem cells can be for example, but not limited to, neoplastic cells, tumor cells and cancer cells or alternatively induced reprogrammed cells such as induced pluripotent stem cells or iPS cells.

In some embodiments, the pancreatic β cell as described herein can be derived from one or more of trichocytes, keratinocytes, gonadotropes, corticotropes, thyrotropes, somatotropes, lactotrophs, chromaffin cells, parafollicular cells, *glomus* cells melanocytes, nevus cells, Merkel cells, odontoblasts, cementoblasts corneal keratocytes, retina Muller cells, retinal pigment epithelium cells, neurons, glias (e.g., oligodendrocyte astrocytes), ependymocytes, pinealocytes, pneumocytes (e.g., type I pneumocytes, and type II pneumocytes), clara cells, goblet cells, G cells, D cells, ECL cells, gastric chief cells, parietal cells, foveolar cells, K cells, D cells, I cells, goblet cells, paneth cells, enterocytes, microfold cells, hepatocytes, hepatic stellate cells (e.g., Kupffer cells from mesoderm), cholecystocytes, centroacinar cells, pancreatic stellate cells, pancreatic α cells, pancreatic β cells, pancreatic δ cells, pancreatic F cells (e.g., PP cells), pancreatic ε cells, thyroid (e.g., follicular cells), parathyroid (e.g., parathyroid chief cells), oxyphil cells, urothelial cells, osteoblasts, osteocytes, chondroblasts, chondrocytes, fibroblasts, fibrocytes, myoblasts, myocytes, myosatellite cells, tendon cells, cardiac muscle cells, lipoblasts, adipocytes, interstitial cells of cajal, angioblasts, endothelial cells, mesangial cells (e.g., intraglomerular mesangial cells and extraglomerular mesangial cells), juxtaglomerular cells, macula *densa* cells, stromal cells, interstitial cells, telocytes simple epithelial cells, podocytes, kidney proximal tubule brush border cells, sertoli cells, leydig cells, granulosa cells, peg cells, germ cells, spermatozoon ovums, lymphocytes, myeloid cells, endothelial progenitor cells, endothelial stem cells, angioblasts, mesoangioblasts, pericyte mural cells, splenocytes (e.g., T lymphocytes, B lymphocytes, dendritic cells, microphages, leukocytes), trophoblast stem cells, or any combination thereof.

Reprogramming

The term "reprogramming" as used herein can refer to the process that alters or reverses the differentiation state of a somatic cell. The cell can either be partially or terminally differentiated prior to the reprogramming. Reprogramming can encompass complete reversion of the differentiation state of a somatic cell to a pluripotent cell. Such complete reversal of differentiation can produce an induced pluripotent (iPS) cell. Reprogramming as used herein can also encompass partial reversion of a cells differentiation state, for example to a multipotent state or to a somatic cell that is neither pluripotent or multipotent, but is a cell that has lost one or more specific characteristics of the differentiated cell from which it arises, e.g. direct reprogramming of a differentiated cell to a different somatic cell type. Reprogramming can involve alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

As used herein, the term "reprogramming factor" can refer to a molecule that is associated with cell "reprogramming," that is, differentiation, and/or de-differentiation, and/or transdifferentiation, such that a cell converts to a different cell type or phenotype. Reprogramming factors generally affect expression of genes associated with cell differentiation, de-differentiation and/or transdifferentiation. Transcription factors are examples of reprogramming factors.

The term "differentiation" and their grammatical equivalents as used herein can refer to the process by which a less specialized cell (e.g., a more naive cell with a higher cell potency) becomes a more specialized cell type (e.g., a less naive cell with a lower cell potency); and that the term "de-differentiation" can refer to the process by which a more specialized cell becomes a less specialized cell type (e.g., a more naive cell with a higher cell potency); and that the term "transdifferentiation" refers to the process by which a cell of a particular cell type converts to another cell type without significantly changing its "cell potency" or "naivety" level. Without wishing to be bound by theory, it is thought that cells "transdifferentiate" when they convert from one lineage-committed cell type or terminally differentiated cell type to another lineage-committed cell type or terminally differentiated cell type, without significantly changing their "cell potency" or "naivety" level.

As used herein, the term "cell potency" is to be understood as referring to the ability of a cell to differentiate into cells of different lineages. For example, a pluripotent cell (e.g., a stem cell) has the potential to differentiate into cells of any of the three germ layers, that is, endoderm (interior stomach lining, gastrointestinal tract, the lungs), mesoderm (muscle, bone, blood, urogenital), or ectoderm (epidermal tissues and nervous system), and accordingly has high cell potency; a multipotent cell (e.g., a stem cell or an induced stem cell of a certain type) has the ability to give rise to cells from a multiple, but limited, number of lineages (such as hematopoietic stem cells, cardiac stem cells, or neural stem cells, etc) comparatively has a lower cell potency than pluripotent cells. Cells that are committed to a particular lineage or are terminally differentiated can have yet a lower cell potency. Specific examples of transdifferentiation known in the art include the conversion of e.g., fibroblasts beta cells or from pancreatic exocrine cells to beta cells etc.

Accordingly, the cell may be caused to differentiate into a more naive cell (e.g., a terminally differentiated cell may be differentiated to be multipotent or pluripotent); or the cell may be caused to de-differentiate into a less naive cell (e.g., a multipotent or pluripotent cell can be differentiated into a lineage-committed cell or a terminally differentiated cell). However, in an embodiment, the cell may be caused to convert or transdifferentiate from one cell type (or phenotype) to another cell type (or phenotype), for example, with a similar cell potency level. Accordingly, in an embodiment of the present disclosure, the inducing steps of the present disclosure can reprogram the cells of the present disclosure to differentiate, de-differentiate and/or transdifferentiate. In an embodiment of the present disclosure, the inducing steps of the present disclosure may reprogram the cells to transdifferentiate.

Methods of reprogramming or inducing a particular type of cell to become another type of cell, for example, by differentiation, de-differentiation and/or transdifferentiation using one or more exogenous polynucleotide or polypeptide reprogramming factors are known to the person skilled in the art. Such methods may rely on the introduction of genetic material encoding one or more transcription factor(s) or other polypeptide(s) associated with cell reprogramming. For example, Pdx1, Ngn3 and MafA, or functional fragments thereof are all known to encode peptides that can induce cell differentiation, de-differentiation and/or transdifferentiation of the cells of the present disclosure. In some methods known to the person skilled in the art, exogenous polypeptides (e.g. recombinant polypeptides) encoded by reprogramming genes (such as the above genes) are contacted with the cells to induce, for example, cells of the present disclosure. The person skilled in the art will appreciate that other genes may be associated with reprogramming of cells, and exogenous molecules encoding such genes (or functional fragments thereof) and the encoded polypeptides are also considered to be polynucleotide or polypeptide reprogramming factors (e.g. polynucleotides or polypeptides that in turn affect expression levels of another gene associated with cell reprogramming). For example, it has been shown that the introduction of exogenous polynucleotide or polypeptide epigenetic gene silencers that decrease p53 inactivation increase the efficiency of inducing induced pluripotent stem cells (iPSC). Accordingly, exogenous polynucleotides or polypeptides encoding epigenetic silencers and other genes or proteins that may be directly or indirectly involved in cell reprogramming or increasing cell programming efficiency would be considered to constitute an exogenous polynucleotide or polypeptide reprogramming factor. The person skilled in the art will appreciate that other methods of influencing cell reprogramming exist, such as introducing RNAi molecules (or genetic material encoding RNAi molecules) that can knock down expression of genes involved in inhibiting cell reprogramming. Accordingly, any exogenous polynucleotide molecule or polypeptide molecule that is associated with cell reprogramming, or enhances cell reprogramming, is to be understood to be an exogenous polynucleotide or polypeptide reprogramming factor as described herein.

In some embodiments of the present disclosure, the method excludes the use of reprogramming factor(s) that are not small molecules. However, it will be appreciated that the method can utilize "routine" tissue culture components such as culture media, serum, serum substitutes, supplements, antibiotics, etc, such as RPMI, Renal Epithelial Basal Medium (REBM), Dulbecco's Modified Eagle Medium (DMEM), MCDB131 medium, CMRL 1066 medium, F12, foetal calf serum (FCS), foetal bovine serum (FBS), bovine serum albumin (BSA), D-glucose, L-glutamine, GlutaMAX™-1 (dipeptide, L-alanine-L-glutamine), B27, heparin, progesterone, putrescine, laminin, nicotinamide, insulin, transferrin, sodium selenite, selenium, ethanolamine, human epidermal growth factor (hEGF), basic fibroblast growth factor (bFGF), hydrocortisone, epinephrine, normacin, penicillin, streptomycin, gentamicin and amphotericin, etc. It is to be understood that these typical tissue culture components (and other similar tissue culture components that are routinely used in tissue culture) are not small molecule reprogramming molecules for the purposes of the present disclosure. These components are either not small molecules as defined herein and/or are not reprogramming factors as defined herein.

Accordingly, in an embodiment, the present disclosure does not involve a culturing step of the cell(s) with one or more exogenous polynucleotide or polypeptide reprogramming factor(s). Accordingly, in an embodiment, the method of the present disclosure does not involve the introduction of one or more exogenous polynucleotide or polypeptide reprogramming factor(s), e.g., by introducing transposons, viral transgenic vectors (such as retroviral vectors), plasmids, mRNA, miRNA, peptides, or fragments of any of these molecules, that are involved in producing induced β cells or, otherwise, inducing cells of the present disclosure to differentiate, de-differentiation and/or transdifferentiate.

That is, in an embodiment, the method occurs in the absence of one or more exogenous polynucleotide or polypeptide reprogramming factor(s). Accordingly, it is to be understood that in an embodiment, the method of the present disclosure utilizes small molecules (e.g., HDAC inhibitors) to reprogram cells, without the addition of polypeptide transcription factors; other polypeptide factors specifically associated with inducing differentiation, de-differentiation, and/or transdifferentiation; polynucleotide sequences encoding polypeptide transcription factors, polynucleotide sequences encoding other polypeptide factors specifically associated with inducing differentiation, de-differentiation, and/or transdifferentiation; mRNA; interference RNA; microRNA and fragments thereof.

V. Xeno-Free Culture Medium

In aspects, the present disclosure relates to a method of generating pancreatic β cells, e.g., SC-β cells, which comprises differentiating progenitor cells (e.g., stem cells like iPSC cells, definitive endoderm cells, primitive gut tube cells, Pdx1-positive pancreatic progenitor cells, NKX6.1-positive pancreatic progenitor cells, or insulin-positive endocrine cells) in a xeno-free culture medium. A xeno-free medium for culturing cells and/or cell clusters of originated from an animal can have no product from other animals. In some cases, a xeno-free medium for culturing human cells and/or cell clusters can have no products from any non-human animals. For example, a xeno-free medium for culturing human cells and/or cell clusters can comprise human serum albumin (HSA) or human platelet lysate (PLT) instead of fetal bovine serum (FBS) or bovine serum albumin (BSA).

In some embodiments, a method provided herein comprises generating pancreatic 13 cells, e.g., SC-β cells, by differentiating progenitor cells (e.g., stem cells like iPSC cells, definitive endoderm cells, primitive gut tube cells, Pdx1-positive pancreatic progenitor cells, NKX6.1-positive pancreatic progenitor cells, or insulin-positive endocrine cells) in a culture medium lacking serum albumin. In some cases, a population of cells or cell cluster comprising pancreatic β cells generated by a method provided herein that does not use serum albumin or uses HSA in the culture medium can have significant improvement as compared to a population of cells or cell cluster comprising pancreatic β cells generated by an otherwise identical method but using BSA instead. The improvement can include higher percentage of pancreatic β cells in the final cell population obtained, higher GSIS responses (e.g., more insulin release in response to glucose challenge), higher GSIS stimulation index, more homogeneity of distribution of pancreatic β cells in the cell cluster generated, or any combination thereof.

In some embodiments, a method provided herein comprises differentiating a population of cells comprising a stem cell, e.g., a hES cell or iPS cell, in a culture medium comprising human serum albumin (HSA). In some cases, the stem cell is differentiated into a definitive endoderm cell. In some embodiments, a method provided herein comprises differentiating a population of cells comprising a definitive endoderm cell in a culture medium comprising human serum albumin (HSA). In some cases, the definitive endoderm cell is differentiated into a primitive gut tube cell. In some embodiments, a method provided herein comprises differentiating a population of cells comprising a primitive gut tube cell in a culture medium comprising human serum albumin (HSA). In some cases, the primitive gut tube cell is differentiated into a Pdx1-positive pancreatic progenitor cell (e.g., Pdx1-positive, NKX6.1-negative pancreatic progenitor cell or Pdx1-positive, NKX6.1-positive pancreatic progenitor cell). In some embodiments, a method provided herein comprises differentiating a population of cells comprising a Pdx1-positive, NKX6.1-negative pancreatic progenitor cell in a culture medium comprising human serum albumin (HSA). In some case, the Pdx1-positive, NKX6.1-negative pancreatic progenitor cell is differentiated into a Pdx1-positive, NKX6.1-positive pancreatic progenitor cell. In some embodiments, a method provided herein comprises differentiating a population of cells comprising a Pdx1-positive, NKX6.1-positive pancreatic progenitor cell in a culture medium comprising human serum albumin (HSA). In some cases, the Pdx1-positive, NKX6.1-positive pancreatic progenitor cell is differentiated into an insulin-positive endocrine cell. In some embodiments, a method provided herein comprises differentiating a population of cells comprising an insulin-positive endocrine cell in a culture medium comprising human serum albumin (HSA). In some cases, the insulin-positive endocrine cell is differentiated into a pancreatic β cell, e.g., SC-β cell.

In some embodiments, the methods provided herein comprise use of culture medium comprising about 0.001% (w/v) to about 5% (w/v), about 0.005% (w/v) to about 4% (w/v), about 0.01% (w/v) to about 3% (w/v), about 0.02% (w/v) to about 2.5% (w/v), about 0.03% (w/v) to about 2% (w/v), about 0.04% (w/v) to about 1% (w/v), about 0.045% (w/v) to about 0.5% (w/v), or about 0.05% (w/v) to about 0.1% (w/v) HSA. In some embodiments, the methods provided herein comprise use of culture medium comprising about 0.001%, 0.002%, 0.0025%, 0.005%, 0.0075%, 0.01%, 0.0125%, 0.015%, 0.0175%, 0.02%, 0.0225%, 0.025%, 0.0275%, 0.03%, 0.0325%, 0.035%, 0.0375%, 0.04%, 0.0425%, 0.045%, 0.0475%, 0.05%, 0.0525%, 0.055%, 0.575%, 0.06%, 0.0625%, 0.065%, 0.0675%, 0.07%, 0.0725%, 0.075%, 0.0775%, 0.08%, 0.085%, 0.09%, 0.1%, 0.12%, 0.15%, 0.2%, 0.25%, 0.3%, 0.4%, 0.5%, 0.6%, 0.7%, 0.8%, 0.9%, 1%, 1.5%, 2%, 2.5%, 3%, or 4%, 5% (w/v) HSA. The term "w/v" is short for percentage of weight/volume or weight per volume. For instance, 1 mg HSA in 100 mL culture medium has a concentration of 1% (w/v).

In some cases, the method provided herein can obtain a population of cells or cell cluster that comprises at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, or at least about 95% Pdx1-positive cells by differentiating a population of cells comprising primitive gut tube cells into a population of cells or cell cluster comprising Pdx1-positive, NKX6.1-negative pancreatic progenitor cells. In some cases, the method provided herein can obtain a population of cells or cell cluster that comprises at most about 60%, at most about 50%, at most about 40%, at most about 35%, at most about 30%, at most about 25%, at most about 22%, at most about 20%, at most about 18%, at most about 15%, at most about 14%, at most about 13%, at most about 11%, at most about 12%, at most about 10%, or at most about 5% CDX2-positive cells by differentiating a population of cells comprising primitive gut tube cells into a population of cells or cell cluster comprising Pdx1-positive, NKX6.1-negative pancreatic progenitor cells.

VI. Method of Generating Stem Cell Derived Beta Cells

Provided herein are methods of generating SC-β cells (e.g., pancreatic β cells). The detailed protocols of generating endocrine cells the stem cells to provide at least one SC-β cell are described in U.S. Patent Application Publication No. US20150240212 and US20150218522, each of which is herein incorporated by reference in its entirety.

The endoderm can give rise to digestive and respiratory tracts, thyroid, liver, and pancreas. Representative disease of endoderm lineages is type 1 diabetes resulting from destruction of the insulin-producing β cells. Generation of functional β cells from human pluripotent stem cells (hPSC) in vitro can be practical, renewable cell source for replacement cell therapy for type 1 diabetes. The embryotic stem (ES) cells that are generated from the inner cell mass of blastocyst-stage embryos represent a promising source of cells for transplantation or cell-based therapy of any damaged cells. They can be maintained in culture, renew for themselves, and proliferate unlimitedly as undifferentiated ES cells. The ES cells are capable of differentiating into all cell types of the body as the ectoderm, mesoderm, and endoderm lineage cells or tissues. The major benefit of ES cells is stable self-renewal in culture and the potential to differentiate.

The definitive endoderm can be generated in vivo from the inner cell mass by the process of gastrulation of embryogenesis, in which epiblast cells are instructed to form the three germ layers. Definitive endoderm can give rise to diverse cells and tissues that contribute to vital organs as the pancreatic β cells, liver hepatocytes, lung alveolar cells, thyroid, thymus, and the epithelial lining of the alimentary and respiratory tract. It is different from the primitive endoderm of extraembryonic tissues, which can give rise to the visceral and parietal endoderm. The definitive endoderm derived from ES cells is theoretically capable of becoming any endoderm derivatives, and directing ES cells into the endoderm lineage is a prerequisite for generating therapeutic endoderm derivatives.

Precise patterning of anterior-posterior axis of the definitive endoderm can eventually form the primitive gut tube. The definitive endoderm-derived primitive gut tube induces the pharynx, esophagus, stomach, duodenum, small and large intestine along the anterior-posterior axis as well as associated organs, including pancreas, lung, thyroid, thymus, parathyroid, and liver. The anterior portion of the foregut of the primitive gut tube becomes lung, thyroid, esophagus, and stomach. The pancreas, liver, and duodenum originate from the posterior portion of the foregut. The midgut and hindgut of primitive gut tube gives rise to the small and large intestine. The anterior foregut expresses developmental markers, NK2 homeobox 1 (NKX2-1) and SRY (sex determining region Y)-box 2 (SOX2); the posterior foregut expresses hematopoietically expressed homeobox (HHEX), pancreatic and duodenal homeobox 1 (PDX1), one cut homeobox 1 (ONECUT1, known as HNF6), and hepatocyte nuclear factor 4 alpha (HNF4A); and the midgut/hindgut expresses caudal type homeobox 1 (CDX1), caudal type homeobox 2 (CDX2), and motor neuron and pancreas homeobox 1 (MNX1) (3, 19, 20).

The successful differentiation to pancreatic β cells should require that differentiated cells synthesize and secrete physiologically appropriate amounts of insulin. An exemplary stepwise protocol directing hPSC cell differentiation is developed, which entails differentiation processes that recapitulates the major stages of normal pancreatic endocrine development (FIG. 5). The differentiation of hPSC cells to hormone-expressing pancreatic endocrine cells is conducted by transiting hPSC cells through major stages of embryonic development; differentiation to mesendoderm and definitive endoderm, establishment of the primitive gut endoderm, patterning of the posterior foregut, and specification and maturation of pancreatic endoderm and endocrine precursors. Through these stages, hPSC cells can obtain pancreatic endocrine phenotype and ability of glucose responsive insulin secretion in vitro.

Generally, the at least one SC-β cell or precursor thereof, e.g., pancreatic progenitors produced according to the methods disclosed herein can comprise a mixture or combination of different cells, e.g., for example a mixture of cells such as a Pdx1-positive pancreatic progenitors, pancreatic progenitors co-expressing Pdx1 and NKX6-1, a Ngn3-positive endocrine progenitor cell, an insulin-positive endocrine cell (e.g., a (3-like cell), and an insulin-positive endocrine cell, and/or other pluripotent or stem cells.

The at least one SC-β cell or precursor thereof can be produced according to any suitable culturing protocol to differentiate a stem cell or pluripotent cell to a desired stage of differentiation. In some embodiments, the at least one SC-β cell or the precursor thereof are produced by culturing at least one pluripotent cell for a period of time and under conditions suitable for the at least one pluripotent cell to differentiate into the at least one SC-β cell or the precursor thereof.

In some embodiments, the at least one SC-β cell or precursor thereof is a substantially pure population of SC-β cells or precursors thereof. In some embodiments, a population of SC-β cells or precursors thereof comprises a mixture of pluripotent cells or differentiated cells. In some embodiments, a population SC-β cells or precursors thereof are substantially free or devoid of embryonic stem cells or pluripotent cells or iPS cells.

In some embodiments, a somatic cell, e.g., fibroblast can be isolated from a subject, for example as a tissue biopsy, such as, for example, a skin biopsy, and reprogrammed into an induced pluripotent stem cell for further differentiation to produce the at least one SC-β cell or precursor thereof for use in the compositions and methods described herein. In some embodiments, a somatic cell, e.g., fibroblast is maintained in culture by methods known by one of ordinary skill in the art, and in some embodiments, propagated prior to being converted into SC-β cells by the methods as disclosed herein.

In some embodiments, the at least one SC-β cell or precursor thereof are maintained in culture by methods known by one of ordinary skill in the art, and in some embodiments, propagated prior to being converted into SC-β cells by the methods as disclosed herein.

Further, at least one SC-β cell or precursor thereof, e.g., pancreatic progenitor can be from any mammalian species, with non-limiting examples including a murine, bovine, simian, porcine, equine, ovine, or human cell. For clarity and simplicity, the description of the methods herein refers to a mammalian at least one SC-β cell or precursor thereof but it should be understood that all of the methods described herein can be readily applied to other cell types of at least one SC-β cell or precursor thereof. In some embodiments, the at least one SC-β cell or precursor thereof is derived from a human individual.

Provided herein is a method for generating a stem cell-derived β (SC-β) cell comprising contacting a cell population comprising pancreatic progenitor cells or precursors thereof with a histone deacetylase (HDAC) inhibitor to generate the SC-β cell, wherein the cell population is derived in vitro from stem cells. In some embodiments, the stem cells are human pluripotent stem cells. In some embodiments, the method further comprises contacting the cell population with at least one of betacellulin, thiazovinin, retinoic acid, SANT1, XXI, Alk5i II, GC-1, LDN, staurosporine, or any combination thereof. In some embodiments, the SC-β cell expresses C-PEP and NKX6-1. In some embodiments, the SC-β cell exhibits an in vitro glucose-stimulated insulin secretion response to a glucose challenge. In some embodiments, the method further comprises contracting the cell population with a histone methyltransferase inhibitor.

Provided herein is a method for generating a stem cell-derived β (SC-β) cell comprising contacting a cell population comprising pancreatic progenitor cells or precursors thereof with a histone methyltransferase inhibitor to generate the SC-β cell, wherein the cell population is derived in vitro from stem cells, and wherein the SC-β cell exhibits an in vitro glucose-stimulated insulin secretion response to a glucose challenge. In some embodiments, the stem cells are human pluripotent stem cells. In some embodiments, the method further comprises contacting the cell population with at least one of betacellulin, thiazovinin, retinoic acid, SANT1, XXI, Alk5i II, GC-1, LDN, staurosporine, or any combination thereof. In some embodiments, the method further comprises contacting the cell population with a histone deacetylase (HDAC) inhibitor.

Non-limiting exemplary epigenetic modifying compound include a DNA methylation inhibitor, a histone acetyltransferase inhibitor, a histone deacetylase inhibitor, a histone methyltransferase inhibitor, a bromodomain inhibitor, or any combination thereof.

In an embodiment, the histone methyltransferase inhibitor is an inhibitor of enhancer of zeste homolog 2 (EZH2). EZH2 is a histone-lysine N-methyltransferase enzyme. Non-limiting examples of an EZH2 inhibitor include 3-deazaneplanocin A (DZNep), EPZ6438, EPZ005687 (an S-adenosylmethionine (SAM) competitive inhibitor), EIL GSK126, and UNC1999. DZNep inhibits the hydrolysis of S-adenosyl-L-homocysteine (SAH), which is a product-based inhibitor of all protein methyltransferases, leading to increased cellular concentrations of SAH which in turn inhibits EZH2. DZNep is not specific to EZH2 and also inhibits other DNA methyltransferases. GSK126 is a SAM-competitive EZH2 inhibitor that has 150-fold selectivity over EZH1. UNC1999 is an analogue of GSK126, and it is less selective than its counterpart GSK126.

In an embodiment, the histone methyltransferase inhibitor is DZNep. In an embodiment, the HDAC inhibitor is a class I HDAC inhibitor, a class II HDAC inhibitor, or a combination thereof. In an embodiment, the histone methyltransferase inhibitor is KD5170 (mercaptoketone-based HDAC inhibitor), MC1568 (class IIa HDAC inhibitor), TMP195 (class IIa HDAC inhibitor), or any combination thereof. In some embodiments, HDAC inhibitor is vorinostat, romidepsin (Istodax), chidamide, panobinostat (farydak), belinostat (PXD101), panobinostat (LBH589), valproic acid, mocetinostat (MGCD0103), abexinostat (PCI-24781), entinostat (MS-275), SB939, resminostat (4SC-201), givinostat (ITF2357), quisinostat (JNJ-26481585), HBI-8000, (a benzamide HDI), kevetrin, CUDC-101, AR-42, CHR-2845, CHR-3996, 4SC-202, CG200745, ACY-1215, ME-344, sulforaphane, or any variant thereof.

In some cases, the concentration of the histone methyltransferase inhibitor (e.g., DZNep) can be from or from about 0.01 to 10 μM. For example, the concentration of the histone methyltransferase inhibitor (e.g., DZNep) can be about 0.01 to 1, 0.1 to 1, 0.25 to 1, 0.5 to 1, 1 to 5; or 1 to 10 μM. The concentration of the histone methyltransferase inhibitor (e.g., DZNep) can be less than about: 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, 0.05, or 0.01 μM.

Aspects of the disclosure involve definitive endoderm cells. Definitive endoderm cells of use herein can be derived from any source or generated in accordance with any suitable protocol. In some aspects, pluripotent stem cells, e.g., iPSCs or hESCs, are differentiated to endoderm cells. In some aspects, the endoderm cells (stage 1) are further differentiated, e.g., to primitive gut tube cells (stage 2), Pdx1-positive pancreatic progenitor cells (stage 3), NKX6.1-positive pancreatic progenitor cells (stage 4), or Ngn3-positive endocrine progenitor cells or insulin-positive endocrine cells (stage 5), followed by induction or maturation to SC-β cells (stage 6).

In some cases, definitive endoderm cells can be obtained by differentiating at least some pluripotent cells in a population into definitive endoderm cells, e.g., by contacting a population of pluripotent cells with i) at least one growth factor from the TGF-β superfamily, and ii) a WNT signaling pathway activator, to induce the differentiation of at least some of the pluripotent cells into definitive endoderm cells, wherein the definitive endoderm cells express at least one marker characteristic of definitive endoderm.

Any growth factor from the TGF-β superfamily capable of inducing the pluripotent stem cells to differentiate into definitive endoderm cells (e.g., alone, or in combination with a WNT signaling pathway activator) can be used in the method provided herein. In some cases, the growth factor from the TGF-β superfamily comprises Activin A. In some cases, the growth factor from the TGF-β superfamily comprises growth differentiating factor 8 (GDF8). Any WNT signaling pathway activator capable of inducing the pluripotent stem cells to differentiate into definitive endoderm cells (e.g., alone, or in combination with a growth factor from the TGF-β superfamily) can be used in the method provided herein. In some cases, the WNT signaling pathway activator comprises CHIR99Q21. In some cases, the WNT signaling pathway activator comprises Wnt3a recombinant protein.

In some cases, differentiating at least some pluripotent cells in a population into definitive endoderm cells is achieved by a process of contacting a population of pluripotent cells with i) Activin A, and ii) CHIR99021 for a suitable period of time, e.g., about 2 days, about 3 days, about 4 days, or about 5 days to induce the differentiation of at least some of the pluripotent cells in the population into definitive endoderm cells, wherein the definitive endoderm cells express at least one marker characteristic of definitive endoderm.

In some examples, the method comprises differentiating pluripotent cells into definitive endoderm cells by contacting a population of pluripotent cells with a suitable concentration of the growth factor from the TGF-β superfamily (e.g., Activin A), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL. In some cases, the method comprises use of about 100 ng/mL Activin A for differentiation of pluripotent cells into definitive endoderm cells. In some cases, the method comprises use of about 200 ng/mL Activin A for differentiation of pluripotent cells into definitive endoderm cells.

In some examples, the method comprises differentiating pluripotent cells into definitive endoderm cells by contacting a population of pluripotent cells with a suitable concentration of the WNT signaling pathway activator (e.g., CHIR99021), such as, about 0.01 μM, about 0.05 μM, about 0.1 μM, about 0.2 μM, about 0.5 μM, about 0.8 μM, about 1 μM, about 1.5 μM, about 2 μM, about 2.5 μM, about 3 μM, about 3.5 μM, about 4 μM, about 5 μM, about 8 μM, about 10 μM, about 12 μM, about 15 μM, about 20 μM, about 30 μM, about 50 μM, about 100 μM, or about 200 μM. In some cases, the method comprises use of about 2 μM CHIR99021 for differentiation of pluripotent cells into definitive endoderm cells. In some cases, the method comprises use of about 5 μM CHIR99021 for differentiation of pluripotent cells into definitive endoderm cells.

In some cases, a definitive endoderm cell produced by the methods as disclosed herein expresses at least one marker selected from the group consisting of: Nodal, Tmprss2, Tmem30b, St14, Spink3, Sh3gl2, Ripk4, Rab1S, Npnt, Clic6, Cldn5, Cacna1b, Bnip1, Anxa4, Emb, FoxA1, Sox17, and Rbm35a, wherein the expression of at least one marker is unregulated to by a statistically significant amount in the definitive endoderm cell relative to the pluripotent stem cell from which it was derived. In some cases, a definitive endoderm cell produced by the methods as disclosed herein does not express by a statistically significant amount at least one marker selected the group consisting of: Gata4, SPARC, AFP and Dab2 relative to the pluripotent stem cell from which it was derived. In some cases, a definitive endoderm cell produced by the methods as disclosed herein does not express by a statistically significant amount at least one marker selected the group consisting of: Zic1, Pax6, Flk1 and CD31 relative to the pluripotent stem cell from which it was derived. In some cases, a definitive endoderm cell produced by the methods as disclosed herein has a higher level of phosphorylation of Smad2 by a statistically significant amount relative to the pluripotent stem cell from which it was derived. In some cases, a definitive endoderm cell produced by the methods as disclosed herein has the capacity to form gut tube in vivo. In some cases, a definitive endoderm cell produced by the methods as disclosed herein can differentiate into a cell with morphology characteristic of a gut cell, and wherein a cell with morphology characteristic of a gut cell expresses FoxA2 and/or Claudin6, In some cases, a definitive endoderm cell produced by the methods as disclosed herein can be further differentiated into a cell of endoderm origin.

In some cases, a population of pluripotent stem cells are cultured in the presence of at least one β cell differentiation factor prior to any differentiation or during the first stage of differentiation. One can use any pluripotent stem cell, such as a human pluripotent stem cell, or a human iPS cell or any of pluripotent stem cell as discussed herein or other suitable pluripotent stem cells. In some cases, a β cell differentiation factor as described herein can be present in the culture medium of a population of pluripotent stem cells or may be added in bolus or periodically during growth (e.g. replication or propagation) of the population of pluripotent stem cells. In certain examples, a population of pluripotent stem cells can be exposed to at least one β cell differentiation factor prior to any differentiation. In other examples, a population of pluripotent stem cells may be exposed to at least one β cell differentiation factor during the first stage of differentiation.

Aspects of the disclosure involve primitive gut tube cells. Primitive gut tube cells of use herein can be derived from any source or generated in accordance with any suitable protocol. In some aspects, definitive endoderm cells are differentiated to primitive gut tube cells. In some aspects, the primitive gut tube cells are further differentiated, e.g., to Pdx1-positive pancreatic progenitor cells, NKX6.1-positive pancreatic progenitor cells, Ngn3-positive endocrine progenitor cells, insulin-positive endocrine cells, followed by induction or maturation to SC-β cells.

In some cases, primitive gut tube cells can be obtained by differentiating at least some definitive endoderm cells in a population into primitive gut tube cells, e.g., by contacting definitive endoderm cells with at least one growth factor from the fibroblast growth factor (FGF) family, to induce the differentiation of at least some of the definitive endoderm cells into primitive gut tube cells, wherein the primitive gut tube cells express at least one marker characteristic of primitive gut tube cells.

Any growth factor from the FGF family capable of inducing definitive endoderm cells to differentiate into primitive gut tube cells (e.g., alone, or in combination with other factors) can be used in the method provided herein. In some cases, the at least one growth factor from the FGF family comprises keratinocyte growth factor (KGF). In some cases, the at least one growth factor from the FGF family comprises FGF2. In some cases, the at least one growth factor from the FGF family comprises FGF8B. In some cases, the at least one growth factor from the FGF family comprises FGF 10. In some cases, the at least one growth factor from the FGF family comprises FGF21.

In some cases, primitive gut tube cells can be obtained by differentiating at least some definitive endoderm cells in a population into primitive gut tube cells, e.g., by contacting definitive endoderm cells with KGF for a certain period of time, e.g., about 1 day, about 2 days, about 3 days, or about 4 days, to induce the differentiation of at least some of the definitive endoderm cells into primitive gut tube cells.

In some cases, the method comprises differentiating definitive endoderm cells into primitive gut tube cells by contacting definitive endoderm cells with a suitable concentration of the growth factor from the FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL. In some cases, the method comprises use of about 50 ng/mL KGF for differentiation of definitive endoderm cells into primitive gut tube cells. In some cases, the method comprises use of about 100 ng/mL KGF for differentiation of definitive endoderm cells into primitive gut tube cells.

Aspects of the disclosure involve Pdx1-positive pancreatic progenitor cells. Pdx1-positive pancreatic progenitor cells of use herein can be derived from any source or generated in accordance with any suitable protocol. In some aspects, primitive gut tube cells are differentiated to Pdx1-positive pancreatic progenitor cells. In some aspects, the Pdx1-positive pancreatic progenitor cells are further differentiated, e.g., NKX6.1-positive pancreatic progenitor cells, Ngn3-positive endocrine progenitor cells, insulin-positive endocrine cells, followed by induction or maturation to SC-β cells, In some aspects, Pdx1-positive pancreatic progenitor cells can be obtained by differentiating at least some primitive gut tube cells in a population into Pdx1-positive pancreatic progenitor cells, e.g., by contacting primitive gut tube cells with i) at least one BMP signaling pathway inhibitor, ii) a growth factor from TGF-β superfamily, iii) at least one growth factor from the FGF family, iv) at least one SHH pathway inhibitor, v) at least one retinoic acid (RA) signaling pathway activator; vi) at least one protein kinase C activator, and vii) ROCK inhibitor to induce the differentiation of at least some of the primitive gut tube cells into Pdx1-positive pancreatic progenitor cells, wherein the Pdx1-positive pancreatic progenitor cells express Pdx1.

In some aspects, Pdx1-positive pancreatic progenitor cells can be obtained by differentiating at least some primitive gut tube cells in a population into Pdx1-positive pancreatic progenitor cells, e.g., by contacting primitive gut tube cells with i) at least one BMP signaling pathway inhibitor, ii) a growth factor from TGF-β superfamily, iii) at least one growth factor from the FGF family, iv) at least one SHH pathway inhibitor, v) at least one retinoic acid (RA) signaling pathway activator; and vi) at least one protein kinase C activator, to induce the differentiation of at least some of the primitive gut tube cells into Pdx1-positive pancreatic progenitor cells, wherein the Pdx1-positive pancreatic progenitor cells express Pdx1.

In some cases, Pdx1-positive pancreatic progenitor cells can be obtained by differentiating at least some primitive gut tube cells in a population into Pdx1-positive pancreatic progenitor cells, e.g., by contacting primitive gut tube cells with i) at least one BMP signaling pathway inhibitor, ii) at least one growth factor from the FGF family, iii) at least one SHH pathway inhibitor, iv) at least one retinoic acid (RA) signaling pathway activator; and v) at least one protein kinase C activator, to induce the differentiation of at least some of the primitive gut tube cells into Pdx1-positive pancreatic progenitor cells, wherein the Pdx1-positive pancreatic progenitor cells express Pdx1.

In some cases, Pdx1-positive pancreatic progenitor cells can be obtained by differentiating at least some primitive gut tube cells in a population into Pdx1-positive pancreatic progenitor cells, e.g., by contacting primitive gut tube cells with i) at least one SHH pathway inhibitor, ii) at least one retinoic acid (RA) signaling pathway activator; and iii) at least one protein kinase C activator, wherein the Pdx1-positive pancreatic progenitor cells express Pdx1.

In some cases, Pdx1-positive pancreatic progenitor cells can be obtained by differentiating at least some primitive gut tube cells in a population into Pdx1-positive pancreatic progenitor cells, e.g., by contacting primitive gut tube cells with i) at least one growth factor from the FGF family, and ii) at least one retinoic acid (RA) signaling pathway activator, to induce the differentiation of at least some of the primitive gut tube cells into Pdx1-positive pancreatic progenitor cells, wherein the Pdx1-positive pancreatic progenitor cells express Pdx1.

Any BMP signaling pathway inhibitor capable of inducing primitive gut tube cells to differentiate into Pdx1-positive pancreatic progenitor cells (e.g., alone, or with any combination of a growth factor from TGF-β superfamily, at least one growth factor from the FGF family, at least one SHH pathway inhibitor, at least one retinoic acid signaling pathway activator, at least one protein kinase C activator, and ROCK inhibitor) can be used in the method provided herein. In some cases, the BMP signaling pathway inhibitor comprises LDN193189 or DMH-1. In some examples, the method comprises contacting primitive gut tube cells with a concentration of BMP signaling pathway inhibitor (e.g., LDN1931189), such as, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 280 nM, about 300 nM, about 400 nM, about 500 nM, or about 1 μM. In some examples, the method comprises contacting primitive gut tube cells with a concentration of BMP signaling pathway inhibitor (e.g., DMH-1), such as, about 0.01 μM, about 0.02 μM, about 0.05 μM, about 0.1 μM, about 0.2 μM, about 0.5 μM, about 0.8 μM, about 1 μM, about 1.2 μM, about 1.5 μM, about 1.75 μM, about 2 μM, about 2.2 μM, about 2.5 μM, about 2.75 μM, about 3 μM, about 3.25 μM, about 3.5 μM, about 3.75 μM, about 4 μM, about 4.5 μM, about 5 μM, about 8 μM, about 10 μM, about 15 μM, about 20 μM, about 30 μM, about 40 μM, about 50 μM, or about 100 μM.

Any growth factor from the TGF-β superfamily capable of inducing primitive gut tube cells to differentiate into Pdx1-positive pancreatic progenitor cells (e.g., alone, or with any combination of at least one BMP signaling pathway inhibitor, a growth factor from the FGF family, at least one SHH pathway inhibitor, at least one retinoic acid signaling pathway activator, at least one protein kinase C activator, and ROCK inhibitor) can be used. In some cases, the growth factor from TGF-β family comprises Activin A. In some cases, the growth factor from TGF-β family comprises Activin A or GDF8. In some examples, the method comprises contacting primitive gut tube cells with a concentration of a growth factor from TGF-13 superfamily (e.g., Activin A), such as, about 5 ng/mL, about 7.5 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, about 21 ng/mL, about 22 ng/mL, about 23 ng/mL, about 24 ng/mL, about 25 ng/mL, about 26 ng/mL, about 27 ng/mL, about 28 ng/mL, about 29 ng/mL, about 30 ng/mL, about 35 ng/mL, about 40 ng/mL, about 50 ng/mL, or about 100 ng/mL.

Any growth factor from the FGF family capable of inducing primitive gut tube cells to differentiate into Pdx1-positive pancreatic progenitor cells (e.g., alone, or with any combination of at least one BMP signaling pathway inhibitor, a growth factor from TGF-β superfamily, at least one SHH pathway inhibitor, at least one retinoic acid signaling pathway activator, at least one protein kinase C activator, and ROCK inhibitor) can be used. In some cases, the at least one growth factor from the FGF family comprises keratinocyte growth factor (KGF). In some cases, the at least one growth factor from the FGF family is selected from the group consisting of FGF2, FGF8B, FGF 10, and FGF21. In some examples, the method comprises contacting primitive gut tube cells with a concentration of a growth factor from FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL.

Any SHH pathway inhibitor capable of inducing primitive gut tube cells to differentiate into Pdx1-positive pancreatic progenitor cells (e.g., alone, or with any combination of at least one BMP signaling pathway inhibitor, at least one growth factor from the FGF family, a growth factor from TGF-β superfamily, at least one retinoic acid signaling pathway activator, at least one protein kinase C activator, and ROCK inhibitor) can be used. In some cases, the SHH pathway inhibitor comprises Sant1. In some examples, the method comprises contacting primitive gut tube cells with a concentration of a SHH pathway inhibitor (e.g., Sant1), such as, about 0.001 μM, about 0.002 μM, about 0.005 μM, about 0.01 μM, about 0.02 μM, about 0.03 μM, about 0.05 μM, about 0.08 μM, about 0.1 μM, about 0.12 μM, about 0.13 μM, about 0.14 μM, about 0.15 μM, about 0.16 μM, about 0.17 μM, about 0.18 μM, about 0.19 μM, about 0.2 μM, about 0.21 μM, about 0.22 μM, about 0.23 μM, about 0.24 μM, about 0.25 μM, about 0.26 μM, about 0.27 μM, about 0.28 μM, about 0.29 μM, about 0.3 μM, about 0.31 μM, about 0.32 μM, about 0.33 μM, about 0.34 μM, about 0.35 μM, about 0.4 μM, about 0.45 μM, about 0.5 μM, about 0.6 μM, about 0.8 μM, about 1 μM, about 2 μM, or about 5 μM.

Any RA signaling pathway activator capable of inducing primitive gut tube cells to differentiate into Pdx1-positive pancreatic progenitor cells (e.g., alone, or with any combination of at least one BMP signaling pathway inhibitor, at least one growth factor from the FGF family, at least one SHH pathway inhibitor, at least one protein kinase C activator, and ROCK inhibitor) can be used. In some cases, the RA signaling pathway activator comprises retinoic acid. In some examples, the method comprises contacting primitive gut tube cells with a concentration of an RA signaling pathway activator (e.g., retinoic acid), such as, about 0.02 μM, about 0.1 μM, about 0.2 μM, about 0.25 μM, about 0.3 μM, about 0.4 μM, about 0.45 μM, about 0.5 μM, about 0.55 μM, about 0.6 μM, about 0.65 μM, about 0.7 μM, about 0.75 μM, about 0.8 μM, about 0.85 μM, about 0.9 μM, about 1

μM, about 1.1 μM, about 1.2 μM, about 1.3 μM, about 1.4 μM, about 1.5 μM, about 1.6 μM, about 1.7 μM, about 1.8 μM, about 1.9 μM, about 2 μM, about 2.1 μM, about 2.2 μM, about 2.3 μM, about 2.4 μM, about 2.5 μM, about 2.6 μM, about 2.7 μM, about 2.8 μM, about 3 μM, about 3.2 μM, about 3.4 μM, about 3.6 μM, about 3.8 μM, about 4 μM, about 4.2 μM, about 4.4 μM, about 4.6 μM, about 4.8 μM, about 5 μM, about 5.5 μM, about 6 μM, about 6.5 μM, about 7 μM, about 7.5 μM, about 8 μM, about 8.5 μM, about 9 μM, about 9.5 μM, about 10 μM, about 12 μM, about 14 μM, about 15 μM, about 16 μM, about 18 μM, about 20 μM, about 50 μM, or about 100 μM.

Any PKC activator capable of inducing primitive gut tube cells to differentiate into Pdx1-positive pancreatic progenitor cells (e.g., alone, or with any combination of at least one BMP signaling pathway inhibitor, at least one growth factor from the FGF family, at least one SHH pathway inhibitor, at least one RA signaling pathway activator, and ROCK inhibitor) can be used. In some cases, the PKC activator comprises PdBU. In some cases, the PKC activator comprises TPB. In some examples, the method comprises contacting primitive gut tube cells with a concentration of a PKC activator (e.g., PdBU), such as, about 10 μM, about 20 μM, about 50 μM, about 75 μM, about 80 μM, about 100 μM, about 120 μM, about 140 μM, about 150 μM, about 175 μM, about 180 μM, about 200 μM, about 210 μM, about 220 μM, about 240 μM, about 250 μM, about 260 μM, about 280 μM, about 300 μM, about 320 μM, about 340 μM, about 360 μM, about 380 μM, about 400 μM, about 420 μM, about 440 μM, about 460 μM, about 480 μM, about 500 μM, about 520 μM, about 540 μM, about 560 μM, about 580 μM, about 600 μM, about 620 μM, about 640 μM, about 660 μM, about 680 μM, about 700 μM, about 750 μM, about 800 μM, about 850 μM, about 900 μM, about 1 mM, about 2 mM, about 3 mM, about 4 mM, or about 5 mM.

Any ROCK inhibitor capable of inducing primitive gut tube cells to differentiate into Pdx1-positive pancreatic progenitor cells (e.g., alone, or with any combination of at least one BMP signaling pathway inhibitor, at least one growth factor from the FGF family, at least one SHH pathway inhibitor, PKC activator, and at least one RA signaling pathway activator) can be used. In some cases, the ROCK inhibitor comprises Thiazovivin, Y-27632, Fasudil/HA1077, or H-1152. In some cases, the ROCK inhibitor comprises Y-27632. In some cases, the ROCK inhibitor comprises Thiazovivin. In some examples, the method comprises contacting primitive gut tube cells with a concentration of a ROCK inhibitor (e.g., Y-27632 or Thiazovivin), such as, about 0.2 μM, about 0.5 μM, about 0.75 μM, about 1 μM, about 2 μM, about 3 μM, about 4 μM, about 5 μM, about 6 μM, about 7 μM, about 7.5 μM, about 8 μM, about 9 μM, about 10 μM, about 11 μM, about 12 μM, about 13 μM, about 14 μM, about 15 μM, about 16 μM, about 17 μM, about 18 μM, about 19 μM, about 20 μM, about 21 μM, about 22 μM, about 23 μM, about 24 μM, about 25 μM, about 26 μM, about 27 μM, about 28 μM, about 29 μM, about 30 μM, about 35 μM, about 40 μM, about 50 μM, or about 100 μM.

In some cases, Pdx1-positive pancreatic progenitor cells can be obtained by differentiating at least some primitive gut tube cells in a population into Pdx1-positive pancreatic progenitor cells, e.g., by contacting primitive gut tube cells with retinoic acid, KGF, Sant1, LDN193189, PdBU, Y-27632, and Activin A, for a suitable period of time, e.g., about 1 day, about 2 days, about 3 days, or about 4 days. In some cases, Pdx1-positive pancreatic progenitor cells can be obtained by differentiating at least some primitive gut tube cells in a population into Pdx1-positive pancreatic progenitor cells, e.g., by contacting primitive gut tube cells with retinoic acid, KGF, Sant1, LDN193189, PdBU, Y-27632, and Activin A, for about 2 days. In some cases, Pdx1-positive pancreatic progenitor cells can be obtained by differentiating at least some primitive gut tube cells in S3 medium.

Aspects of the disclosure involve NKX6.1-positive pancreatic progenitor cells. NKX6.1-positive pancreatic progenitor cells of use herein can be derived from any source or generated in accordance with any suitable protocol. In some aspects, Pdx1-positive pancreatic progenitor cells are differentiated to NKX6.1-positive pancreatic progenitor cells. In some aspects, the NKX6.1-positive pancreatic progenitor cells are further differentiated, e.g., to Ngn3-positive endocrine progenitor cells, or insulin-positive endocrine cells, followed by induction or maturation to SC-β cells.

In some aspects, a method of producing a NKX6.1-positive pancreatic progenitor cell from a Pdx1-positive pancreatic progenitor cell comprises contacting a population of cells (e.g., under conditions that promote cell clustering and/or promoting cell survival) comprising Pdx1-positive pancreatic progenitor cells with at least two β cell-differentiation factors comprising a) at least one growth factor from the fibroblast growth factor (FGF) family, b) a sonic hedgehog pathway inhibitor, and optionally c) a low concentration of a retinoic acid (RA) signaling pathway activator, to induce the differentiation of at least one Pdx1-positive pancreatic progenitor cell in the population into NKX6.1-positive pancreatic progenitor cells, wherein the NKX6.1-positive pancreatic progenitor cells expresses NKX6.1.

In some cases, the Pdx1-positive, NKX6.1-positive pancreatic progenitor cells are obtained by contacting Pdx1-positive pancreatic progenitor cells with i) at least one growth factor from the FGF family, ii) at least one SHH pathway inhibitor, and optionally iii) a low concentration of a RA signaling pathway activator, to induce the differentiation of at least some of the Pdx1-positive pancreatic progenitor cells into Pdx1-positive, NKX6.1-positive pancreatic progenitor cells, wherein the Pdx1-positive, NKX6.1-positive pancreatic progenitor cells expresses Pdx1 and NKX6.1.

In some cases, the Pdx1-positive, NKX6.1-positive pancreatic progenitor cells are obtained by contacting Pdx1-positive pancreatic progenitor cells with i) at least one growth factor from the FGF family, ii) at least one SHH pathway inhibitor, and optionally iii) a low concentration of a RA signaling pathway activator, iv) ROCK inhibitor, and v) at least one growth factor from the TGF-β superfamily, to induce the differentiation of at least some of the Pdx1-positive pancreatic progenitor cells into Pdx1-positive, NKX6.1-positive pancreatic progenitor cells. In some cases, the Pdx1-positive, NKX6.1-positive pancreatic progenitor cells are obtained by contacting Pdx1-positive pancreatic progenitor cells under conditions that promote cell clustering with at least one growth factor from the FGF family.

In some cases, the Pdx1-positive pancreatic progenitor cells are produced from a population of pluripotent cells. In some cases, the Pdx1-positive pancreatic progenitor cells are produced from a population of iPS cells. In some cases, the Pdx1-positive pancreatic progenitor cells are produced from a population of ESC cells. In some cases, the Pdx1-positive pancreatic progenitor cells are produced from a population of definitive endoderm cells. In some cases, the Pdx1-positive pancreatic progenitor cells are produced from a population of primitive gut tube cells.

Any growth factor from the FGF family capable of inducing Pdx1-positive pancreatic-progenitor cells to differentiate into NKX6.1-positive pancreatic progenitor cells (e.g., alone, or with any combination of at least one SHH pathway inhibitor, a ROCK inhibitor, a growth factor from the TGF-β superfamily, and at least one retinoic acid signaling pathway activator) can be used in the method provided herein. In some cases, the at least one growth factor from the FGF family comprises keratinocyte growth factor (KGF). In some cases, the at least one growth factor from the FGF family is selected from the group consisting of FGF2, FGF8B, FGF 10, and FGF21. In some examples, the method comprises contacting Pdx1-positive pancreatic progenitor cells with a concentration of a growth factor from FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL.

Any SHH pathway inhibitor capable of inducing Pdx1-positive pancreatic progenitor cells to differentiate into NKX6.1-positive pancreatic progenitor cells (e.g., alone, or with any combination of at least one growth factor from the FGF family, at least one retinoic acid signaling pathway activator, ROCK inhibitor, and at least one growth factor from the TGF-β superfamily) can be used in the method provided herein. In some cases, the SHH pathway inhibitor comprises Sant1. In some examples, the method comprises contacting Pdx1-positive pancreatic progenitor cells with a concentration of a SHH pathway inhibitor (e.g., Sant1), such as, about 0.001 μM, about 0.002 μM, about 0.005 μM, about 0.01 μM, about 0.02 μM, about 0.03 μM, about 0.05 μM, about 0.08 μM, about 0.1 μM, about 0.12 μM, about 0.13 μM, about 0.14 μM, about 0.15 μM, about 0.16 μM, about 0.17 μM, about 0.18 μM, about 0.19 μM, about 0.2 μM, about 0.21 μM, about 0.22 μM, about 0.23 μM, about 0.24 μM, about 0.25 μM, about 0.26 μM, about 0.27 μM, about 0.28 μM, about 0.29 μM, about 0.3 μM, about 0.31 μM, about 0.32 μM, about 0.33 μM, about 0.34 μM, about 0.35 μM, about 0.4 μM, about 0.45 μM, about 0.5 μM, about 0.6 μM, about 0.8 μM, about 1 μM, about 2 μM, or about 5 μM.

Any RA signaling pathway activator capable of inducing Pdx1-positive pancreatic progenitor cells to differentiate into NKX6.1-positive pancreatic progenitor cells (e.g., alone, or with any combination of at least one growth factor from the FGF family, at least one SHH pathway inhibitor, ROCK inhibitor, and at least one growth factor from the TGF-β superfamily) can be used. In some cases, the RA signaling pathway activator comprises retinoic acid. In some examples, the method comprises contacting Pdx1-positive pancreatic progenitor cells with a concentration of an RA signaling pathway activator (e.g., retinoic acid), such as, about 0.02 μM, about 0.1 μM, about 0.2 μM, about 0.25 μM, about 0.3 μM, about 0.4 μM, about 0.45 μM, about 0.5 μM, about 0.55 μM, about 0.6 μM, about 0.65 μM, about 0.7 μM, about 0.75 μM, about 0.8 μM, about 0.85 μM, about 0.9 μM, about 1 μM, about 1.1 μM, about 1.2 μM, about 1.3 μM, about 1.4 μM, about 1.5 μM, about 1.6 μM, about 1.7 μM, about 1.8 μM, about 1.9 μM, about 2 μM, about 2.1 μM, about 2.2 μM, about 2.3 μM, about 2.4 μM, about 2.5 μM, about 2.6 μM, about 2.7 μM, about 2.8 μM, about 3 μM, about 3.2 μM, about 3.4 μM, about 3.6 μM, about 3.8 μM, about 4 μM, about 4.2 μM, about 4.4 μM, about 4.6 μM, about 4.8 μM, about 5 μM, about 5.5 μM, about 6 μM, about 6.5 μM, about 7 μM, about 7.5 μM, about 8 μM, about 8.5 μM, about 9 μM, about 9.5 μM, about 10 μM, about 12 μM, about 14 μM, about 15 μM, about 16 μM, about 18 μM, about 20 μM, about 50 μM, or about 100 μM.

Any ROCK inhibitor capable of inducing Pdx1-positive pancreatic progenitor cells to differentiate into NKX6.1-positive pancreatic progenitor cells (e.g., alone, or with any combination of at least one growth factor from the FGF family, at least one SHH pathway inhibitor, a RA signaling pathway activator, and at least one growth factor from the TGF-β superfamily) can be used. In some cases, the ROCK inhibitor comprises Thiazovivin, Y-27632, Fasudil/HA1077, or 14-1152. In some examples, the method comprises contacting Pdx1-positive pancreatic progenitor cells with a concentration of a ROCK inhibitor (e.g., Y-27632 or Thiazovivin), such as, about 0.2 μM, about 0.5 μM, about 0.75 μM, about 1 μM, about 2 μM, about 3 μM, about 4 μM, about 5 μM, about 6 μM, about 7 μM, about 7.5 μM, about 8 μM, about 9 μM, about 10 μM, about 11 μM, about 12 μM, about 13 μM, about 14 μM, about 15 μM, about 16 μM, about 17 μM, about 18 μM, about 19 μM, about 20 μM, about 21 μM, about 22 μM, about 23 μM, about 24 μM, about 25 μM, about 26 μM, about 27 μM, about 28 μM, about 29 μM, about 30 μM, about 35 μM, about 40 μM, about 50 μM, or about 100 μM.

Any activator from the TGF-β superfamily capable of inducing Pdx1-positive pancreatic progenitor cells to differentiate into NKX6.1-positive pancreatic progenitor cells (e.g., alone, or with any combination of at least one growth factor from the FGF family, at least one SHH pathway inhibitor, a RA signaling pathway activator, and ROCK inhibitor) can be used. In some cases, the activator from the TGF-β superfamily comprises Activin A or GDF8. In some examples, the method comprises contacting Pdx1-positive pancreatic progenitor cells with a concentration of a growth factor from TGF-β superfamily (e.g., Activin A), such as, about 0.1 ng/mL, about 0.2 ng/mL, about 0.3 ng/mL, about 0.4 ng/mL, about 0.5 ng/mL, about 0.6 ng/mL, about 0.7 ng/mL, about 0.8 ng/mL, about 1 ng/mL, about 1.2 ng/mL, about 1.4 ng/mL, about 1.6 ng/mL, about 1.8 ng/mL, about 2 ng/mL, about 2.2 ng/mL, about 2.4 ng/mL, about 2.6 ng/mL, about 2.8 ng/mL, about 3 ng/mL, about 3.2 ng/mL, about 3.4 ng/mL, about 3.6 ng/mL, about 3.8 ng/mL, about 4 ng/mL, about 4.2 ng/mL, about 4.4 ng/mL, about 4.6 ng/mL, about 4.8 ng/mL, about 5 ng/mL, about 5.2 ng/mL, about 5.4 ng/mL, about 5.6 ng/mL, about 5.8 ng/mL, about 6 ng/mL, about 6.2 ng/mL, about 6.4 ng/mL, about 6.6 ng/mL, about 6.8 ng/mL, about 7 ng/mL, about 8 ng/mL, about 9 ng/mL, about 10 ng/mL, about 20 ng/mL, about 30 ng/mL, or about 50 ng/mL. In some examples, the method comprises contacting Pdx1-positive pancreatic progenitor cells with a concentration of a growth factor from TGF-β superfamily (e.g., Activin A), such as, about 5 ng/mL.

In some cases, the Pdx1-positive, NKX6.1-positive pancreatic progenitor cells are obtained by contacting Pdx1-positive pancreatic progenitor cells under conditions that promote cell clustering with KGF, Sant1, and RA, for a period of 5 days. In some cases, the Pdx1-positive, NKX6.1-positive pancreatic progenitor cells are obtained by contacting Pdx1-positive pancreatic progenitor cells under conditions that promote cell clustering with KGF, Sant1, RA, Y27632, and Activin A, for a period of 5 days. In some cases, the Pdx1-positive, NKX6.1-positive pancreatic progenitor cells are obtained by contacting Pdx1-positive pancreatic progenitor cells under conditions that promote cell clustering with KGF for a period of 5 days. In some cases, the Pdx1-positive, NKX6.1-positive pancreatic progenitor cells are obtained by contacting Pdx1-positive pancreatic progenitor cells in a S3 medium.

Aspects of the disclosure involve insulin-positive endocrine cells. Insulin-positive endocrine cells of use herein can be derived from any source or generated in accordance with any suitable protocol, In some aspects, NKX6.1-positive pancreatic progenitor cells are differentiated to insulin-positive endocrine cells, In some aspects, the insulin-positive endocrine cells are further differentiated, e.g., by induction or maturation to SC-β cells.

In some aspects, a method of producing an insulin-positive endocrine cell from an NKX6.1-positive pancreatic progenitor cell comprises contacting a population of cells (e.g., under conditions that promote cell clustering) comprising NKX6-1-positive pancreatic progenitor cells with a) a TGF-β signaling pathway inhibitor, and b) a thyroid hormone signaling pathway activator, to induce the differentiation of at least one NKX6.1-positive pancreatic progenitor cell in the population into an insulin-positive endocrine cell, wherein the insulin-positive endocrine ceil expresses insulin. In some cases, insulin-positive endocrine cells express Pdx1, NKX6.1, NKX2.2, Math, glis3, Sur1, Kir6.2, Znt8, SLC2A1, SLC2A3 and/or insulin.

Any TGF-β signaling pathway inhibitor capable of inducing the differentiation of NKX6.1-positive pancreatic progenitor cells to differentiate into insulin-positive endocrine cells (e.g., alone, or in combination with other β cell-differentiation factors, e.g., a thyroid hormone signaling pathway activator) can be used. In some cases, the TGF-β signaling pathway comprises TGF-β receptor type I kinase signaling. In some cases, the TGF-β signaling pathway inhibitor comprises Alk5 inhibitor II.

Any thyroid hormone signaling pathway activator capable of inducing the differentiation of NKX6.1-positive pancreatic progenitor cells to differentiate into insulin-positive endocrine cells (e.g., alone, or in combination with other β cell-differentiation factors, e.g., a TGF-β signaling pathway inhibitor) can be used. In some cases, the thyroid hormone signaling pathway activator comprises triiodothyronine (T3). In some cases, the thyroid hormone signaling pathway activator comprises GC-1.

In some cases, the method comprises contacting the population of cells (e.g., NKX6.1-positive pancreatic progenitor cells) with at least one additional factor. In some cases, the method comprises contacting the Pdx1-positive NKX6.1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, v) a protein kinase inhibitor, vi) a TGF-β signaling pathway inhibitor, or vii) a thyroid hormone signaling pathway activator.

In some cases, the method comprises contacting the Pdx1-positive NKX6.1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) a protein kinase inhibitor, or ix) a ROCK inhibitor.

In some cases, the method comprises contacting the Pdx1-positive NKX6.1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) an epigenetic modifying compound, ix) a protein kinase inhibitor, or x) a ROCK inhibitor.

In some embodiments, in the method of generating the insulin-positive endocrine cells from the Pdx1-positive NKX6.1-positive pancreatic progenitor cells, some of the differentiation factors are present only for the first 1, 2, 3, 4, or 5 days during the differentiation step. In some cases, some of the differentiation factors, such as the SHH pathway inhibitor, the RA signaling pathway activator, and the at least one growth factor from the EGF family are removed from the culture medium after the first 3 days of incubation.

Any γ-secretase inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator). In some cases, the γ-secretase inhibitor comprises XXI. In some cases, the γ-secretase inhibitor comprises DAPT. In some examples, the method comprises contacting NKX6.1-positive pancreatic progenitor cells with a concentration of a γ-secretase inhibitor (e.g., XXI), such as, about 0.01 μM, about 0.02 μM, about 0.05 μM, about 0.075 μM, about 0.1 μM, about 0.2 μM, about 0.3 μM, about 0.4 μM, about 0.5 μM, about 0.6 μM, about 0.7 μM, about 0.8 μM, about 0.9 μM, about 1 μM, about 1.1 μM, about 1.2 μM, about 1.3 μM, about 1.4 μM, about 1.5 μM, about 1.6 μM, about 1.7 μM, about 1.8 μM, about 1.9 μM, about 2 μM, about 2.1 μM, about 2.2 μM, about 2.3 μM, about 2.4 μM, about 2.5 μM, about 2.6 μM, about 2.7 μM, about 2.8 μM, about 2.9 μM, about 3 μM, about 3.2 μM, about 3.4 μM, about 3.6 μM, about 3.8 μM, about 4 μM, about 4.2 μM, about 4.4 μM, about 4.6 μM, about 4.8 μM, about 5 μM, about 5.2 μM, about 5.4 μM, about 5.6 μM, about 5.8 μM, about 6 μM, about 6.2 μM, about 6.4 μM, about 6.6 μM, about 6.8 μM, about 7 μM, about 8 μM, about 9 μM, about 10 μM, about 20 μM, about 30 μM, or about 50 μM.

Any growth factor from the EGF family capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some cases, the at least one growth factor from the EG F family comprises betacellulin. In some cases, at least one growth factor from the EGF family comprises EGF. In some examples, the method comprises contacting NKX6.1-positive pancreatic progenitor cells with a concentration of a growth factor from EGF family (e.g., betacellulin), such as, about 1 ng/mL, about 2 ng/mL, about 4 ng/mL, about 6 ng/mL, about 8 ng/mL, about 10 ng/mL, about 12 ng/mL, about 14 ng/mL, about 16 ng/mL, about 18 ng/mL, about 20 ng/mL, about 22 ng/mL, about 24 ng/mL, about 26 ng/mL, about 28 ng/mL, about 30 ng/mL, about 40 ng/mL, about 50 ng/mL, about 75 ng/mL, about 80 ng/mL, about 90 ng/mL, about 95 ng/mL, about 100 ng/mL, about 150 ng/mL, about 200 ng/mL, about 250 ng/mL, or about 300 ng/mL.

Any RA signaling pathway activator capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used. In some cases, the RA signaling pathway activator comprises RA. In some examples, the method comprises contacting NKX6.1-positive pancreatic progenitor cells with a concentration of an RA signaling pathway activator (e.g., retinoic acid), such as, about 0.02 μM, about 0.1 μM, about 0.2 μM, about 0.25 μM, about 0.3 μM, about 0.4 μM, about 0.45 μM, about 0.5 μM, about 0.55 μM, about 0.6 μM, about 0.65 μM, about 0.7 μM, about 0.75 μM, about 0.8 μM, about 0.85 μM, about 0.9 μM, about 1 μM, about 1.1 μM, about 1.2 μM, about 1.3 μM, about 1.4 μM, about 1.5 μM, about 1.6 μM, about 1.7 μM, about 1.8 μM, about 1.9 μM, about 2 μM, about 2.1 μM, about 2.2 μM, about 2.3 μM, about 2.4 μM, about 2.5 μM, about 2.6 μM, about 2.7 μM, about 2.8 μM, about 3 μM, about 3.2 μM, about 3.4 μM, about 3.6 μM, about 3.8 μM, about 4 μM, about 4.2 μM, about 4.4 μM, about 4.6 μM, about 4.8 μM, about 5 μM, about 5.5 μM, about 6 μM, about 6.5 μM, about 7 μM, about 7.5 μM, about 8 μM, about 8.5 μM, about 9 μM, about 9.5 μM, about 10 μM, about 12 μM, about 14 μM, about 15 μM, about 16 μM, about 18 μM, about 20 μM, about 50 μM, or about 100 μM.

Any SHH pathway inhibitor capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used in the method provided herein. In some cases, the SHH pathway inhibitor comprises Sant1. In some examples, the method comprises contacting NKX6.1-positive pancreatic progenitor cells with a concentration of a SHH pathway inhibitor (e.g., Sant1), such as, about 0.001 μM, about 0.002 μM, about 0.005 μM, about 0.01 μM, about 0.02 μM, about 0.03 μM, about 0.05 μM, about 0.08 μM, about 0.1 μM, about 0.12 μM, about 0.13 μM, about 0.14 μM, about 0.15 μM, about 0.16 μM, about 0.17 μM, about 0.18 μM, about 0.19 μM, about 0.2 μM, about 0.21 μM, about 0.22 μM, about 0.23 μM, about 0.24 μM, about 0.25 μM, about 0.26 μM, about 0.27 μM, about 0.28 μM, about 0.29 μM, about 0.3 μM, about 0.31 μM, about 0.32 μM, about 0.33 μM, about 0.34 μM, about 0.35 μM, about 0.4 μM, about 0.45 μM, about 0.5 μM, about 0.6 μM, about 0.8 μM, about 1 μM, about 2 μM, or about 5 μM.

Any BMP signaling pathway inhibitor capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used. In some cases, the BMP signaling pathway inhibitor comprises LDN193189 or DMH-1. In some examples, the method comprises contacting NKX6.1-positive pancreatic progenitor cells with a concentration of BMP signaling pathway inhibitor (e.g., LDN1931189), such as, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 280 nM, about 300 nM, about 400 nM, about 500 nM, or about 1 μM.

Any ROCK inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some cases, the ROCK inhibitor comprises Thiazovivin, Y-27632, Fasudil/HA1077, or H-1152. In some cases, the ROCK inhibitor comprises Y-27632. In some cases, the ROCK inhibitor comprises Thiazovivin. In some examples, the method comprises contacting Pdx1-positive, NKX6.1-positive pancreatic progenitor cells with a concentration of a ROCK inhibitor (e.g., Y-27632 or Thiazovivin), such as, about 0.2 μM, about 0.5 μM, about 0.75 μM, about 1 μM, about 2 μM, about 3 μM, about 4 μM, about 5 μM, about 6 μM, about 7 μM, about 7.5 μM, about 8 μM, about 9 μM, about 10 μM, about 11 μM, about 12 μM, about 13 μM, about 14 μM, about 15 μM, about 16 μM, about 17 μM, about 18 μM, about 19 μM, about 20 μM, about 21 μM, about 22 μM, about 23 μM, about 24 μM, about 25 μM, about 26 μM, about 27 μM, about 28 μM, about 29 μM, about 30 μM, about 35 μM, about 40 μM, about 50 μM, or about 100 μM.

Any epigenetic modifying compound that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some cases, the epigenetic modifying compound comprises a histone methyltransferase inhibitor or a HDAC inhibitor. In some cases, the epigenetic modifying compound comprises a histone methyltransferase inhibitor, e.g., DZNep. In some cases, the epigenetic modifying compound comprises a HDAC inhibitor, e.g., KD5170. In some examples, the method comprises contacting Pdx1-positive, NKX6.1-positive pancreatic progenitor cells with a concentration of an epigenetic modifying compound (e.g., DZNep or KD5170), such as, about 0.01 μM, about 0.025 μM, about 0.05 μM, about 0.075 μM, about 0.1 μM, about 0.15 μM, about 0.2 μM, about 0.5 μM, about 0.75 μM, about 1 μM, about 2 μM, about 3 μM, about 4 μM, about 5 μM, about 6 μM, about 7 μM, about 7.5 μM, about 8 μM, about 9 μM, about 10 μM, about 15 μM, about 20 μM, about 25 μM, about 30 μM, about 35 μM, about 40 μM, about 50 μM, or about 100 μM.

In some cases, the population of cells is optionally contacted with a protein kinase inhibitor. In some cases, the population of cells is not contacted with the protein kinase inhibitor. In some cases, the population of cells is contacted with the protein kinase inhibitor. Any protein kinase inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator). In some cases, the protein kinase inhibitor comprises staurosporine.

In some cases, the method comprises contacting the population of cells (e.g., NKX6.1-positive pancreatic progenitor cells) with XXI, Alk5i, T3 or GC-1, RA, Sant1, and betacellulin for a period of 7 days, to induce the differentiation of at least one NKX6.1-positive pancreatic progenitor cell in the population into an insulin-positive endocrine cell, wherein the insulin-positive endocrine cell expresses insulin. In some cases, the method comprises contacting the population of cells (e.g., NKX6.1-positive pancreatic progenitor cells) with XXI, Alk5i, T3 or GC-1, RA, Sant1, betacellulin, and LDN193189 for a period of 7 days, to induce the differentiation of at least one NKX6.1-positive pancreatic progenitor cell in the population into an insulin-positive endocrine cell, wherein the insulin-positive endocrine ceil expresses insulin. In some embodiments, one or more differentiation factors are added in a portion of the Stage 5, for instance, only the first 1, 2, 3, 4, 5, or 6 days of the period of time for Stage 5, or the last 1, 2, 3, 4, 5, or 6 days of the period of time for Stage 5. In one example, the cells are contacted with SHH signaling pathway inhibitor for only the first 2, 3, 4, or 5 days during Stage 5, after which the SHH signaling pathway inhibitor is removed from the culture medium. In another example, the cells are contacted with BMP signaling pathway inhibitor for only the first 1, 2, or 3 days during Stage 5, after which the BMP signaling pathway inhibitor is removed from the culture medium.

In some cases, the method comprises culturing the population of cells (e.g., NKX6.1-positive pancreatic progenitor cells) in a BE5 medium, to induce the differentiation of at least one NKX6.1-positive pancreatic progenitor cell in the population into an insulin-positive endocrine cell, wherein the insulin-positive endocrine cell expresses insulin.

Aspects of the disclosure involve generating pancreatic β cells (e.g., non-native pancreatic β cells). Non-native pancreatic β cells, in some cases, resemble endogenous mature 13 cells in form and function, but nevertheless are distinct from native β cells.

In some cases, the insulin-positive pancreatic endocrine cells generated using the method provided herein can form a cell cluster, alone or together with other types of cells, e.g., precursors thereof, e.g., stem cell, definitive endoderm cells, primitive gut tube cell, Pdx1-positive pancreatic progenitor cells, or NKX6.1-positive pancreatic progenitor cells.

In some cases, the cell population comprising the insulin-positive endocrine cells can be directly induced to mature into SC-β cells without addition of any exogenous differentiation factors (such as inhibitor of TGF-β signaling pathway, thyroid hormone signaling pathway activator, PKC activator, growth factors from TGF-β superfamily, FGF family, or EGF family, SHH signaling pathway inhibitor, γ-secretase inhibitor, ROCK inhibitor, or BMP signaling pathway inhibitor).

In some cases, the cell population comprising the insulin-positive endocrine cells can be directly induced to mature into SC-β cells by contacting the insulin-positive endocrine cells with differentiation factors. The differentiation factors can comprise at least one inhibitor of TGF-β signaling pathway and thyroid hormone signaling pathway activator as described herein. In some cases, SC-β cells can be obtained by contacting a population of cells comprising insulin-positive endocrine cells with Alk5i and T3 or GC-1.

In some examples, insulin-positive endocrine cells can be matured in a NS-GFs medium, MCDB131 medium, DMEM medium, or CMRL medium. In some cases, the insulin-positive endocrine cells can be matured in a CMRLs medium supplemented with 10% FBS. In some cases, the insulin-positive endocrine cells can be matured in a DMEM medium supplemented with 1% HSA. In other cases, SC-β cells can be obtained by culturing the population of cells containing the insulin-positive endocrine cells in a MCDB131 medium that can be supplemented by 2% BSA. In some cases, the MCDB131 medium with 2% BSA for maturation of insulin-positive endocrine cells into SC-β cells can be comprise no small molecule factors as described herein. In some case, the MCDB131 medium with 2% BSA for maturation of insulin-positive endocrine cells into SC-β cells can comprise no serum (e.g., no FBS).

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into Pdx1-positive pancreatic progenitor cells by a process of contacting the primitive gut tube cells with i) retinoic acid signaling pathway activator, ii) at least one factor from the FGF family, iii) a SHH pathway inhibitor, iv) a BMP signaling pathway inhibitor (e.g., DMH-1 or LDN193189), v) a PKC activator, and vi) a ROCK inhibitor; d) differentiating at least some of the Pdx1-positive pancreatic progenitor cells into Pdx1-positive, NKX6.1-positive pancreatic progenitor cells by a process of contacting the Pdx1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, every other day for a period of 5 days, wherein the NKX6.1-positive pancreatic progenitor cells expresses Pdx1 and NKX6.1; e) differentiating at least some of the Pdx1-positive, NKX6.1-positive pancreatic progenitor cells into Pdx1-positive, NKX6.1-positive, insulin-positive endocrine cells by a process of contacting the Pdx1-positive, NKX6.1-positive pancreatic progenitor cells with i) a TGF-β signaling pathway inhibitor, ii) a TH signaling pathway activator, iii) at least one SHH pathway inhibitor, iv) a RA signaling pathway activator, v) a γ-secretase inhibitor, optionally vi) at least one growth factor from the epidermal growth factor (EGF) family, and optionally vii) a BMP signaling pathway inhibitor, every other day for a period of between five and seven days; and f) differentiating at least some of the Pdx1-positive, NKX6.1-positive, insulin-positive endocrine cells into SC-β cells by a process of culturing the Pdx1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, every other day for a period of between 7 and 14 days to induce the in vitro maturation of at least some of the Pdx1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature 13 cells.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into Pdx1-positive pancreatic progenitor cells by a process of contacting the primitive gut tube cells with i) retinoic acid signaling pathway activator, ii) at least one factor from the FGF family, iii) a SHH pathway inhibitor, iv) a BMP signaling pathway inhibitor, v) a PKC activator, vi) a ROCK inhibitor, and vii) a growth factor from TGFβ superfamily, for a period of 2 days; d) differentiating at least some of the Pdx1-positive pancreatic progenitor cells into Pdx1-positive, NKX6.1-positive pancreatic progenitor cells by a process of contacting the Pdx1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, every other day for a period of 5 days, wherein the NKX6.1-positive pancreatic progenitor cells expresses Pdx1 and NKX6.1; e) differentiating at least some of the Pdx1-positive, NKX6.1-positive pancreatic progenitor cells into Pdx1-positive, NKX6.1-positive, insulin-positive endocrine cells by a process of contacting the Pdx1-positive, NKX6.1-positive pancreatic progenitor cells with i) a TGF-β signaling pathway inhibitor, ii) a TH signaling pathway activator, iii) at least one SHH pathway inhibitor, iv) a RA signaling pathway activator, v) a γ-secretase inhibitor, optionally vi) at least one growth factor from the epidermal growth factor (EGF) family, and optionally vii) a BMP signaling pathway inhibitor, every other day for a period of between five and seven days; and f) differentiating at least some of the Pdx1-positive, NKX6.1-positive, insulin-positive endocrine cells into SC-β cells by a process of culturing the Pdx1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, every other day for a period of between 7 and 14 days to induce the in vitro maturation of at least some of the Pdx1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature β cells.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into Pdx1-positive pancreatic progenitor cells by a process of contacting the primitive gut tube cells with i) retinoic acid signaling pathway activator, ii) at least one factor from the FGF family, iii) a SHH pathway inhibitor, iv) a PKC activator, and v) a ROCK inhibitor; d) differentiating at least some of the Pdx1-positive pancreatic progenitor cells into Pdx1-positive, NKX6.1-positive pancreatic progenitor cells by a process of contacting the Pdx1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, every other day for a period of 5 days, wherein the NKX6.1-positive pancreatic progenitor cells expresses Pdx1 and NKX6.1; e) differentiating at least some of the Pdx1-positive, NKX6.1-positive pancreatic progenitor cells into Pdx1-positive, NKX6.1-positive, insulin-positive endocrine cells by a process of contacting the Pdx1-positive, NKX6.1-positive pancreatic progenitor cells with i) a TGF-β signaling pathway inhibitor, ii) a TH signaling pathway activator, iii) at least one SHH pathway inhibitor, iv) a RA signaling pathway activator, v) a γ-secretase inhibitor, and optionally vi) at least one growth factor from the epidermal growth factor (EGF) family, every other day for a period of between five and seven days; and f) differentiating at least some of the Pdx1-positive, NKX6.1-positive, insulin-positive endocrine cells into SC-β cells by a process of culturing the Pdx1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, every other day for a period of between 7 and 14 days to induce the in vitro maturation of at least some of the Pdx1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature β cells.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into Pdx1-positive pancreatic progenitor cells by a process of contacting the primitive gut tube cells with i) retinoic acid signaling pathway activator, ii) at least one factor from the FGF family, iii) a SHH pathway inhibitor, iv) a BMP signaling pathway inhibitor (e.g., DMH-1 or LDN193189), v) a PKC activator, and vi) a ROCK inhibitor; d) differentiating at least some of the Pdx1-positive pancreatic progenitor cells into Pdx1-positive, NKX6.1-positive pancreatic progenitor cells by a process of contacting the Pdx1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, every other day for a period of 5 or 6 days, wherein the NKX6.1-positive pancreatic progenitor cells expresses Pdx1 and NKX6.1; e) differentiating at least some of the Pdx1-positive, NKX6.1-positive pancreatic progenitor cells into Pdx1-positive, NKX6.1-positive, insulin-positive endocrine cells by a process of contacting the Pdx1-positive, NKX6.1-positive pancreatic progenitor cells with i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) an epigenetic modifying compound (e.g., DZNep or KD5170), ix) a protein kinase inhibitor, and x) a ROCK inhibitor, every other day for a period of between five and seven days; and f) differentiating at least some of the Pdx1-positive, NKX6.1-positive, insulin-positive endocrine cells into SC-β cells by a process of culturing the Pdx1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, every other day for a period of between 7 and 14 days to induce the in vitro maturation of at least some of the Pdx1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature β cells.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into Pdx1-positive pancreatic progenitor cells by a process of contacting the primitive gut tube cells with i) retinoic acid signaling pathway activator, ii) at least one factor from the FGF family, iii) a SHH pathway inhibitor, iv) a BMP signaling pathway inhibitor (e.g., DMH-1 or LDN193189), v) a PKC activator, and vi) a ROCK inhibitor; d) differentiating at least some of the Pdx1-positive pancreatic progenitor cells into Pdx1-positive, NKX6.1-positive pancreatic progenitor cells by a process of contacting the Pdx1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, every other day for a period of 5 or 6 days, wherein the NKX6.1-positive pancreatic progenitor cells expresses Pdx1 and NKX6.1; e) differentiating at least some of the Pdx1-positive, NKX6.1-positive pancreatic progenitor cells into Pdx1-positive, NKX6.1-positive, insulin-positive endocrine cells by a process of contacting the Pdx1-positive, NKX6.1-positive pancreatic progenitor cells with i) a γ-secretase inhibitor, ii) at least one bone morphogenetic protein (BMP) signaling pathway inhibitor, iii) a TGF-β signaling pathway inhibitor, iv) a thyroid hormone signaling pathway activator, v) an epigenetic modifying compound (e.g., DZNep or KD5170), vi) a protein kinase inhibitor, and vii) a ROCK inhibitor, every other day for a period of between five and seven days, and within first three days of the period of between five and seven days, contacting the the Pdx1-positive, NKX6.1-positive pancreatic progenitor cells with a SHH pathway inhibitor, a RA signaling pathway, and at least one growth factor from the EGF family, which are removed from the Pdx1-positive, NKX6.1-positive pancreatic progenitor cells thereafter; and f) differentiating at least some of the Pdx1-positive, NKX6.1-positive, insulin-positive endocrine cells into SC-β cells by a process of culturing the Pdx1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, every other day for a period of between 7 and 14 days to induce the in vitro maturation of at least some of the Pdx1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature β cells.

The medium used to culture the cells dissociated from the first cell cluster can be xeno-free. A xeno-free medium for culturing cells and/or cell clusters of originated from an animal can have no product from other animals. In some cases, a xeno-free medium for culturing human cells and/or cell clusters can have no products from any non-human animals. For example, a xeno-free medium for culturing human cells and/or cell clusters can comprise human platelet lysate (PLT) instead of fetal bovine serum (FBS). For example, a medium can comprise from about 1% to about 20%, from about 5% to about 15%, from about 8% to about 12%, from about 9 to about 11% serum. In some cases, medium can comprise about 10% of serum. In some cases, the medium can be free of small molecules and/or FBS. For example, a medium can comprise MCDB131 basal medium supplemented with 2% BSA. In some cases, the medium is serum-free. In some examples, a medium can comprise no exogenous small molecules or signaling pathway agonists or antagonists, such as, growth factor from fibroblast growth factor family (FGF, such as FGF2, FGF8B, FGF 10, or FGF21), Sonic Hedgehog Antagonist (such as Sant1, Sant2, Sant4, Sant4, Cur61414, forskolin, tomatidine, AY9944, triparanol, cyclopamine, or derivatives thereof), Retinoic Acid Signaling agonist (e.g., retinoic acid, CD1530, AM580, TTHPB, CD437, Ch55, BMS961, AC261066, AC55649, AM80, BMS753, tazarotene, adapalene, or CD2314), inhibitor of Rho-associated, coiled-coil containing protein kinase (ROCK) (e.g., Thiazovivin, Y-27632, Fasudil/HA1077, or 14-1152), activator of protein kinase C (PKC) (e.g., phorbol 12,13-dibutyrate (PDBU), TPB, phorbol 12-myristate 13-acetate, bryostatin 1, or derivatives thereof), antagonist of TGF β super family (e.g., Alk5 inhibitor II (CAS 446859-33-2), A83-01, SB431542, D4476, GW788388, LY364947, LY580276, SB505124, GW6604, SB-525334, SD-208, SB-505124, or derivatives thereof), inhibitor of Bone Morphogenetic Protein (BMP) type 1 receptor (e.g., LDN193189 or derivatives thereof), thyroid hormone signaling pathway activator (e.g., T3, GC-1 or derivatives thereof), gamma-secretase inhibitor (e.g., XXI, DAPT, or derivatives thereof), activator of TGF-β signaling pathway (e.g., WNT3a or Activin A) growth factor from epidermal growth factor (EGF) family (e.g., betacellulin or EGF), broad kinase (e.g., staurosporine or derivatives thereof), non-essential amino acids, vitamins or antioxidants (e.g., cyclopamine, vitamin D, vitamin C, vitamin A, or derivatives thereof), or other additions like N-acetyl cysteine, zinc sulfate, or heparin. In some cases, the reaggregation medium can comprise no exogenous extracellular matrix molecule. In some cases, the reaggregation medium does not comprise Matrigel™. In some cases, the reaggregation medium does not comprise other extracellular matrix molecules or materials, such as, collagen, gelatin, poly-L-lysine, poly-D-lysine, vitronectin, laminin, fibronectin, PLO laminin, fibrin, thrombin, and RetroNectin and mixtures thereof, for example, or lysed cell membrane preparations.

A person of ordinary skill in the art will appreciate that that the concentration of serum albumin supplemented into the medium may vary. For example, a medium (e.g., MCDB131) can comprise about 0.01%, 0.05%, 0.1%, 1%, about 2%, about 3%, about 4%, about 5%, about 10%, or about 15% BSA. In other cases, a medium can comprise about 0.01%, 0.05%, 0.1%, 1%, about 2%, about 3%, about 4%, about 5%, about 10%, or about 15% HSA. The medium used (e.g., MCDB131 medium) can contain components not found in traditional basal media, such as trace elements, putrescine, adenine, thymidine, and higher levels of some amino acids and vitamins. These additions can allow the medium to be supplemented with very low levels of serum or defined components. The medium can be free of proteins and/or growth factors, and may be supplemented with EGF, hydrocortisone, and/or glutamine. The medium can comprise one or more extracellular matrix molecules (e.g., extracellular proteins). Non-limiting exemplary extracellular matrix molecules used in the medium can include collagen, placental matrix, fibronectin, laminin, merosin, tenascin, heparin, heparin sulfate, chondroitin sulfate, dermatan sulfate, aggrecan, biglycan, thrombospondin, vitronectin, and decorin. In some cases, the medium comprises laminin, such as LN-332. In some cases, the medium comprises heparin.

The medium can be changed periodically in the culture, e.g., to provide optimal environment for the cells in the medium. When culturing the cells dissociated from the first cell cluster for re-aggregation, the medium can be changed at least or about every 4 hours, 12 hours, 24 hours, 48 hours, 3 days or 4 days. For example, the medium can be changed about every 48 hours.

In some cases, cells can be cultured under dynamic conditions (e.g., under conditions in which the cells are subject to constant movement or stirring while in the suspension culture). For dynamic culturing of cells, the cells can be cultured in a container (e.g., an non-adhesive container such as a spinner flask (e.g., of 200 ml to 3000 ml, for example 250 ml; of 100 ml; or in 125 ml Erlenmeyer), which can be connected to a control unit and thus present a controlled culturing system. In some cases, cells can be cultured under non-dynamic conditions (e.g., a static culture) while preserving their proliferative capacity. For non-dynamic culturing of cells, the cells can be cultured in an adherent culture vessel. An adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, vitronectin, laminin, fibronectin, PLO laminin, fibrin, thrombin, and RetroNectin and mixtures thereof, for example, Matrigel™, and lysed cell membrane preparations.

Medium in a dynamic cell culture vessel (e.g., a spinner flask) can be stirred (e.g., by a stirrer). The spinning speed can correlate with the size of the re-aggregated second cell cluster. The spinning speed can be controlled so that the size of the second cell cluster can be similar to an endogenous pancreatic islet. In some cases, the spinning speed is controlled so that the size of the second cell cluster can be from about 75 μm to about 250 μm. The spinning speed of a dynamic cell culture vessel (e.g., a spinner flask) can be about 20 rounds per minute (rpm) to about 100 rpm, e.g., from about 30 rpm to about 90 rpm, from about 40 rpm to about 60 rpm, from about 45 rpm to about 50 rpm. In some cases, the spinning speed can be about 50 rpm.

Stage 6 cells as provided herein may or may not be subject to the dissociation and reaggregation process as described herein. In some cases, the cell cluster comprising the insulin-positive endocrine cells can be reaggregated. The reaggregation of the cell cluster can enrich the insulin-positive endocrine cells. In some cases, the insulin-positive endocrine cells in the cell cluster can be further matured into pancreatic β cells. For example, after reaggregation, the second cell cluster can exhibit in vitro GSIS, resembling native pancreatic islet. For example, after reaggregation, the second cell cluster can comprise non-native pancreatic β cell that exhibits in vitro GSIS. In some embodiments, the reaggregation process can be performed according to the disclosure of PCT application PCT/US2018/043179, which is incorporated herein by reference in its entirety.

Stage 6 cells obtained according to methods provided herein can have high recovery yield after cryopreservation and reaggregation procedures. In some cases, stage 6 cells that are obtained in a differentiation process that involves treatment of a BMP signaling pathway inhibitor (e.g., DMH-1 or LDN) and a growth factor from TGF-β superfamily (e.g., Activin A) at stage 3 and treatment of an epigenetic modifying compound (e.g., histone methyltransferase inhibitor, e.g., EZH2 inhibitor, e.g., DZNep) at stage 5 can have a higher recovery yield after cryopreservation post stage 5, as compared to a corresponding cell population without such treatment. In some cases, stage 6 cells that are obtained in a differentiation process that involves treatment of a BMP signaling pathway inhibitor (e.g., DMH-1 or LDN) and a growth factor from TGF-β superfamily (e.g., Activin A) at stage 3 and treatment of an epigenetic modifying compound (e.g., histone methyltransferase inhibitor, e.g., EZH2 inhibitor, e.g., DZNep) at stage 5 can have a higher recovery yield after cryopreservation post stage 5, as compared to a corresponding cell population without treatment of a BMP signaling pathway inhibitor (e.g., DMH-1 or LDN) and a growth factor from TGF-β superfamily (e.g., Activin A) at stage 3. In some cases, stage δ cells that are obtained in a differentiation process that involves treatment of a BMP signaling pathway inhibitor (e.g., DMH-1 or LDN) and a growth factor from TGF-β superfamily (e.g., Activin A) at stage 3 and treatment of an epigenetic modifying compound (e.g., histone methyltransferase inhibitor, e.g., EZH2 inhibitor, e.g., DZNep) at stage 5 can have a recovery yield after cryopreservation post stage 5 that is at least about 35%, 37.5%, 40%, 42.5%, 45%, 47.5%, 48%, 49%, or 50%. The recovery yield can be calculated as a percentage of cells that survive and form reaggregated cell clusters after cryopreservation, thawing and recovery, and reaggregation procedures, as compared to the cells before the cryopreservation.

In some embodiments, the present disclosure relates to cryopreservation of the non-native pancreatic β cells or precursors thereof obtained using the methods provided herein. In some embodiments, the cell population comprising non-native pancreatic β cells can be stored via cryopreservation. For instances, the cell population comprising non-native β cells, e.g., Stage δ cells in some cases, can be dissociated into cell suspension, e.g., single cell suspension, and the cell suspension can be cryopreserved, e.g., frozen in a cryopreservation solution. The dissociation of the cells can be conducted by any of the technique provided herein, for example, by enzymatic treatment. The cells can be frozen at a temperature of at highest −20° C., at highest −30° C., at highest −40° C., at highest −50° C., at highest −60° C., at highest −70° C., at highest −80° C., at highest −90° C., at highest −100° C., at highest −110° C., at highest −120° C., at highest −130° C., at highest −140° C., at highest −150° C., at highest −160° C., at highest −170° C., at highest −180° C., at highest −190° C., or at highest −200° C. In some cases, the cells are frozen at a temperature of about −80° C. In some cases, the cells are frozen at a temperature of about −195° C. Any cooling methods can be used for providing the low temperature needed for cryopreservation, such as, but not limited to, electric freezer, solid carbon dioxide, and liquid nitrogen. In some cases, any cryopreservation solution available to one skilled in the art can be used for incubating the cells for storage at low temperature, including both custom made and commercial solutions. For example, a solution containing a cryoprotectant can be used. The cryoprotectant can be an agent that is configured to protect the cell from freezing damage. For instance, a cryoprotectant can be a substance that can lower the glass transition temperature of the cryopreservation solution. Exemplary cryoprotectants that can be used include DMSO (dimethyl sulfoxide), glycols (e.g., ethylene glycol, propylene glycol and glycerol), dextran (e.g., dextran-40), and trehalose. Additional agents can be added in to the cryopreservation solution for other effects. In some cases, commercially available cryopreservation solutions can be used in the method provided herein, for instance, FrostaLife™, pZerve™, Prime-XV®, Gibco Synth-a-Freeze Cryopreservation Medium, STEM-CELL- BANKER®, CryoStor® Freezing Media, HypoThermosol® FRS Preservation Media, and CryoDefend® Stem Cells Media.

During the differentiation process, the cells can be subject to irradiation treatment as provided herein. In some cases, the cell population at Stage 6, e.g., the cell population or cell cluster that has cells being differentiated from insulin-positive endocrine cells into pancreatic β cells, is irradiated for a period of time. In some cases, the cell population at Stage 6 after reaggregation following the recovery from cryopreservation is irradiated for a period of time. In some cases, the cryopreserved cells (e.g., the cells that are cryo-preserved at the end of Stage 5) are irradiated for a certain period of time prior to thawing and recovery for subsequent differentiation process.

V. Differentiation Factors

Aspects of the disclosure relate to contacting progenitor cells (e.g., stem cells, e.g., iPS cells, definitive endoderm cells, primitive gut tube cells, Pdx1-positive pancreatic progenitor cells, NKX6.1-positive pancreatic progenitor cells, insulin-positive endocrine cells) with β cell differentiation factors, for example, to induce the maturation of the insulin-positive endocrine cells or differentiation of other progenitor cells into SC-β cells (e.g., mature pancreatic β cells). In some embodiments, the differentiation factor can induce the differentiation of pluripotent cells (e.g., iPSCs or hESCs) into definitive endoderm cells, e.g., in accordance with a method described herein. In some embodiments, the differentiation factor can induce the differentiation of definitive endoderm cells into primitive gut tube cells, e.g., in accordance with a method described herein. In some embodiments, the differentiation factor can induce the differentiation of primitive gut tube cells into Pdx1-positive pancreatic progenitor cells, e.g., in accordance with a method described herein. In some embodiments, the differentiation factor can induce the differentiation of Pdx1-positive pancreatic progenitor cells into NKX6-1-positive pancreatic progenitor cells, e.g., in accordance with a method described herein. In some embodiments, the differentiation factor can induce the differentiation of NKX6-1-positive pancreatic progenitor cells into insulin-positive endocrine cells, e.g., in accordance with a method described herein. In some embodiments, the differentiation factor can induce the maturation of insulin-positive endocrine cells into SC-β cells, e.g., in accordance with a method described herein.

At least one differentiation factor described herein can be used alone, or in combination with other differentiation actors, to generate SC-β cells according to the methods as disclosed herein. In some embodiments, at least two, at least three, at least four, at least five, at least six, at least seven, at least eight, at least nine, or at least ten differentiation factors described herein are used in the methods of generating SC-β cells.

Transforming Growth Factor-β (TGF-β) Superfamily

Aspects of the disclosure relate to the use of growth factors from the transforming growth factor-β (TGF-β) superfamily as differentiation factors. The "TGF-β superfamily" means proteins having structural and functional characteristics of known TGFβ family members. The TGFβ family of proteins can include the TGFβ series of proteins, the Inhibins (including Inhibin A and Inhibin B), the Activins (including Activin A, Activin B, and Activin AB), MIS (Müllerian inhibiting substance), BMP (bone morphogenetic proteins), dpp (decapentaplegic), Vg-1, MNSF (monoclonal nonspecific suppressor factor), and others. Activity of this family of proteins can be based on specific binding to certain receptors on various cell types. Members of this family can share regions of sequence identity, particularly at the C-terminus, that correlate to their function. The TGFβ family can include more than one hundred distinct proteins, all sharing at least one region of amino acid sequence identity. Members of the family that can be used in the method disclosed herein can include, but are not limited to, the following proteins, as identified by their GenBank accession numbers: P07995, P18331, P08476, Q04998, P03970, P43032, P55102, P27092, P42917, P09529, P27093, P04088, Q04999, P17491, P55104, Q9WUK5, P55103, O88959, O08717, P58166, O61643, P35621, P09534, P48970, Q9NR23, P25703, P30884, P12643, P49001, P21274, O46564, O19006, P22004, P20722, Q04906, Q07104, P30886, P18075, P23359, P22003, P34821, P49003, Q90751, P21275, Q06826, P30885, P34820, Q29607, P12644, Q90752, 046576, P27539, P48969, Q26974, P07713, P91706, P91699, P27091, O42222, Q24735, P20863, O18828, P55106, Q9PTQ2, O14793, O08689, O42221, O18830, O18831, O18836, O35312, O42220, P43026, P43027, P43029, O95390, Q9R229, 093449, Q9Z1W4, Q9BDW8, P43028, Q7Z4P5, P50414, P17246, P54831, P04202, P01137, P09533, P18341, 019011, Q9Z1Y6, P07200, Q9Z217, O95393, P55105, P30371, Q9MZE2, Q07258, Q96S42, P97737, AAA97415.1, NP-776788.1, NP-058824.1, EAL24001.1, 1 S4Y, NP-001009856.1, NP-1-032406.1, NP-999193.1, XP-519063.1, AAG17260.1, CAA40806.1, NP-1-001009458.1, AAQ55808.1, AAK40341.1, AAP33019.1, AAK21265.1, AAC59738.1, CAI46003.1, B40905, AAQ55811.1, AAK40342.1, XP-540364.1, P55102, AAQ55810.1, NP-990727.1, CAA51163.1, AAD50448.1, JC4862, PN0504, BAB17600.1, AAH56742.1, BAB17596.1, CAG06183.1, CAG05339.1, BAB17601.1, CAB43091.1, A36192, AAA49162.1, AAT42200.1, NP-789822.1, AAA59451.1, AAA59169.1, XP-541000.1, NP-990537.1, NP-1-002184.1, AAC14187.1, AAP83319.1, AAA59170.1, BAB16973.1, AAM66766.1, WFPGBB, 1201278C, AAH30029.1, CAA49326.1, XP-344131.1, AA-148845.1, XP-1-148966.3, 148235, B41398, AAH77857.1, AAB26863.1, 1706327A, BAA83804.1, NP-571143.1, CAG00858.1, BAB17599.1, BAB17602.1, AAB61468.1, PN0505, PN0506, CAB43092.1, BAB17598.1, BAA22570.1, BAB16972.1, BAC81672.1, BAA12694.1, BAA08494.1, B36192, C36192, BAB16971.1, NP-034695.1, AAA49160.1, CAA62347.1, AAA49161.1, AAD30132.1, CAA58290.1, NP-005529.1, XP-522443.1, AAM27448.1, XP-538247.1, AAD30133. I, AAC36741.1, AAH10404.1, NP-032408.1, AAN03682.1, XP-509161.1, AAC32311.1, NP-651942.2, AAL51005.1, AAC39083.1, AAH85547.1, NP-571023.1, CAF94113.1, EAL29247.1, AAW30007.1, AAH90232.1, A29619, NP-001007905.1, AAH73508.1, AAD02201.1, NP-999793.1, NP-990542.1, AAF19841.1, AAC97488.1, AAC60038.1, NP 989197.1, NP-571434.1, EAL41229.1, AAT07302.1, CAI19472.1, NP-031582.1, AAA40548.1, XP-535880.1, NP-1-037239.1, AAT72007.1, XP-418956.1, CAA41634.1, BAC30864.1, CAA38850.1, CAB81657.2, CAA45018.1, CAA45019.1, BAC28247.1, NP-031581.1, NP-990479.1, NP-999820.1, AAB27335.1, 545355, CAB82007.1, XP-534351.1, NP-058874.1, NP-031579.1, 1REW, AAB96785.1, AAB46367.1, CAA05033.1, BAA89012.1, IES7, AAP20870.1, BAC24087.1, AAG09784.1, BAC06352.1, AAQ89234.1, AAM27000.1, AAH30959.1, CAG01491.1, NP-571435.1, 1REU, AAC60286.1, BAA24406.1, A36193, AAH55959.1, AAH54647.1, AAH90689.1, CAG09422.1, BAD16743.1, NP-032134.1, XP-532179.1, AAB24876.1, AAH57702.1, AAA82616.1, CAA40222.1, CAB90273.2, XP-342592.1, XP-534896.1, XP-534462.1, 1LXI, XP-417496.1, AAF34179.1, AAL73188.1, CAF96266.1, AAB34226.1, AAB33846.1, AAT12415.1, AA033819.1, AAT72008.1, AAD38402.1, BAB68396.1, CAA45021.1, AAB27337.1, AAP69917.1, AATI2416.1, NP-571396.1, CAA53513.1, AA033820.1, AAA48568.1, BAC02605.1, BAC02604.1, BAC02603.1, BAC02602.1, BAC02601.1, BAC02599.1, BAC02598.1, BAC02597.1, BAC02595.1, BAC02593.1, BAC02592.1, BAC02590.1, AAD28039.1, AAP74560.1, AAB94786.1, NP-001483.2, XP-528195.1, NP-571417.1, NP-001001557. I, AAH43222.1, AAM33143.1, CAG10381.1, BAA31132.1, EAL39680.1, EAA12482.2, P34820, AAP88972.1, AAP74559.1, CAI16418.1, AAD30538.1, XP-345502.1, NP-1-038554.1, CAG04089.1, CAD60936.2, NP-031584.1, B55452, AAC60285.1, BAA06410.1, AAH52846.1, NP-031580.1, NP-1-036959.1, CAA45836.1, CAA45020.1, Q29607, AAB27336.1, XP-547817.1, AAT12414.1, AAM54049.1, AAH78901.1, AA025745.1, NP-570912.1, XP-392194.1, AAD20829.1, AAC97113.1, AAC61694.1, AAH60340.1, AAR97906.1, BAA32227.1, BAB68395.1, BAC02895.1, AAWS 1451.1, AAF82188.1, XP-544189.1, NP-990568.1, BAC80211.1, AAW82620.1, AAF99597.1, NP-571062.1, CAC44179.1, AAB97467.1, AAT99303.1, AAD28038.1, AAH52168.1, NP-001004122.1, CAA72733.1, NP-032133.2, XP-394252.1, XP-224733.2, JH0801, AAP97721.1, NP-989669.1, 543296, P43029, A55452, AAH32495.1, XP-542974.1, NP-032135.1, AAK30842.1, AAK27794.1, BAC30847.1, EAA12064.2, AAP97720.1, XP-525704.1, AAT07301.1, BAD07014.1, CAF94356.1, AAR27581.1, AAG13400.1, AAC60127.1, CAF92055.1, XP-540103.1, AA020895.1, CAF97447.1, AAS01764.1, BAD08319.1, CAA10268.1, NP-998140.1, AAR03824.1, AAS48405.1, AAS48403.1, AAK53545.1, AAK84666.1, XP-395420.1, AAK56941.1, AAC47555.1, AAR88255.1, EAL33036.1, AAW47740.1, AAW29442.1, NP-722813.1, AARO8901.1, AAO 15420.2, CAC59700.1, AAL26886.1, AAK71708.1, AAK71707.1, CAC51427.2, AAK67984.1, AAK67983.1, AAK28706.1, P07713, P91706, P91699, CAG02450.1, AAC47552.1, NP-005802.1, XP-343149.1, AW34055.1, XP-538221.1, AAR27580.1, XP-125935.3, AAF21633.1, AAF21630.1, AAD05267.1, Q9Z1 W4, NP-1-031585.2, NP-571094.1, CAD43439.1, CAF99217.1, CAB63584.1, NP-722840.1, CAE46407.1, XP-1-417667.1, BAC53989.1, BAB19659.1, AAM46922.1, AAA81169.1, AAK28707.1, AAL05943.1, AAB17573.1, CAH25443.1, CAG10269.1, BAD16731.1, EAA00276.2, AAT07320.1, AAT07300.1, AAN15037.1, CAH25442.1, AAK08152.2, 2009388A, AAR12161.1, CAGO1961.1, CAB63656.1, CAD67714.1, CAF94162.1, NP-477340.1, EAL24792.1, NP-1-001009428.1, AAB86686.1, AAT40572.1, AAT40571.1, AAT40569.1, NP-033886.1, AAB49985.1, AAG39266.1, Q26974, AAC77461.1, AAC47262.1, BAC05509.1, NP-055297.1, XP-546146.1, XP-525772.1, NP-060525.2, AAH33585.1, AAH69080.1, CAG12751.1, AAH74757.2, NP-034964.1, NP-038639.1, 042221, AAF02773.1, NP-062024.1, AAR18244.1, AAR14343.1, XP-228285.2, AAT40573.1, AAT94456.1, AAL35278.1, AAL35277.1, AAL17640.1, AAC08035.1, AAB86692.1, CAB40844.1, BAC38637.1, BAB16046.1, AAN63522.1, NP-571041.1, AAB04986.2, AAC26791.1, AAB95254.1, BAA11835.1, AAR18246.1, XP-538528.1, BAA31853.1, AAK18000.1, XP-1-420540.1, AAL35276.1, AAQ98602.1, CAE71944.1, AAW50585.1, AAV63982.1, AAW29941.1, AAN87890.1, AAT40568.1, CAD57730.1, AAB81508.1, AAS00534.1, AAC59736.1, BAB79498.1, AAA97392.1, AAP85526.1, NP-999600.2, NP-878293.1, BAC82629.1, CAC60268.1, CAG04919.1, AAN10123.1, CAA07707.1 AAK20912.1, AAR88254.1, CAC34629.1, AAL35275.1, AAD46997. I, AAN03842.1, NP-571951.2, CAC50881.1, AAL99367.1, AAL49502.1, AAB71839.1, AAB65415.1, NP-624359.1, NP-990153.1, AAF78069.1, AAK49790.1, NP-919367.2, NP-001192.1, XP-544948.1, AAQ18013.1, AAV38739.1, NP-851298.1, CAA67685.1, AAT67171.1, AAT37502.1, AAD27804.1, AAN76665.1, BAC11909.1, XP-1-421648.1, CAB63704.1, NP-037306.1, A55706, AAF02780.1, CAG09623.1, NP-067589.1, NP-035707.1, AAV30547.1, AAP49817.1, BAC77407.1, AAL87199.1, CAG07172.1, B36193, CAA33024.1, NP-1-001009400.1, AAP36538.1, XP-512687.1, XP-510080.1, AAH05513.1, 1KTZ, AAH14690.1, AAA31526.1.

The growth factor from the TGF-β superfamily in the methods and compositions provided herein can be naturally obtained or recombinant. In some embodiments, the growth factor from the TGF-β superfamily comprises Activin A. The term "Activin A" can include fragments and derivatives of Activin A. The sequence of an exemplary Activin A (SEQ ID NO: 1) is disclosed as SEQ ID NO: 1 in U.S. Pub. No. 2009/0155218 (the '218 publication). Other non-limiting examples of Activin A (SEQ ID NOS: 2-16) are provided in SEQ ID NO: 2-16 of the '218 publication, and non-limiting examples of nucleic acids encoding Activin A (SEQ ID NOS: 17-18) are provided in SEQ ID NO:33-34 of the '218 publication. In some embodiments, the growth factor from the TGF-β superfamily can comprise a polypeptide having an amino acid sequence at least 30%, at least 40%, at least 50%, at least 60%, at least 70%, at least 80%, at least 90%, at least 95%, or at least 99%, or greater identical to SEQ ID NO: 1 of the '218 publication (SEQ ID NO: 1).

In some embodiments, the growth factor from the TGF-β superfamily comprises growth differentiation factor 8 (GDF8). The term "GDF8" can include fragments and derivatives of GDF8. The sequences of GDF8 polypeptides are available to the skilled artisan. In some embodiments, the growth factor from the TGF-β superfamily comprises a polypeptide having an amino acid sequence at least 30%, at least 40%, at least 50%, at least 60%, at least 70%, at least 80%, at least 90%, at least 95%, or at least 99%, or greater identical to the human GDF8 polypeptide sequence (GenBank Accession EAX10880).

In some embodiments, the growth factor from the TGF-β superfamily comprises a growth factor that is closely related to GDF8, e.g., growth differentiation factor 11 (GDF11). In some embodiments, the growth factor from the TGF-β superfamily comprises a polypeptide having an amino acid sequence at least 30%, at least 40%, at least 50%, at least 60%, at least 70%, at least 80%, at least 90%, at least 95%, or at least 99%, or greater identical to the human GDF11 polypeptide sequence (GenBank Accession AAF21630).

In some embodiments, the growth factor from the TGF-β superfamily can be replaced with an agent mimics the at least one growth factor from the TGF-β superfamily. Exemplary agents that mimic the at least one growth factor from the TGF-β superfamily, include, without limitation, IDE1 and IDE2.

Bone Morphogenetic Protein (BMP) Signaling Pathway Inhibitors

Aspects of the disclosure relate to the use of BMP signaling pathway inhibitors as (3 cell differentiation factors. The BMP signaling family is a diverse subset of the TGF-β superfamily (Sebald et al. Biol. Chem. 385:697-710, 2004). Over twenty known BMP ligands are recognized by three distinct type II (BMPRII, ActRIIa, and ActRIIb) and at least three type I (ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR−) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner (Nohe et al. Cell Signal 16:291-299, 2004). Soluble BMP antagonists such as noggin, chordin, gremlin, and follistatin limit BMP signaling by ligand sequestration.

In some embodiments, the BMP signaling pathway inhibitor in the methods and composition provided herein comprises DMH-1, or a derivative, analogue, or variant thereof. In some embodiments, the BMP signaling pathway inhibitor in the methods and composition provided herein comprises the following compound or a derivative, analogue, or variant of the following compound:

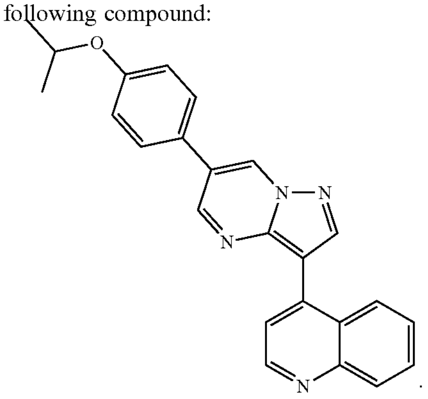

In some embodiments, the BMP signaling pathway inhibitor in the methods and composition provided herein comprises LDN193189 (also known as LDN193189, 1062368-24-4, LDN-193189, DM 3189, DM-3189, IUPAC Name: 4-[6-(4-piperazin-1-ylphenyl)pyrazolo[1,5-a]pyrimidin-3-yl]quinolone). In some embodiments, the BMP signaling pathway inhibitor in the methods and composition provided herein comprises the following compound or a derivative, analogue, or variant of the following compound:

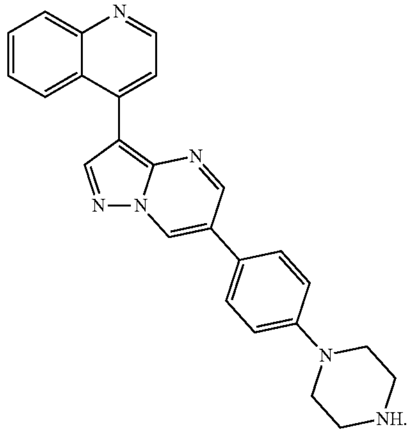 [SMILES: c1ccc2c(-c3cnn4cc(-c5ccc(N6CCNCC6)cc5)cnc34)ccnc2c1]

In some cases, DMH-1 can be more selective as compared to LDN193189. In some embodiments of the present disclosure, DMH-1 can be particularly useful for the methods provided herein. In some embodiments, the methods and compositions provided herein exclude use of LDN193189. In some embodiments, the methods and compositions provided herein exclude use of LDN193189, or a derivative, analogue, or variant thereof for generating Pdx1-positive pancreatic progenitor cells from primitive gut tube cells. In some embodiments, the methods and compositions provided herein relate to use of DMH-1, or a derivative, analogue, or variant thereof for generating Pdx1-positive pancreatic progenitor cells from primitive gut tube cells.

In some embodiments, the BMP signaling pathway inhibitor in the methods and composition provided herein comprise an analog or derivative of LDN193189, e.g., a salt, hydrate, solvent, ester, or prodrug of LDN193189. In some embodiments, a derivative (e.g., salt) of LDN193189 comprises LDN193189 hydrochloride.

In some embodiments, the BMP signaling pathway inhibitor in the methods and composition provided herein comprises a compound of Formula I from U.S. Patent Publication No. 2011/0053930.

TGF-β Signaling Pathway Inhibitors

Aspects of the disclosure relate to the use of TGF-β signaling pathway inhibitors as (3 cell differentiation factors.

In some embodiments, the TGF-β signaling pathway comprises TGF-β receptor type I kinase (TGF-β RI) signaling. In some embodiments, the TGF-β signaling pathway inhibitor comprises ALK5 inhibitor II (CAS 446859-33-2, an ATP-competitive inhibitor of TGF-B RI kinase, also known as RepSox, IUPAC Name: 2-[5-(6-methylpyridin-2-yl)-1H-pyrazol-4-yl]-1,5-naphthyridine. In some embodiments, the TGF-β signaling pathway inhibitor is an analog or derivative of ALK5 inhibitor II.

In some embodiments, the analog or derivative of ALK5 inhibitor II (also named "ALK5i") is a compound of Formula I as described in U.S. Patent Publication No. 2012/0021519, incorporated by reference herein in its entirety.

In some embodiments, the TGF-β signaling pathway inhibitor in the methods and compositions provided herein is a TGF-β receptor inhibitor described in U.S. Patent Publication No. 2010/0267731. In some embodiments, the TGF-β signaling pathway inhibitor in the methods and compositions provided herein comprises an ALK5 inhibitor described in U.S. Patent Publication Nos. 2009/0186076 and 2007/0142376. In some embodiments, the TGF-β signaling pathway inhibitor in the methods and compositions provided herein is A 83-01. In some embodiments, the TGF-β signaling pathway inhibitor in the methods and compositions provided herein is not A 83-01. In some embodiments, the compositions and methods described herein exclude A 83-01. In some embodiments, the TGF-β signaling pathway inhibitor in the methods and compositions provided herein is SB 431542. In some embodiments, the TGF-β signaling pathway inhibitor is not SB 431542. In some embodiments, the compositions and methods described herein exclude SB 431542. In some embodiments, the TGF-β signaling pathway inhibitor in the methods and compositions provided herein is D 4476. In some embodiments, the TGF-β signaling pathway inhibitor is not D 4476. In some embodiments, the compositions and methods described herein exclude D 4476. In some embodiments, the TGF-β signaling pathway inhibitor in the methods and compositions provided herein is GW 788388. In some embodiments, the TGF-β signaling pathway inhibitor is not GW 788388. In some embodiments, the compositions and methods described herein exclude GW 788388. In some embodiments, the TGF-β signaling pathway inhibitor in the methods and compositions provided herein is LY 364947. In some embodiments, the TGF-β signaling pathway inhibitor is not LY 364947. In some embodiments, the compositions and methods described herein exclude LY 364947. In some embodiments, the TGF-β signaling pathway inhibitor in the methods and compositions provided herein is LY 580276. In some embodiments, the TGF-β signaling pathway inhibitor is not LY 580276. In some embodiments, the compositions and methods described herein exclude LY 580276. In some embodiments, the TGF-β signaling pathway inhibitor in the methods and compositions provided herein is SB 525334. In some embodiments, the TGF-β signaling pathway inhibitor is not SB 525334. In some embodiments, the compositions and methods described herein exclude SB 525334. In some embodiments, the TGF-β signaling pathway inhibitor in the methods and compositions provided herein is SB 505124. In some embodiments, the TGF-β signaling pathway inhibitor is not SB 505124. In some embodiments, the compositions and methods described herein exclude SB 505124. In some embodiments, the TGF-β signaling pathway inhibitor in the methods and compositions provided herein is SD 208. In some embodiments, the TGF-β signaling pathway inhibitor is not SD 208. In some embodiments, the compositions and methods described herein exclude SD 208. In some embodiments, the TGF-β signaling pathway inhibitor in the methods and compositions provided herein is GW 6604. In some embodiments, the TGF-β signaling pathway inhibitor is not GW 6604. In some embodiments, the compositions and methods described herein exclude GW 6604. In some embodiments, the TGF-β signaling pathway inhibitor in the methods and compositions provided herein is GW 788388. In some embodiments, the TGF-β signaling pathway inhibitor in the methods and compositions provided herein is not GW 788388. In some embodiments, the compositions and methods described herein exclude GW 788388.

From the collection of compounds described above, the following can be obtained from various sources: LY-364947, SB-525334, SD-208, and SB-505124 available from Sigma, P.O. Box 14508, St. Louis, Mo., 63178-9916; 616452 and 616453 available from Calbiochem (EMD Chemicals, Inc.), 480 S. Democrat Road, Gibbstown, N.J., 08027; GW788388 and GW6604 available from GlaxoSmithKline, 980 Great West Road, Brentford, Middlesex, TW8 9GS, United Kingdom; LY580276 available from Lilly Research, Indianapolis, Ind. 46285; and SM16 available from Biogen Idec, P.O. Box 14627, 5000 Davis Drive, Research Triangle Park, N.C., 27709-4627.

WNT Signaling Pathway

Aspects of the disclosure relate to the use of activators of the WNT signaling pathway as β cell differentiation factors.

In some embodiments, the WNT signaling pathway activator in the methods and compositions provided herein comprises CHIR99021. In some embodiments, the WNT signaling pathway activator in the methods and compositions provided herein comprises a derivative of CHIR99021, e.g., a salt of CHIR99021, e.g., trihydrochloride, a hydrochloride salt of CHIR99021. In some embodiments, the WNT signaling pathway activator in the methods and compositions provided herein comprises Wnt3a recombinant protein. In some embodiments, the WNT signaling pathway activator in the methods and compositions provided herein comprises a glycogen synthase kinase 3 (GSK3) inhibitor. Exemplary GSK3 inhibitors include, without limitation, 3F8, A 1070722, AR-A 014418, BIO, BIO-acetoxime, FRATide, 10Z-Hymenialdisine, Indirubin-3' oxime, kenpaullone, L803, L803-mts, lithium carbonate, NSC 693868, SB 216763, SB 415286, TC-G 24, TCS 2002, TCS 21311, TWS 119, and analogs or derivatives of any of these. In certain embodiments, the methods, compositions, and kits disclosed herein exclude a WNT signaling pathway activator.

Fibroblast Growth Factor (FGF) Family

Aspects of the disclosure relate to the use of growth factors from the FGF family as 13 cell differentiation factors.

In some embodiments, the growth factor from the FGF family in the methods and compositions provided herein comprises keratinocyte growth factor (KGF). The polypeptide sequences of KGF are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human KGF polypeptide sequence (GenBank Accession AAB21431).

In some embodiments, the growth factor from the FGF family in the methods and composition provided herein comprises FGF2. The polypeptide sequences of FGF2 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF2 polypeptide sequence (GenBank Accession NP-001997).

In some embodiments, the at least one growth factor from the FGF family in the methods and composition provided herein comprises FGF8B. The polypeptide sequences of FGF8B are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF8B polypeptide sequence (GenBank Accession AAB40954).

In some embodiments, the at least one growth factor from the FGF family in the methods and composition provided herein comprises FGF10. The polypeptide sequences of FGF10 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF10 polypeptide sequence (GenBank Accession CAG46489).

In some embodiments, the at least one growth factor from the FGF family in the methods and composition provided herein comprises FGF21. The polypeptide sequences of FGF21 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF21 polypeptide sequence (GenBank Accession AAQ89444.1).

Sonic Hedgehog (SHH) Signaling Pathway

Aspects of the disclosure relate to the use of SHH signaling pathway inhibitors as 13 cell differentiation factors.

In some embodiments, the SHH signaling pathway inhibitor in the methods and composition provided herein comprises Sant1. In some embodiments, the SHH signaling pathway inhibitor in the methods and composition provided herein comprises SANT2. In some embodiments, the SHH signaling pathway inhibitor in the methods and composition provided herein comprises SANT3. In some embodiments, the SHH signaling pathway inhibitor in the methods and composition provided herein comprises SANT4. In some embodiments, the SHH signaling pathway inhibitor comprises Cur61414. In some embodiments, the SHH signaling pathway inhibitor in the methods and composition provided herein comprises forskolin. In some embodiments, the SHH signaling pathway inhibitor in the methods and composition provided herein comprises tomatidine. In some embodiments, the SHH signaling pathway inhibitor in the methods and composition provided herein comprises AY9944. In some embodiments, the SHH signaling pathway inhibitor in the methods and composition provided herein comprises triparanol. In some embodiments, the SHH signaling pathway inhibitor in the methods and composition provided herein comprises compound A or compound B (as disclosed in U.S. Pub. No. 2004/0060568). In some embodiments, the SHH signaling pathway inhibitor in the methods and composition provided herein comprises a steroidal alkaloid that antagonizes hedgehog signaling (e.g., cyclopamine or a derivative thereof) as disclosed in U.S. Pub. No. 2006/0276391. In certain embodiments, the methods, compositions, and kits disclosed herein exclude a SHH signaling pathway inhibitor.

Rho Kinase (ROCK) Signaling Pathway

Aspects of the disclosure relate to the use of ROCK signaling pathway inhibitors (ROCK inhibitors) as β cell differentiation factors.

In some embodiments, the ROCK inhibitor in the methods and composition provided herein comprises Y-27632 or Thiazovivin. In some embodiments, the ROCK inhibitor in the methods and composition provided herein comprises Thiazovivin. In some embodiments, the ROCK inhibitor in the methods and composition provided herein comprises Y-27632. In some cases, the ROCK inhibitor in the methods and composition provided herein comprises the following compound or a derivative thereof:

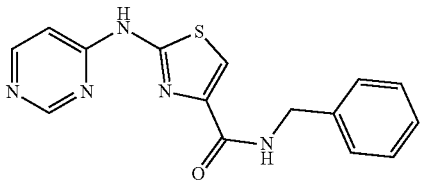 [SMILES: O=C(NCc1ccccc1)c1csc(Nc2ccncn2)n1]

In some cases, the ROCK inhibitor in the methods and composition provided herein comprises the following compound or a derivative thereof:

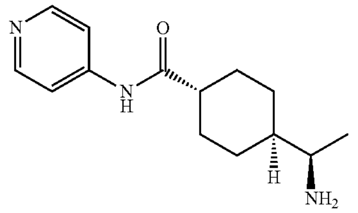 [SMILES: C[C@@H](N)[C@H]1CC[C@H](C(=O)Nc2ccncc2)CC1]

Non-limiting examples of ROCK inhibitor that can be used in the methods and compositions provided herein include Thiazovivin, Y-27632, Fasudil/HA1077, H-1152, Ripasudil, Y39983, Wf-536, SLx-2119, Azabenzimidazole-aminofurazans, DE-104, Olefins, Isoquinolines, Indazoles, and pyridinealkene derivatives, ROKa inhibitor, XD-4000, HMN-1152, 4-(1-aminoalkyl)-N-(4-pyridyl)cyclohexane-carboxamides, Rhostatin, BA-210, BA-207, BA-215, BA-285, BA-1037, Ki-23095, VAS-012, and quinazoline.

Retinoic Acid Signaling Pathway

Aspects of the disclosure relate to the use of modulators of retinoic acid signaling as 13 cell differentiation factors.

In some embodiments, the modulator of retinoic acid signaling in the methods and composition provided herein comprises an activator of retinoic acid signaling. In some embodiments, the RA signaling pathway activator in the methods and composition provided herein comprises retinoic acid. In some embodiments, the RA signaling pathway activator in the methods and composition provided herein comprises a retinoic acid receptor agonist. Exemplary retinoic acid receptor agonists in the methods and composition provided herein include, without limitation, CD 1530, AM 580, TTNPB, CD 437, Ch 55, BMS 961, AC 261066, AC 55649, AM 80, BMS 753, tazarotene, adapalene, and CD 2314.

In some embodiments, the modulator of retinoic acid signaling in the methods and composition provided herein comprises an inhibitor of retinoic acid signaling. In some embodiments, the retinoic acid signaling pathway inhibitor comprises DEAB (IUPAC Name: 2-[2-(diethylamino) ethoxy]-3-prop-2-enylbenzaldehyde). In some embodiments, the retinoic acid signaling pathway inhibitor comprises an analog or derivative of DEAB.

In some embodiments, the retinoic acid signaling pathway inhibitor in the methods and composition provided herein comprises a retinoic acid receptor antagonist. In some embodiments, the retinoic acid receptor antagonist in the methods and composition provided herein comprises (E)-4-[2-(5,6-dihydro-5,5-dimethyl-8-phenyl-2-naphthalenyl) ethenyl]benzoic acid, (E)-4-[[(5,6-dihydro-5,5-dimethyl-8-phenylethynyl)-2-naphthalenyl]ethenyl]benzoic acid, (E)-4-[2-[5,6-dihydro-5,5-dimethyl-8-(2-naphthalenyl)-2-naphthalenyl]ethenyl]-benzoic acid, and (E)-4-[2-[5,6-dihydro-5,5-dimethyl-8-(4-methoxyphenyl)-2-naphthalenyl]ethenyl]benzoic acid. In some embodiments, the retinoic acid receptor antagonist comprises BMS 195614 (CAS #253310-42-8), ER 50891 (CAS #187400-85-7), BMS 493 (CAS #170355-78-9), CD 2665 (CAS #170355-78-9), LE 135 (CAS #155877-83-1), BMS 453 (CAS #166977-43-1), or MM 11253 (CAS #345952-44-5).

In certain embodiments, the methods, compositions, and kits disclosed herein exclude a modulator of retinoic acid signaling. In certain embodiments, the methods, compositions, and kits disclosed herein exclude a retinoic acid signaling pathway activator. In certain embodiments, the methods, compositions, and kits disclosed herein exclude a retinoic acid signaling pathway inhibitor.

Protein Kinase C

Aspects of the disclosure relate to the use of protein kinase C activators as β cell differentiation factors. Protein kinase C is one of the largest families of protein kinase enzymes and is composed of a variety of isoforms. Conventional isoforms include a, βI, βII, γ; novel isoforms include δ, ε, η, Θ; and atypical isoforms include ξ and ι/λ PKC enzymes are primarily cytosolic but translocate to the membrane when activated. In the cytoplasm, PKC is phosphorylated by other kinases or autophosphorylates. In order to be activated, some PKC isoforms (e.g., PKC-ε) require a molecule to bind to the diacylglycerol ("DAG") binding site or the phosphatidylserine ("PS") binding site. Others are able to be activated without any secondary binding messengers at all. PKC activators that bind to the DAG site include, but are not limited to, bryostatin, picologues, phorbol esters, aplysiatoxin, and gnidimacrin. PKC activators that bind to the PS site include, but are not limited to, polyunsaturated fatty acids and their derivatives. It is contemplated that any protein kinase C activator that is capable, either alone or in combination with one or more other β cell differentiation factors, of inducing the differentiation of at least one insulin-producing, endocrine cell or precursor thereof into a SC-β cell can be used in the methods, compositions, and kits described herein.

In some embodiments, the PKC activator in the methods and composition provided herein comprises PdbU. In some embodiments, the PKC activator in the methods and composition provided herein comprises TPB. In some embodiments, the PKC activator in the methods and composition provided herein comprises cyclopropanated polyunsaturated fatty acids, cyclopropanated monounsaturated fatty acids, cyclopropanated polyunsaturated fatty alcohols, cyclopropanated monounsaturated fatty alcohols, cyclopropanated polyunsaturated fatty acid esters, cyclopropanated monounsaturated fatty acid esters, cyclopropanated polyunsaturated fatty acid sulfates, cyclopropanated monounsaturated fatty acid sulfates, cyclopropanated polyunsaturated fatty acid phosphates, cyclopropanated monounsaturated fatty acid phosphates, macrocyclic lactones, DAG derivatives, isoprenoids, octylindolactam V, gnidimacrin, iripallidal, ingenol, napthalenesulfonamides, diacylglycerol kinase inhibitors, fibroblast growth factor 18 (FGF-18), insulin growth factor, hormones, and growth factor activators, as described in WIPO Pub. No. WO/2013/071282. In some embodiments, the bryostain comprises bryostatin-1, bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, or bryostatin-18. In certain embodiments, the methods, compositions, and kits disclosed herein exclude a protein kinase C activator.

γ-Secretase Inhibitors

Aspects of the disclosure relate to the use of γ-secretase inhibitors as β cell differentiation factors.

In some embodiments, the γ-secretase inhibitor in the methods and composition provided herein comprises XXI. In some embodiments, the γ-secretase inhibitor in the methods and composition provided herein comprises DAPT. Additional exemplary γ-secretase inhibitors in the methods and composition provided herein include, without limitation, the γ-secretase inhibitors described in U.S. Pat. Nos. 7,049,296, 8,481,499, 8,501,813, and WIPO Pub. No. WO/2013/052700. In certain embodiments, the methods, compositions, and kits disclosed herein exclude a γ-secretase inhibitor.

Thyroid Hormone Signaling Pathway Activators

Aspects of the disclosure relate to the use of thyroid hormone signaling pathway activators as β cell differentiation factors.

In some embodiments, the thyroid hormone signaling pathway activator in the methods and composition provided herein comprises triiodothyronine (T3). In some embodiments, the thyroid hormone signaling pathway activator in the methods and composition provided herein comprises GC-1. In some embodiments, the thyroid hormone signaling pathway activator in the methods and composition provided herein comprises an analog or derivative of T3 or GC-1. Exemplary analogs of T3 in the methods and composition provided herein include, but are not limited to, selective and non-selective thyromimetics, TRβ selective agonist-GC-1, GC-24, 4-Hydroxy-PCB 106, MB07811, MB07344,3,5-diiodothyropropionic acid (DITPA); the selective TR-0 agonist GC-1; 3-Iodothyronamine (T(1)AM) and 3,3',5-triiodothyroacetic acid (Triac) (bioactive metabolites of the hormone thyroxine (T(4)); KB-2115 and KB-141; thyronamines; SKF L-94901; DIBIT; 3'-AC-T2; tetraiodothyroacetic acid (Tetrac) and triiodothyroacetic acid (Triac) (via oxidative deamination and decarboxylation of thyroxine [T4] and triiodothyronine [T3] alanine chain), 3,3',5'-triiodothyronine (rT3) (via T4 and T3 deiodination), 3,3'-diiodothyronine (3,3'-T2) and 3,5-diiodothyronine (T2) (via T4, T3, and rT3 deiodination), and 3-iodothyronamine (T1AM) and thyronamine (TOAM) (via T4 and T3 deiodination and amino acid decarboxylation), as well as for TH structural analogs, such as 3,5,3'-triiodothyropropionic acid (Triprop), 3,5-dibromo-3-pyridazinone-1-thyronine (L-940901), N-[3,5-dimethyl-4-(4'-hydroxy-3'-isopropylphenoxy)-phenyl]-oxamic acid (CGS 23425), 3,5-dimethyl-4-[(4'-hydroxy-3'-isopropylbenzyl)-phenoxy]acetic acid (GC-1), 3,5-dichloro-4-[(4-hydroxy-3-isopropylphenoxy)phenyl]acetic acid (KB-141), and 3,5-diiodothyropropionic acid (DITPA).

In some embodiments, the thyroid hormone signaling pathway activator in the methods and composition provided herein comprises a prodrug or prohormone of T3, such as T4 thyroid hormone (e.g., thyroxine or L-3,5,3',5'-tetraiodothyronine).

In some embodiments, the thyroid hormone signaling pathway activator in the methods and composition provided herein is an iodothyronine composition described in U.S. Pat. No. 7,163,918.

Epidermal Growth Factor (EGF) Family

Aspects of the disclosure relate to the use of growth factors from the EGF family as β cell differentiation factors.

In some embodiments, the at least one growth factor from the EGF family in the methods and composition provided herein comprises betacellulin. In some embodiments, at least one growth factor from the EGF family in the methods and composition provided herein comprises EGF. Epidermal growth factor (EGF) is a 53 amino acid cytokine which is proteolytically cleaved from a large integral membrane protein precursor. In some embodiments, the growth factor from the EGF family in the methods and composition provided herein comprises a variant EGF polypeptide, for example an isolated epidermal growth factor polypeptide having at least 90% amino acid identity to the human wild-type EGF polypeptide sequence, as disclosed in U.S. Pat. No. 7,084,246. In some embodiments, the growth factor from the EGF family in the methods and composition provided herein comprises an engineered EGF mutant that binds to and agonizes the EGF receptor, as is disclosed in U.S. Pat. No. 8,247,531. In some embodiments, the at least one growth factor from the EGF family in the methods and composition provided herein is replaced with an agent that activates a signaling pathway in the EGF family. In some embodiments, the growth factor from the EGF family in the methods and composition provided herein comprises a compound that mimics EGF. In certain embodiments, the methods, compositions, and kits disclosed herein exclude a growth factor from the EGF family.

Protein Kinase Inhibitors

Aspects of the disclosure relate to the use of protein kinase inhibitors as β cell differentiation factors.

In some embodiments, the protein kinase inhibitor in the methods and composition provided herein comprises staurosporine. In some embodiments, the protein kinase inhibitor in the methods and composition provided herein comprises an analog of staurosporine. Exemplary analogs of staurosporine in the methods and composition provided herein include, without limitation, Ro-31-8220, a bisindolylmaleimide (Bis) compound, 10'-{5"-[(methoxycarbonyl) amino]-2"-methyl}-phenylaminocarbonylstaurosporine, a staralog (see, e.g., Lopez et al., "Staurosporine-derived inhibitors broaden the scope of analog-sensitive kinase technology", *J. Am. Chem. Soc.* 2013; 135(48):18153-18159), and, cgp41251.

In some embodiments, the protein kinase inhibitor in the methods and composition provided herein is an inhibitor of PKCβ. In some embodiments, the protein kinase inhibitor in the methods and composition provided herein is an inhibitor of PKCβ with the following structure or a derivative, analogue or variant of the compound as follows:

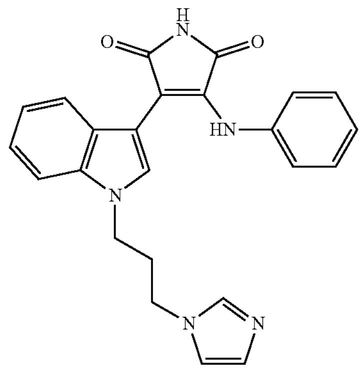 [SMILES: O=C1NC(=O)C(c2cn(CCCn3ccnc3)c3ccccc23)=C1Nc1ccccc1]

In some embodiments, the inhibitor of PKCβ is a GSK-2 compound with the following structure or a derivative, analogue or variant of the compound as follows:

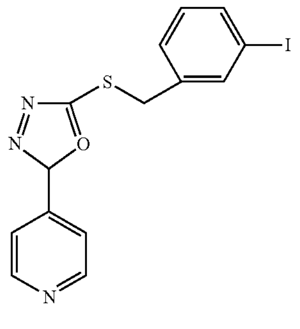

In some embodiments, the inhibitor of PKC in the methods and composition provided herein is a bisindolylmaleimide. Exemplary bisindolylmaleimides include, without limitation, bisindolylmaleimide I, bisindolylmaleimide II, bisindolylmaleimide Ill, hydrochloride, or a derivative, analogue or variant thereof.

In some embodiments, the PKC inhibitor in the methods and composition provided herein is a pseudohypericin, or a derivative, analogue, or variant thereof. In some embodiments, the PKC inhibitor in the methods and composition provided herein is indorublin-3-monoximc, 5-lodo or a derivative, analogue or variant thereof. In certain embodiments, the methods, compositions, and kits disclosed herein exclude a protein kinase inhibitor.

VII. SC-β Cells

The SC-β cells of the disclosure share many characteristic features of β cells which are important for normal β cell function. In some embodiments, the SC-β cell exhibits a glucose stimulated insulin secretion (GSIS) response in vitro. In some embodiments, the SC-β cell exhibits a GSIS response in vivo. In some embodiments, the SC-β cell exhibits in vitro and in vivo GSIS responses. In some embodiments, the GSIS responses resemble the GSIS responses of an endogenous mature pancreatic β cell. In some embodiments, the SC-β cell exhibits a GSIS response to at least one glucose challenge. In some embodiments, the SC-β cell exhibits a GSIS response to at least two sequential glucose challenges. In some embodiments, the SC-β cell exhibits a GSIS response to at least three sequential glucose challenges. In some embodiments, the GSIS responses resemble the GSIS response of endogenous human islets to multiple glucose challenges. In some embodiments, the GSIS response is observed immediately upon transplanting the cell into a human or animal. In some embodiments, the GSIS response is observed within approximately 24 hours of transplanting the cell into a human or animal. In some embodiments, the GSIS response is observed within approximately one week of transplanting the cell into a human or animal. In some embodiments, the GSIS response is observed within approximately two weeks of transplanting the cell into a human or animal. In some embodiments, the stimulation index of the cell as characterized by the ratio of insulin secreted in response to high glucose concentrations compared to low glucose concentrations is similar to the stimulation index of an endogenous mature pancreatic β cell. In some embodiments, the SC-β cell exhibits a stimulation index of greater than 1. In some embodiments, the SC-β cell exhibits a stimulation index of greater than or equal to 1. In some embodiments, the SC-β cell exhibits a stimulation index of greater than 1.1. In some embodiments, the SC-β cell exhibits a stimulation index of greater than or equal to 1.1. In some embodiments, the SC-β cell exhibits a stimulation index of greater than 2. In some embodiments, the SC-β cell exhibits a stimulation index of greater than or equal to 1. In some embodiments, the SC-β cell exhibits a stimulation index of at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 or greater.

Some embodiments of the present disclosure relate to cell compositions, such as cell cultures or cell populations, comprising SC-β cells, wherein the SC-β cells have been derived from at least one insulin-positive endocrine cell or a precursor thereof. In some embodiments, the cell compositions comprise insulin-positive endocrine cells. In some embodiments, the cell compositions comprise NKX6.1-pancreatic progenitor cells. In some embodiments, the cell compositions comprise PDX1-pancreatic progenitor cells. In some embodiments, the cell compositions comprise primitive gut tube cells. In some embodiments, the cell compositions comprise definitive endoderm cells.

In accordance with certain embodiments, the chemically induced SC-β cells are mammalian cells, and in a preferred embodiment, such SC-β cells are human SC-β cells. In some embodiments, the insulin-positive endocrine cells have been derived from definitive endoderm cells e.g. human definitive endoderm stem cells. In accordance with certain embodiments, the chemically induced PDX1-positive pancreatic progenitors are mammalian cells, and in a preferred embodiment, such PDX1-positive pancreatic progenitors are human PDX1-positive pancreatic progenitors.

Other embodiments of the present disclosure relate to compositions, such as an isolated cell population or cell culture, comprising SC-β cells produced by the methods as disclosed herein. In some embodiments of the present disclosure relate to compositions, such as isolated cell populations or cell cultures, comprising chemically-induced SC-β cells produced by the methods as disclosed herein. In such embodiments, the SC-β cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the SC-β cells population. In some embodiments, the composition comprises a population of SC-β cells which make up more than about 90% of the total cells in the cell population, for example about at least 95%, or at least 96%, or at least 97%, or at least 98% or at least about 99%, or about at least 100% of the total cells in the cell population are SC-β cells.

Certain other embodiments of the present disclosure relate to compositions, such as an isolated cell population or cell cultures, comprise a combination of SC-β cells and insulin-positive endocrine cells or precursors thereof from which the SC-β cells were derived. In some embodiments, the insulin-positive endocrine cells from which the SC-β cells are derived comprise less than about 25%, less than about 20%, less than about 15%, less than about 10%, less than about 5%, less than about 4%, less than about 3%, less than about 2% or less than about 1% of the total cells in the isolated cell population or culture.

Additional embodiments of the present disclosure relate to compositions, such as isolated cell populations or cell cultures, produced by the processes described herein and which comprise chemically induced SC-β cells as the majority cell type. In some embodiments, the methods and processes described herein produces an isolated cell culture and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% SC-β cells.

In another embodiment, isolated cell populations or compositions of cells (or cell cultures) comprise human SC-β cells. In other embodiments, the methods and processes as described herein can produce isolated cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% SC-β cells. In preferred embodiments, isolated cell populations can comprise human SC-β cells. In some embodiments, the percentage of SC-β cells in the cell cultures or populations is calculated without regard to the feeder cells remaining in the culture.

Yet another aspect of the present disclosure relates to cell populations or compositions of cells (or cell cultures) that comprise at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% NKX6.1$^+$/C-peptide$^+$ cells. In some embodiments, the cell population or composition of cells as provided herein comprises at least about 20% NKX6.1$^+$/C-peptide$^+$ cells. In some embodiments, the cell population or composition of cells as provided herein comprises at least about 40% NKX6.1$^+$/C-peptide$^+$ cells. In some embodiments, the cell population or composition of cells as provided herein comprises at least about 50% NKX6.1$^+$/C-peptide$^+$ cells. In some embodiments, the cell population or composition of cells as provided herein comprises about 17.9% NKX6.1$^+$/C-peptide$^+$ cells. In some embodiments, the cell population or composition of cells as provided herein comprises about 41.5% NKX6.1$^+$/C-peptide$^+$ cells. In some embodiments, the cell population or composition of cells as provided herein comprises about 50.6% NKX6.1$^+$/C-peptide$^+$ cells.

In some embodiments, the cell population or composition of cells as provided herein comprises at least about 90%, at least about 89%, at least about 88%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% NKX6.1$^+$ cells. In some embodiments, the cell population or composition of cells as provided herein comprises at least about 40% NKX6.1$^+$ cells. In some embodiments, the cell population or composition of cells as provided herein comprises at least about 60% NKX6.1$^+$ cells. In some embodiments, the cell population or composition of cells as provided herein comprises at least about 85% NKX6.1$^+$ cells. In some embodiments, the cell population or composition of cells as provided herein comprises about 36.9% NKX6.1+ cells. In some embodiments, the cell population or composition of cells as provided herein comprises about 63.4% NKX6.1$^+$ cells. In some embodiments, the cell population or composition of cells as provided herein comprises about 89.5% NKX6.1$^+$ cells.

In some embodiments, the cell population or composition of cells as provided herein comprises at least about 55%, at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% C-peptide cells. In some embodiments, the cell population or composition of cells as provided herein comprises at least about 30% C-peptide cells. In some embodiments, the cell population or composition of cells as provided herein comprises at least about 55% C-peptide cells. In some embodiments, the cell population or composition of cells as provided herein comprises about 26.8% C-peptide cells. In some embodiments, the cell population or composition of cells as provided herein comprises about 57.7% C-peptide$^+$ cells. In some embodiments, the cell population or composition of cells as provided herein comprises about 55.2% C-peptide cells.

In some embodiments, the cell population or composition of cells as provided herein comprises at least about 99%, at least about 98%, at least about 95%, at least about 90%, at least about 89%, at least about 88%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% Chromogranin A (CHGA)$^+$ cells. In some embodiments, the cell population or composition of cells as provided herein comprises at least about 40% CHGA$^+$ cells. In some embodiments, the cell population or composition of cells as provided herein comprises at least about 85% CHGA$^+$ cells. In some embodiments, the cell population or composition of cells as provided herein comprises at least about 95% CHGA$^+$ cells. In some embodiments, the cell population or composition of cells as provided herein comprises about 37.7% CHGA$^+$ cells. In some embodiments, the cell population or composition of cells as provided herein comprises about 87.5% CHGA$^+$ cells. In some embodiments, the cell population or composition of cells as provided herein comprises about 96.4% CHGA$^+$ cells.

Still other embodiments of the present disclosure relate to compositions, such as isolated cell populations or cell cultures, comprising mixtures of SC-β cells and insulin-positive endocrine cells or precursors thereof from which they were differentiated from. For example, cell cultures or cell populations comprising at least about 5 SC-β cells for about every 95 insulin-positive endocrine cells or precursors thereof can be produced. In other embodiments, cell cultures or cell populations comprising at least about 95 SC-β cells for about every 5 insulin-positive endocrine cells or precursors thereof can be produced. Additionally, cell cultures or cell populations comprising other ratios of SC-β cells to insulin-positive endocrine cells or precursors thereof are contemplated. For example, compositions comprising at least about 1 SC-β cell for about every 1,000,000, or at least 100,000 cells, or at least 10,000 cells, or at least 1000 cells or 500, or at least 250 or at least 100 or at least 10 insulin-positive endocrine cells or precursors thereof can be produced.

In some aspects, the present disclosure provides a cell cluster comprising at least about 50% Pdx1-positive, NKX6.1-positive pancreatic progenitor cells, at most about 30%, 28%, 26%, 25%, 24%, 22%, 20%, 18%, 16%, 14%, 12%, 10%, 9%, 8%, 7%, 6%, 5%, 4%, 3%, or 2% chromogranin A (CHGA)-positive cells, and at most about 30%, 28%, 26%, 25%, 24%, 22%, 20%, 18%, 16%, or 15% CDX2-positive cells. In some cases, the cell cluster comprises at most about 20% the CDX2-positive, NKX6.1-positive cells. In some cases, the cell cluster comprises at most about 5% the CHGA-positive cells. In some embodiments, the cell cluster comprises at most about 20% the CDX2-positive, NKX6.1-positive cells and at most about 5% the CHGA-positive cells. In some embodiments, the cell cluster comprises at least about 60%, 62%, 64%, 65%, 68%, 70%, 72%, 74%, 76%, 78%, 80%, 82%, 84%, 86%, 88%, 90%, 92%, or 95% the Pdx1-positive, NKX6.1-positive pancreatic progenitor cells. In some embodiments, the cell cluster comprises at least about 65% the Pdx1-positive, NKX6.1-positive pancreatic progenitor cells.

In some embodiments, the cell cluster comprising at least about 50% Pdx1-positive, NKX6.1-positive pancreatic progenitor cells, at most about 30% chromogranin A (CHGA)-positive cells, and at most about 30% CDX2-positive cells can have particular functional features as compared to a comparable cell cluster having more than about 30% chromogranin A (CHGA)-positive cells or more than about 30% CDX2-positive cells. For instance, in some cases, further differentiation of the cell cluster comprising at least about 50% Pdx1-positive, NKX6.1-positive pancreatic progenitor cells, at most about 30% chromogranin A (CHGA)-positive cells, and at most about 30% CDX2-positive cells results in a first cell cluster comprising non-native pancreatic β cells that has a higher glucose-stimulated insulin secretion (GSIS) stimulation index than a second cell cluster comprising the non-native pancreatic β cells differentiated from a comparable cell cluster comprising at least about 50% the Pdx1-positive, NKX6.1-positive pancreatic progenitor cells, and more than 30% the chromogranin A (CHGA)-positive cells or more than 30% the CDX2-positive cells as measured by flow cytometry.

In some aspects, the present disclosure provides a cell cluster comprising at least about 60%, 62%, 64%, 65%, 68%, 70%, 72%, 74%, 76%, 78%, 80%, 82%, 84%, 86%, 88%, or 90% Pdx1-positive, NKX6.1-negative pancreatic progenitor cells and at most about 40%, 38%, 36%, 34%, 32%, 30%, 28%, 26%, 25%, 24%, 22%, 20%, 18%, 16%, 15%, 14%, 12%, or 10% CDX2-positive cells. In some embodiments, the cell cluster comprises at least about 85% the Pdx1-positive, NKX6.1-negative pancreatic progenitor cells. In some embodiments, the cell cluster comprises at most about 15% the CDX2-positive cells. In some cases, the cell cluster comprises at least about 85% the Pdx1-positive, NKX6.1-negative pancreatic progenitor cells and at most about 15% the CDX2-positive cells.

In some embodiments, the cell cluster comprising at least about 60% Pdx1-positive, NKX6.1-negative pancreatic progenitor cells and at most about 40% CDX2-positive cells can have particular functional features as compared to a comparable cell cluster having more than about 40% CDX2-positive cells. For instance, in some cases, further differentiation of the cell cluster comprising at least about 60% Pdx1-positive, NKX6.1-negative pancreatic progenitor cells and at most about 40% CDX2-positive cells results in a first cell cluster comprising non-native pancreatic β cells that has a higher glucose-stimulated insulin secretion (GSIS) stimulation index than a second cell cluster comprising the non-native pancreatic β cells differentiated from a comparable cell cluster comprising at least about 60% Pdx1-positive, NKX6.1-negative pancreatic progenitor cells and more than 40% the CDX2-positive cells as measured by flow cytometry.

In some aspects, the present disclosure provides a cell cluster comprising non-native pancreatic β cells. In some embodiments, the cell cluster disclosed herein is obtained from differentiation of primitive gut tube cells by contacting the primitive gut tube cells with a bone morphogenetic protein (BMP) signaling pathway inhibitor and a growth factor from transformation growth factor 13 (TGF-β) superfamily. In some embodiments, the cell cluster has a higher number of the non-native pancreatic β cells per cubic micrometer as compared to a comparable second cell cluster obtained from differentiation of primitive gut tube cells without the contacting. In some embodiments, cell cluster has an at least about 1.1, 1.2, 1.3, 1.4, 1.5, or 1.6 fold higher number of the non-native pancreatic β cells per cubic micrometer as compared to the comparable second cell cluster.

In some cases, the cell cluster comprising non-native pancreatic β cells disclosed herein exhibits higher insulin secretion in response to glucose challenge as compared to a comparable cell cluster obtained from differentiation of primitive gut tube cells without contacting with BMP signaling pathway inhibitor or growth factor from TGF-β family. In some embodiments, the cell cluster exhibits at least about 1.2, 1.5, 2, 2.5, 3, 3.5, 4, 4.5, or 5 fold higher an insulin secretion as compared to the comparable second cell cluster. In some embodiments, the cell cluster exhibits a higher GSIS stimulation index as compared to the comparable second cell cluster. In some embodiments, the GSIS stimulation index of the cell cluster is at least about 1.2 fold, at least about 1.5 fold, at least about 1.8 fold, at least about 2 fold, at least about 2.2 fold, at least about 2.4 fold, at least about 2.8 fold, or at least about 3 fold higher than that of the second cell cluster. In some embodiments, GSIS stimulation index of the cell cluster is at least about 3 fold higher than that of the second population. In some embodiments, GSIS stimulation index is calculated as a ratio of insulin secretion in response to 20 mM glucose challenge to insulin secretion in response to 2 mM glucose challenge. In some embodiments, the non-native pancreatic β cells exhibit an in vitro glucose-stimulated insulin secretion response when exposed to a glucose challenge. In some cases, non-native pancreatic 13 cells exhibit an insulin secretion in response to a first concentration of $K^+$. In some embodiments, the cell cluster exhibits a higher insulin secretion as compared to the comparable second cell cluster in response to a first concentration of $K^+$. In some embodiments, cell cluster exhibits at least about 1.2 fold, at least about 1.5 fold, at least about 1.8 fold, at least about 2 fold, at least about 2.2 fold, at least about 2.4 fold, at least about 2.8 fold, at least about 3 fold, at least about 3.2 fold, at least about 3.4 fold, at least about 3.6 fold, at least about 3.8 fold, at least about 4 fold higher an insulin secretion as compared to the comparable second cell cluster in response to a first concentration of $K^+$.

In some cases, cell populations or cell clusters disclosed herein are unsorted, e.g., isolated cell populations or cell clusters that have not been through cell sorting process. In some embodiments, the cell cluster disclosed herein can refer to a cell cluster formed by self-aggregation of cells cultured in a given environment, for instance, in a 3D suspension culture. In some embodiments, cell clusters disclosed herein are intermediate cell clusters formed during the differentiation process as described herein. In some cases, the intermediate cell clusters, e.g., cell clusters comprising Pdx1-positive, NKX6.1-negative pancreatic progenitor cells (e.g., Stage 3 cell clusters) or cell clusters comprising Pdx1-positive, NKX6.1-positive pancreatic progenitor cells (e.g., Stage 4 cell clusters), are not subjected to cell sorting. In some case, cell populations going through cell sorting may not be able to form the intermediate cell clusters disclosed herein. For instance, Pdx1-positive pancreatic progenitor cells, after going through cell sorting, may not be able to form a cell cluster as disclosed herein.

Cell sorting as described herein can refer to a process of isolating a group of cells from a plurality of cells by relying on differences in cell size, shape (morphology), surface protein expression, endogenous signal protein expression, or any combination thereof. In some cases, cell sorting comprises subjecting the cells to flow cytometry. Flow cytometry can be a laser- or impedance-based, biophysical technology. During flow cytometry, one can suspend cells in a stream of fluid and pass them through an electronic detection apparatus. In one type of flow cytometry, fluorescent-activated cell sorting (FACS), based on one or more parameters of the cells' optical properties (e.g., emission wave length upon laser excitation), one can physically separate and thereby purify cells of interest using flow cytometry. As described herein, an unsorted cell cluster can be cell cluster that formed by a plurality of cells that have not been subject to an active cell sorting process, e.g., flow cytometry. In some cases, flow cytometry as discussed herein can be based on one or more signal peptides expressed in the cells. For example, a cell cluster can comprise cells that express a signal peptide (e.g., a fluorescent protein, e.g., green fluorescent protein (GFP) or tdTomato). In some cases, the signal peptide is expressed as an indicator of insulin expression in the cells. For instance, a cell cluster can comprise cell harboring an exogenous nucleic acid sequence coding for GFP under the control of an insulin promoter. The insulin promoter can be an endogenous or exogenous promoter. In some cases, the expression of GFP in these cells can be indicative of insulin expression in the cells. The GFP signal can thus be a marker of a pancreatic β cell. In some cases, cell sorting as described herein can comprise magnetic-activated flow cytometry, where magnetic antibody or other ligand is used to label cells of different types, and the differences in magnetic properties can be used for cell sorting.

The percentage of cells expressing one or more particular markers, like Pdx1, NKX6.1, insulin, NGN3, or CHGA, described herein can be the percentage value detected using techniques like flow cytometry assay. In some cases, during a flow cytometry assay, cell population or cell cluster discussed herein are dispersed into single-cell suspension by incubation in digesting enzyme like trypsin or TrypLE™ Express. Dispersed cell can be washed in suitable buffer like PBS, centrifuged and then re-suspended in fixation buffer like 4% PFA. Incubation with primary antibodies against the cell markers of interest can then be conducted, which can be followed by incubation with the secondary antibodies. After antibody incubation, the cells can be washed and the subject to segregation by flow cytometry. Techniques other than flow cytometry can also be used to characterize the cells described herein, e.g., determine the cell percentages. Non-limiting examples of cell characterization methods include gene sequencing, microscopic techniques (fluorescence microscopy, atomic force microscopy), karyotyping, isoenzyme analysis, DNA properties, viral susceptibility.

In some aspects, the disclosure relates to a composition comprising a population of glucose-responsive insulin secreting cells, wherein the cells secrete a higher amount of insulin upon induction with KCl (e.g., about 20 to about 50 mM, e.g., about 30 mM) as compared to the amount of insulin secreted upon induction with glucose. In some embodiments, the population of glucose-responsive insulin secreting cells secrete at least 1.5 times, 2 times, 2.5 times, 3 times higher amount of insulin upon induction with KCl as compared to the amount of insulin secreted upon induction with glucose.

In some aspects, the disclosure relates to a composition comprising a population of glucose-responsive insulin secreting cells, wherein the cells secrete a higher amount of insulin upon induction with KCl and/or glucose, in the presence of a signaling factor as compared to comparable cells in the absence of the signaling factor. In some embodiments, the cells secrete higher amount of insulin in the presence of high glucose, but not in the presence of low glucose. In some embodiments, the high glucose concentration is about 10-20 mM. In some embodiments, the low glucose concentration is about 2-5 mM.

In some aspects, the disclosure relates to a composition comprising a population of differentiated pancreatic progenitor cells, wherein the population comprises at least 60% pancreatic β cells as determined by flow cytometry. In some embodiments, the population comprises at least 65%, 70%, 75%, 80%, 85%, or 90% pancreatic β cells. In some embodiments, the population comprises a higher percentage of pancreatic β cells upon being contacted with a predetermined basal medium component as compared to a comparable population not contacted with the basal medium component.

The in vitro-matured, SC-β cell (e.g., pancreatic β cells) generated according to the disclosed methods described herein demonstrate many advantages, for example, they perform glucose stimulated insulin secretion in vitro, resemble human islet β cells by gene expression and ultrastructure, secrete human insulin and ameliorate hyperglycemia when transplanted into mice, provide a new platform for cell therapy (e.g., transplantation into a subject in need of additional and/or functional β cells), drug screening (e.g., for insulin production/secretion, survival, dedifferentiation, etc.), research (e.g., determining the differences in function between normal and diabetic β cell), and tissue engineering (e.g., using the SC-β cells as the first cell type in reconstructing an islet).

VIII. Methods of Reducing Proliferation

Provided herein is a method to reduce proliferation in cell population of SC-β cells that is generated according to the methods described herein. A method can comprise irradiating an in vitro cell population comprising endocrine cells. In some cases, the irradiation of the cell population comprising endocrine cells is at a dose of about 100 rads to about 100,000 rads for a time period of about 1 min to about 60 min.

In some cases, the irradiation of the cell population comprising endocrine cells is at a dose of about 100 rads to about 50,000 rads, about 100 rads to about 25,000 rads, about 100 rads to about 10,000 rads, about 250 rads to about 25,000 rads, about 500 rads to about 25,000 rads, about 1,000 rads to about 25,000 rads, about 2,500 rads to about 25,000 rads, about 5,000 rads to about 25,000 rads, or about 10,000 rads to about 15,000 rads. In some cases, the irradiation of the cell population comprising endocrine cells is at a dose of about 10,000 rads. In some cases, the irradiation of the cell population comprising endocrine cells is conducted for about 1 min to about 55 min, about 1 min to about 50 min, about 1 min to about 45 min, about 1 min to about 40 min, about 1 min to about 35 min, about 1 min to about 30 min, about 1 min to about 25 min, about 1 min to about 20 min, about 1 min to about 10 min, about 1 min to about 5 min, about 10 min to about 55 min, about 15 min to about 55 min, about 20 min to about 55 min, about 25 min to about 55 min, about 30 min to about 55 min, about 20 min to about 40 min, or about 25 min to about 35 min. In some cases, the irradiation of the cell population comprising endocrine cells is for about 30 min.

As used herein, irradiation can refer to ionizing irradiation. It can be conducted by exposing the cell population to gamma rays, x-rays, ultraviolet radiation, alpha rays, beta rays (electron beams), or neutron rays. Without wishing to be bound by a certain theory, the ionizing irradiation can control cell growth by damaging DNA of cells, e.g., proliferating cells, and consequentially cell death. In some cases, the cell population comprising endocrine cells that has been subject to the irradiation as described herein has a lower proportion of cells capable of proliferation or proliferating cells as compared to a corresponding cell population that has not been subject to the irradiation. In some cases, there is at least about 10%, 20%, 30%, 40%, 50%, 60%, 70%, 80%, 90%, 100%, 120%, 150%, 180%, 200%, 220%, 250%, 280%, 300%, 320%, 350%, 380%, 400%, 420%, 450%, 480%, or 500% lower proportion of cells capable of proliferation or proliferating cells in the cell population comprising endocrine cells that has been exposed to the irradiation as compared to a corresponding cell population that has not been exposed to the irradiation.

In some cases, the methods provided herein can comprise exposing to irradiation a cell population during pancreatic differentiation that comprises stem cells, definitive endoderm cells, primitive gut tube cells, pancreatic progenitor cells, or endocrine cells. In some cases, the irradiation results in a cell population that has reduced proliferative capability as compared to a corresponding cell population that is not subject to irradiation.

In some cases, the cell population comprising endocrine cells is a cell population obtained via any of the differentiation methods provided herein. In some cases, the cell population comprising endocrine cells is a cell population obtained by the stepwise differentiation methods provided herein. In some cases, the cell population comprising endocrine cells is a cell population at Stage 6 of the differentiation protocol. In some cases, the cell population comprising endocrine cells is a cell population on day 1 at Stage 6 (S6d1), S6d2, S6d3, S6d4, S6d5, S6d6, or S6d7. In some cases, the cell population comprising endocrine cells is a cell population thawed and recovered from cryopreservation. In some cases, the cell population comprising endocrine cells is cryopreserved while being exposed to the irradiation. The cell population comprising endocrine cells can be thawed and recovered for further differentiation into pancreatic β cells after exposure to the irradiation as described herein.

In some cases, the cell population comprising endocrine cells can be further differentiated/matured into a cell population comprising pancreatic β cells, which can have a lower proportion of cells capable of proliferation or proliferating cells as compared to a corresponding cell population without being the same exposure to the irradiation. In some cases, there is at least about 10%, 20%, 30%, 40%, 50%, 60%, 70%, 80%, 90%, 100%, 120%, 150%, 180%, 200%, 220%, 250%, 280%, 300%, 320%, 350%, 380%, 400%, 420%, 450%, 480%, or 500% lower proportion of cells capable of proliferation or proliferating cells in the cell population comprising pancreatic β cells that is obtained from the irradiated cell population comprising endocrine as compared to a corresponding cell population that has not been exposed to the irradiation.

In some cases, the cell population comprising pancreatic β cells that is obtained from the irradiated cell population comprising endocrine is implanted into as subject in need thereof. The cell population comprising pancreatic β cells can help control the blood glucose level in the subject. In some cases, the cell population comprising pancreatic β cells that is obtained from the irradiated cell population comprising endocrine can maintain the blood glucose control in the subject for at least about 50 days, 60 days, 70 days, 80 days, 90 days, or even longer. In some cases, the cell population comprising pancreatic β cells that is obtained from the irradiated cell population comprising endocrine can maintain the blood glucose control in the subject for 60 days. In some cases, the cell population comprising pancreatic β cells that is obtained from the irradiated cell population comprising endocrine can maintain the blood glucose control in the subject for 90 days.

IX. Methods of Enriching Stem Cell Derived Beta Cells

Provided herein is a method to isolate of a population of SC-β cells from a heterogeneous population of cells, such a mixed population of cells comprising SC-β cells and insulin-positive endocrine cells or precursors thereof from which the SC-β cells were derived. A population of SC-β cells produced by any of the above-described processes can be enriched, isolated and/or purified by using any cell surface marker, e.g., polysialylated-neural cell adhesion molecule (PSA-NCAM), present on the SC-β cells which is not present on the insulin-positive endocrine cell or precursor thereof from which it was derived. Such cell surface markers are also referred to as an affinity tag which is specific for a SC-β cell.

In some embodiments, the cell surface marker is an inducible cell surface marker. For example, PSA-NCAM can be induced to the surface by certain signals. Different types of endocrine cells can respond to different signals. In some embodiments, PSA-NCAM can be selectively cleaved off the surface by an enzyme, e.g., endoneuraminidase or Endo-N. Endo-N is an endosialidase which degrades rapidly and specifically linear polymers of sialic acid with α-2,8-linkage with a minimum length of 7-9 residues characteristic of sialic acid residues associated with NCAM.

Cell Sorting

The methods provided herein relates to a cell composition comprising a first population of endocrine cells and a second population of endocrine cells, wherein a reduced proportion of cells of the first population of endocrine cells express $VMAT^+$ or $Cdx2^+$ as compared to a second population of endocrine cells. In some embodiments, the first and second populations of endocrine cells comprise beta cells which can be induced by glucose and stem cells (e.g., hPSC or EC). In some embodiments, the stem cells are induced by isoproterenol. In some embodiments, the populations of cells comprise a mixture of cells that are induced insulin producing beta cells and non-insulin producing cells. In some embodiments, PSA-NCAM can be cleaved off from all cells to create a "blank slate", can be induced to the cell surface with a cell type specific stimulant resulting in only one cell type having PSA-NCAM on the surface in large quantities, and can be used to selectively sort using an affinity tag, e.g., an anti-PSA-NCAM antibody, for the induced SC-β cells. In this manner, the differentiated SC-β cells can be sorted and enriched from other endocrine cells in the population of endocrine cells. SC-β cells. In some embodiments, one or more cells of the population of cells fails to localize the selectable marker to a cell surface when contacted with the stimulating compound.

Examples of affinity tags specific for SC-β cells are antibodies (e.g., an anti-PSA-NCAM antibody), ligands or other binding agents that are specific to a marker molecule, such as a polypeptide, that is present on the cell surface of a SC-β cells but which is not substantially present on other cell types (e.g. insulin-positive endocrine cells or precursors thereof). In some processes, an antibody which binds to a cell surface antigen on a SC-β cell (e.g. a human SC-β cell) is used as an affinity tag for the enrichment, isolation or purification of chemically induced (e.g. by contacting with at least one β cell maturation factor as described herein) SC-β cells produced by the methods described herein. Such antibodies are known and commercially available.

The skilled artisan will readily appreciate the processes for using antibodies for the enrichment, isolation and/or purification of SC-β cell. For example, in some embodiments, the reagent, such as an antibody, is incubated with a cell population comprising SC-β cells, wherein the cell population has been treated to reduce intercellular and substrate adhesion. The cell population are then washed, centrifuged and resuspended. In some embodiments, if the antibody is not already labeled with a label, the cell suspension is then incubated with a secondary antibody, such as an FACS-conjugated antibody that is capable of binding to the primary antibody. The SC-β cells are then washed, centrifuged and resuspended in buffer. The SC-β cell suspension is then analyzed and sorted using a fluorescence activated cell sorter (FACS). Antibody-bound, fluorescent reprogrammed cells are collected separately from non-bound, non-fluorescent cells (e.g. immature, insulin-producing cells), thereby resulting in the isolation of SC-β cells from other cells present in the cell suspension, e.g. insulin-positive endocrine cells or precursors thereof, or immature, insulin-producing cell (e.g. other differentiated cell types).

In another embodiment of the processes described herein, the isolated cell composition comprising SC-β cells can be further purified by using an alternate affinity-based method or by additional rounds of sorting using the same or different markers that are specific for SC-β cells. For example, in some embodiments, FACS sorting is used to first isolate a SC-β cell which expresses NKX6-1, either alone or with the expression of C-peptide, or alternatively with a (3 cell marker disclosed herein from cells that do not express one of those markers (e.g. negative cells) in the cell population. A second FAC sorting, e.g. sorting the positive cells again using FACS to isolate cells that are positive for a different marker than the first sort enriches the cell population for reprogrammed cells. In an alternative embodiment, FACS sorting is used to separate cells by negatively sorting for a marker that is present on most insulin-positive endocrine cells or precursors thereof but is not present on SC-β cells.

In some embodiments of the processes described herein, SC-β cells are fluorescently labeled without the use of an antibody then isolated from non-labeled cells by using a fluorescence activated cell sorter (FACS). In such embodiments, a nucleic acid encoding GFP, YFP or another nucleic acid encoding an expressible fluorescent marker gene, such as the gene encoding luciferase, is used to label reprogrammed cells using the methods described above. For example, in some embodiments, at least one copy of a nucleic acid encoding GFP or a biologically active fragment thereof is introduced into at least one insulin-positive endocrine cell which is first chemically induced into a SC-β cell, where a downstream of a promoter expressed in SC-β cell, such as the insulin promoter, such that the expression of the GFP gene product or biologically active fragment thereof is under control of the insulin promoter.

In addition to the procedures just described, chemically induced SC-β cells may also be isolated by other techniques for cell isolation. Additionally, SC-β cells may also be enriched or isolated by methods of serial subculture in growth conditions which promote the selective survival or selective expansion of the SC-β cell. Such methods are known by persons of ordinary skill in the art, and may include the use of agents such as, for example, insulin, members of the TGF-beta family, including Activin A, TGF-beta1, 2, and 3, bone morphogenic proteins (BMP-2, -3, -4, -5, -6, -7, -11, -12, and -13), fibroblast growth factors-1 and -2, platelet-derived growth factor-AA, and —BB, platelet rich plasma, insulin-like growth factors (IGF-I, II) growth differentiation factor (GDF-5, -6, -7, -8, -10, -11, -15), vascular endothelial cell-derived growth factor (VEGF), Hepatocyte growth factor (HGF), pleiotrophin, endothelin, Epidermal growth factor (EGF), beta-cellulin, among others. Other pharmaceutical compounds can include, for example, nicotinamide, glucagon like peptide-1 (GLP-1) and II, GLP-1 and 2 mimetibody, Exendin-4, retinoic acid, parathyroid hormone.

Using the methods described herein, enriched, isolated and/or purified populations of SC-β cells can be produced in vitro from insulin-positive endocrine cells or precursors thereof (which were differentiated from pluripotent stem cells by the methods described herein). In some embodiments, preferred enrichment, isolation and/or purification methods relate to the in vitro production of human SC-β cell from human insulin-positive endocrine cells or precursors thereof, which were differentiated from human pluripotent stem cells, or from human induced pluripotent stem (iPS) cells. In such an embodiment, where SC-β cells are differentiated from insulin-positive endocrine cells, which were previously derived from definitive endoderm cells, which were previously derived from iPS cells, the SC-β cell can be autologous to the subject from whom the cells were obtained to generate the iPS cells.

Using the methods described herein, isolated cell populations of SC-β cells are enriched in SC-β cell content by at least about 2- to about 1000-fold as compared to a population of cells before the chemical induction of the insulin-positive endocrine cell or precursor population. In some embodiments, SC-β cells can be enriched by at least about 5- to about 500-fold as compared to a population before the chemical induction of an insulin-positive endocrine cell or precursor population. In other embodiments, SC-β cells can be enriched from at least about 10- to about 200-fold as compared to a population before the chemical induction of insulin-positive endocrine cell or precursor population. In still other embodiments, SC-β cell can be enriched from at least about 20- to about 100-fold as compared to a population before the chemical induction of insulin-positive endocrine cell or precursor population. In yet other embodiments, SC-β cell can be enriched from at least about 40- to about 80-fold as compared to a population before the chemical induction of insulin-positive endocrine cell or precursor population. In certain embodiments, SC-β cell can be enriched from at least about 2- to about 20-fold as compared to a population before the chemical induction of insulin-positive endocrine cell or precursor population.

Provided herein is a method of selecting a target cell (e.g., SC-β cell) from a population of cells comprising contacting the target cell with a stimulating compound, wherein the contacting induces a selectable marker (e.g., PSA-NCAM) of the target cell to localize to a cell surface of the target cell, and selecting the target cell (e.g., SC-β cell) based on the localization of the selectable marker (e.g., PSA-NCAM) at the cell surface. In some embodiments, the selectable marker comprises PSA-NCAM. In some embodiments, the selecting the target cell is by cell sorting. In some embodiments, the selecting comprises contacting the selectable marker of the target cell with an antigen binding polypeptide when the selectable marker is localized to the surface of the target cell. In some embodiments, the antigen binding polypeptide comprises an antibody. In some embodiments, the antigen binding polypeptide binds to the PSA-NCAM. In some embodiments, the method further comprises treating the population of cells with a compound (e.g., enzyme) that removes the selectable marker from a cell surface of at least one cell of the target cell population. In some embodiments, the population of target cells is treated with the compound prior to the contacting of the target cell with the stimulating compound. In some embodiments, the compound cleaves the selectable marker from the cell surface of the at least one cell. In some embodiments, the target cell is an endocrine cell. In some embodiments, the stimulating compound comprises glucose. In some embodiments, the endocrine cell is a (3 cell. In some embodiments, the β cell is an SC-β cell. In some embodiments, the stimulating compound comprises isoproterenol. In some embodiments, the endocrine cell is an EC cell. In aspects, the stimulating compound is glucose and the one or more cells is an EC cell. In some embodiments, the stimulating compound is isoproterenol and the one or more cells is a β cell. In some embodiments, selecting the target cell separates the target cell from the one or more cells of the population of cells.

Irradiation

In some embodiments, the insulin producing endocrine cells (e.g., stem cell derived beta cells) can be cultured in the presence of a feeder layer of cells. Such cells may, for example, be of murine or human origin. The insulin producing endocrine cells (e.g., stem cell derived beta cells) can also be irradiated, chemically inactivated by treatment with a chemical inactivator such as mitomycin c, or otherwise treated to inhibit their proliferation if desired. In other embodiments, the insulin producing endocrine cells (e.g., stem cell derived beta cells) are cultured without feeder cells.

The pluripotent stem cells can be maintained in an undifferentiated state even without feeder cells. The environment for feeder-free cultures includes a suitable culture substrate, particularly an extracellular matrix such as Matrigel® or laminin. Typically, enzymatic digestion is halted before cells become completely dispersed (~5 mM with collagenase IV). Clumps of ~10 to 2,000 cells are then plated directly onto the substrate without further dispersal. Feeder-free cultures are supported by a nutrient medium containing factors that support proliferation of the cells without differentiation.

Such factors may be introduced into the medium by culturing the medium with cells secreting such factors, such as irradiated (~4,000 rad) primary mouse embryonic fibroblasts, telomerized mouse fibroblasts, or fibroblast-like cells derived from pPS cells. Medium can be conditioned by plating the feeders at a density of ~5-6×104 $cm^{-2}$ in a serum free medium such as KO DMEM supplemented with 20% serum replacement and 4 ng/mL bFGF. Medium that has been conditioned for 1-2 days is supplemented with further bFGF, and used to support pluripotent stem cell culture for 1-2 days. Features of the feeder-free culture method are further discussed in International Patent Publication WO 01/51616; and Xu et al., Nat. Biotechnol. 19:971, 2001.

X. Pharmaceutical Compositions

The present disclosure relates to a therapeutic composition containing cells produced by any of the foregoing methods or containing any of the foregoing cell populations. The therapeutic compositions can further comprise a physiologically compatible solution including, for example, artificial cerebrospinal fluid or phosphate-buffered saline. The therapeutic composition can be used to treat, prevent, or stabilize diabetes. For example, somatic cells or stem cells can be obtained from an individual in need of treatment or from a healthy individual and reprogrammed to stem cell derived beta cells by the method of the present disclosure. In one embodiment of the present disclosure the stem cell derived beta cells are sorted and enriched and introduced into the individual to treat the condition. In another embodiment the stem cells are cultured under conditions suitable for differentiation into beta cells prior to introduction into the individual, and can be used to replace or assist the normal function of diseased or damaged tissue. The great advantage of the present disclosure is that it provides an essentially limitless supply of patient specific human beta cells or compatible stem cell derived beta cells from healthy individuals with the same HLA type suitable for transplantation. The use of autologous and/or compatible cells in cell therapy offers a major advantage over the use of non-autologous cells, which are likely to be subject to immunological rejection. In contrast, autologous cells are unlikely to elicit significant immunological responses.

In some cases, the present disclosure provides pharmaceutical compositions that can utilize non-native pancreatic β cell (beta cells) populations and cell components and products in various methods for treatment of a disease (e.g., diabetes). Certain cases encompass pharmaceutical compositions comprising live cells (e.g., non-native pancreatic β cells alone or admixed with other cell types). Other cases encompass pharmaceutical compositions comprising non-native pancreatic β cell components (e.g., cell lysates, soluble cell fractions, conditioned medium, ECM, or components of any of the foregoing) or products (e.g., trophic and other biological factors produced by non-native pancreatic β cells or through genetic modification, conditioned medium from non-native pancreatic β cell culture). In either case, the pharmaceutical composition may further comprise other active agents, such as anti-inflammatory agents, exogenous small molecule agonists, exogenous small molecule antagonists, anti-apoptotic agents, antioxidants, and/or growth factors known to a person having skill in the art.

Pharmaceutical compositions of the present disclosure can comprise non-native pancreatic β cell, or components or products thereof, formulated with a pharmaceutically acceptable carrier (e.g. a medium or an excipient). The term pharmaceutically acceptable carrier (or medium), which may be used interchangeably with the term biologically compatible carrier or medium, can refer to reagents, cells, compounds, materials, compositions, and/or dosage forms that are not only compatible with the cells and other agents to be administered therapeutically, but also are suitable for use in contact with the tissues of human beings and animals without excessive toxicity, irritation, allergic response, or other complication. Suitable pharmaceutically acceptable carriers can include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical compositions comprising cellular components or products, but not live cells, can be formulated as liquids. Pharmaceutical compositions comprising living non-native pancreatic β cells can be formulated as liquids, semisolids (e.g., gels, gel capsules, or liposomes) or solids (e.g., matrices, scaffolds and the like).

As used here, the term "pharmaceutically acceptable" can refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" can refer to a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient," "carrier," "pharmaceutically acceptable carrier" or the like are used interchangeably herein.

The phrase "therapeutically-effective amount" as used herein in respect to a population of cells means that amount of relevant cells in a population of cells, e.g., SC-β cells or mature pancreatic β cells, or composition comprising SC-β cells of the present disclosure which is effective for producing some desired therapeutic effect in at least a sub-population of cells in an animal at a reasonable benefit/risk ratio applicable to any medical treatment. For example, an amount of a population of SC-β cells administered to a subject that is sufficient to produce a statistically significant, measurable change in at least one symptom of Type 1, Type 1.5 or Type 2 diabetes, such as glycosylated hemoglobin level, fasting blood glucose level, hypoinsulinemia, etc. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In some instances, pharmaceutical compositions of the stem cell derived beta cells are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions can also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical compositions described herein are administered by any suitable administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes. In some instances, the pharmaceutical composition is formulated for parenteral (e.g., intravenous, subcutaneous, intramuscular, intracerebral, intracerebroventricular, intra-articular, intraperitoneal, or intracranial) administration.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the pharmaceutical compositions are formulated into capsules. In some embodiments, the pharmaceutical compositions are formulated into solutions (for example, for IV administration). In some cases, the pharmaceutical composition is formulated as an infusion. In some cases, the pharmaceutical composition is formulated as an injection.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, a composition of the present disclosure can comprise the stem cell derived beta cells, in an amount that is effective to treat or prevent e.g., diabetes. A pharmaceutical composition can comprise the stem cell derived beta cells as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Pharmaceutical compositions can comprise auxiliary components as would be familiar to a person having skill in the art. For example, they can contain antioxidants in ranges that vary depending on the kind of antioxidant used. Reasonable ranges for commonly used antioxidants are about 0.01% to about 0.15% weight by volume of EDTA, about 0.01% to about 2.0% weight volume of sodium sulfite, and about 0.01% to about 2.0% weight by volume of sodium metabisulfite. One skilled in the art may use a concentration of about 0.1% weight by volume for each of the above. Other representative compounds include mercaptopropionyl glycine, N-acetyl cysteine, β-mercaptoethylamine, glutathione and similar species, although other antioxidant agents suitable for renal administration, e.g. ascorbic acid and its salts or sulfite or sodium metabisulfite may also be employed.

A buffering agent can be used to maintain the pH of formulations in the range of about 4.0 to about 8.0; so as to minimize irritation in the target tissue. For direct intraperitoneal injection, formulations should be at pH 7.2 to 7.5, preferably at pH 7.35-7.45. The compositions may also include tonicity agents suitable for administration to the kidney. Among those suitable is sodium chloride to make formulations approximately isotonic with blood.

In certain cases, pharmaceutical compositions are formulated with viscosity enhancing agents. Exemplary agents are hydroxyethylcellulose, hydroxypropylcellulose, methylcellulose, and polyvinylpyrrolidone. The pharmaceutical compositions may have cosolvents added if needed. Suitable cosolvents may include glycerin, polyethylene glycol (PEG), polysorbate, propylene glycol, and polyvinyl alcohol. Preservatives may also be included, e.g., benzalkonium chloride, benzethonium chloride, chlorobutanol, phenylmercuric acetate or nitrate, thimerosal, or methyl or propylparabens.

Pharmaceutical compositions comprising cells, cell components or cell products may be delivered to the kidney of a patient in one or more of several methods of delivery known in the art. In some cases, the compositions are delivered to the kidney (e.g., on the renal capsule and/or underneath the renal capsule). In another embodiment, the compositions may be delivered to various locations within the kidney via periodic intraperitoneal or intrarenal injection. Alternatively, the compositions may be applied in other dosage forms known to those skilled in the art, such as pre-formed or in situ-formed gels or liposomes.

Pharmaceutical compositions comprising live cells in a semi-solid or solid carrier are may be formulated for surgical implantation on or beneath the renal capsule. It should be appreciated that liquid compositions also may be administered by surgical procedures. In particular cases, semi-solid or solid pharmaceutical compositions may comprise semi-permeable gels, lattices, cellular scaffolds and the like, which may be non-biodegradable or biodegradable. For example, in certain cases, it may be desirable or appropriate to sequester the exogenous cells from their surroundings, yet enable the cells to secrete and deliver biological molecules (e.g., insulin) to surrounding cells or the blood stream. In these cases, cells may be formulated as autonomous implants comprising living non-native pancreatic β cells or cell population comprising non-native pancreatic β cell surrounded by a non-degradable, selectively permeable barrier that physically separates the transplanted cells from host tissue. Such implants are sometimes referred to as "immunoprotective," as they have the capacity to prevent immune cells and macromolecules from killing the transplanted cells in the absence of pharmacologically induced immunosuppression.

In other cases, various degradable gels and networks can be used for the pharmaceutical compositions of the present disclosure. For example, degradable materials particularly suitable for sustained release formulations include biocompatible polymers, such as poly(lactic acid), poly (lactic-co-glycolic acid), methylcellulose, hyaluronic acid, collagen, and the like.

In other cases, it may be desirable or appropriate to deliver the cells on or in a biodegradable, preferably bioresorbable or bioabsorbable, scaffold or matrix. These typically three-dimensional biomaterials contain the living cells attached to the scaffold, dispersed within the scaffold, or incorporated in an extracellular matrix entrapped in the scaffold. Once implanted into the target region of the body, these implants become integrated with the host tissue, wherein the transplanted cells gradually become established.

Examples of scaffold or matrix (sometimes referred to collectively as "framework") material that may be used in the present disclosure include nonwoven mats, porous foams, or self-assembling peptides. Nonwoven mats, for example, may be formed using fibers comprising a synthetic absorbable copolymer of glycolic and lactic acids (PGA/PLA), foams, and/or poly(epsilon-caprolactone)/poly(glycolic acid) (PCL/PGA) copolymer.

In another embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another embodiment, cells are seeded onto foam scaffolds that may be composite structures. In many of the abovementioned cases, the framework may be molded into a useful shape. Furthermore, it will be appreciated that non-native pancreatic β cells may be cultured on pre-formed, non-degradable surgical or implantable devices.

The matrix, scaffold or device may be treated prior to inoculation of cells in order to enhance cell attachment. For example, prior to inoculation, nylon matrices can be treated with 0.1 molar acetic acid and incubated in polylysine, PBS, and/or collagen to coat the nylon. Polystyrene can be similarly treated using sulfuric acid. The external surfaces of a framework may also be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In one aspect, the present disclosure provided devices comprising a cell cluster comprising at least one pancreatic β cell. A device provided herein can be configured to produce and release insulin when implanted into a subject. A device can comprise a cell cluster comprising at least one pancreatic β cell, e.g., a non-native pancreatic β cell. A cell cluster in the device can exhibit in vitro GSIS. A device can further comprise a semipermeable membrane. The semipermeable membrane can be configured to retain the cell cluster in the device and permit passage of insulin secreted by the cell cluster. In some cases of the device, the cell cluster can be encapsulated by the semipermeable membrane. The encapsulation can be performed by any technique available to one skilled in the art. The semipermeable membrane can also be made of any suitable material as one skilled in the art would appreciate and verify. For example, the semipermeable membrane can be made of polysaccharide or polycation. In some cases, the semipermeable membrane can be made of poly(lactide) (PLA), poly(glycolic acid) (PGA), poly(lactide-co-glycolide) (PLGA), and other polyhydroxy-acids, poly(caprolactone), polycarbonates, polyamides, polyanhydrides, polyphosphazene, polyamino acids, poly-ortho esters, polyacetals, polycyanoacrylates, biodegradable polyurethanes, albumin, collagen, fibrin, polyamino acids, prolamines, alginate, agarose, agarose with gelatin, dextran, polyacrylates, ethylene-vinyl acetate polymers and other acyl-substituted cellulose acetates and derivatives thereof, polyurethanes, polystyrenes, polyvinyl chloride, polyvinyl fluoride, poly(vinyl imidazole), chlorosulphonated polyolefins, polyethylene oxide, or any combinations thereof. In some cases, the semipermeable membrane comprises alginate. In some cases, the cell cluster is encapsulated in a microcapsule that comprises an alginate core surrounded by the semipermeable membrane. In some cases, the alginate core is modified, for example, to produce a scaffold comprising an alginate core having covalently conjugated oligopeptides with an RGD sequence (arginine, glycine, aspartic acid). In some cases, the alginate core is modified, for example, to produce a covalently reinforced microcapsule having a chemoenzymatically engineered alginate of enhanced stability. In some cases, the alginate core is modified, for example, to produce membrane-mimetic films assembled by in-situ polymerization of acrylate functionalized phospholipids. In some cases, microcapsules are composed of enzymatically modified alginates using epimerases, In some cases, microcapsules comprise covalent links between adjacent layers of the microcapsule membrane. In some embodiment, the microcapsule comprises a subsieve-size capsule comprising alginate coupled with phenol moieties. In some cases, the microcapsule comprises a scaffold comprising alginate-agarose. In some cases, the SC-β cell is modified with PEG before being encapsulated within alginate. In some cases, the isolated populations of cells, e.g., SC-β cells are encapsulated in photoreactive liposomes and alginate. It should be appreciated that the alginate employed in the microcapsules can be replaced with other suitable biomaterials, including, without limitation, polyethylene glycol (PEG), chitosan, polyester hollow fibers, collagen, hyaluronic acid, dextran with ROD, BHD and polyethylene glycol-diacrylate (PEGDA), poly(MPC-co-n-butyl methacrylate-co-4-vinylphenyl boronic acid) (PMBV) and poly (vinyl alcohol) (PVA), agarose, agarose with gelatin, and multilayer cases of these. In some cases, the device provided herein comprise extracorporeal segment, e.g., part of the device can be outside a subject's body when the device is implanted in the subject. The extracorporeal segment can comprise any functional component of the device, with or without the cells or cell cluster provided herein.

XI. Methods of Treating

Further provided herein are methods for treating or preventing a disease in a subject. A composition comprising the cell clusters or cells provided herein or generated according to the methods provided herein can be administered into a subject to restore a degree of pancreatic function in the subject. For example, the cell clusters resembling endogenous pancreatic islets, or the cells resembling endogenous pancreatic β cells (e.g., non-native pancreatic β cells or SC-β cells) or the precursors thereof can be transplanted to a subject to treat diabetes.

The methods can comprise transplanting the cell cluster or the cell disclosed in the application to a subject, e.g., a subject in need thereof. The term "transplanting" can refer to the placement of cells or cell clusters, any portion of the cells or cell clusters thereof, or any compositions comprising cells, cell clusters or any portion thereof, into a subject, by a method or route which results in at least partial localization of the introduced cells or cell clusters at a desired site. The cells or cell clusters can be implanted directly to the pancreas, or alternatively be administered by any appropriate route which results in delivery to a desired location in the subject where at least a portion of the implanted cells or cell remain viable. The period of viability of the cells or cell clusters after administration to a subject can be as short as a few hours, e.g. twenty-four hours, to a few days, to as long as several years. In some instances, the cells or cell clusters, or any portion of the cells or cell clusters thereof, can also be transadministered at a non-pancreatic location, such as in the liver or subcutaneously, for example, in a capsule (e.g., microcapsule) to maintain the implanted cells or cell clusters at the implant location and avoid migration.

As used herein, the term "treating" and "treatment" can refer to administering to a subject an effective amount of a composition (e.g., cell clusters or a portion thereof) so that the subject as a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (e.g., partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, suhcuticular, intraarticular, sub capsular, subarachnoid, intraspinal, intracerebro spinal, and intrasternal injection and infusion. In preferred embodiments, the compositions are administered by intravenous infusion or injection.

By "treatment," "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Treatment of Diabetes is determined by standard medical methods. A goal of Diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycosylated hemoglobin level (HbA1c; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with complications relating to Diabetes, such as diseases of the eye, kidney disease, or nerve disease.

Delaying the onset of diabetes in a subject refers to delay of onset of at least one symptom of diabetes, e.g., hyperglycemia, hypoinsulinemia, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, or combinations thereof, for at least 1 week, at least 2 weeks, at least 1 month, at least 2 months, at least 6 months, at least 1 year, at least 2 years, at least 5 years, at least 10 years, at least 20 years, at least 30 years, at least 40 years or more, and can include the entire lifespan of the subject.

In some aspects, the disclosure relates to a method comprising implanting in a subject a device comprising a cell or cell cluster provided herein (e.g., insulin producing cells), wherein the device releases insulin in an amount sufficient for a reduction of blood glucose levels in the subject. In some embodiments, the insulin producing cells are glucose responsive insulin producing cells.

In some embodiments, the reduction of blood glucose levels in the subject, as induced by the transplantation of the cell or cell cluster, or the device provided herein, results in an amount of glucose which is lower than the diabetes threshold. In some embodiments, the subject is a mammalian subject. In some embodiments, the mammalian subject is human. In some embodiments, the amount of glucose is reduced to lower than the diabetes threshold in 1, 2, 3, 4, 5, 6, 7, 8, 9, or 10 days after the implanting.

As described in detail above, the pharmaceutical compositions of the present disclosure can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

A subject that can be treated by the methods herein can be a human or a non-human animal. In some cases, a subject can be a mammal. Examples of a subject include but are not limited to primates, e.g., a monkey, a chimpanzee, a bamboo, or a human. In some cases, a subject is a human. A subject can be non-primate animals, including, but not limited to, a dog, a cat, a horse, a cow, a pig, a sheep, a goat, a rabbit, and the like. In some cases, a subject receiving the treatment is a subject in need thereof, e.g., a human in need thereof.

In certain embodiments, the subject is a mammal, e.g., a primate, e.g., a human. The terms, "patient" and "subject" are used interchangeably herein. Preferably, the subject is a mammal. The mammal can be a human, non-human primate, mouse, rat, dog, cat, horse, or cow, but are not limited to these examples. Mammals other than humans can be advantageously used as subjects that represent animal models of Type 1 diabetes, Type 2 Diabetes Mellitus, or pre-diabetic conditions. In addition, the methods described herein can be used to treat domesticated animals and/or pets. A subject can be male or female. A subject can be one who has been previously diagnosed with or identified as suffering from or having Diabetes (e.g., Type 1 or Type 2), one or more complications related to Diabetes, or a pre-diabetic condition, and optionally, but need not have already undergone treatment for the Diabetes, the one or more complications related to Diabetes, or the pre-diabetic condition. A subject can also be one who is not suffering from Diabetes or a pre-diabetic condition. A subject can also be one who has been diagnosed with or identified as suffering from Diabetes, one or more complications related to Diabetes, or a pre-diabetic condition, but who show improvements in known Diabetes risk factors as a result of receiving one or more treatments for Diabetes, one or more complications related to Diabetes, or the pre-diabetic condition. Alternatively, a subject can also be one who has not been previously diagnosed as having Diabetes, one or more complications related to Diabetes, or a pre-diabetic condition. For example, a subject can be one who exhibits one or more risk factors for Diabetes, complications related to Diabetes, or a pre-diabetic condition, or a subject who does not exhibit Diabetes risk factors, or a subject who is asymptomatic for Diabetes, one or more Diabetes-related complications, or a pre-diabetic condition. A subject can also be one who is suffering from or at risk of developing Diabetes or a pre-diabetic condition. A subject can also be one who has been diagnosed with or identified as having one or more complications related to Diabetes or a pre-diabetic condition as defined herein, or alternatively, a subject can be one who has not been previously diagnosed with or identified as having one or more complications related to Diabetes or a pre-diabetic condition.

The methods can comprise transplanting the cell cluster to a subject using any means in the art. For example the methods can comprise transplanting the cell cluster via the intraperitoneal space, renal subcapsule, renal capsule, omentum, subcutaneous space, or via pancreatic bed infusion. For example, transplanting can be subcapsular transplanting, intramuscular transplanting, or intraportal transplanting, e.g., intraportal infusion. Immunoprotective encapsulation can be implemented to provide immunoprotection to the cell clusters. In some cases, the methods of treatment provided herein can comprise administer immune response modulator for modulating or reducing transplant rejection response or other immune response against the implant (e.g., the cells or the device). Examples of immune response modulator that can be used in the methods can include purine synthesis inhibitors like Azathioprine and Mycophenolic acid, pyrimidine synthesis inhibitors like Leflunomide and Teriflunomide, antifolate like Methotrexate, Tacrolimus, Ciclosporin, Pimecrolimus, Abetimus, Gusperimus, Lenalidomide, Pomalidomide, Thalidomide, PDE4 inhibitor, Apremilast, Anakinra, Sirolimus, Everolimus, Ridaforolimus, Temsirolimus, Umirolimus, Zotarolimus, Anti-thymocyte globulin antibodies, Anti-lymphocyte globulin antibodies, CTLA-4, fragment thereof, and fusion proteins thereof like Abatacept and Belatacept, TNF inhibitor like Etanercept and Pegsunercept, Aflibercept, Alefacept, Rilonacept, antibodies against complement component 5 like Eculizumab, anti-TNF antibodies like Adalimumab, Afelimomab, Certolizumab pegol, Golimumab, Infliximab, and Nerelimomab, antibodies against Interleukin 5 like Mepolizumab, anti-Ig E antibodies like Omalizumab, anti-Interferon antibodies like Faralimomab, anti-IL-6 antibodies like Elsilimomab, antibodies against IL-12 and IL-23 like Lebrikizumab and Ustekinumab, anti-IL-17A antibodies like Secukinumab, anti-CD3 antibodies like Muromonab-CD3, Otelixizumab, Teplizumab, and Visilizumab, anti-CD4 antibodies like Clenoliximab, Keliximab, and Zanolimumab, anti-CD11a antibodies like Efalizumab, anti-CD18 antibodies like Erlizumab, anti-CD20 antibodies like Obinutuzumab, Rituximab, Ocrelizumab and Pascolizumab, anti-CD23 antibodies like Gomiliximab and Lumiliximab, anti-CD40 antibodies like Teneliximab and Toralizumab, antibodies against CD62L/L-selectin like Aselizumab, anti-CD80 antibodies like Galiximab, anti-CD147/Basigin antibodies like Gavilimomab, anti-CD154 antibodies like Ruplizumab, anti-BLyS antibodies like Belimumab and Blisibimod, anti-CTLA-4 antibodies like Ipilimumab and Tremelimumab, anti-CAT antibodies like Bertilimumab, Lerdelimumab, and Metelimumab, anti-Integrin antibodies like Natalizumab, antibodies against Interleukin-6 receptor like Tocilizumab, anti-LFA-1 antibodies like Odulimomab, antibodies against IL-2 receptor/CD25 like Basiliximab, Daclizumab, and Inolimomab, antibodies against T-lymphocyte (Zolimomab aritox) like Atorolimumab, Cedelizumab, Fontolizumab, Maslimomab, Morolimumab, Pexelizumab, Reslizumab, Rovelizumab, Siplizumab, Talizumab, Telimomab aritox, Vapaliximab, and Vepalimomab.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

The disclosure is not limited to the embodiments described and exemplified above, but is capable of variation and modification within the scope of the appended claims.

EXEMPLARY EMBODIMENTS

[1] A method comprising:

contacting a population of pancreatic progenitor cells or precursors thereof with a composition comprising at least one epigenetic modifying compound, wherein said contacting results in a population of endocrine cells with a reduced proportion of cells expressing VMAT or Cdx2 as compared to a corresponding population of endocrine cells which is not contacted with said at least one epigenetic modifying compound.

[2] The method of paragraph [1], wherein said at least one epigenetic modifying compound comprises one or more of a DNA methylation inhibitor, a histone acetyltransferase inhibitor, a histone deacetylase inhibitor, a histone methyltransferase inhibitor, or a bromodomain inhibitor.

[3] The method of paragraph [2], wherein said at least one epigenetic modifying compound comprises a histone methyltransferase inhibitor.

[4] The method of paragraph [3], wherein said histone methyltransferase inhibitor is an EZH2 inhibitor.

[5] The method of paragraph [3] or [4], wherein said histone methyltransferase inhibitor is at least one of DZNep, GSK126, or EPZ6438.

[6] The method of paragraph [5], wherein said histone methyltransferase inhibitor is DZNep.

[7] The method of paragraph [6], wherein a concentration of said DZNep in said composition is greater than 0.1 μM.

[8] The method of paragraph [7], wherein said concentration of said DZNep is at least 0.5 μM.

[9] The method of paragraph [7], wherein said concentration of said DZNep is about 1 μM.

[10] The method of any one of paragraphs [1] to [9], wherein said at least one epigenetic modifying compound comprises a histone deacetylase (HDAC) inhibitor.

[11] The method of paragraph [10], wherein said HDAC inhibitor is a Class I HDAC inhibitor, a Class II HDAC inhibitor, or a combination thereof.

[12] The method of paragraph [11], wherein said HDAC inhibitor is at least one of KD5170, MC1568, or TMP195.

[13] The method of paragraph [12], wherein said HDAC inhibitor is KD5170.

[14] The method of paragraph [1], wherein said at least one epigenetic modifying compound comprises an HDAC inhibitor and an EZH2 inhibitor.

[15] The method of paragraph [1], wherein said at least one epigenetic modifying compound comprises DZNep and KD5170.

[16] The method of any one of paragraphs [1]-[15], wherein at least one of said cells expressing VMAT is INS−.

[17] The method of any one of paragraphs [1]-[16], wherein at least some cells of said population of pancreatic progenitor cells differentiate into a population of PH cells.

[18] The method of paragraph [17], wherein an increased proportion of cells of said population of endocrine cells are $NKX6.1^-$ or $ChromA^+$ as compared to said corresponding population of endocrine cells which is not contacted with said at least one epigenetic modifying compound.

[19] The method of paragraph [18], wherein at least one cell of said increased proportion of cells is $NKX6.1^-$ and $ChromA^+$.

[20] The method of any one of paragraphs [1]-[19], wherein at least some cells of said population of pancreatic progenitor cells differentiate into a population of β cells.

[21] The method of paragraph [20], wherein said β cells are stem-cell derived β (SC-β) cells.

[22] The method of paragraph [20] or [21], wherein said β cells express C-PEP and NKX6-1.

[23] The method of any one of paragraphs [20]-[22], wherein said β cells exhibit an in vitro glucose-stimulated insulin secretion response to a glucose challenge.

[24] The method of any one of paragraphs [1]-[23], wherein said method is performed in vitro.

[25] The method of paragraph [24], wherein said composition comprises at least one of betacellulin, thiazovinin, retinoic acid, SANT1, XXI, Alk5i II, GC-1, LDN or staurosporine.

[26] The method of paragraph [24] or [25], wherein said contacting is for at least three days.

[27] The method of paragraph [24] or [25], wherein said contacting is for at least five days.

[28] The method of paragraph [24] or [25], wherein said contacting is for about seven days.

[29] The method of any one of paragraphs [1]-[28], wherein at least one pancreatic progenitor cell of said population of pancreatic progenitor cells expresses at least one of PDX1 and NKX6-1.

[30] The method of any one of paragraphs [1]-[29], wherein at least one endocrine cell of said population of endocrine cells expresses CHGA.

[31] A cell produced by the method of any one of paragraphs [1]-[30].

[32] A composition that comprises a pancreatic progenitor cell, a histone deacetylase (HDAC) inhibitor, a histone methyltransferase inhibitor and optionally an endocrine cell.

[33] The composition of paragraph [32], wherein said HDAC inhibitor is a Class I HDAC inhibitor, a Class II HDAC inhibitor, or a combination thereof.

[34] The composition of paragraph [33], wherein said HDAC inhibitor is at least one of KD5170, MC1568, or TMP195.

[35] The composition of paragraph [34], wherein said HDAC inhibitor is KD5170.

[36] The composition of paragraph [35], wherein a concentration of said KD5170 in said composition is at least 0.1 μM.

[37] The composition of paragraph [36], wherein said concentration of said KD5170 is at least 0.5 μM.

[38] The composition of paragraph [37], wherein said concentration of said KD5170 is about [1 μM.

[39] The composition of any one of paragraphs [32]-[38], wherein said histone methyltransferase inhibitor is an EZH2 inhibitor.

[40] The composition of paragraph [39], wherein said histone methyltransferase inhibitor is at least one of DZNep, GSK126, or EPZ6438.

[41] The composition of paragraph [40], wherein said histone methyltransferase inhibitor is DZNep.

[42] The composition of paragraph [41], wherein a concentration of said DZNep is at least 0.1 μM.

[43] The composition of paragraph [42], wherein said concentration of said DZNep is at least 0.5 μM.

[44] The composition of paragraph [42], wherein said concentration of said DZNep is about [1 μM.

[45] The composition of paragraph [32], wherein said HDAC inhibitor is KD5170 and said histone methyltransferase inhibitor is DZNep.

[46] The composition of any one of paragraphs [32]-[45], wherein said composition is an in vitro composition.

[47] The composition of paragraph [46], wherein said composition further comprises at least one of betacellulin, thiazovinin, retinoic acid, SANT1, XXI, Alk5i II, GC-1, LDN or staurosporine.

[48] A method comprising contacting a pancreatic progenitor cell or precursor thereof with a histone deacetylase (HDAC) inhibitor and a histone methyltransferase inhibitor, wherein said contacting induces differentiation of said pancreatic progenitor cell.

[49] The method of paragraph [48], wherein said pancreatic progenitor cell differentiates into a β cell.

[50] The method of paragraph [49], wherein said β cell is a stem-cell derived β (SC-β) cell.

[51] The method of paragraph [49] or [50], wherein said β cell expresses C-PEP and NKX6-1.

[52] The method of any one of paragraphs [49]-[51], wherein said β cells exhibit an in vitro glucose-stimulated insulin secretion response to a glucose challenge.

[53] The method of any one of paragraphs [48]-[52], wherein said HDAC inhibitor is a Class I HDAC inhibitor, a Class II HDAC inhibitor, or a combination thereof.

[54] The method of paragraph [53], wherein said HDAC inhibitor is at least one of KD5170, MC1568, or TMP195.

[55] The method of paragraph [54], wherein said HDAC inhibitor is KD5170.

[56] The method of any one of paragraphs [48]-[55], wherein said histone methyltransferase inhibitor is an EZH2 inhibitor.

[57] The method of paragraph [56], wherein said histone methyltransferase inhibitor is at least one of DZNep, GSK126, or EPZ6438.

[58] The method of paragraph [57], wherein said histone methyltransferase inhibitor is DZNep.

[59] The method of paragraph [48], wherein said HDAC inhibitor is KD5170 and said histone methyltransferase inhibitor is DZNep.

[60] The method of any one of paragraphs [48]-[59], wherein said method is performed in vitro.

[61] A method comprising contacting a pancreatic progenitor cell or precursor thereof with KD5170 in an amount sufficient to result in differentiation of said cell.

[62] The method of paragraph [61], further comprising contracting said pancreatic progenitor cell with a histone methyltransferase inhibitor.

[63] The method of paragraph [62], wherein said histone methyltransferase inhibitor is at least one of DZNep, GSK126, or EPZ6438.

[64] The method of paragraph [63], wherein said histone methyltransferase inhibitor is DZNep.

[65] The method of any one of paragraphs [61]-[64], wherein said pancreatic progenitor cell differentiates into an endocrine cell.

[66] The method of any one of paragraphs [61]-[65], wherein said pancreatic progenitor cell differentiates into a β cell.

[67] The method of paragraph [66], wherein said 3 cell is a stem-cell derived β (SC-β) cell.

[68] The method of paragraph [66] or [67], wherein said β cell expresses C-PEP and NKX6-1.

[69] The method of any one of paragraphs [66]-[68], wherein said β cell exhibits an in vitro glucose-stimulated insulin secretion response to a glucose challenge.

[70] A method comprising:

a) differentiating a plurality of stem cells in vitro to obtain a cell population comprising pancreatic progenitor cells or precursors thereof;

b) contacting in vitro said cell population with a histone deacetylase (HDAC) inhibitor to generate at least one endocrine cell; and c) maturing said endocrine cell in vitro to obtain at least one SC-β cell.

[71] The method of paragraph [70], wherein said stem cells are human pluripotent stem cells.

[72] The method of paragraph [70] or [71], further comprising contacting said cell population with at least one of betacellulin, thiazovinin, retinoic acid, SANT1, XXI, Alk5i II, GC-1, LDN or staurosporine.

[73] The method of any one of paragraphs [70]-[72], wherein said SC-β cell expresses C-PEP and NKX6-1.

[74] The method of any one of paragraphs [70]-[73], wherein said SC-β cell exhibits an in vitro glucose-stimulated insulin secretion response to a glucose challenge.

[75] The method of any one of paragraphs [70]-[74], further comprising contracting said cell population with a histone methyltransferase inhibitor.

[76] The method of paragraph [75], wherein said histone methyltransferase inhibitor is at least one of DZNep, GSK126, or EPZ6438.

[77] The method of paragraph [76], wherein said histone methyltransferase inhibitor is DZNep.

[78] The method of any one of paragraphs [70]-[77], wherein said HDAC inhibitor is KD5170.

[79] A method comprising contacting a cell population comprising pancreatic progenitor cells or precursors thereof with a histone methyltransferase inhibitor in vitro in an amount sufficient to generate endocrine cells; and maturing said endocrine cells in vitro to obtain at least one SC-β cell that exhibits an in vitro glucose-stimulated insulin secretion response to a glucose challenge.

[80] The method of paragraph [79], further comprising differentiating a plurality of stem cells in vitro to obtain said cell population comprising said pancreatic progenitor cells or precursors thereof.

[81] The method of paragraph [79] or [80], further comprising contacting said cell population with at least one of betacellulin, thiazovinin, retinoic acid, SANT1, XXI, Alk5i II, GC-1, LDN or staurosporine.

[82] The method of any one of paragraphs [79]-[81], further comprising contacting said cell population with a histone deacetylase (HDAC) inhibitor.

[83] The method of paragraph [82], wherein said HDAC inhibitor is KD5170.

[84] The method of any one of paragraphs [79]-[83], wherein said histone methyltransferase inhibitor is at least one of DZNep, GSK126, or EPZ6438.

[85] The method of paragraph [84], wherein said histone methyltransferase inhibitor is DZNep.

[86] A method for selecting a target cell from a population of cells comprising:

(i) contacting said target cell with a stimulating compound, wherein said contacting induces a selectable marker of said target cell to localize to a cell surface of said target cell; and (ii) selecting said target cell based on said localization of said selectable marker at said cell surface.

[87] The method of paragraph [86], wherein said selectable marker comprises PSA-NCAM.

[88] The method of paragraph [87], wherein said selecting said target cell is by cell sorting.

[89] The method of paragraph [88], wherein said selecting comprises contacting said selectable marker of said target cell with an antigen binding polypeptide when said selectable marker is localized to said surface of said target cell.

[90] The method of paragraph [89], wherein said antigen binding polypeptide comprises an antibody.

[91] The method of paragraph [90], wherein said antigen binding polypeptide binds to said PSA-NCAM.

[92] The method of any one of paragraphs [86]-[91], wherein said method further comprises treating said population of cells with a compound that removes said selectable marker from a cell surface of at least one cell of said population of cells.

[93] The method of paragraph [92], wherein said population of cells is treated with said compound prior to said contacting said target cell with said stimulating compound.

[94] The method of paragraph [92] or [93], wherein said compound cleaves said selectable marker from said cell surface of said at least one cell.

[95] The method of paragraph [94], wherein said compound is an enzyme.

[96] The method of paragraph [95], wherein said compound is an endosialidase.

[97] The method of paragraph [96], wherein said endosialidase is endoneuraminidase (Endo-N).

[98] The method of any one of paragraphs [86]-[97], wherein said target cell is an endocrine cell.

[99] The method of any one of paragraphs [86]-[98], wherein said stimulating compound comprises at least one of arginine or glucose.

[100] The method of paragraph [98], wherein said endocrine cell is a β cell.

[101] The method of paragraph [101], wherein said β cell is an SC-β cell.

[102] The method of paragraph [98], wherein said stimulating compound comprises isoproterenol.

[103] The method of paragraph [98], wherein said endocrine cell is an EC cell.

[104] The method of any one of paragraphs [86]-[103], wherein one or more cells of said population of cells fails to localize said selectable marker to a cell surface when contacted with said stimulating compound.

[105] The method of paragraph [104], wherein said stimulating compound is at least one of glucose or arginine and said one or more cells is an EC cell.

[106] The method of paragraph [104], wherein said stimulating compound is isoproterenol and said one or more cells is a β cell.

[107] The method of any one of paragraphs [104]-[106], wherein said selecting said target cell separates said target cell from said one or more cells of said population of cells.

[108] A method comprising:

contacting a population of pancreatic progenitor cells or precursors thereof with a composition comprising at least one epigenetic modifying compound, wherein said contacting results in an increased proportion of islet cells as compared to a corresponding population of pancreatic progenitor cells which is not contacted with said at least one epigenetic modifying compound.

[109] The method of paragraph [108], wherein said islet cells comprise at least one 3 cell.

[110] The method of paragraph [109], wherein said β cell comprises an SC-β cell.

[111] The method of paragraph [110], wherein said SC-β cell exhibits an in vitro glucose-stimulated insulin secretion response to a glucose challenge.

[112] The method of paragraph [108], wherein said islet cells comprise at least one alpha cell.

[113] The method of paragraph [108], wherein said islet cells comprise a delta cell.

[114] The method of paragraph [108], wherein said islet cells comprise a polyhormonal (PH) cell.

[115] The method of any one of paragraphs [108]-[114], further comprising differentiating a plurality of stem cells in vitro to obtain said population of pancreatic progenitor cells or precursors thereof.

[116] The method of paragraph [115], wherein said stem cells are human pluripotent stem cells.

[117] The method of any one of paragraphs [108]-[116], wherein said at least one epigenetic modifying compound comprises one or more of a DNA methylation inhibitor, a histone acetyltransferase inhibitor, a histone deacetylase inhibitor, a histone methyltransferase inhibitor, or a bromodomain inhibitor.

[118] The method of paragraph [117], wherein said at least one epigenetic modifying compound comprises a histone methyltransferase inhibitor.

[119] The method of paragraph [118], wherein said histone methyltransferase inhibitor is an EZH2 inhibitor.

[120] The method of paragraph [118] or [119], wherein said histone methyltransferase inhibitor is at least one of DZNep, GSK126, or EPZ6438.

[121] The method of paragraph [120], wherein said histone methyltransferase inhibitor is DZNep.

[122] The method of paragraph [121], wherein a concentration of said DZNep in said composition is greater than 0.1 μM.

[123] The method of paragraph [122], wherein said concentration of said DZNep is at least 0.5 μM.

[124] The method of paragraph [123], wherein said concentration of said DZNep is about 1 μM.

[125] The method of any one of paragraphs [108] to [124], wherein said at least one epigenetic modifying compound comprises a histone deacetylase (HDAC) inhibitor.

[126] The method of paragraph [125], wherein said HDAC inhibitor is a Class I HDAC inhibitor, a Class II HDAC inhibitor, or a combination thereof.

[127] The method of paragraph [126], wherein said HDAC inhibitor is at least one of KD5170, MC1568, or TMP195.

[128] The method of paragraph [127], wherein said HDAC inhibitor is KD5170.

[129] The method of paragraph [108], wherein said at least one epigenetic modifying compound comprises an HDAC inhibitor and an EZH2 inhibitor.

[130] The method of paragraph [108], wherein said at least one epigenetic modifying compound comprises DZNep and KD5170.

EXAMPLES

These examples are provided for illustrative purposes only and not to limit the scope of the claims provided herein.

Example 1. Histone Acetylation in hPSC-Derived Beta Cells

Systems approach (for instance Arda et al. (Cell Metabolism 23: 909-920, 2016)) are used to identify age-dependent gene expression programs in human islet cells that includes (1) procurement of pancreatic tissue from children and adults, (2) developing robust and reliable cell purification methods, (3) generation of comprehensive transcriptome and histone modification maps, and (4) systematic assays of islet physiology and function. Distinct modes of histone mediated regulation of age-dependent genes in juvenile and adult human islet cells are revealed on the described genome wide histone map. Xu et al. (EMBO J 2014) describes that histone methylation is reduced in NGN3, NKX6.1, and NKX2.2 genes in endocrine progenitors. In NGN3 cells, H3K27me3 is depleted from the NGN3, NeuroD1, and NKX6.1 elements, consistent with the activation of the respective genes. Haumaitre et al. (MCB 2013) reports global reduction in HDAC expression and activity during pancreas differentiation. Xie (Cell Stem Cell, 2013) reports that chromatin architecture is inappropriately remodeled during in vitro differentiation. EZH2 inhibition and HDAC inhibition increases NGN3 expression and leads to more stem cell derived beta cells, suggesting that NGN3 is important for beta cell development.

Example 2. Inhibition of Histone Methylation and Deacetylation

Figure 6:
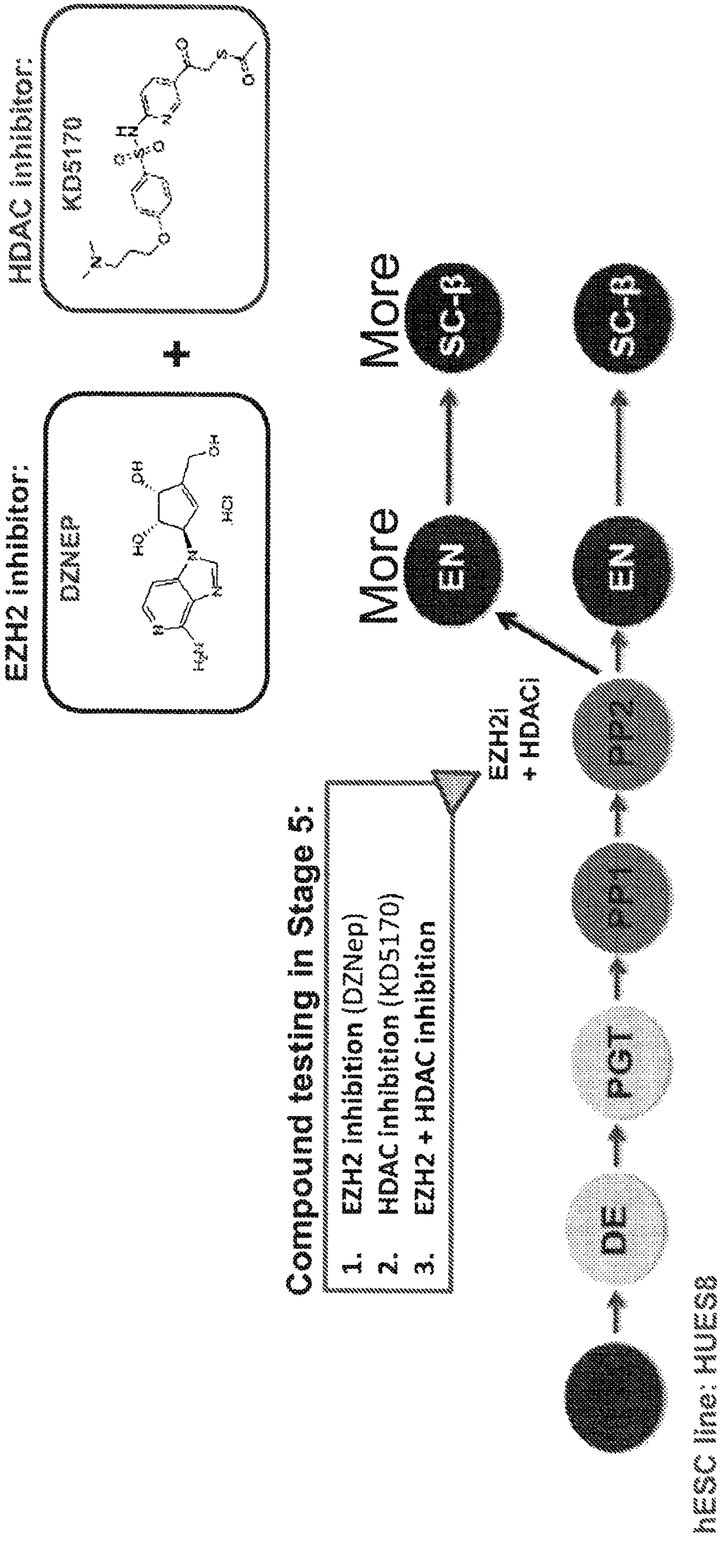
FIG. 6 is a schematic of directed differentiation from hPSC into INS+ cells, comprising inhibition of histone methylation and deacetylation of stage 5 as described herein. DE: definitive endoderm; PGT; primitive gut tube; PPT1; early pancreatic progenitor; PPT2; PDX1+/NKX6.1+ pancreatic progenitors; EN: NKX6.1/C peptide+ cells; SC-β: stem cell derived beta cell.
Figure 7:
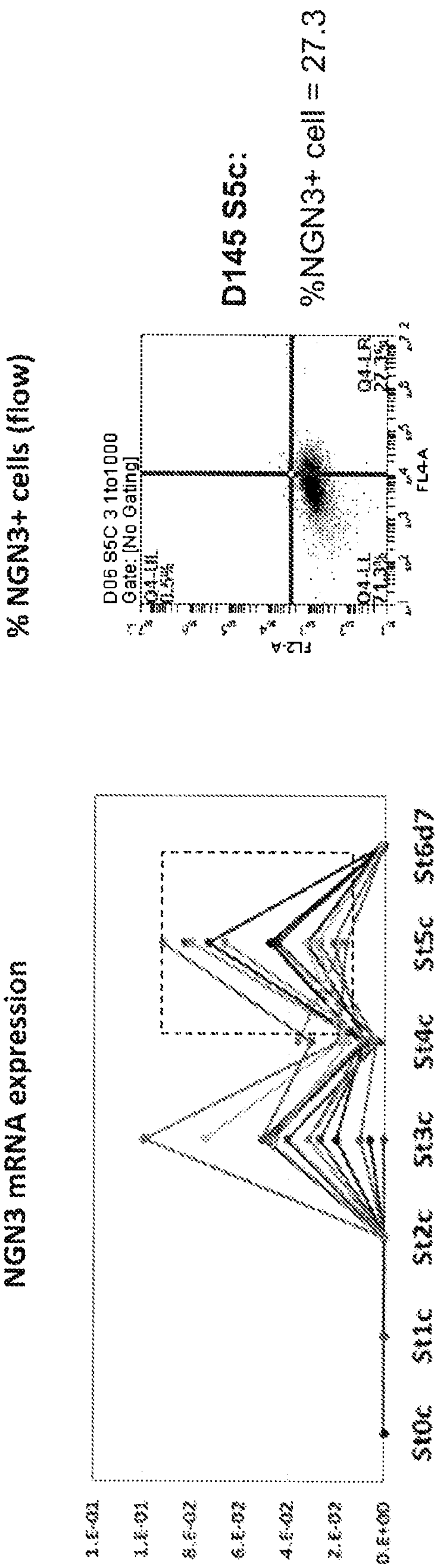
FIG. 7 shows that stage 5 cells express NGN3 to initiate stem cell (SC) islet cell differentiation.

The mRNA expression of NGN3 was investigated in each steps of directed differentiation described herein (FIG. 5), and it was observed that cells expressed NGN3 to initiate SC-β cell differentiation (FIG. 7). The effects of inhibition of histone methylation and deacetylation on SC-β cell differentiation were investigated (FIG. 6). Stage 5 of the directed differentiation as described herein (FIGS. 5-6) in hESC line (D97, D114, and D241 HUES8) was treated with an EZH2 inhibitor (DZNep), HDAC inhibitor (KD5170), and a combination thereof (FIG. 6).

Figure 9:
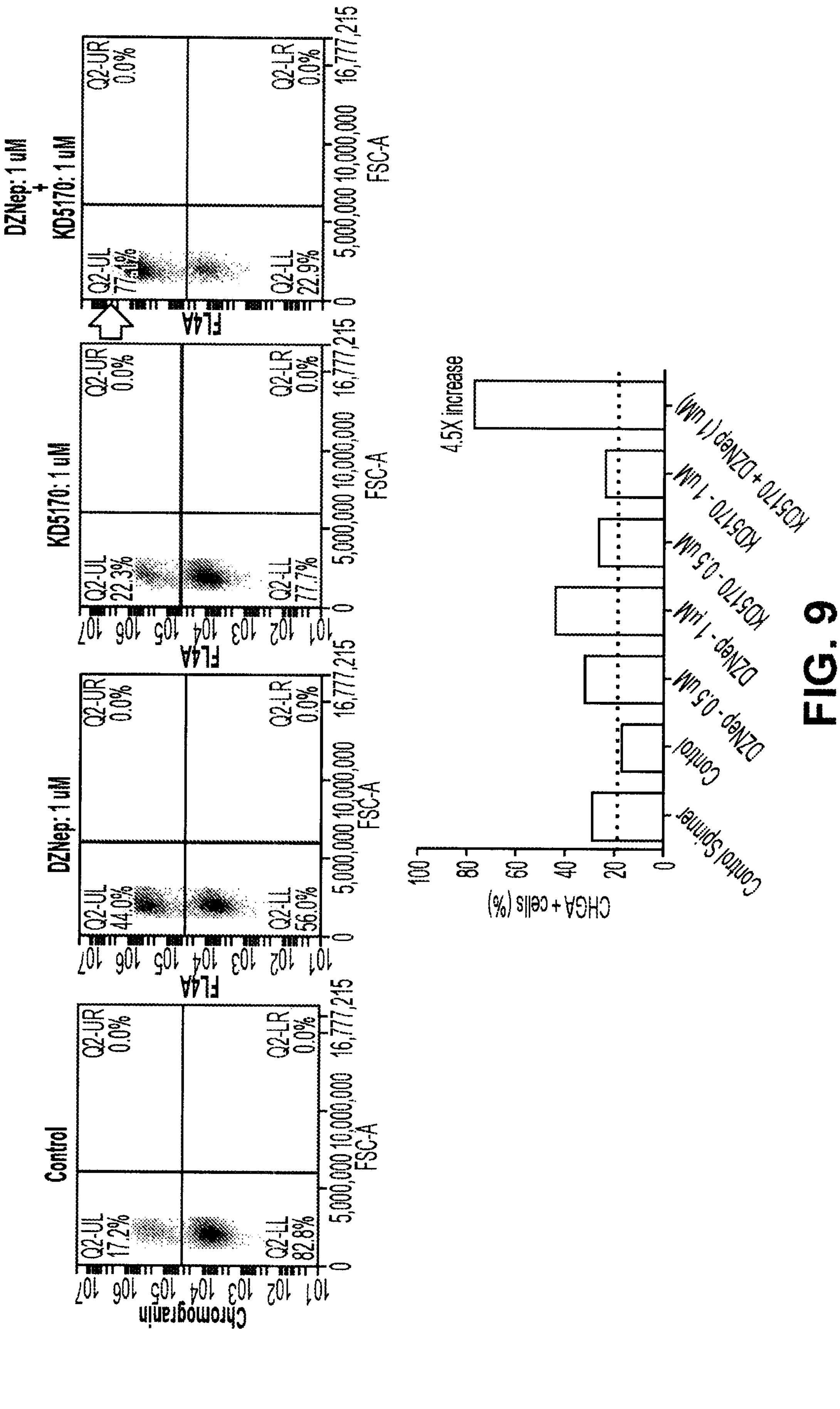
FIG. 9 shows that combined inhibition of EZH2 and HDAC in stage 5 significantly increases endocrine cells.
Figure 10:
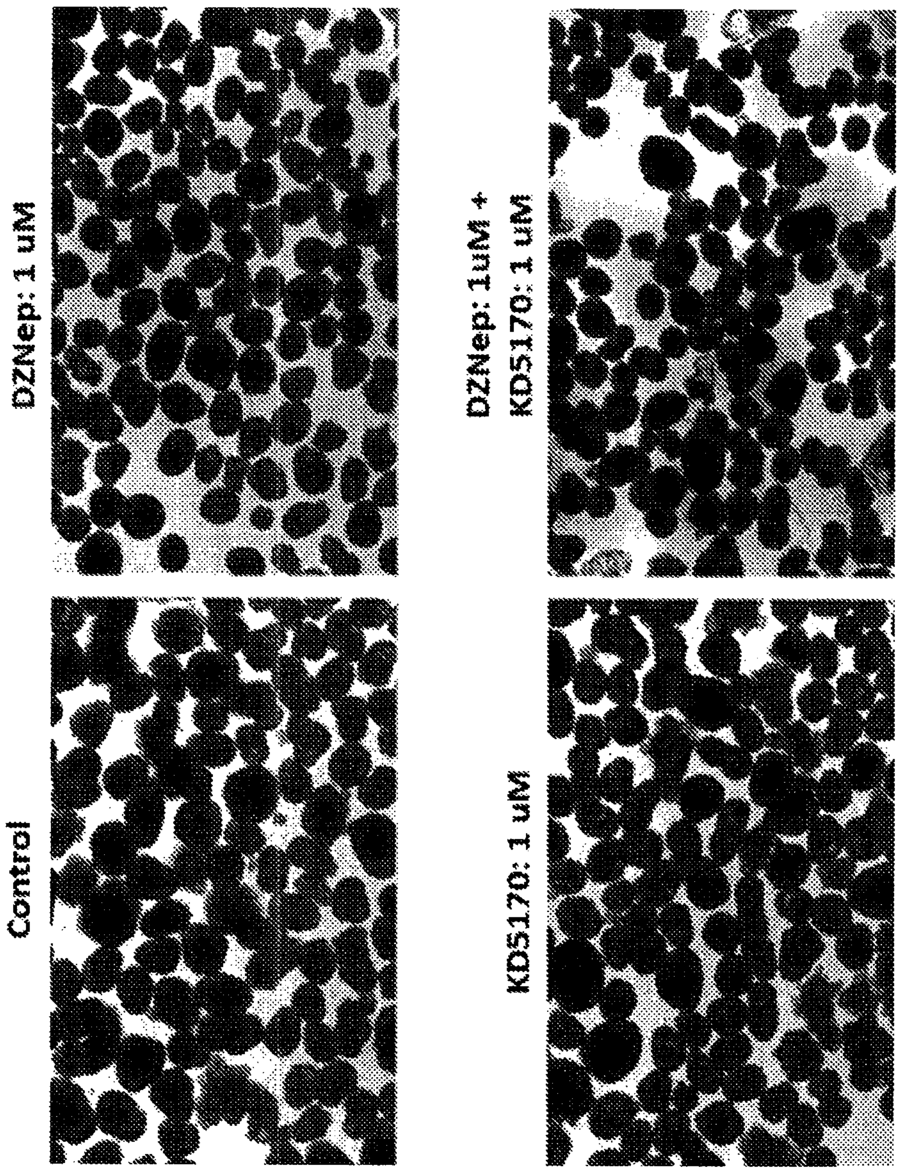
FIG. 10 shows that combined inhibition of EZH2 and HDAC in stage 5 significantly increases endocrine cells.
Figure 11:
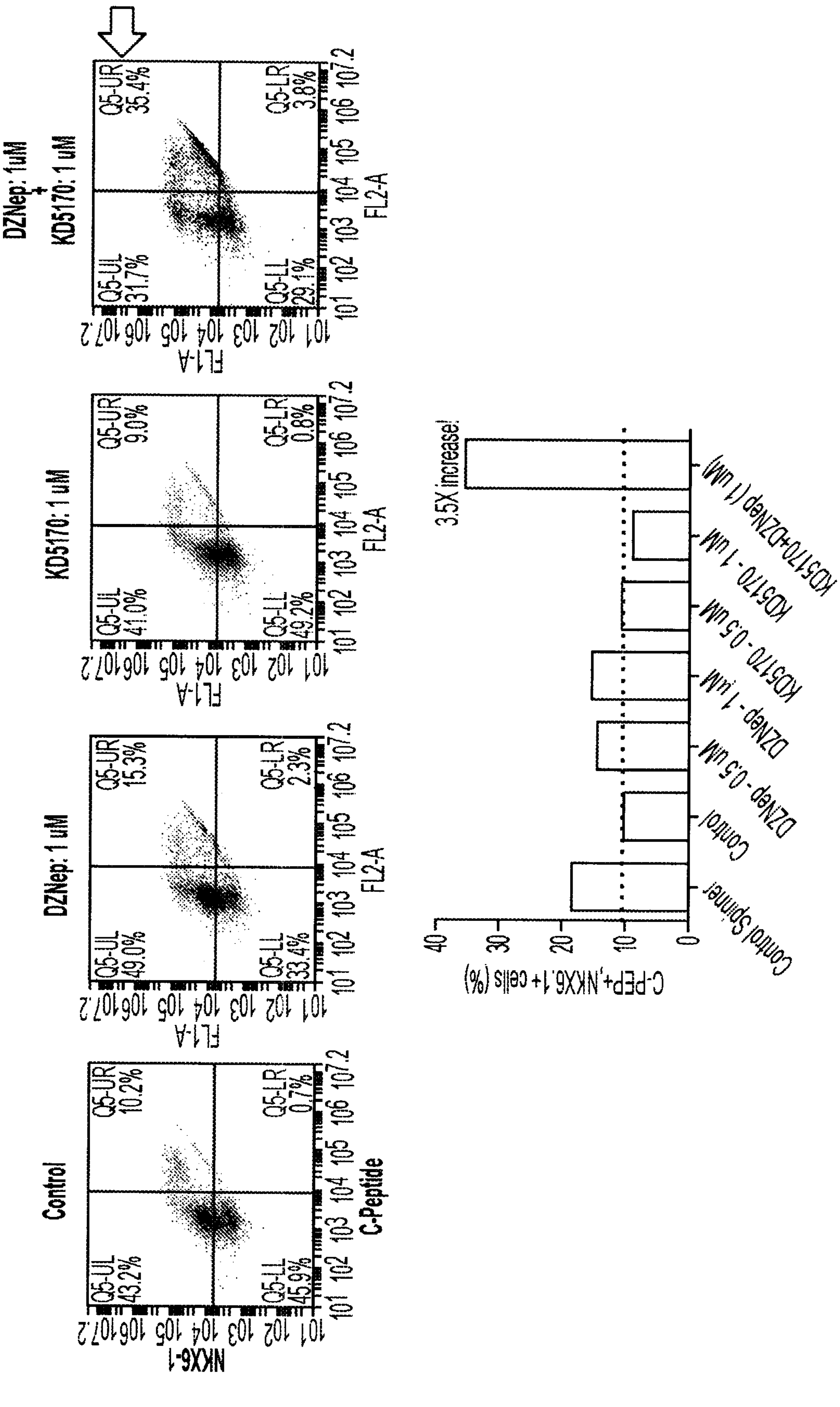
FIG. 11 shows that combined inhibition of EZH2 and HDAC in stage 5 significantly increases SC β cells.
Figure 12:
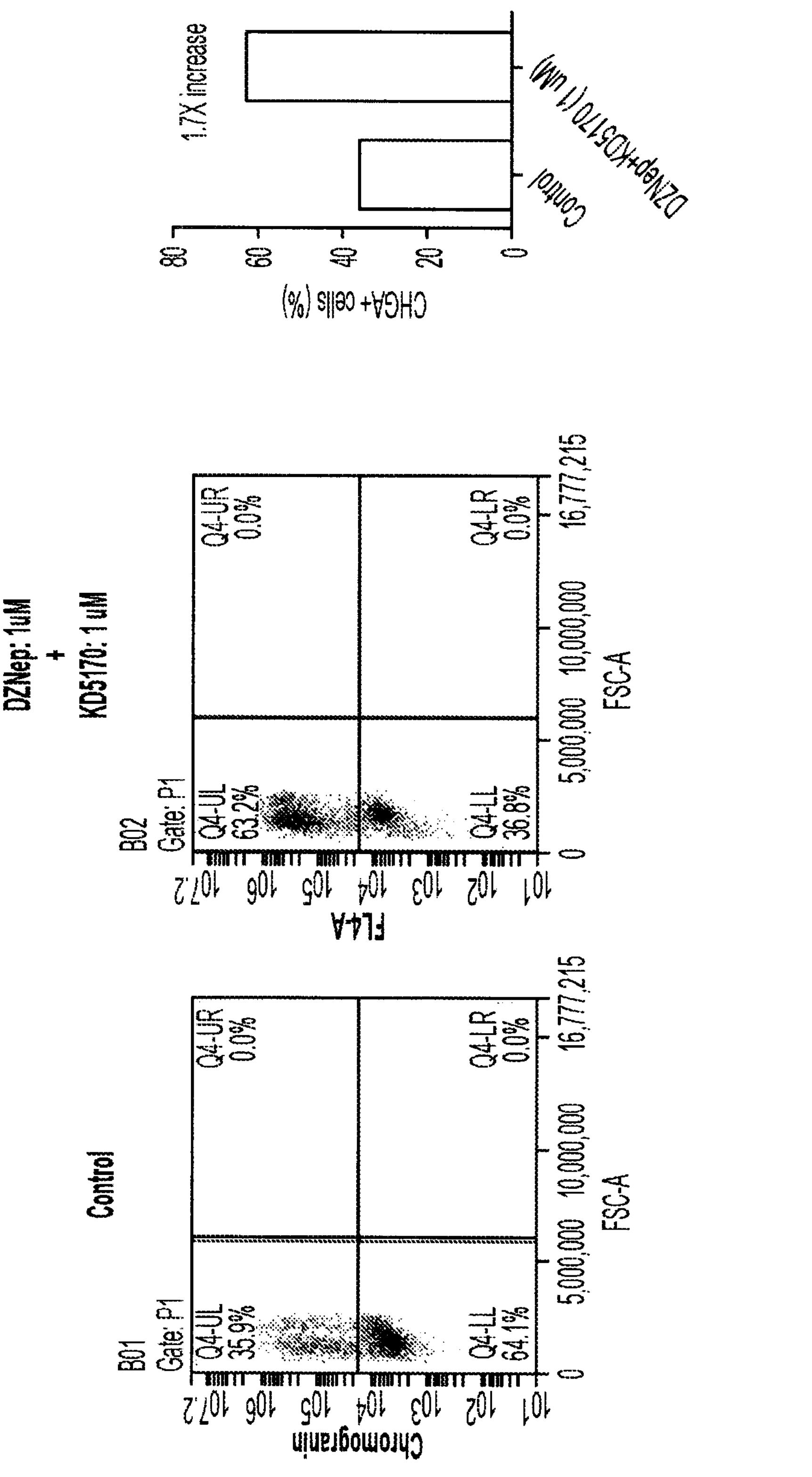
FIG. 12 shows increased endocrine cells in stage 5 (n=2).
Figure 13:
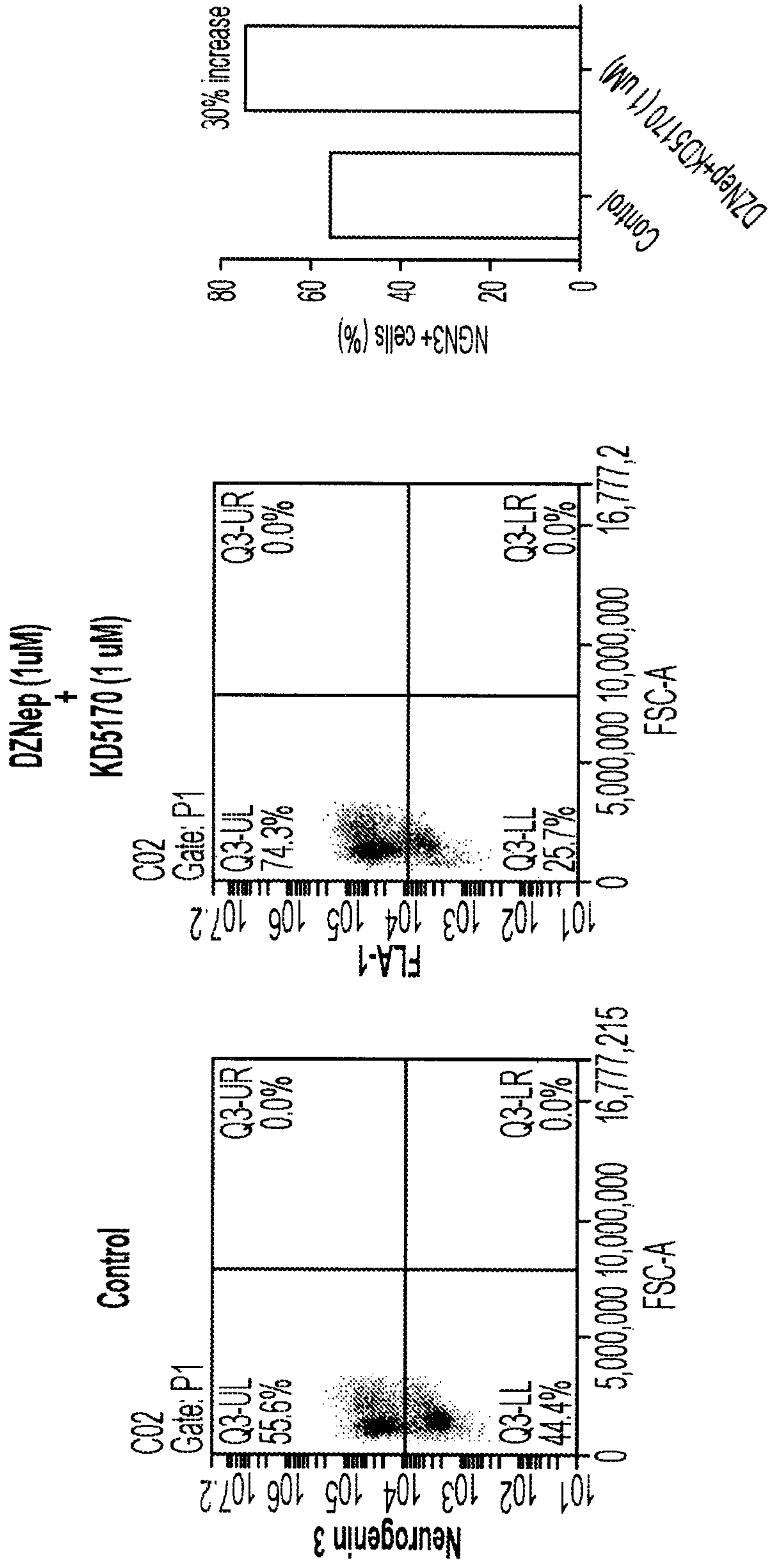
FIG. 13 shows combined EZH2 and HDAC inhibition increases neurogenin3+ progenitors in stage 5.
Figure 16:
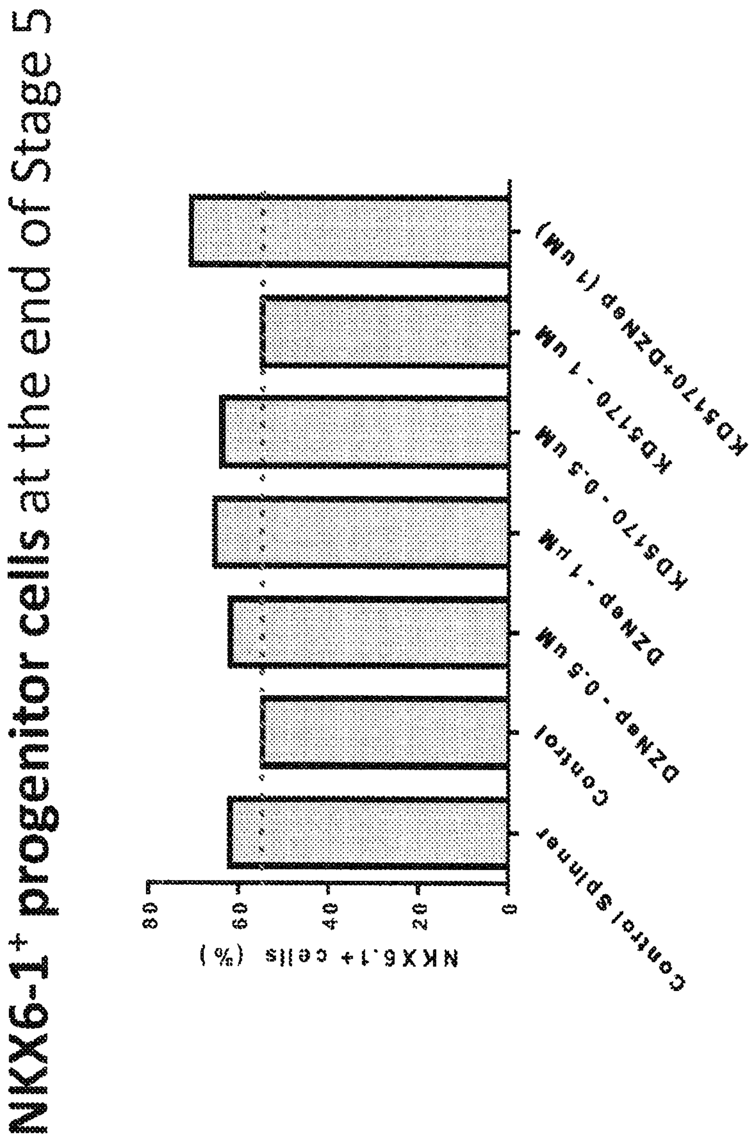
FIG. 16 shows that combined inhibition of EZH2 and HDAC in stage 5 increases NKX6-1+ progenitors.
Figure 17:
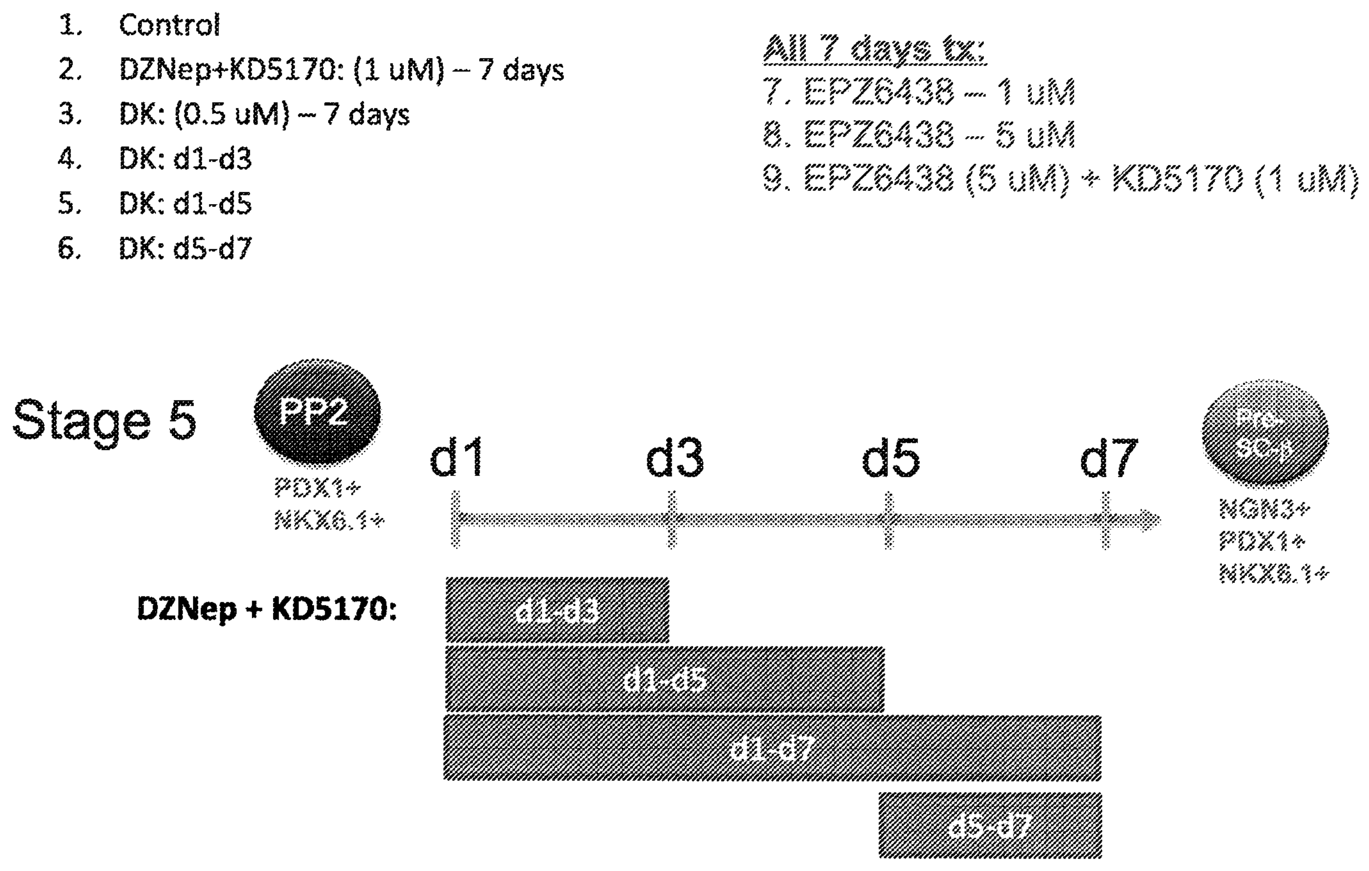
FIG. 17 is an experiment outline for testing EZH2 and HDAC inhibitors in stage 5.
Figure 18:
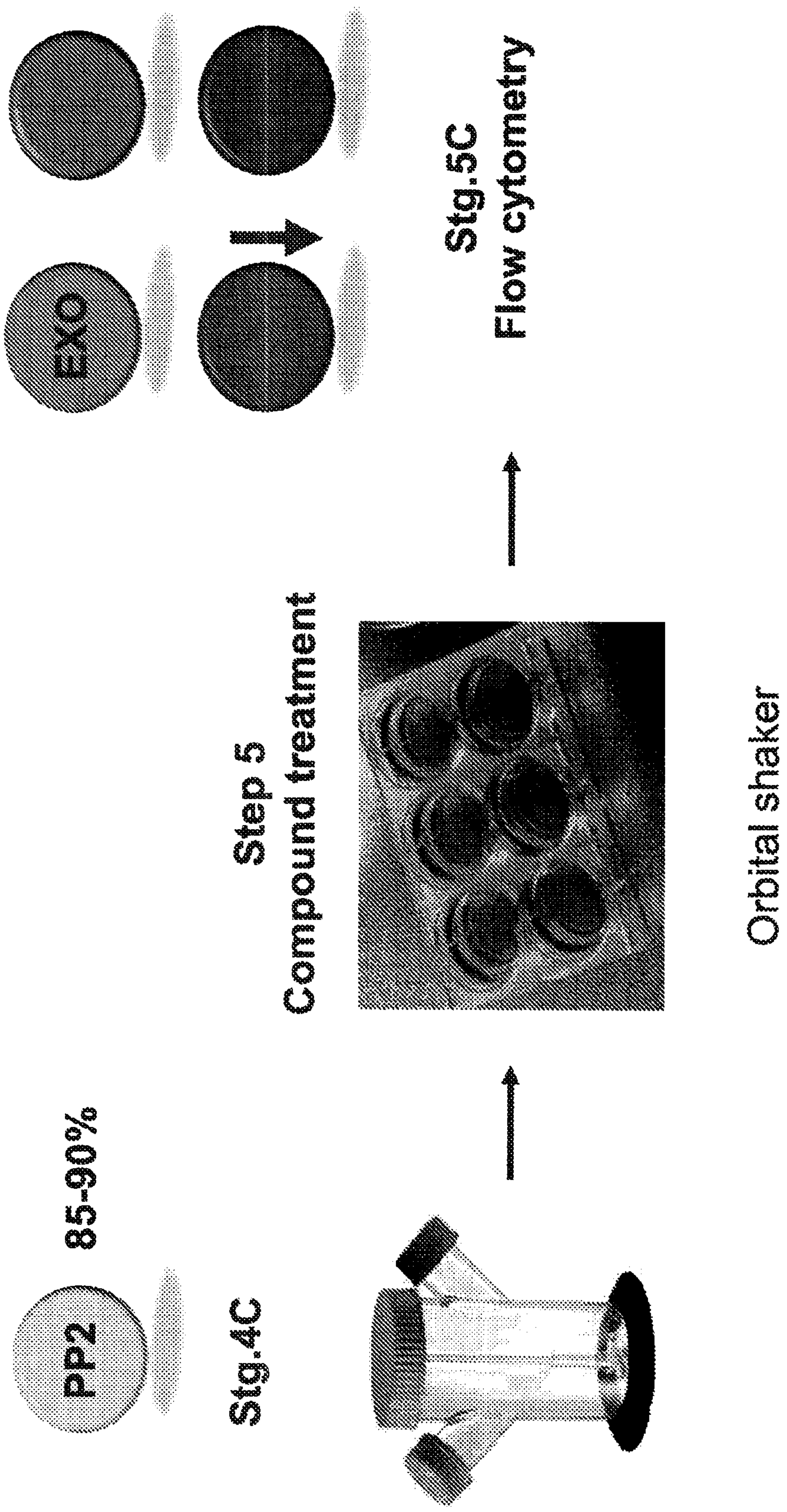
FIG. 18 is a schematic of candidate screen set up.

Candidate inhibitor screening was performed as described in FIG. 18. Inhibition of EZH2 or HDAC in stage 5 (D97 HUES8) increased endocrine cells and SC-β cells (FIG. 8). Combined inhibition of EZH2 and HDAC in stage 5 (D114 HUES8) significantly increased endocrine cells (FIGS. 9-11). SC-β cells comprised 35.4% at the end of stage 5 with DZNep and KD5170. The total percentage of C-peptide positive cells was 39.6%, which suggested that there were at most 4% C-peptide positive, NKX6.1 polyhormonal cells (FIG. 11). Combined inhibition of EZH2 and HDAC in stage 5 was tested as described in FIG. 17. Combined inhibition of EZH2 and HDAC in stage 5 (D241 HUES8) increased Neorogenin3+ progenitors in stage 5 (FIGS. 12-13). Combined inhibition of EZH2 and HDAC in stage 5 increased NKX6.1+ progenitor cells (FIG. 16).

Figure 19:
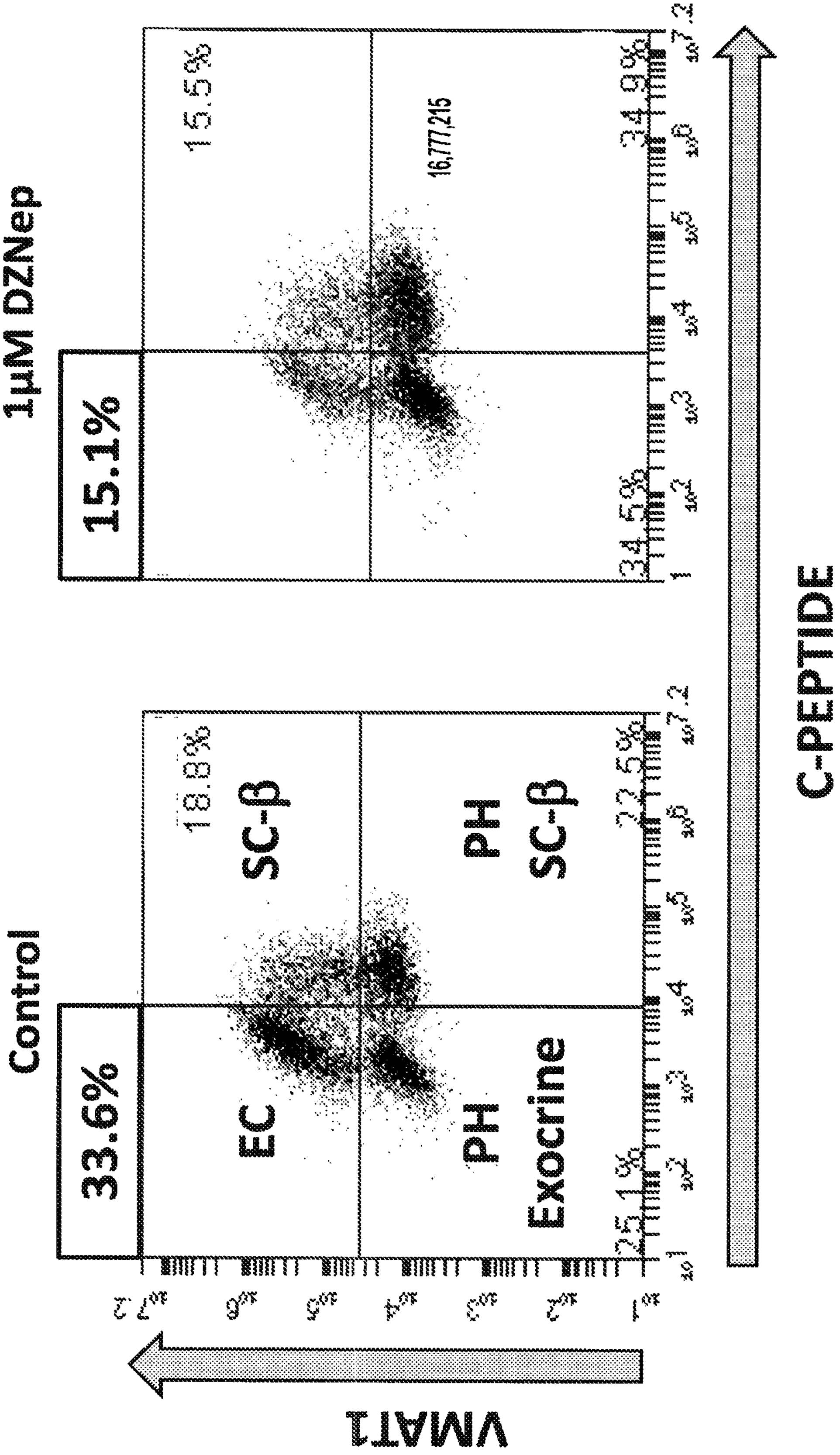
FIG. 19 shows specific decrease in (VMAT1+ INS−) EC population.
Figure 20:
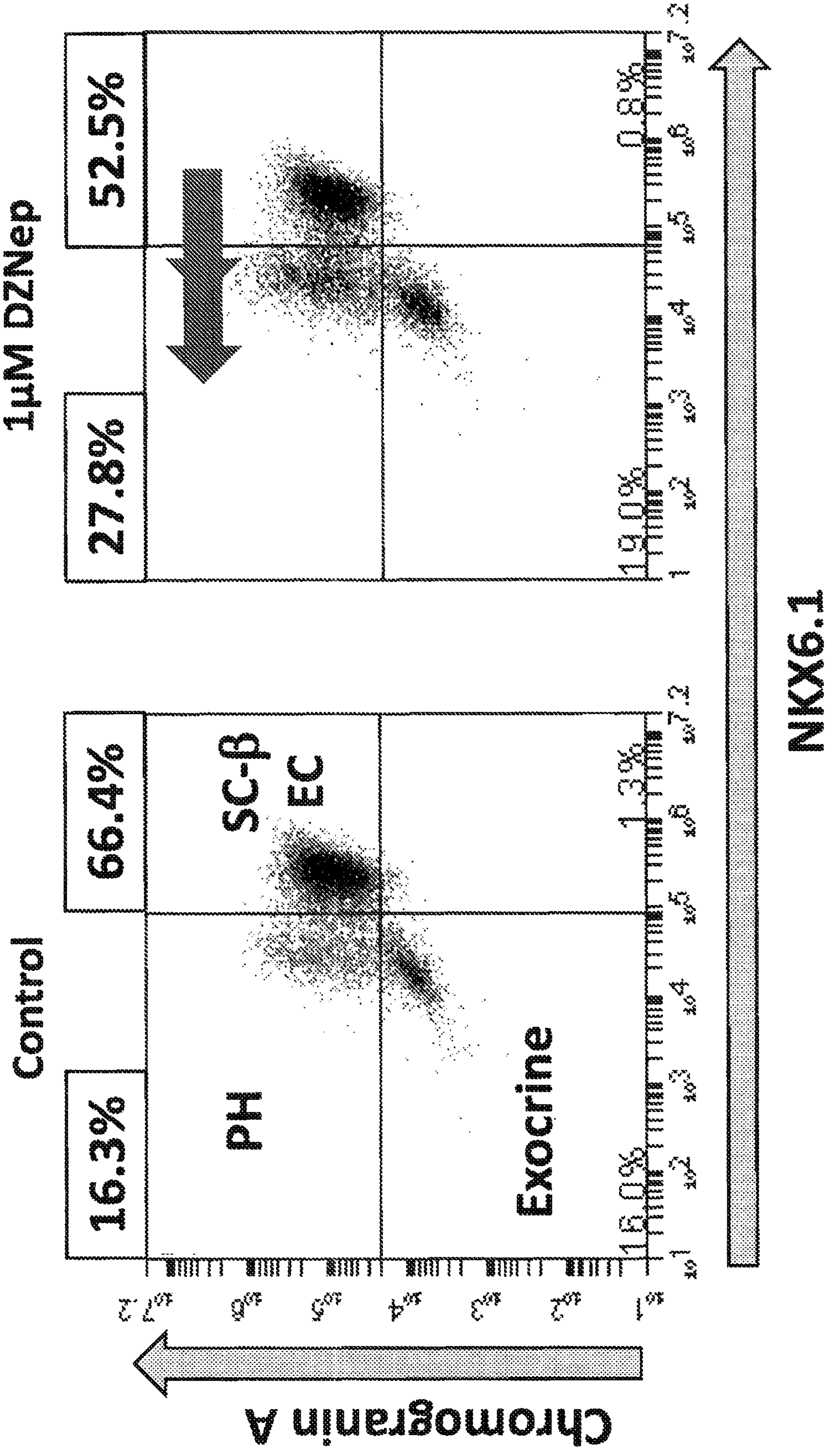
FIG. 20 shows concomitant increase of (NKX6.1−ChromA+) PH cells. PH: polyhormonal cells.
Figure 21:
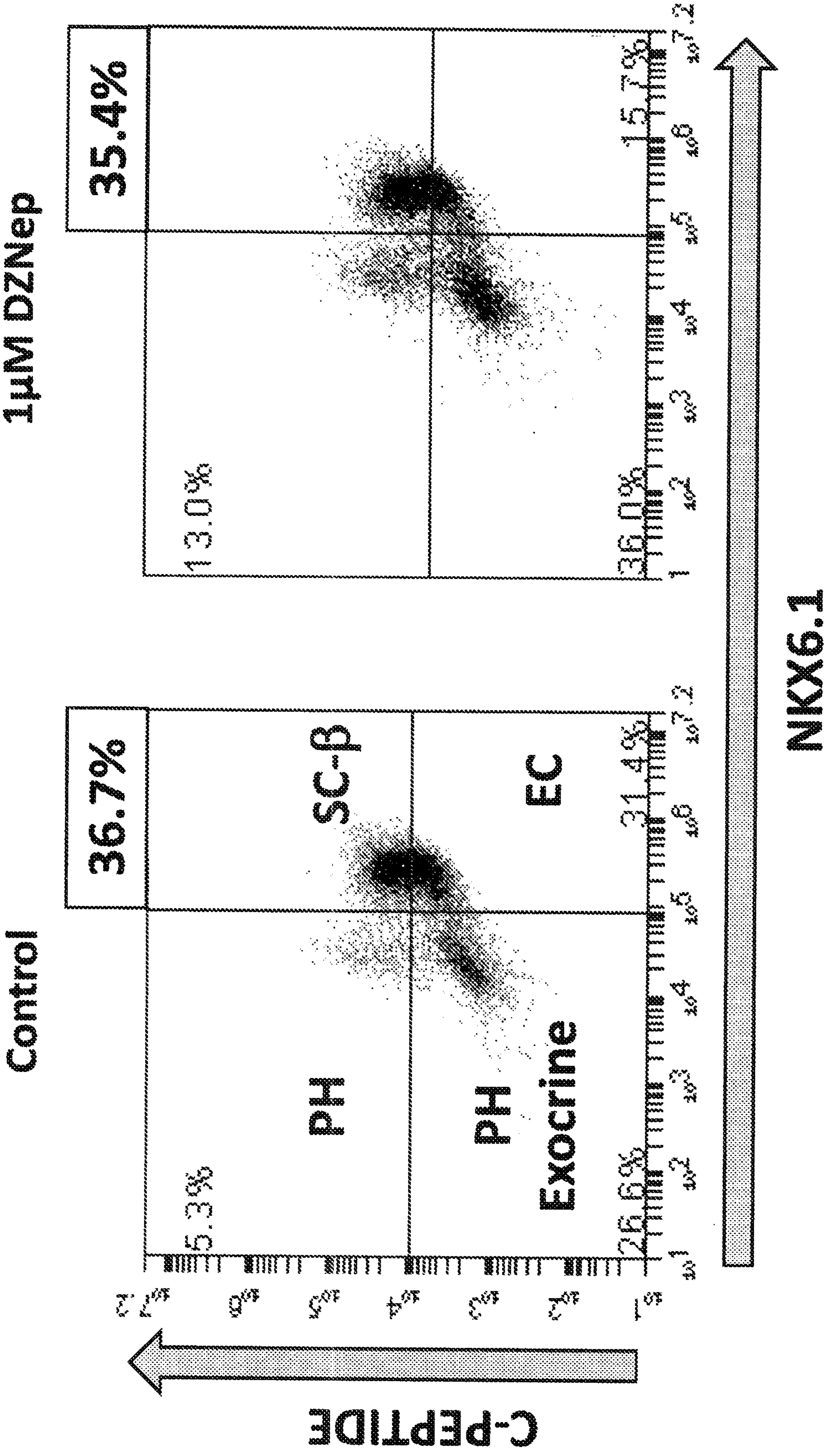
FIG. 21 shows that the (NKX6.1+ INS+) SC-β population percentage is not affected.

Inhibition with DZNep showed specific decrease in VMAT1+INS− EC population (FIG. 19), concomitant increase of NKX6.1-ChromA+PH cells (FIG. 20), and unaffected NKX6.1+INS+SC-β cell population (FIG. 21). Inhibition with DZNep (1 μM) throughout stage 5 removed more than half of the (VMAT1+INS−) EC population without affecting viability (FIGS. 19-21).

Figure 14:
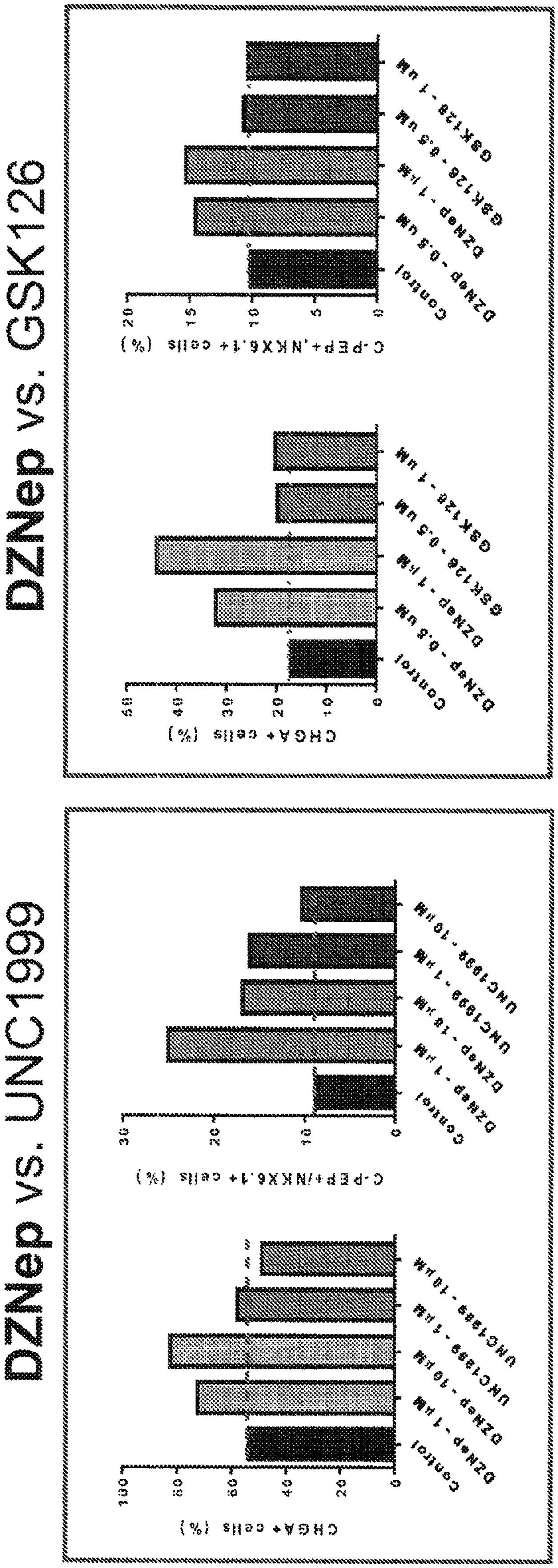
FIG. 14 shows that DZNep outperforms other EZH2 inhibitors.

In summary, histone methyltransferase and deacetylase inhibitors increased NGN3 expression and beta cell differentiation, and EZH2 inhibition by DZNep in stage 5 increased the proportion of endocrine cells (CHGA+), progenitors cells (NKX6-1+) and pre-SC-b cells (C-PEP+, NKX6-1+). Other EZH2 inhibitors (UNC1999, GSK126) did not increase the proportion of all β cell types (FIG. 14). HDAC inhibition by KD5170 in stage 5 increased the percentage of pre-SC-β cells (C-PEP+, NKX6-1+). Other HDAC inhibitors (sodium butyrate, TSA, SAHA) did not increase the percentage of pre-SC-β cells (FIG. 15). Combined EZH2 and HDAC inhibition by DZNep and KD5170 in stage 5 (HUES8) synergistically and significantly enhanced differentiation of endocrine cells (CHGA+), progenitors cells (NKX6-1+) and pre-SC-b cells (C-PEP+, NKX6.1+).

Example 3. Differentiation of Stem Cell into Pancreatic β Cells (SC-β Cells

Figure 39:
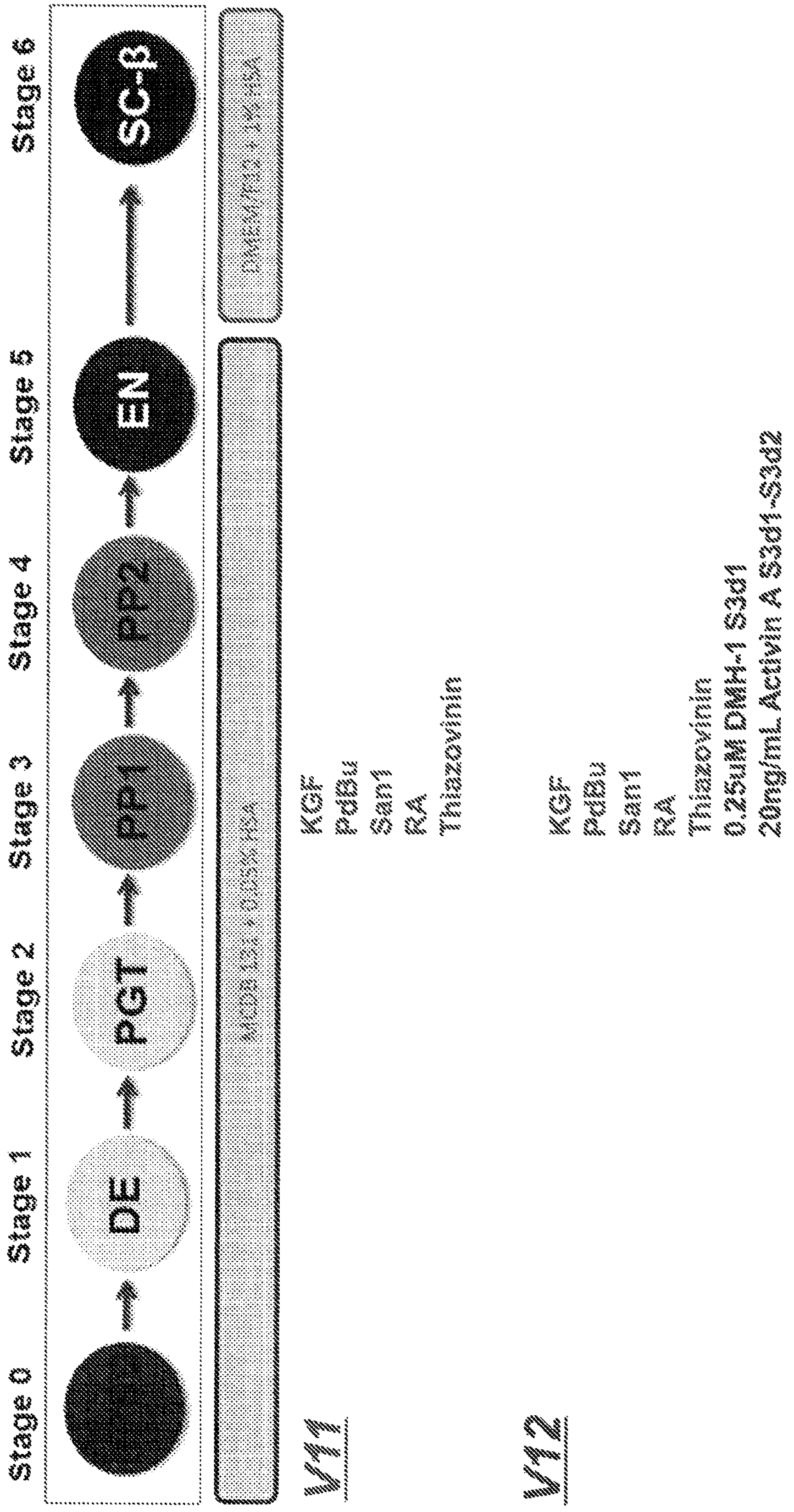
FIG. 39 shows diagrams of two exemplary protocols (v11 and v12) for differentiating human pluripotent stem cells into stem cell-derived pancreatic β cells according to the present disclosure.

Two exemplary differentiation protocols v11 and v12, as illustrated in FIG. 39, were tested. The two protocols are both 6-stage stepwise protocols that share similar reagents and their differentiation steps of the first 5 stages are largely based on the differentiation protocol as shown in FIG. 5, and their differences are as follows: (a) in v12 protocol, 0.25 μM DMH-1 was present in the culture medium on day 1 of Stage 3 (S3d1) and 20 ng/mL Activin A was present in the culture medium on day 1 and day 2 of Stage 3 (S3d1-S3d2); (b) in vii protocol there was no DMH-1 or Activin A added in Stage 3; (c) in both v11 and v12 protocols, DZNep was present in the culture medium at 100 nM on day 1, 3, 5, 7 at Stage 5. Stage 6 of both v11 and v12 protocols was carried out by culturing product cells from Stage 5 in DMEM/F12 medium that is supplemented with 1% HAS without exogenous differentiation factors. The medium was changed every other day throughout the Stage 6.

Figure 40:
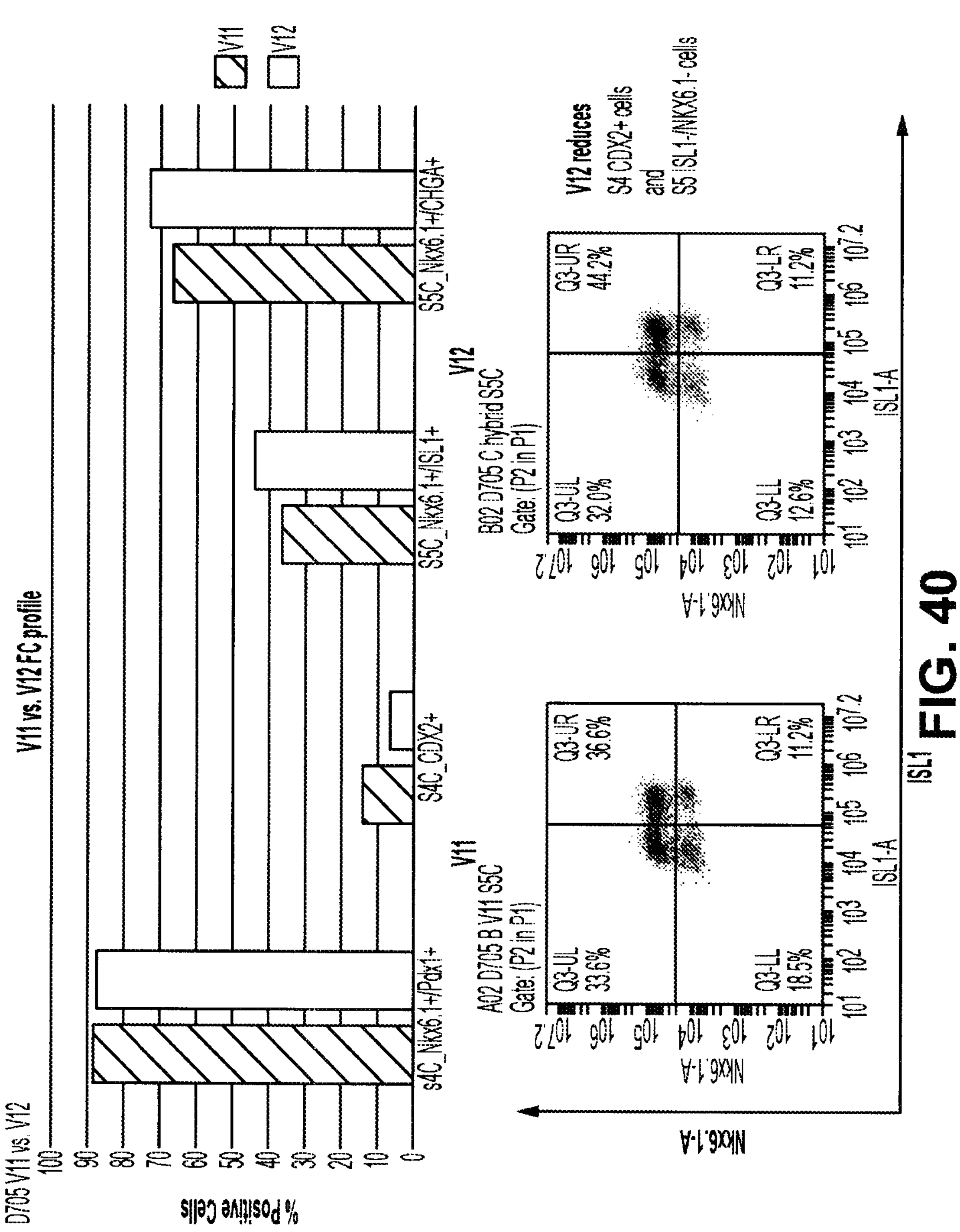
FIG. 40 shows that v12 protocol generated a higher proportion of cells expressing ISL1 and NKX6.1 (ISL1-positive, NKX6.1-positive) and a lower proportion of ISL-negative, NKX6.1-negative cells at Stage 5, and a lower proportion of CDX2-positive cells at Stage 4, as compared to v11 protocol.

In one experiment, the cell cultures derived from stem cell line D705 according to the two different protocols were examined at different stages. FIG. 40 shows the flow cytometry results when surface expression level of NKX6.1, Pdx1, Cdx2, ISL1, and CHGA were examined in the differentiated cells at Stage 4 (S4) and Stage 5 (S5), respectively. As shown in the figure, the v12 protocol reduced the percentages of Cdx2+ cells at S4 and ISL1−/NKX6.1− cells at S5, and increased the percentage of the differentiated ISL+/NKX6.1+ cells at S5.

Figure 41:
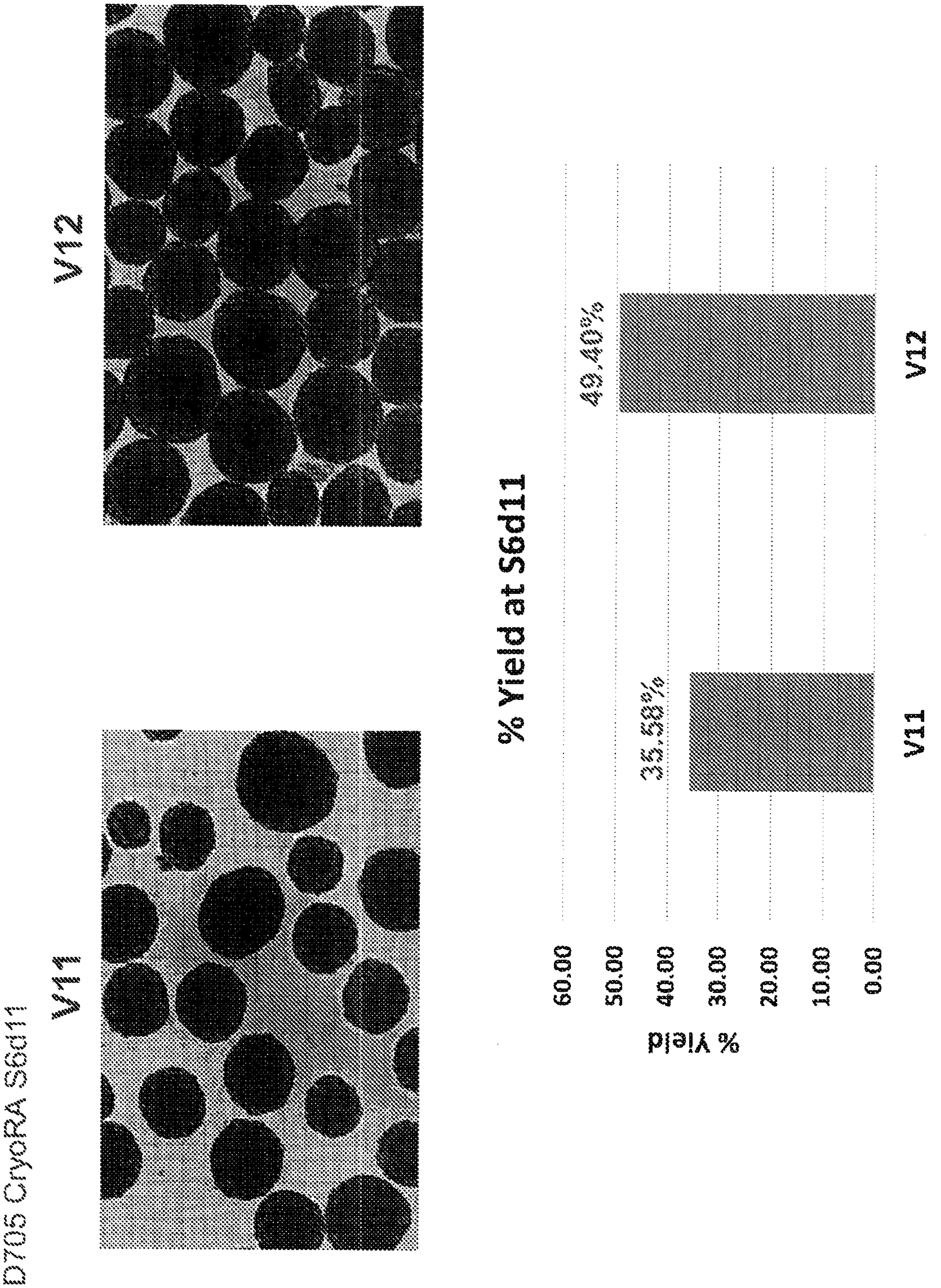
FIG. 41 shows that cell clusters generated via v12 protocol had a higher recovery yield after cryopreservation as compared to v11 protocol.
Figure 42:
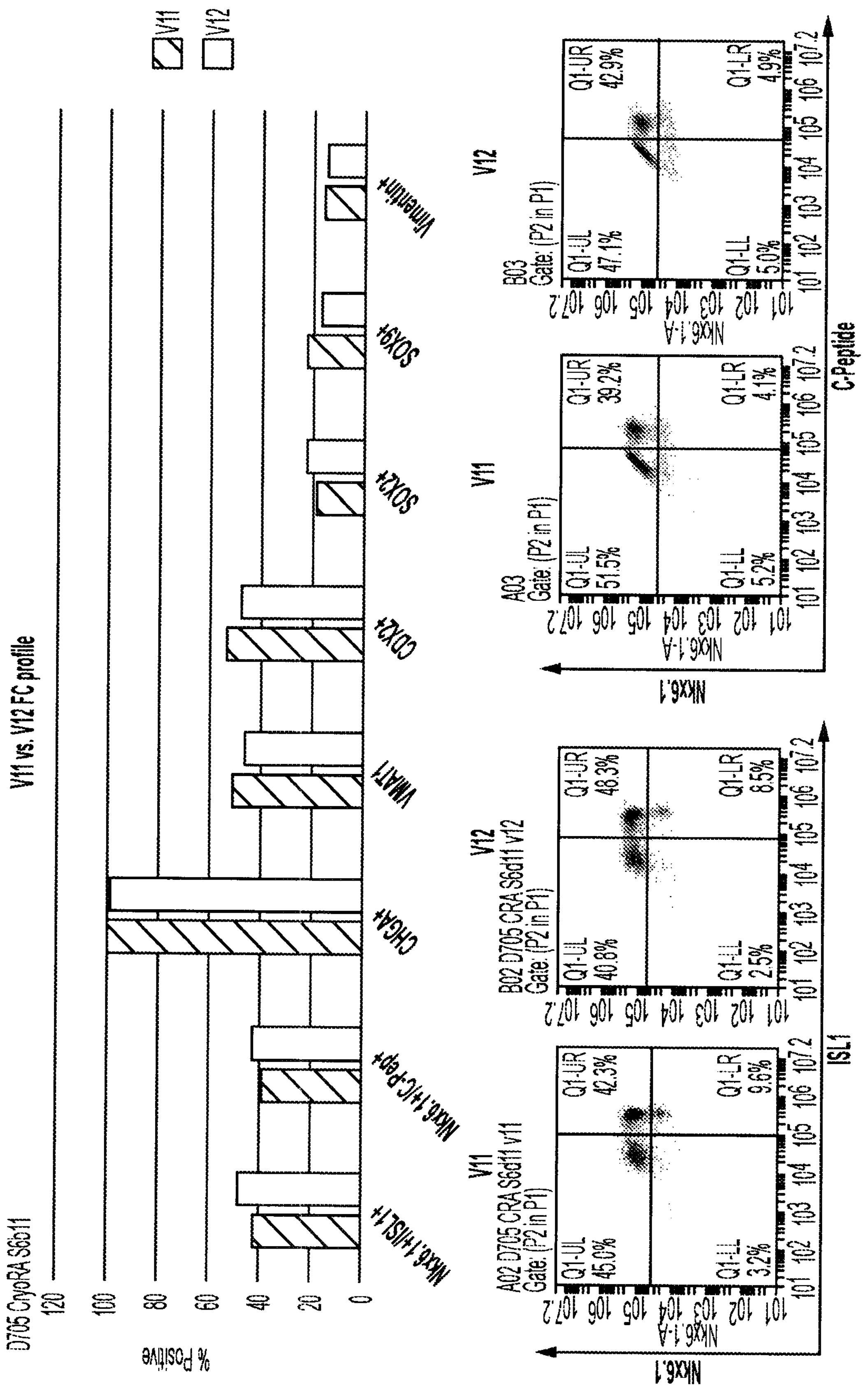
FIG. 42 shows that v11 and v12 protocols generated comparable proportion of SC-β cells.
Figure 43:
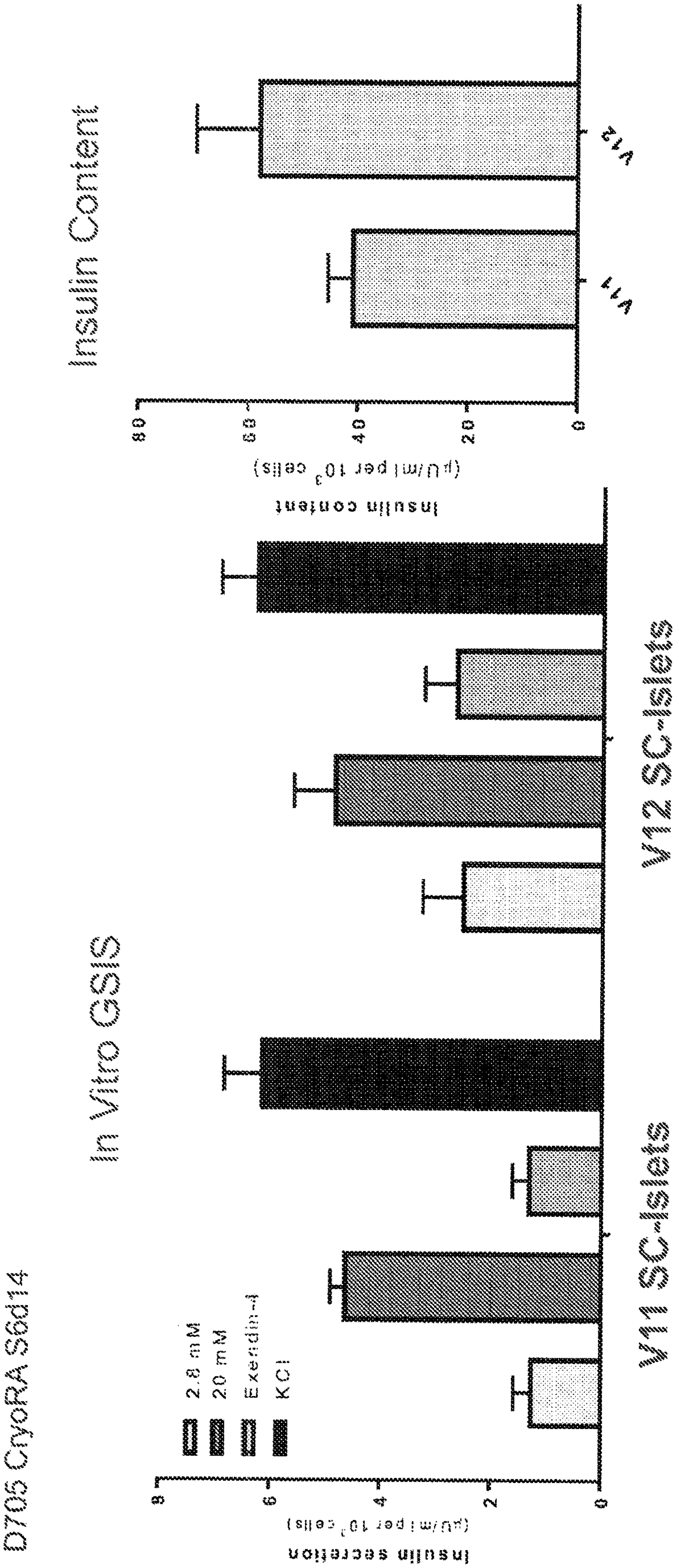
FIG. 43 shows that v11 and v12 protocols generated cell clusters having comparable GSIS response and insulin content.

The cell cultures were also examined after cryopreservation and reaggregation procedure (CryoRA cells) after Stage 5 and before recovery of the cells for Stage 6 (S6) differentiation. In this experiment, as summarized in the graph in FIG. 41, cell counting of the CryoRA cell clusters on day 11 of Stage 6 (S6d11) showed that the cell recovery yield was much higher with the cells obtained via the v12 protocol as compared to the cells obtained via the v11 protocol. Flow cytometry analysis (FIG. 42) of the S6d11 cells obtained via the two protocols indicated that the Sc-β cell composition constitutes comparable percentage, about 40%. In vitro GSIS assay was also conducted to examine the glucose response in S6d14 cells obtained via the two protocols, which showed comparable results between the two protocols. The insulin content was also shown to be comparable (FIG. 43).

Figure 44:
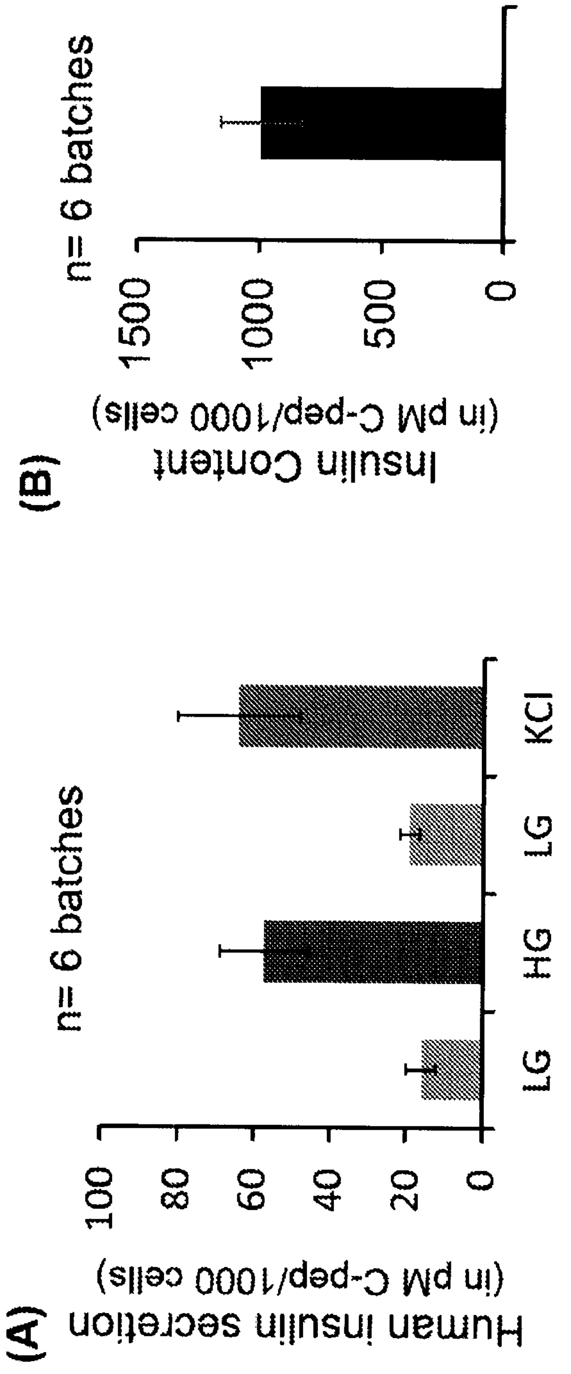
FIG. 44 summarizes insulin release performance of an exemplary cell population generated according to the methods provided herein in a bioreactor in response to low glucose (LG), high glucose (HG), and potassium chloride (KCl) challenges, respectively, and the insulin content of the cell populations.

In one experiment, cell clusters comprising the pancreatic β cells were generated in bioreactors according to the exemplary protocol. In a glucose stimulated insulin secretion (GSIS) assay (FIG. 44A), SC-islet cell clusters were exposed sequentially to low (LG, 2.8 mM) or high (HG, 20 mM) glucose conditions or a combination of 2.8 mM glucose and 30 mM KCl (KCl). An average of 6 independent batches is shown. SC-islet cells clusters were also lysed and analyzed for total insulin content as another method of analyzing activity (FIG. 44B). Data are Mean+/−SEM.

Example 4. SC-β Cell Surface Marker Identification Screen and Sorting

Figure 22A:
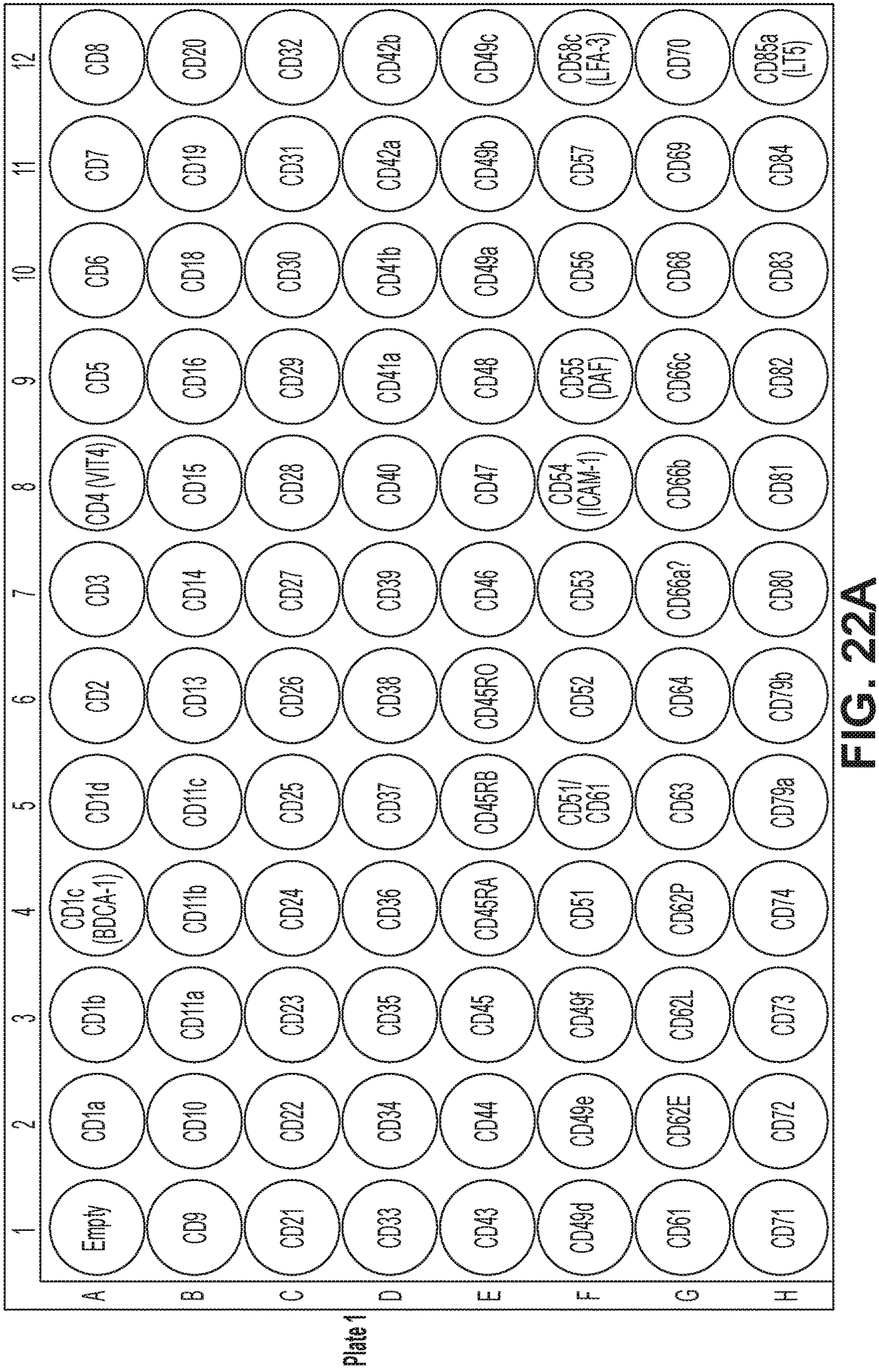
FIG. 22 shows different plates of cell surface marker discovery screen.
Figure 22B:
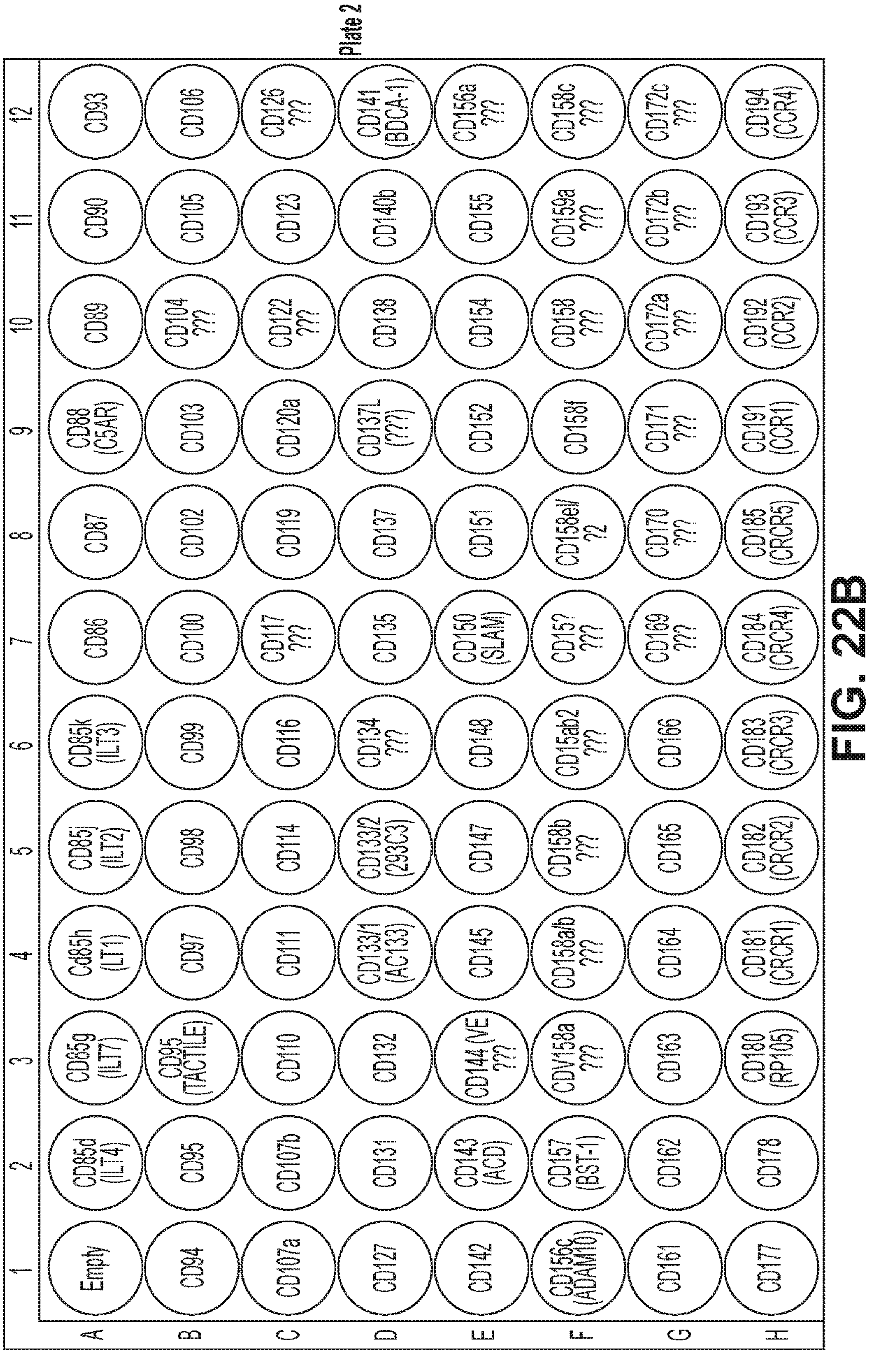
Figure 22C:
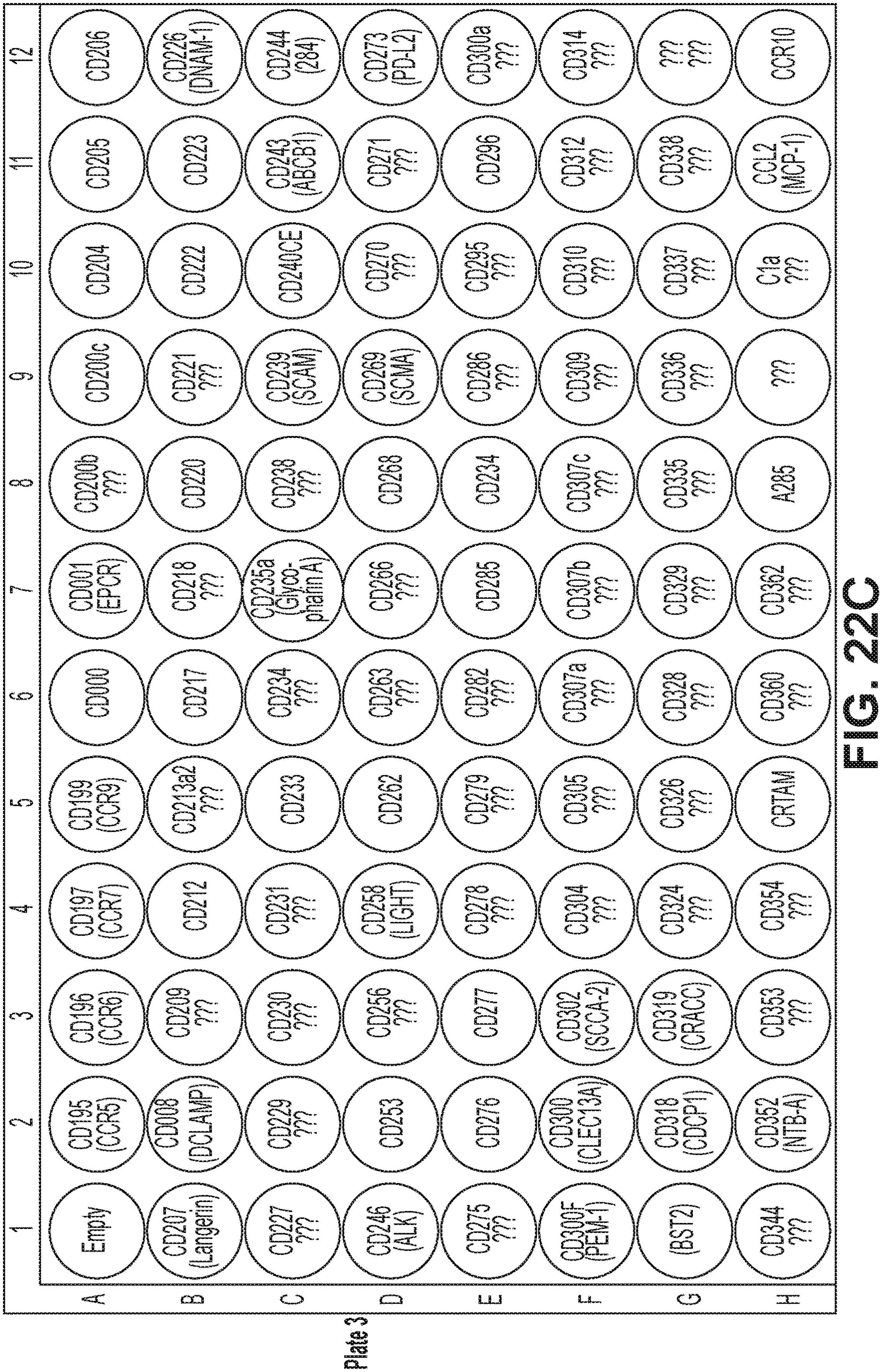
Figure 23:
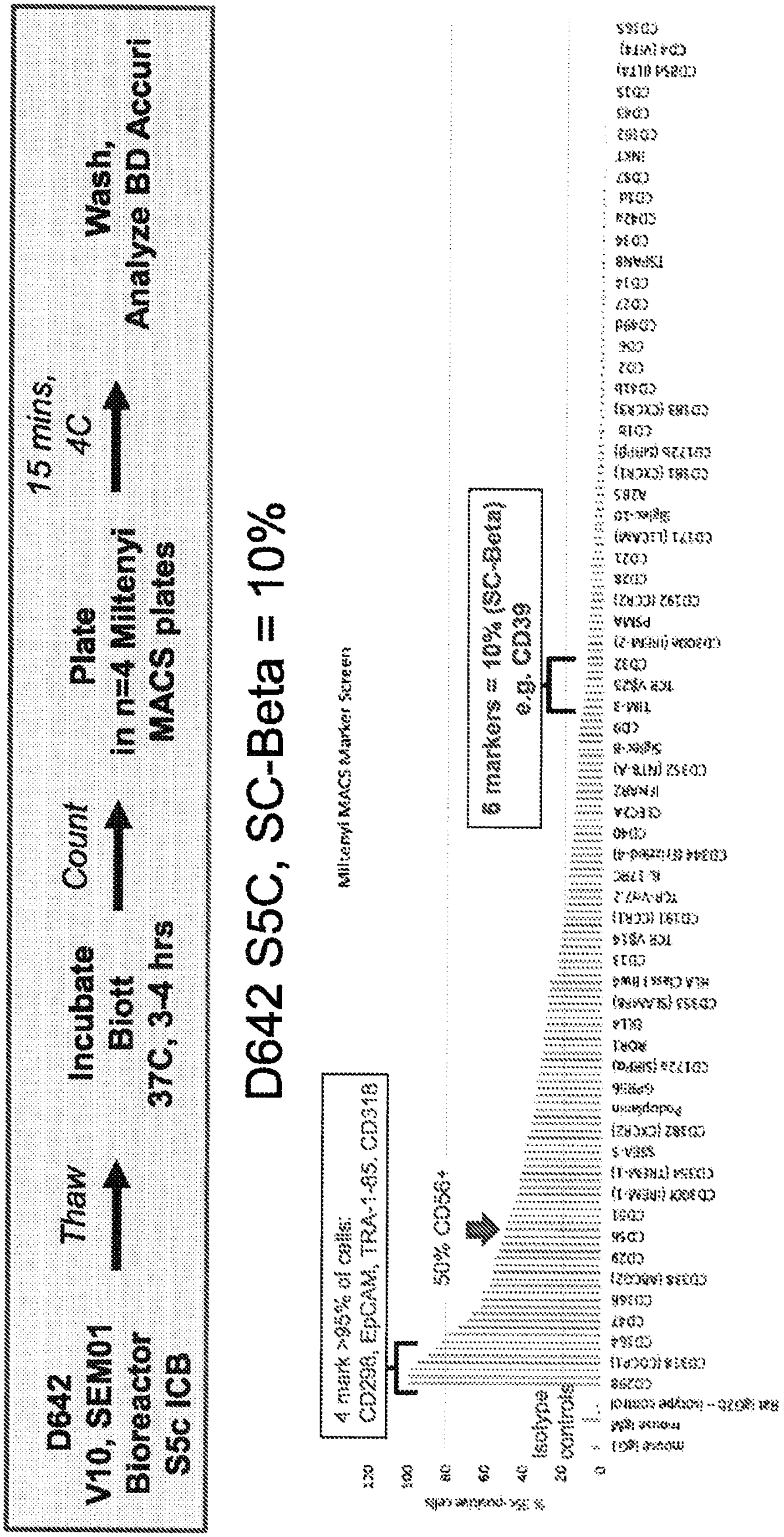
FIG. 23 shows MACS marker screening of stage 5.
Figure 24:
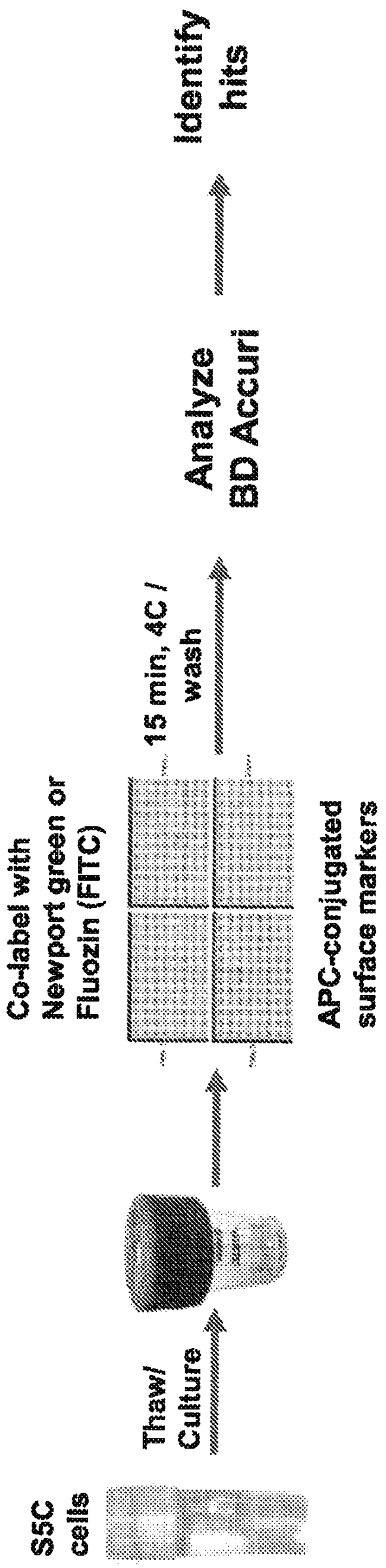
FIG. 24 shows a schematic of SC-beta cell labeling and MACS maker screening.

The cell surface marker library screen (Miltenyi MACS marker screen) for identification of selective SC-β cell surface markers was performed with 371 APC-conjugated monoclonal antibodies (FIGS. 22-23). The screening showed that 52.3% (194 out of 371) of wells contained sufficient cells for analysis. Live SC-β cell labeling with Newport green or fluozin-3 and MACS marker screening can be performed as described in FIG. 24.

Figure 25:
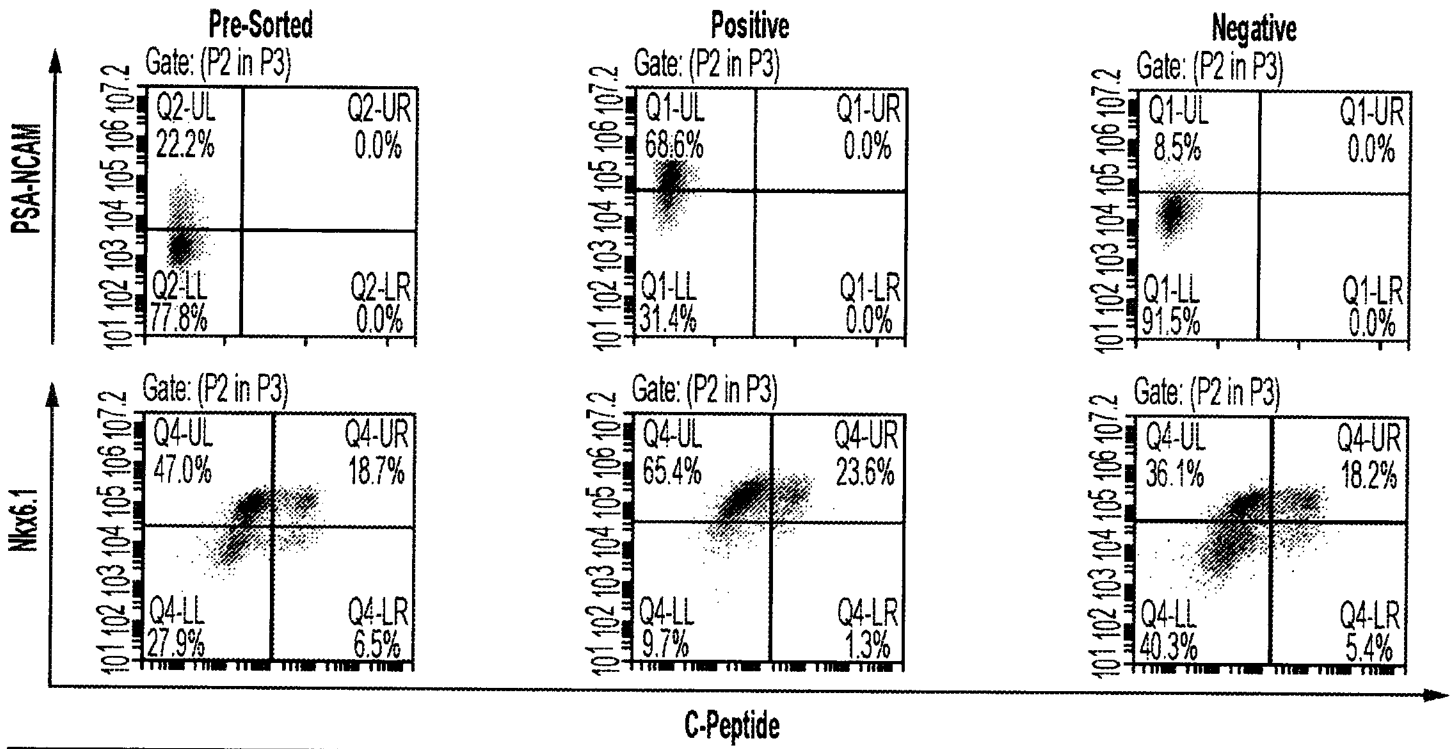
FIG. 25 shows that PSA-NCAM microbead based soring enriches on-target cells and reduces SOX9+ cells.
Figure 26:
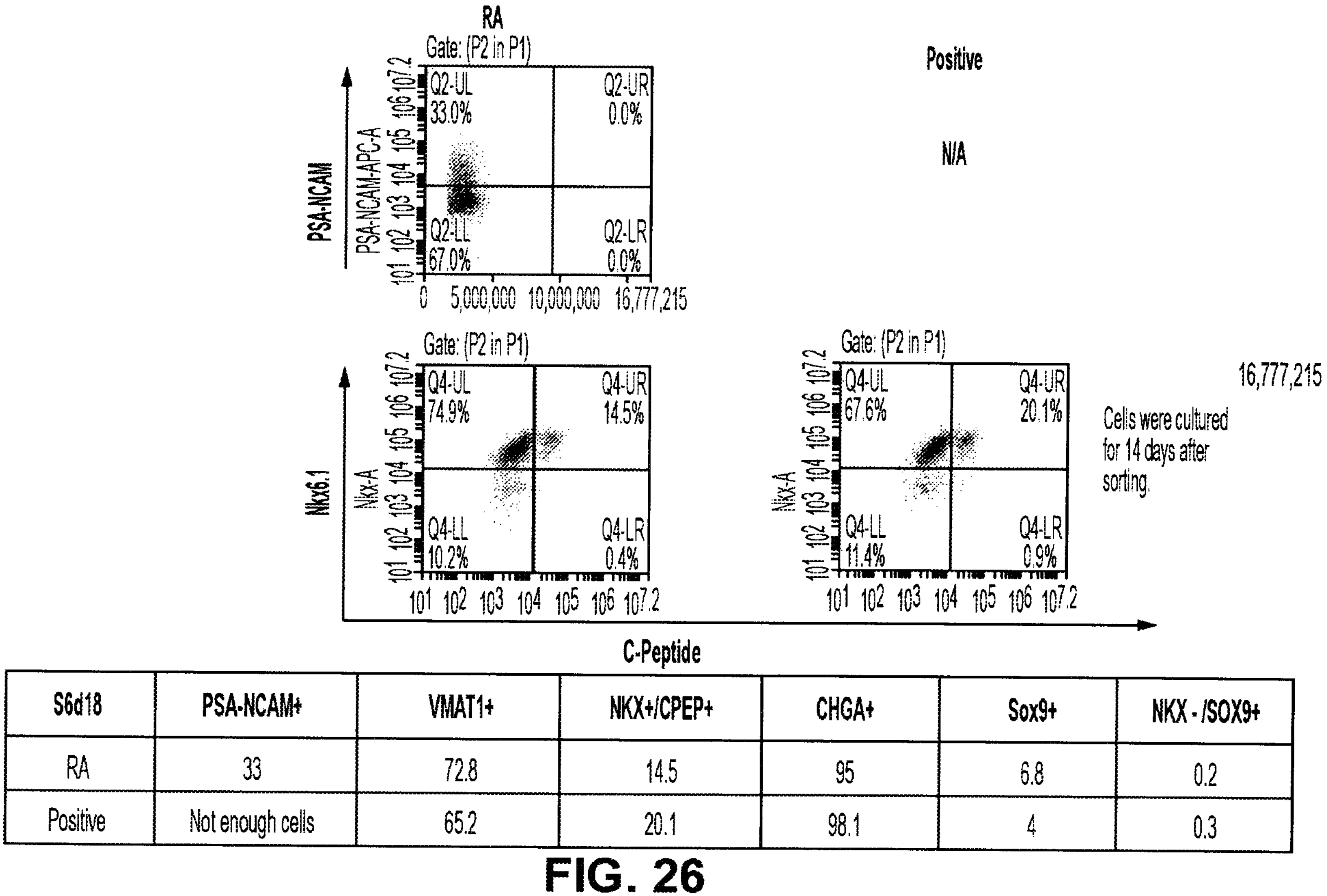
FIG. 26 shows that EC cells (VMAT1+) remain after PSA-NCAM sorting.
Figure 27:
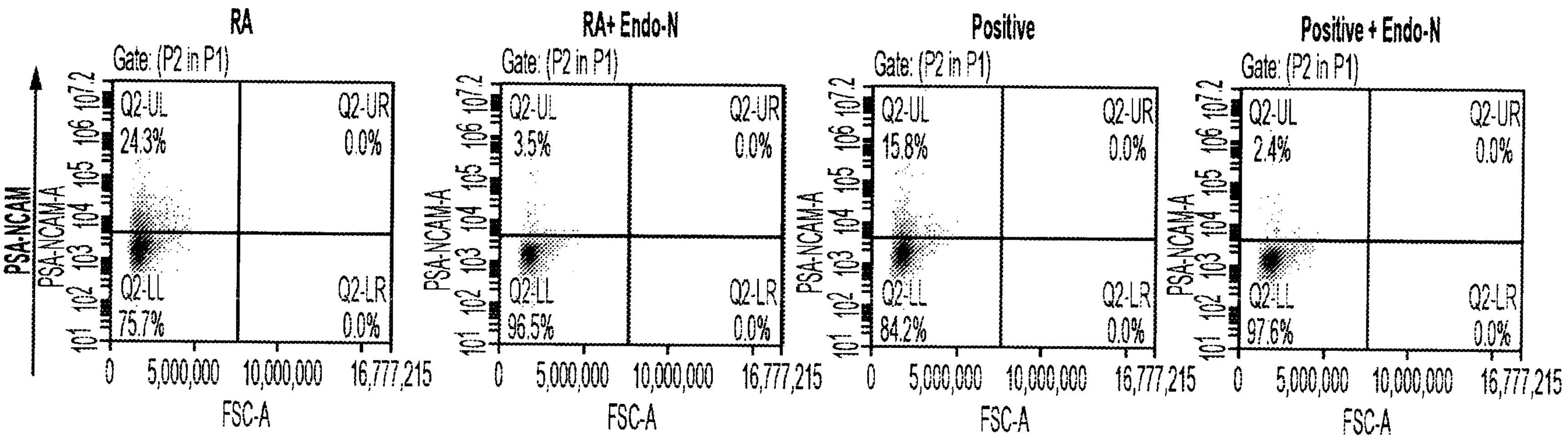
FIG. 27 shows that PSA-NCAM expression decreases significantly upon Endo-N enzyme treatment. Endo-N is an endosialidase which degrades rapidly and specifically linear polymers of sialic acid with α-2,8-linkage with a minimum length of 7-9 residues characteristic of sialic acid residues associated with NCAM. Cleavage of PSA on NCAM in physiological conditions.
Figure 28:
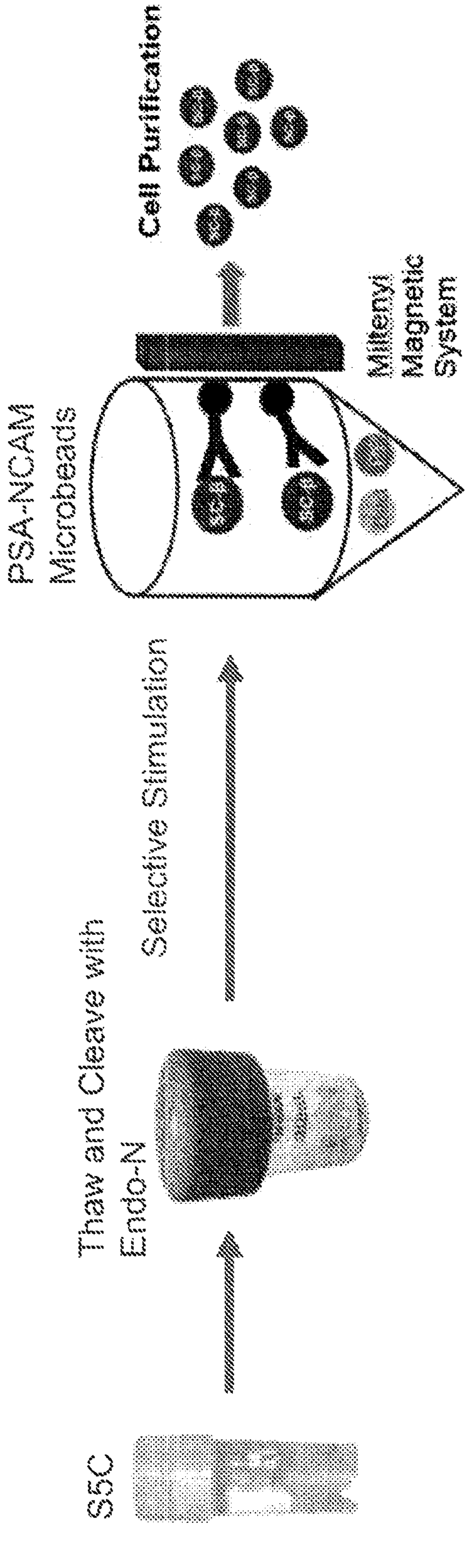
FIG. 28 is a schematic of removing EC cells using PSA-NCAM microbeads sorting.

Purification of SC-β cells by PSA-NCAM microbeads sorting was performed as described in FIG. 28. PSA-NCAM micro-bead based sorting enriched on-target cells and reduced SOX9+ cells (FIG. 25). EC cells (VMAT1+) remained after PSA-NCAM sorting (FIG. 26). The cells were cultured for 14 days after sorting. PSA-NCAM expression decreased significantly upon Endo-N enzyme treatment (FIG. 27). Endo-N is an endosialidase which degrades rapidly and specifically linear polymers of sialic acid with α-2,8-linkage with a minimum length of 7-9 residues characteristic of sialic acid residues associated with NCAM. Cleavage of PSA on NCAM in physiological conditions.

To remove EC cells using PSA-NCAM, pre-exiting PSA-NCAM can be removed with Endo-N enzyme, and PSA-NCAM can be selectively expressed on SC-β cells by stimulating with arginine. SC-β cells expressing PSA-NCAM can be sorted using microbeads as described in FIG. 28.

Example 5. Improving hESC Quality and DE Induction

Figure 29:
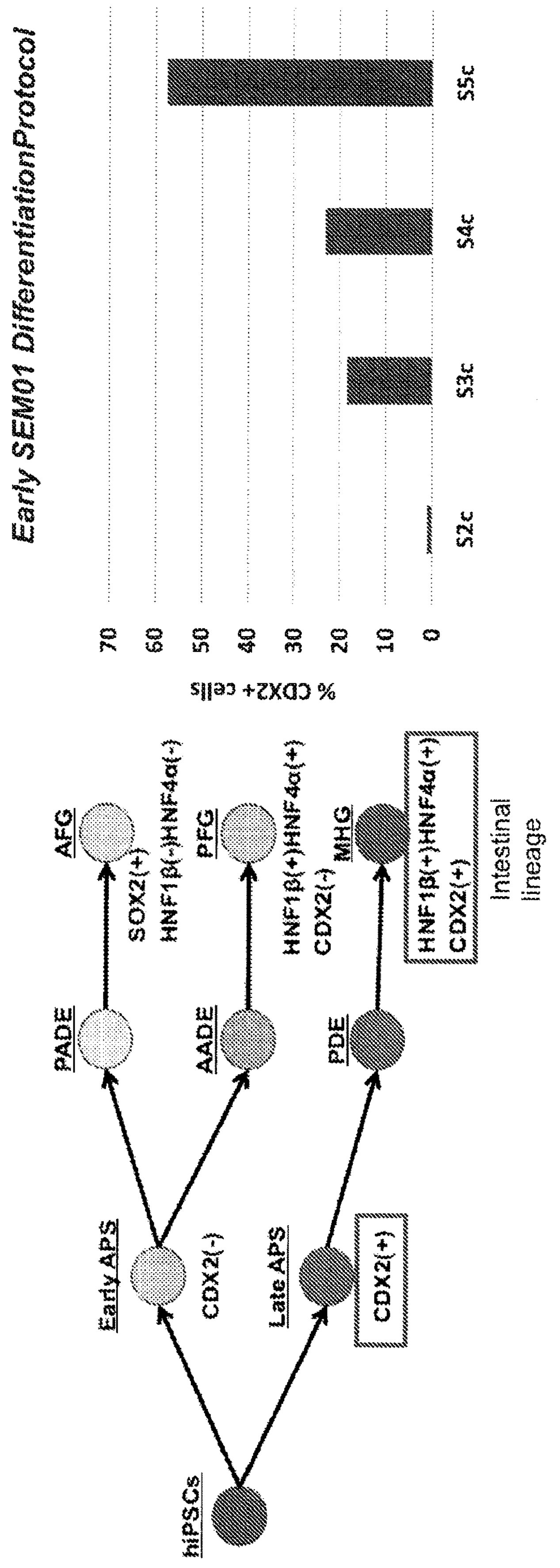
FIG. 29 shows that EC cells can arise from intestinal progenitor specified early in the differentiation process.
Figure 30:
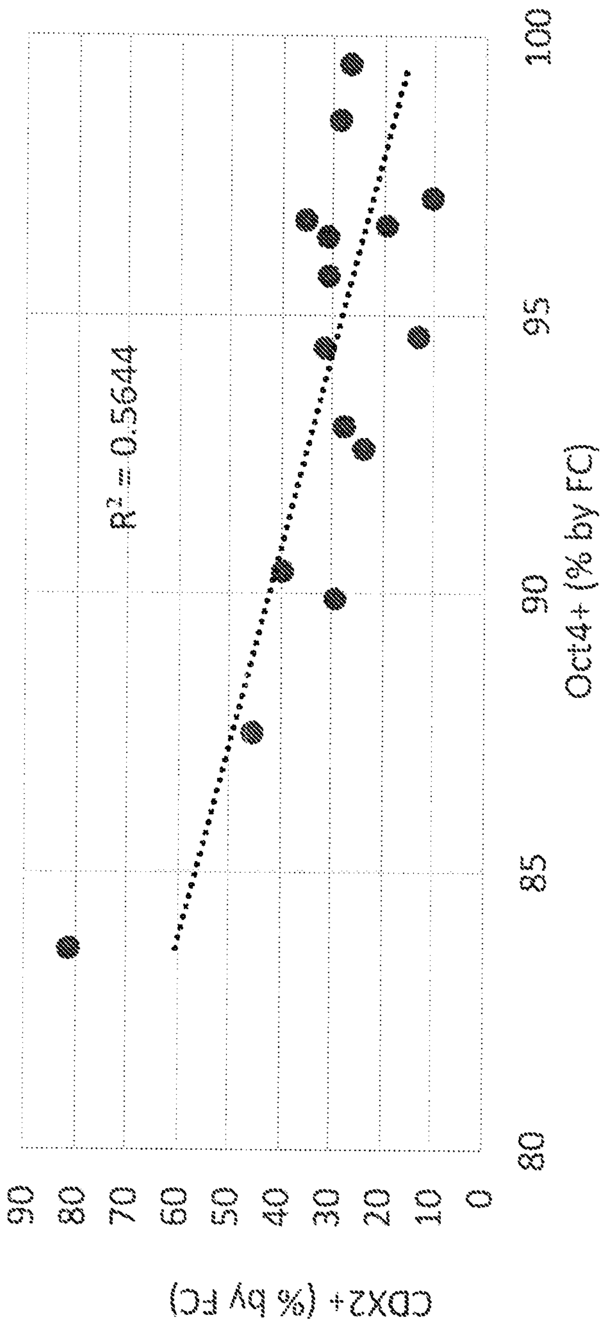
FIG. 30 shows that low OCT4 percentage at stage 0 complete leads to higher CDX2 percentage in later stages. High Oct4% is required for robust differentiation. Variability in Sox17 induction remains even with high Oct4%.

Intestinal lineage is specified early in differentiation, and EC cells can arise from the specified intestinal progenitors (FIG. 29). Low Oct4% at stage 0 led to higher CDX2 percentage in later stages. High Oct4% was required for robust differentiation. Variability in Sox17 induction remained even with high Oct4% (FIG. 30). CDX2+ intestinal population dictated by stage 1 factor concentrations. Fine-tuning Chir/AA concentration and timing can reduce CDX2 population and improve SC-β cell differentiation.

Example 6. Screening of EC Cell Differentiation Inhibitors

Figure 31:
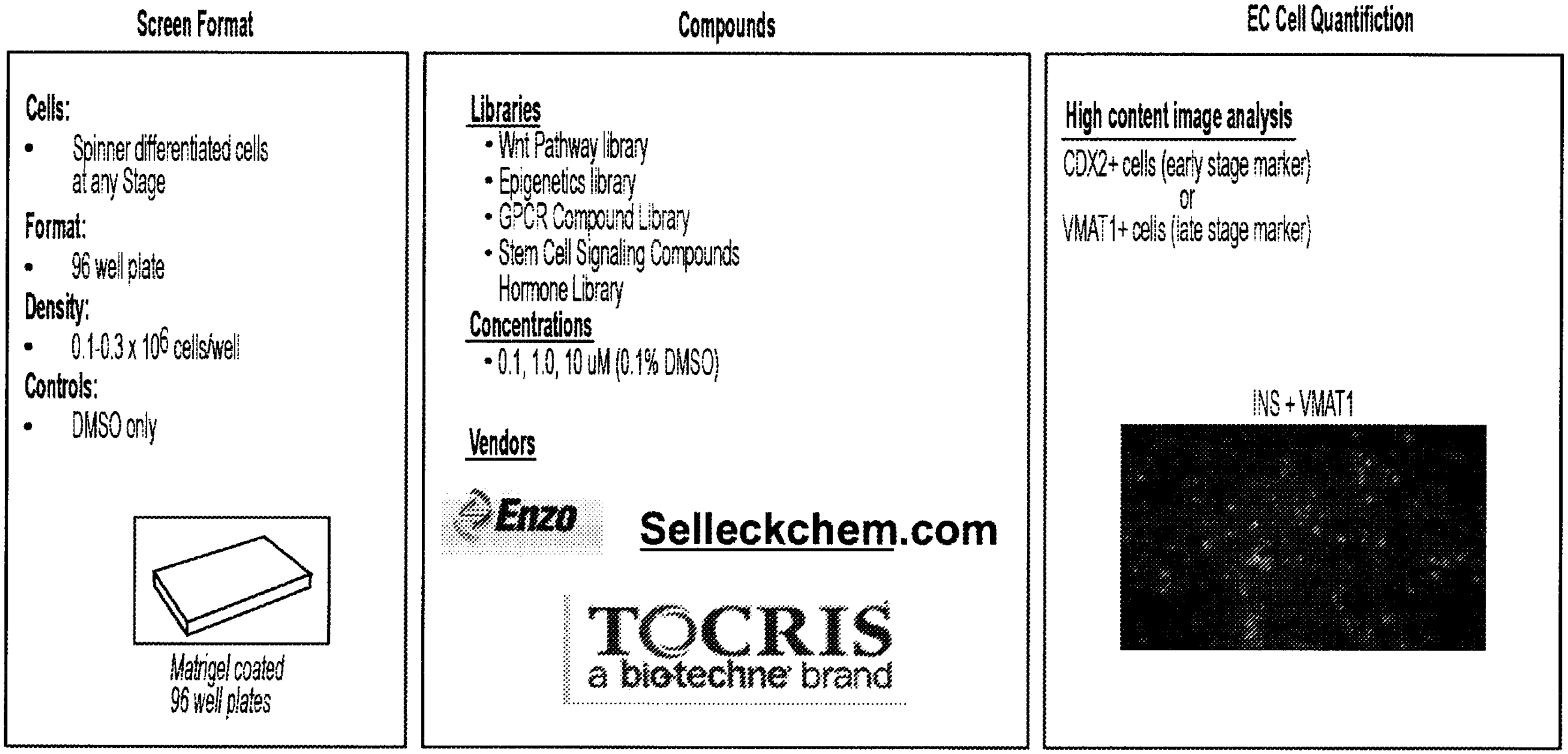
FIG. 31 is a schematic of compound screening based approach to identify inhibitors of EC cell differentiation.
Figure 32:
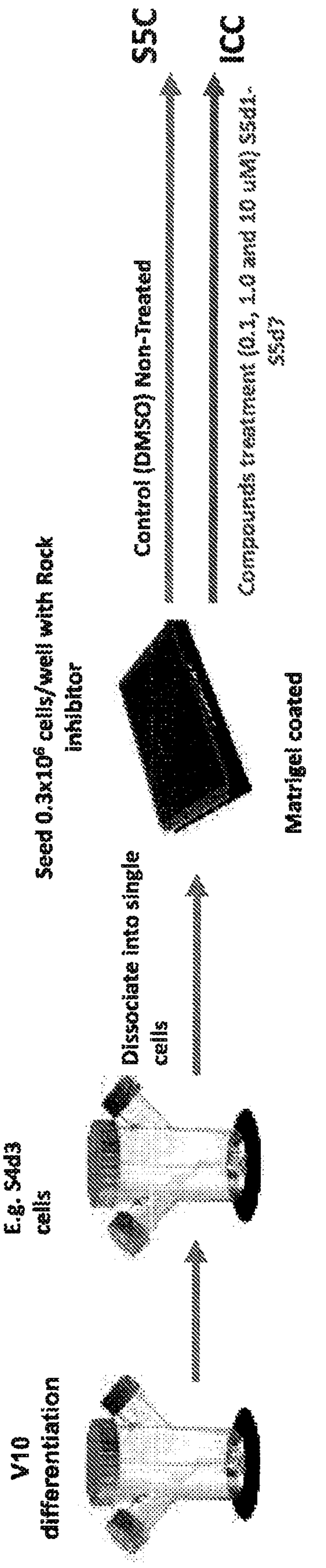
FIG. 32 is a schematic of compounds screening on stage 5 cells.

Further compound screening strategies on stage 5 cells to identify inhibitors of EC cell differentiation are shown in FIGS. 31-32. Matrigel coated 96 well plates are used to seed differentiated cells. Cells are plated at $0.1\text{-}0.3\times10^6$ cells/well. For control, DMSO only is used. Wnt pathway library, epigenetics library, GPCR compound library, and stem cell signaling compound hormone library are screened at concentrations 0.1 μM, 1.0 μM, and 10 μM in 0.1% DMSO. EC cell quantification is determined with high content image analysis with CDX2+ as an early stage marker and VMAT+ as a late stage marker.

Example 7. γ-Irradiation of Stem Cell Derived Islet Cells

Figure 33:
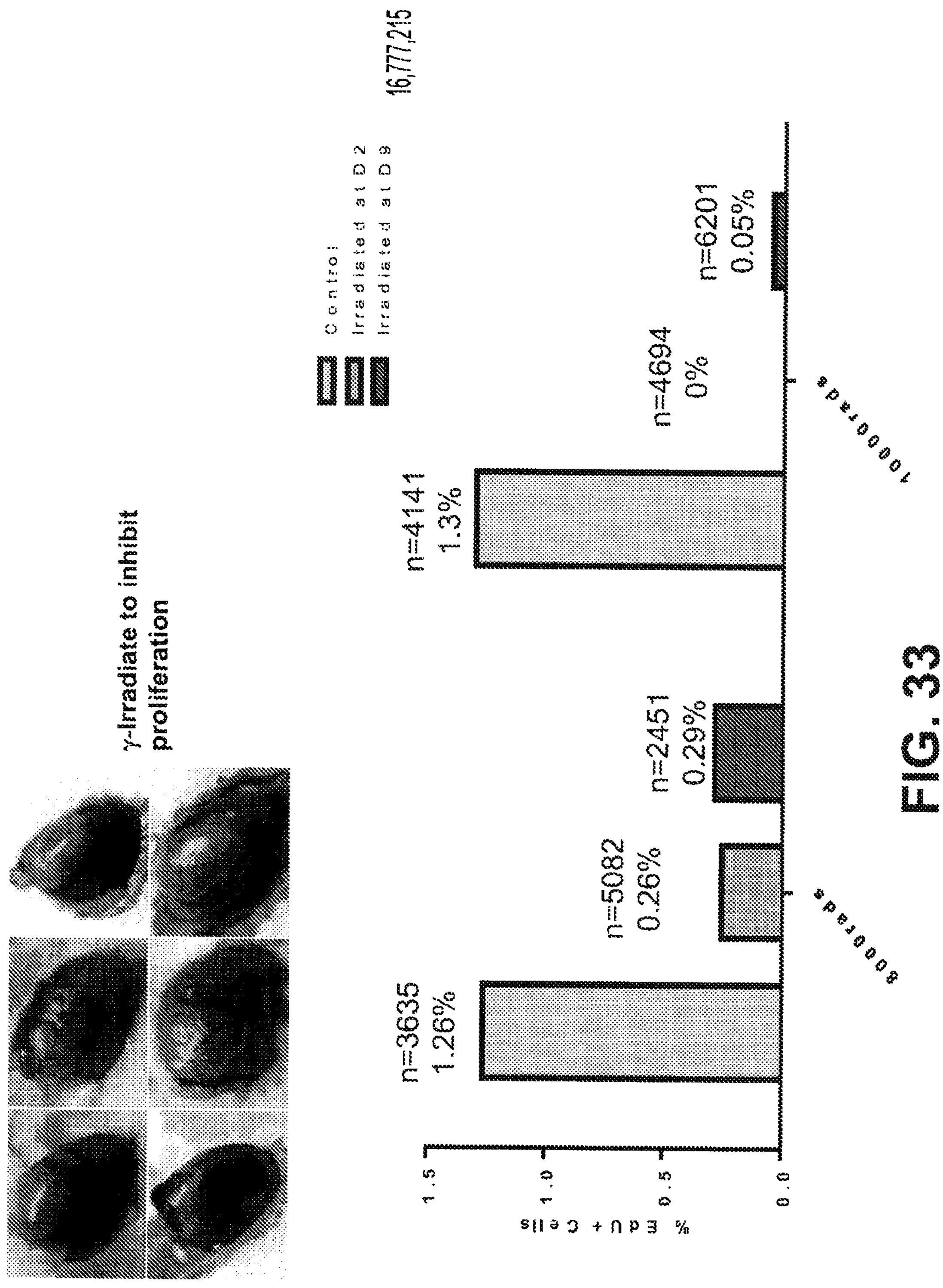
FIG. 33 shows irradiation dose dependent reduction of proliferating cells.
Figure 35:
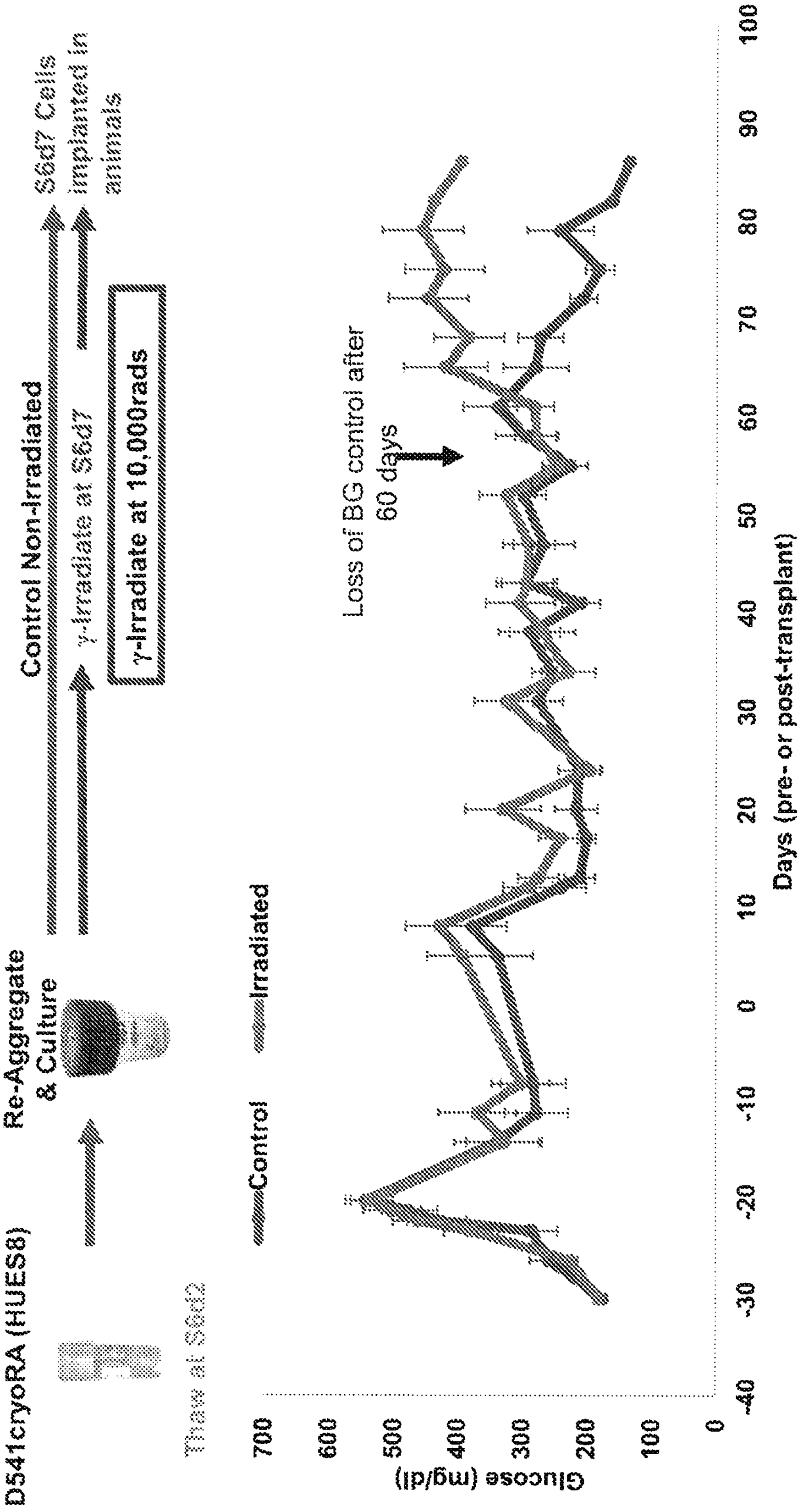
FIG. 35 shows that cryopreserved SC-islets lost ability to control BG after 60 days after irradiation.
Figure 36:
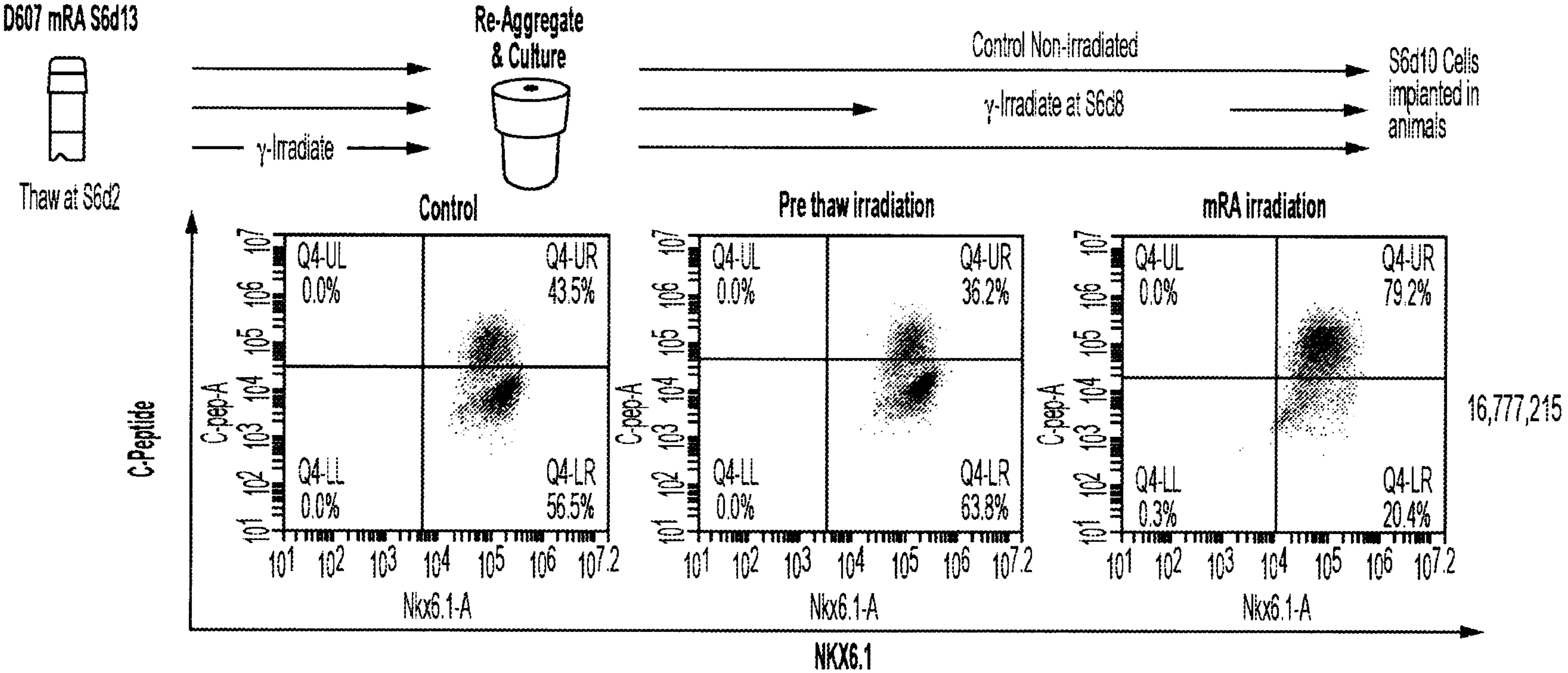
FIG. 36 shows beta cell numbers in irradiated sample as compared to control sample.
Figure 37:
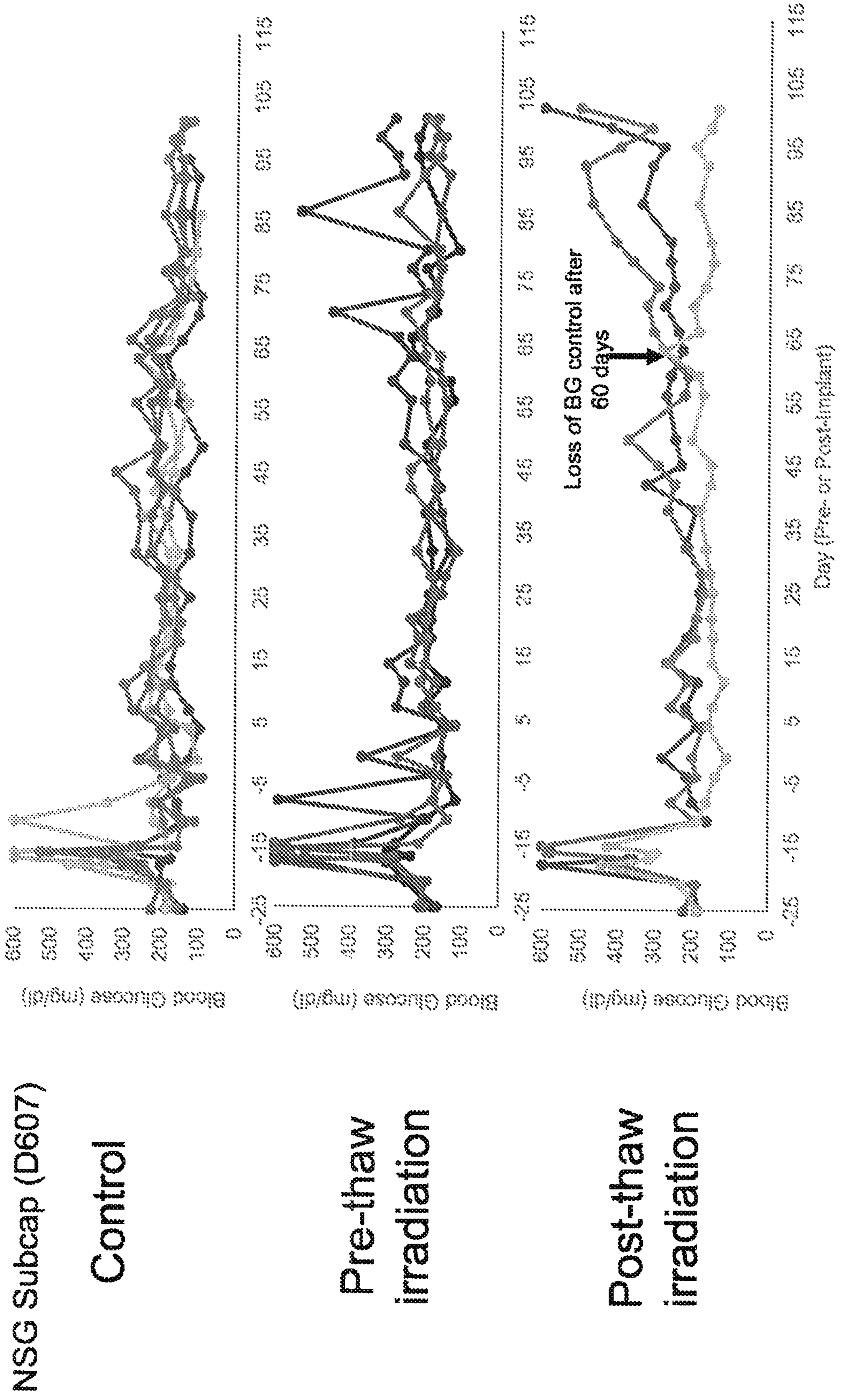
FIG. 37 shows glycemic control maintained by implanted irradiated mRA islet cells.
Figure 38:
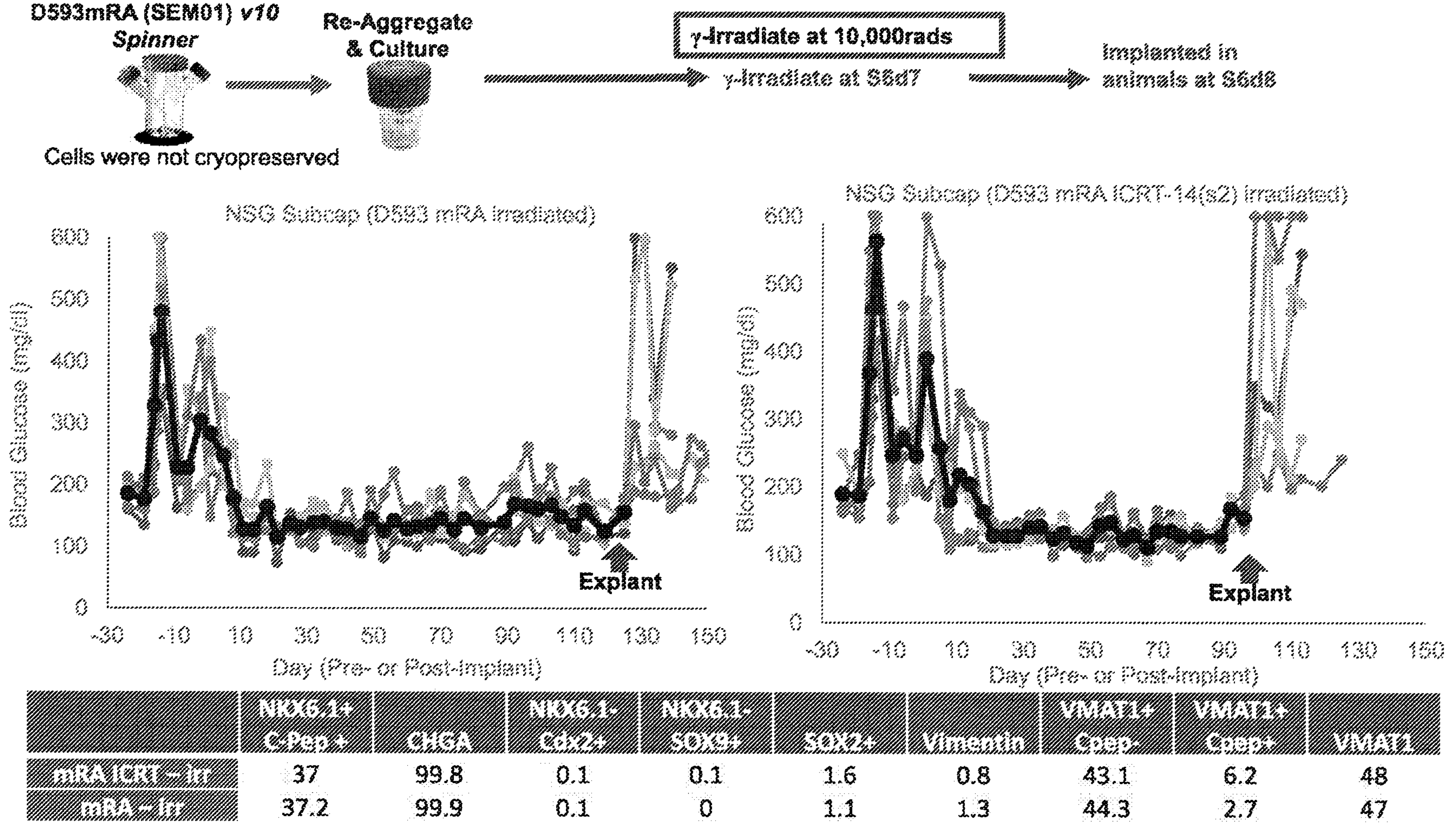
FIG. 38 shows glycemic control in all animals with irradiated SC-islets.

Proliferation of the population of stem cell derived islet cells was inhibited with varying irradiation doses (8,000 rads and 10,000 rads). When no irradiation was performed, proliferation of cells and enlargement of the implant was observed (FIG. 33). High dose γ-irradiation (10,000 rads) had no significant impact on stem cell derived islet cell composition and function (FIG. 34). The ability to control blood glucose was investigated for irradiated cryopreserved stem cell derived islet cells. The cryopreserved cells were thawed, irradiated, and implanted immediately after irradiation without recovery. The cryopreserved stem cell derived islet cells lost ability to control blood glucose 60 days after irradiation (FIG. 35). Enhanced beta cell numbers was observed in irradiated sample (FIGS. 35-36). In one experiment, γ-irradiation was conducted before thawing the cryopreserved stem cell derived islet cells, after which the cells were recovered from cryopreservation and re-aggregated before being implanted into animal models (Pre-thaw irradiation). As shown in FIG. 37, as compared to animals receiving implantation of stem cell derived islet cells that were irradiated after recovery from cryopreservation (Post-thaw irradiation), animals implanted with stem cell derived islet cells receiving Pre-thaw irradiation exhibited glycemic control for a longer period. All animals implanted with irradiated stem cell derived islet cells showed glycemic control until the implant was explanted (FIG. 38).

In summary, the number of proliferating cells was dependent on dosage of γ-irradiation. The number of proliferating cells was lower when the stem cell derived islet cells were irradiated with higher irradiation. γ-irradiation had no significant impact on composition and function of the stem cell derived islet cells. When γ-irradiation was conducted while the cells are frozen, the resultant stem cell derived islet cell implants had longer glycemic control effect in the implanted animal models.

While preferred embodiments of the present disclosure have been shown and described herein, such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

What is claimed is:

1. A method of treating a subject with Type 1 Diabetes, comprising administering to the subject a plurality of autologous or HLA compatible cell clusters comprising cells differentiated from pluripotent stem cells in vitro, wherein the cell clusters comprise NKX6.1-positive and ISL1-positive cells, NKX6.1-negative and ISL1-negative cells, CHGA-positive cells, and C-peptide-positive cells, wherein:

a) at least 35% of the cells in the cell clusters are NKX6.1-positive and ISL1-a) positive cells;

b) at most 3.2% of the cells in the cell clusters are NKX6.1-negative and ISL1-negative cells;

c) at least 60% of the cells in the cell clusters are CHGA-positive cells; and d) at least 30% of the cells in the cell clusters are C-peptide-positive cells; and e) the cells were not subjected to a cell sorting process comprising subjecting the cells to flow cytometry based on a fluorescent protein expressed in the cells.

2. The method of claim 1, wherein at least 40% of the cells in the cell clusters are NKX6.1-positive and ISL1-positive cells.

3. The method of claim 1, wherein at least 40% of the cells in the cell clusters are C-peptide positive.

4. The method of claim 1, wherein at least 50% of the cells in the cell clusters are C-peptide positive.

5. The method of claim 1, wherein at least 55% of the cells in the cell clusters are C-peptide positive.

6. The method of claim 1, wherein at least 70% of the cells in the cell clusters are CHGA-positive cells.

7. The method of claim 1, wherein at least 80% of the cells in the cell clusters are CHGA-positive cells.

8. The method of claim 1, wherein at least 85% of the cells in the cell clusters are CHGA-positive cells.

9. The method of claim 1, wherein at least 40% of the cells in the cell clusters are NKX6.1-positive and C-peptide-positive cells.

10. The method of claim 1, wherein:
- a) at least 35% of the cells in the cell clusters are NKX6.1-positive and ISL1-positive cells;
- b) at most 3.2% of the cells in the cell clusters are NKX6.1-negative and ISL1-negative cells;
- c) at least 80% of the cells in the cell clusters are CHGA-positive cells; and
- d) at least 40% of the cells in the cell clusters are C-peptide-positive cells.

11. The method of claim 1, wherein:
- a) at least 40% of the cells in the cell clusters are NKX6.1-positive and ISL1-positive cells;
- b) at most 3.2% of the cells in the cell clusters are NKX6.1-negative and ISL1-negative cells;
- c) at least 85% of the cells in the cell clusters are CHGA-positive cells; and
- d) at least 40% of the cells in the cell clusters are C-peptide-positive cells.

12. The method of claim 10, wherein at least 40% of the cells in the cell clusters are NKX6.1-positive and C-peptide-positive cells.

13. The method of claim 1, wherein the cell clusters comprise cells that express NKX6.1 and ISL1 and that exhibit glucose stimulated insulin secretion (GSIS) in vitro.

14. The method of claim 1, wherein the expression levels of NKX6.1, ISL1, CHGA, and C-peptide are determined utilizing flow cytometry.

15. The method of claim 1, wherein the cell clusters are in a device suitable for implantation into a human subject.

16. The method of claim 10, wherein the cell clusters are in a device suitable for implantation into the subject.

17. The method of claim 15, wherein the device comprises a semipermeable membrane.

18. The method of claim 16, wherein the device comprises a semipermeable membrane.

19. The method of claim 1, wherein the composition is administered by intraportal infusion.

20. The method of claim 10, wherein the composition is administered by intraportal infusion.

21. The method of claim 11, wherein the composition is administered by intraportal infusion.

22. The method of claim 1, wherein the composition is in a device suitable for implantation into the subject.

23. The method of claim 11, wherein the composition is in a device suitable for implantation into the subject.

24. The method of claim 1, wherein the cells were not subjected to a cell sorting process comprising subjecting the cells to flow cytometry based on a green fluorescent protein expressed in the cells.

25. The method of claim 11, wherein the cells were not subjected to a cell sorting process comprising subjecting the cells to flow cytometry based on a green fluorescent protein expressed in the cells.

26. The method of claim 1, wherein less than 90% of the cells in the cell clusters are NKX6.1-positive, ISL1-positive SC-β cells.

27. The method of claim 11, wherein less than 90% of the cells in the cell clusters are NKX6.1-positive, ISL1-positive SC-β cells.

28. The method of claim 19, wherein less than 90% of the cells in the cell clusters are NKX6.1-positive, ISL1-positive SC-β cells.

29. The method of claim 21, wherein less than 90% of the cells in the cell clusters are NKX6.1-positive, ISL1-positive SC-β cells.

30. The method of claim 1, wherein the cell clusters are autologous to the subject.

31. The method of claim 1, wherein the cell clusters are HLA compatible with the subject.

32. A method of treating a subject with Type 1 Diabetes, comprising:
- administering to the subject a plurality of cell clusters comprising cells differentiated from pluripotent stem cells in vitro, and
- administering to the subject an immune response modulator for reducing rejection of the cell clusters,
- wherein the cell clusters comprise NKX6.1-positive and ISL1-positive cells, NKX6.1-negative and ISL1-negative cells, CHGA-positive cells, and C-peptide-positive cells, wherein:
  - a) at least 35% of the cells in the cell clusters are NKX6.1-positive and ISL1-positive cells;
  - b) at most 3.2% of the cells in the cell clusters are NKX6.1-negative and ISL1-negative cells;
  - c) at least 60% of the cells in the cell clusters are CHGA-positive cells;
  - d) at least 30% of the cells in the cell clusters are C-peptide-positive cells; and
  - e) the cells were not subjected to a cell sorting process comprising subjecting the cells to flow cytometry based on a fluorescent protein expressed in the cells.

33. The method of claim 32, wherein at least 40% of the cells in the cell clusters are NKX6.1-positive and ISL1-positive cells.

34. The method of claim 32, wherein at least 40% of the cells in the cell clusters are C-peptide positive.

35. The method of claim 32, wherein at least 50% of the cells in the cell clusters are C-peptide positive.

36. The method of claim 32, wherein at least 55% of the cells in the cell clusters are C-peptide positive.

37. The method of claim 32, wherein at least 70% of the cells in the cell clusters are CHGA-positive cells.

38. The method of claim 32, wherein at least 80% of the cells in the cell clusters are CHGA-positive cells.

39. The method of claim 32, wherein at least 85% of the cells in the cell clusters are CHGA-positive cells.

40. The method of claim 32, wherein at least 40% of the cells in the cell clusters are NKX6.1-positive and C-peptide-positive cells.

41. The method of claim 32, wherein:
- a) at least 35% of the cells in the cell clusters are NKX6.1-positive and ISL1-positive cells;
- b) at most 3.2% of the cells in the cell clusters are NKX6.1-negative and ISL1-negative cells;
- c) at least 80% of the cells in the cell clusters are CHGA-positive cells; and d) at least 40% of the cells in the cell clusters are C-peptide-positive cells.

42. The method of claim 32, wherein:

a) at least 40% of the cells in the cell clusters are NKX6.1-positive and ISL1-positive cells;

b) at most 3.2% of the cells in the cell clusters are NKX6.1-negative and ISL1-negative cells;

c) at least 85% of the cells in the cell clusters are CHGA-positive cells; and d) at least 40% of the cells in the cell clusters are C-peptide-positive cells.

43. The method of claim 41, wherein at least 40% of the cells in the cell clusters are NKX6.1-positive and C-peptide-positive cells.

44. The method of claim 32, wherein the cell clusters comprise cells that express NKX6.1 and ISL1 and that exhibit glucose stimulated insulin secretion (GSIS) in vitro.

45. The method of claim 32, wherein the expression levels of NKX6.1, ISL1, CHGA, and C-peptide are determined utilizing flow cytometry.

46. The method of claim 32, wherein the cell clusters are in a device suitable for implantation into a human subject.

47. The method of claim 41, wherein the cell clusters are in a device suitable for implantation into the subject.

48. The method of claim 46, wherein the device comprises a semipermeable membrane.

49. The method of claim 47, wherein the device comprises a semipermeable membrane.

50. The method of claim 32, wherein the composition is administered by intraportal infusion.

51. The method of claim 41, wherein the composition is administered by intraportal infusion.

52. The method of claim 42, wherein the composition is administered by intraportal infusion.

53. The method of claim 32, wherein the composition is in a device suitable for implantation into the subject.

54. The method of claim 42, wherein the composition is in a device suitable for implantation into the subject.

55. The method of claim 32, wherein the cells were not subjected to a cell sorting process comprising subjecting the cells to flow cytometry based on a green fluorescent protein expressed in the cells.

56. The method of claim 42, wherein the cells were not subjected to a cell sorting process comprising subjecting the cells to flow cytometry based on a green fluorescent protein expressed in the cells.

57. The method of claim 32, wherein less than 90% of the cells in the cell clusters are NKX6.1-positive, ISL1-positive SC-β cells.

58. The method of claim 42, wherein less than 90% of the cells in the cell clusters are NKX6.1-positive, ISL1-positive SC-β cells.

59. The method of claim 50, wherein less than 90% of the cells in the cell clusters are NKX6.1-positive, ISL1-positive SC-β cells.

60. The method of claim 52, wherein less than 90% of the cells in the cell clusters are NKX6.1-positive, ISL1-positive SC-β cells.

* * * * *

SEQUENCE LISTING

```
Sequence total quantity: 18
SEQ ID NO: 1             moltype = AA  length = 116
FEATURE                  Location/Qualifiers
source                   1..116
                         mol_type = protein
                         organism = Homo sapiens
SEQUENCE: 1
GLECDGKVNI CCKKQFFVSF KDIGWNDWII APSGYHANYC EGECPSHIAG TSGSSLSFHS  60
TVINHYRMRG HSPFANLKSC CVPTKLRPMS MLYYDDGQNI IKKDIQNMIV EECGCS      116

SEQ ID NO: 2             moltype = DNA  length = 351
FEATURE                  Location/Qualifiers
source                   1..351
                         mol_type = genomic DNA
                         organism = Homo sapiens
SEQUENCE: 2
ggcttggagt gtgatggcaa ggtcaacatc tgctgtaaga aacagttctt tgtcagtttc  60
aaggacatcg gctggaatga ctggatcatt gctccctctg gctatcatgc caactactgc  120
gagggtgagt gcccgagcca tatagcaggc acgtccgggt cctcactgtc cttccactca  180
acagtcatca accactaccg catgcggggc catagcccct ttgccaacct caaatcgtgc  240
tgtgtgccca ccaagctgag acccatgtcc atgttgtact atgatgatgg tcaaaacatc  300
atcaaaaagg acattcagaa catgatcgtg gaggagtgtg ggtgctcata g           351
```

-continued

```
SEQ ID NO: 3           moltype = AA  length = 426
FEATURE                Location/Qualifiers
source                 1..426
                       mol_type = protein
                       organism = Homo sapiens
SEQUENCE: 3
MPLLWLRGFL LASCWIIVRS SPTPGSEGHS AAPDCPSCAL AALPKDVPNS QPEMVEAVKK  60
HILNMLHLKK RPDVTQPVPK AALLNAIRKL HVGKVGENGY VEIEDDIGRR AEMNELMEQT  120
SEIITFAESG TARKTLHFEI SKEGSDLSVV ERAEVWLFLK VPKANRTRTK VTIRLFQQQK  180
HPQGSLDTGE EAEEVGLKGE RSELLLSEKV VDARKSTWHV FPVSSSIQRL LDQGKSSLDV  240
RIACEQCQES GASLVLLGKK KKKEEEGEGK KKGGGEGGAG ADEEKEQSHR PFLMLQARQS  300
EDHPHRRRRR GLECDGKVNI CCKKQFFVSF KDIGWNDWII APSGYHANYC EGECPSHIAG  360
TSGSSLSFHS TVINHYRMRG HSPFANLKSC CVPTKLRPMS MLYYDDGQNI IKKDIQNMIV  420
EECGCS                                                             426

SEQ ID NO: 4           moltype = AA  length = 130
FEATURE                Location/Qualifiers
source                 1..130
                       mol_type = protein
                       organism = Homo sapiens
SEQUENCE: 4
ARQSEDHPHR RRRRGLECDG KVNICCKKQF FVSFKDIGWN DWIIAPSGYH ANYCEGECPS  60
HIAGTSGSSL SFHSTVINHY RMRGHSPFAN LKSCCVPTKL RPMSMLYYDD GQNIIKKDIQ  120
NMIVEECGCS                                                         130

SEQ ID NO: 5           moltype = AA  length = 115
FEATURE                Location/Qualifiers
source                 1..115
                       mol_type = protein
                       organism = Homo sapiens
SEQUENCE: 5
GLECDGKVNI CCKKQFFVSF KDIGWNDWII APSGYHANYC EGECPSHIAG TSGSSLSFHS  60
TVINHYACGH SPFANLKSCC VPTKLRPMSM LYYDDGQNII KKDIQNMIVE ECGCS       115

SEQ ID NO: 6           moltype = AA  length = 426
FEATURE                Location/Qualifiers
source                 1..426
                       mol_type = protein
                       organism = Homo sapiens
SEQUENCE: 6
MPLLWLRGFL LASCWIIVRS SPTPGSEGHS AAPDCPSCAL AALPKDVPNS QPEMVEAVKK  60
HILNMLHLKK RPDVTQPVPK AALLNAIRKL HVGKVGENGY VEIEDDIGRR AEMNELMEQT  120
SEIITFAESG TARKTLHFEI SKEGSDLSVV ERAEVWLFLK VPKANRTRTK VTIRLFQQQK  180
HPQGSLDTGE EAEEVGLKGE RSELLLSEKV VDARKSTWHV FPVSSSIQRL LDQGKSSLDV  240
RIACEQCQES GASLVLLGKK KKKEEEGEGK KKGGGEGGAG ADEEKEQSHR PFLMLQARQS  300
EDHPHRRRRR GLECDGKVNI CCKKQFFVSF KDIGWNDWII APSGYHANYC EGECPSHIAG  360
TSGSSLSFHS TVINHYRMRG HSPFANLKSC CVPTKLRPMS MLYYDDGQNI IKKDIQNMIV  420
EECGCS                                                             426

SEQ ID NO: 7           moltype = AA  length = 424
FEATURE                Location/Qualifiers
source                 1..424
                       mol_type = protein
                       organism = Mus musculus
SEQUENCE: 7
MPLLWLRGFL LASCWIIVRS SPTPGSEGHG SAPDCPSCAL ATLPKDGPNS QPEMVEAVKK  60
HILNMLHLKK RPDVTQPVPK AALLNAIRKL HVGKVGENGY VEIEDDIGRR AEMNELMEQT  120
SEIITFAESG TARKTLHFEI SKEGSDLSVV ERAEVWLFLK VPKANRTRTK VTIRLFQQQK  180
HPQGSLDTGD EAEEMGLKGE RSELLLSEKV VDARKSTWHI FPVSSSIQRL LDQGKSSLDV  240
RIACEQCQES GASLVLLGKK KKKEVDGDGK KKDGSDGGLE EEKEQSHRPF LMLQARQSED  300
HPHRRRRRGL ECDGKVNICC KKQFFVSFKD IGWNDWIIAP SGYHANYCEG ECPSHIAGTS  360
GSSLSFHSTV INHYRMRGHS PFANLKSCCV PTKLRPMSML YYDDGQNIIK KDIQNMIVEE  420
CGCS                                                               424

SEQ ID NO: 8           moltype = AA  length = 424
FEATURE                Location/Qualifiers
source                 1..424
                       mol_type = protein
                       organism = Rattus norvegicus
SEQUENCE: 8
MPLLWLRGFL LASCWIIVRS SPTPGSEGHG AAPDCPSCAL ATLPKDGPNS QPEMVEAVKK  60
HILNMLHLKK RPDVTQPVPK AALLNAIRKL HVGKVGENGY VEIEDDIGRR AEMNELMEQT  120
SEIITFAESG TARKTLHFEI SKEGSDLSVV ERAEVWLFLK VPKANRTRTK VTIRLFQQQK  180
HPQGSLDMGD EAEEMGLKGE RSELLLSEKV VDARKSTWHI FPVSSSIQRL LDQGKSSLDV  240
RIACEQCQES GASLVLLGKK KKKEVDGDGK KKDGSDGGLE EEKEQSHRPF LMLQARQSED  300
HPHRRRRRGL ECDGKVNICC KKQFFVSFKD IGWNDWIIAP SGYHANYCEG ECPSHIAGTS  360
GSSLSFHSTV INHYRMRGHS PFANLKSCCV PTKLRPMSML YYDDGQNIIK KDIQNMIVEE  420
CGCS                                                               424
```

-continued

```
SEQ ID NO: 9            moltype = AA  length = 424
FEATURE                 Location/Qualifiers
source                  1..424
                        mol_type = protein
                        organism = Gallus gallus
SEQUENCE: 9
MPLLWKRGFL LVICWIIVRS SPTPGSEGHS SVADCPSCAL TTLSKDVPSS QPEMVEAVKK  60
HILNMLHLRD RPNITQPVPK AALLNATKKL HVGKVGDDGY VEIEDDVGRR AEMNEVVEQT  120
SEIITFAESG TPKKTLHFEI SKEGSELSVV EHAEVWLFLK VSKANRSRTK VTIRLFQQQR  180
QPKGNSEAAE DMEDMGLKGE RSETLISEKA VDARKSTWHI FPISSSVQRL LDQGQSSLDV  240
RIACDLCQET GASLVLLGKK KKKEDDGEGK EKDGGELTGE EEKEQSHRPF LMMLARHSED  300
RQHRRRERGL ECDGKVNICC KKQFFVSFKD IGWSDWIIAP TGYHANYCEE ECPSHIAGTS  360
GSSLSFHSTV INHYRMRGHS PFANLKSCCV PTKLRPMSML YYDDGQNIIK KDIQNMIVEE  420
CGCS                                                              424

SEQ ID NO: 10           moltype = AA  length = 425
FEATURE                 Location/Qualifiers
source                  1..425
                        mol_type = protein
                        organism = Bos taurus
SEQUENCE: 10
MPLLWLRGFL LASCWIIVRS SPTPGSEGHS AAPDCPSCAL ATLPKDVPNS QPEMVEAVKK  60
HILNMLHLKK RPDVTQPVPK AALLNAIRKL HVGKVGENGY VEIEDDIGRR AEMNELMEQT  120
SEIITFAESG TARKTLHFEI SKEGSDLSVV ERAEIWLFLK VPKANRTRSK VTIRLFQQQK  180
HLQGSLDAGE EAEEVGLKGE KSEMLISEKV VDARKSTWHI FPVSSCIQRL LDQGKSSLDI  240
RIACEQCQET GASLVLLGKK KKKEEEGEGK KRDGEGGAGG DEEKEQSHRP FLMLQARQSE  300
DHPHRRRRRG LECDGKVNIC CKKQFFVSFK DIGWNDWIIA PSGYHANYCE GECPSHIAGT  360
SGSSLSFHST VINHYRMRGH SPFANLKSCC VPTKLRPMSM LYYDDGQNII KKDIQNMIVE  420
ECGCS                                                             425

SEQ ID NO: 11           moltype = AA  length = 426
FEATURE                 Location/Qualifiers
source                  1..426
                        mol_type = protein
                        organism = Equus caballus
SEQUENCE: 11
MPLLWLRGFL LASCWIIVKS SPTPGSEGHS AAPNCPSCAL ATLPKDVPNA QPEMVEAVKK  60
HILNMLHLKK RPDVTQPVPK AALLNAIRKL HVGKVGENGY VEIEDDIGRR AEMNELMEQT  120
SEIITFAESG TARKTLHFEI SKEGSDLSVV ERAEVWLFLK VPKANRTRSK VTIRLLQQQK  180
HPQGSSDTRE EAEEADLMEE RSEQLISEKV VDARKSTWHI FPVSSSIQRL LDQGKSSLDI  240
RIACDQCHET GASLVLLGKK KKKEEEGEGK KKDGGEAGAG VDEEKEQSHR PFLMLQARQS  300
EDHPHRRRRR GLECDGKVNI CCKKQFFVSF KDIGWNDWII APSGYHANYC EGECPSHIAG  360
TSGSSLSFHS TVINQYRLRG HNPFANLKSC CVPTKLRPMS MLYYDDGQNI IKKDIQNMIV  420
EECGCS                                                            426

SEQ ID NO: 12           moltype = AA  length = 424
FEATURE                 Location/Qualifiers
source                  1..424
                        mol_type = protein
                        organism = Sus scrofa
SEQUENCE: 12
MPLLWLRGFL LASCWIIVRS SPTPGSGGHS AAPDCPSCAL ATLPKDVPNS QPEMVEAVKK  60
HILNMLHLKK RPDVTQPVPK AALLNAIRKL HVGKVGENGY VELEDDIGRR AEMNELMEQT  120
SEIITFAEAG TARKTLRFEI SKEGSDLSVV ERAEIWLFLK VPKANRTRTK VSIRLFQQQR  180
RPQGSADAGE EAEDVGFPEE KSEVLISEKV VDARKSTWHI FPVSSSIQRL LDQGKSALDI  240
RTACEQCHET GASLVLLGKK KKKEEEAEGR KRDGEGAGVD EEKEQSHRPF LMLQARQSEE  300
HPHRRRRRGL ECDGKVNICC KKQFFVSFKD IGWNDWIIAP SGYHANYCEG ECPSHIAGTS  360
GSSLSFHSTV INHYRMRGHS PFANLKSCCV PTKLRPMSML YYDDGQNIIK KDIQNMIVEE  420
CGCS                                                              424

SEQ ID NO: 13           moltype = AA  length = 425
FEATURE                 Location/Qualifiers
source                  1..425
                        mol_type = protein
                        organism = Ovis aries
SEQUENCE: 13
MPLLWLRGFL LASCWIIVRS SPTPGSEGHS AAPDCPSCAL ATLPKDVPNS QPEMVEAVKK  60
HILNMLHLKK RPDVTQPVPK AALLNAIRKL HVGKVGENGY VEIEDDIGRR AEMNELMEQT  120
SEIITFAESG TARKTLHFEI SQEGSDLSVV ERAEIWLFLK VPKANRTRSK VTIRLFQQQK  180
HLQGSLDAGE EAEEVGLKGE KSEMLISEKV VDARKSTWHI FPVSSCIQRL LDQGKSSLDI  240
RIACEQCQET GASLVLLGKK KRKEEEGEGK KRDGEGGAGG DEEKEQSHRP FLMLQARQSE  300
DHPHRRRRRG LECDGKVNIC CKKQFYVSFK DIGWNDWIIA PSGYHANYCE GECPSHIAGT  360
SGSSLSFHST VINHYRMRGH SPFANLKSCC VPTKLRPMSM LYYDDGQNII KKDIQNMIVE  420
ECGCS                                                             425

SEQ ID NO: 14           moltype = AA  length = 424
FEATURE                 Location/Qualifiers
source                  1..424
                        mol_type = protein
```

-continued

```
                         organism = Felis catus
SEQUENCE: 14
MPLLWLRGFL LASCWIIVRS SPTPGSEGPG AAPDCPSCAL ATLPKDVPNS QPEMVEAVKK  60
HILNMLHLKK RPEVTQPVPK AALLNAIRKL HVGKVGENGY VEIEDDIGRR AEMNELMEQT  120
SEIITFAESG TARKTLHFEI SKEGSDLSVV ERAEVWLFLK VPKANRTRTK VTIQLLQKQP  180
QGGVDAGEEA EEMGLMEERN EVLISEKVVD ARKSTWHIFP VSSSIQRLLD QGKSSLDVRI  240
ACEQCHETGA SLVLLGKKKK KEEEGEGKKK DGGDGGAGAD EDKEQSHRPF LMLQARQSED  300
HPHRRRRRGL ECDGKVNICC KKQFFVSFKD IGWNDWIIAP SGYHANYCEG ECPSHIAGTS  360
GSSLSFHSTV INHYRMRGHS PFANLKSCCV PTKLRPMSML YYDDGQNIIK KDIQNMIVEE  420
CGCS                                                              424

SEQ ID NO: 15            moltype = AA  length = 395
FEATURE                  Location/Qualifiers
source                   1..395
                         mol_type = protein
                         organism = Danio rerio
SEQUENCE: 15
MSPLPLLSGI LLLLIRSCSL SAMVTKGSLP MSEQQAGATV CPSCALARFR KGVSESEDEG  60
AQQDVVEAVK RHILNMLHLQ ERPNITHPVP RAALLNAIRK VHVGRVAKDG SVLIEDEASN  120
RAETEQAEQT EIITFAETGE APGIVNFLIS KEGGEMSVVD QANVWIFLRL PKGNRTRANV  180
NIRLLLQQGA GEKILAEKSV DTRRSGWHTF PASESVQSLL QRGGSTLSLR VSCPLCADAR  240
ATPVLVSPGG SEREQSHRPF LMAVVRQMDE LSLRRRRKRG LECDGKARVC CKRQFYVNFK  300
DIGWNDWIIA PSGYHANYCE GDCASNVASI TGNSLSFHST VISHYRIRGY SPFTNIKSCC  360
VPTRLRAMSM LYYNEEQKIV KKDIQNMIVE ECGCS                            395

SEQ ID NO: 16            moltype = AA  length = 404
FEATURE                  Location/Qualifiers
source                   1..404
                         mol_type = protein
                         organism = Carassius auratus
SEQUENCE: 16
MSSLTLVNRG TAALRLFVRG LLTHSSREWL SGDGEPDDPV TPCPSCALAQ RQKDSEEQTD  60
MVEAVKRHIL NMLHLNTRPN VTHPVPRAAL LNAIRRLHVG RVGEDGTVEM EEDGGGLGEH  120
REQSEEQPFE IITFAEPGDA PDIMKFDISM EGNTLSVVEQ ANVWLLLKVA KGSRGKGKVS  180
VQLLQHGKAD PGSADGPQEA VVSEKTVDTR RSGWHTLPVS RTVQTLLDGD SSMLSLRVSC  240
PMCAEAGAVP ILVPTESNKG KEREQSHRPF LMVVLKPAEE HPHRRSKRGL ECDGKIRVCC  300
KRQFYVNFKD IGWSDWIIAP SGYHANYCEG DCPSHVASIT GSALSFHSTV INHYRMRGYS  360
PFNNIKSCCV PTRLRAMSML YYNEEQKIIK KDIQNMIVEE CGCS                  404

SEQ ID NO: 17            moltype = DNA  length = 425
FEATURE                  Location/Qualifiers
source                   1..425
                         mol_type = genomic DNA
                         organism = Homo sapiens
SEQUENCE: 17
gcccggcagt ctgaagacca ccctcatcgc cggcgtcggc ggggcttgga gtgtgatggc  60
aaggtcaaca tctgctgtaa gaaacagttc tttgtcagtt tcaaggacat cggctggaat  120
gactggatca ttgctccctc tggctatcat gccaactact gcgagggtga gtgcccgagc  180
catatagcag gcacgtccgg gtcctcactg tccttccact caacagtcat caaccactac  240
cgcatgcggg gccatagccc ctttgccaac ctcaaatcgt gctgtgtgcc caccaagctg  300
agacccatgt ccatgttgta ctatgatgat ggtcaaaaca tcatcaaaaa ggacattcag  360
aacatgatcg tggaggagtg tgggtgctca tagagttgcc cagcccaggg ggaaagggag  420
caaga                                                             425

SEQ ID NO: 18            moltype = DNA  length = 348
FEATURE                  Location/Qualifiers
source                   1..348
                         mol_type = genomic DNA
                         organism = Homo sapiens
SEQUENCE: 18
ggcctggagt gcgacggcaa ggtcaacatc tgctgtaaga aacagttctt tgtcagtttc  60
aaggacatcg gctggaatga ctggatcatt gctccctctg gctatcatgc caactactgc  120
gagggtgagt gcccgagcca tatagcaggc acgtccgggt cctcactgtc cttccactca  180
acagtcatca accactacgc atgcggccat agcccctttg ccaacctcaa atcgtgctgt  240
gtgcccacca agctgagacc catgtccatg ttgtactatg atgatggtca aaacatcatc  300
aaaaaggaca ttcagaacat gatcgtggag gagtgcgggt gctcctaa              348
```